United States Patent
Martina et al.

(10) Patent No.: US 11,945,858 B2
(45) Date of Patent: Apr. 2, 2024

(54) ANTIBODIES AND ANTIBODY FRAGMENTS AGAINST HNAV1.7 CHANNEL AND THEIR USE IN PAIN AND CANCER INDICATIONS

(71) Applicant: NATIONAL RESEARCH COUNCIL OF CANADA, Ottawa (CA)

(72) Inventors: Marzia Martina, Ottawa (CA); Balu Chakravarthy, Ottawa (CA); Yves Durocher, Montreal (CA); Mehdi Arbabi-Ghahroudi, Ottawa (CA); Anne Marcil, Pierrefonds (CA); Danica Stanimirovic, Ottawa (CA); Traian Sulea, Kirkland (CA); Maria Moreno, Ottawa (CA); Umberto Banderali, Ottawa (CA)

(73) Assignee: NATIONAL RESEARCH COUNCIL OF CANADA, Ottawa (CA)

( * ) Notice: Subject to any disclaimer, the term of this patent is extended or adjusted under 35 U.S.C. 154(b) by 140 days.

(21) Appl. No.: 17/056,243

(22) PCT Filed: May 17, 2019

(86) PCT No.: PCT/CA2019/050676
§ 371 (c)(1),
(2) Date: Nov. 17, 2020

(87) PCT Pub. No.: WO2019/218082
PCT Pub. Date: Nov. 21, 2019

(65) Prior Publication Data
US 2021/0206842 A1    Jul. 8, 2021

Related U.S. Application Data

(60) Provisional application No. 62/673,210, filed on May 18, 2018.

(51) Int. Cl.
| | |
|---|---|
| *A61K 39/395* | (2006.01) |
| *A61P 29/00* | (2006.01) |
| *C07K 16/00* | (2006.01) |
| *C07K 16/18* | (2006.01) |
| *C07K 16/46* | (2006.01) |
| *A61K 39/00* | (2006.01) |

(52) U.S. Cl.
CPC ............. *C07K 16/18* (2013.01); *A61P 29/00* (2018.01); *A61K 2039/505* (2013.01); *C07K 2317/22* (2013.01); *C07K 2317/33* (2013.01); *C07K 2317/565* (2013.01); *C07K 2317/569* (2013.01); *C07K 2317/92* (2013.01)

(58) Field of Classification Search
None
See application file for complete search history.

(56) References Cited

U.S. PATENT DOCUMENTS

| 8,383,107 B2 | 2/2013 | Muruganandam et al. |
| 8,715,659 B2 | 5/2014 | Muruganandam et al. |

FOREIGN PATENT DOCUMENTS

| EP | 3805390 A1 | 4/2021 | |
| WO | WO2011051350 A1 | 5/2011 | |
| WO | WO-2011051351 A1 * | 5/2011 | ......... A61K 39/0005 |
| WO | WO2013/134881 A1 | 9/2013 | |
| WO | WO2014159595 A2 | 10/2014 | |
| WO | 2015035173 A1 | 3/2015 | |
| WO | WO2015/032916 A1 | 3/2015 | |
| WO | WO2018/007950 A1 | 1/2018 | |
| WO | WO-2021032078 A1 * | 2/2021 | ......... A61K 39/3955 |

OTHER PUBLICATIONS

International Search Report of PCT/CA2019/050676.
Arbabi-Ghahroudi et al. (2009). Isolation of monoclonal antibody fragments from phage display libraries. Methods Mol Biol 502: 341-364.
Altschul et al. (1997). Gapped BLAST and PSI-BLAST: a new generation of protein database search programs. Nucleic Acids Res 25: 3389-3402.
Baral et al. (2013). Single-domain antibodies and their utility. Curr Protoc Immunol 103: Unit 2 17.
Diss et al. (2001) Expression profiles of voltage-gated Na channel a-subunit genes in rat and human prostate cancer cell lines. Prostate 48: 1-14. doi:10.1002/pros.1095.
Deuis et al. (2016). Analgesic effects of GpTx-1, PF-04856264 and CNV1014802 in a mouse model of NaV1.7mediated main. Toxins 8, 78. doi:10.3390/toxins8030078.
Fraser et al. (2005). Voltage-gated sodium channel expression and potentiation of human breast cancer metastasis. Clin Cancer Res 11: 5381-5389. doi:10.1158/1078-0432.
Grimes et al. (1995). Differential expression of voltage-activated Na+ currents in two prostatic tumour cell lines: contribution to invasiveness in vitro. FEBS Lett 369, 290-294.
Hussack et al. (2011). Neutralization of Clostridium difficile toxin A with single-domain antibodies targeting the cell receptor binding domain. J Biol Chem 286: 8961-8976. doi: 10.1074/jbc.M110.198754.
Hussack et al. (2012). Isolation and characterization of Clostridium difficile toxin-specific single-domain antibodies. Methods Mol Biol 911:211-39.

(Continued)

*Primary Examiner* — Maher M Haddad
(74) *Attorney, Agent, or Firm* — BENOIT & COTE INC; Mathieu Miron

(57) ABSTRACT

The present disclosure concerns antibodies specific for the Na v.7 polypeptides which are capable of antagonizing the biological activity of the Na v.7 polypeptide. The anti-Na v.7 antibodies can be used for alleviating the symptoms of pain and/or for treating or alleviating the symptoms of an hyperproliferative disease. The presence disclosure also concerns immunogens and methods for making antibodies, such as the anti-Na v.7 antibodies, comprising a single-domain antibody.

18 Claims, 32 Drawing Sheets

Specification includes a Sequence Listing.

(56) References Cited

OTHER PUBLICATIONS

Yildirim et al. (2012). Voltage-gated sodium channel activity promotes prostate cancer metastasis in vivo. Cancer Lett 323, 58-61.

Kumaran J et al. (2012). Semi-automated panning of naive camelidae libraries and selection of single-domain antibodies against peptide antigens. Methods Mol Biol 911:105-124. doi: 10.1007/978-1-61779-968-6_7.

Laniado et al. (1997). Expression and functional analysis of voltage-activated Na+ channels in human prostate cancer sell lines and their contribution to invasion in vitro. Am J of Path 150, 1213-1221.

Moreno et al. (2006). Insulin-like growth factor binding protein-4 (IGFBP-4) is a novel anti-angiogenic and anti-tumorigenic mediator secreted by dibutyryl cyclic AMP (dB-cAMP)-differentiated glioblastoma cells. Glia 53, 845-857.

Payandeh et al. (2011). The crystal structure of a voltage-gated sodium channel. Nature 475, 353-358.

Raymond et al. (2015). Production of α2,6-sialylated IgG1 in CHO cells. MAbs 7(3):571-83. doi: 10.1080/19420862.2015.1029215.

Rey et al. (2016). Mass Spec Studio for integrative structural biology. Structure 22(10):1538-48.

Roger et al. (2007). Voltage-gated sodium channels potentiate the invasive capacities of human non-small-cell lung cancer cell lines. Int J Biochem Cell Biol 39: 774-786. doi:10.1016/j biocel. 2006. 12.007.

Shaolong et al. (2018) Hydrogen-deuterium exchange epitope mapping reveals distinct neutralizing mechanisms for two monoclonal antibodies against diphtheria toxin. Biochemistry, 58(6): 646-56.

Shen et al. (2017) Structure of a eukaryotic voltage-gated sodium channel at near-atomic resolution. Science 355, eaal4326; DOI: 10.1126/science.aal4326.

Webster et al. (2016). Brain penetration, target engagement, and disposition of the blood-brain barrier-crossing bispecific antibody antagonist of metabotropic glutamate receptor type 1. FASEB J 30(5), 1927-1940.

Yoneda et al. "Analgesic effects of a novel monoclonal antibody against Nav1.7 sodium channel", Proceedings for Annual Meeting of the Japanese Pharmacological Society, vol. WCP2018, No. 0, Jan. 1, 2018, p. PO3-2-25.

Peng et al. "A General Method for Insertion of Functional Proteins within Proteins via Combinatorial Selection of Permissive Junctions", Chemistry & Biologie, vol. 22, Aug. 20, 2015, pp. 1134-1143.

Extended European Search Report from corresponding European Patent Application No. 19802903.5; Munich; Jun. 24, 2022; Domingues, Helena.

* cited by examiner

A pep#40a. KHKCFRNSLENNETLESIMNTLESEEDFRKYFYYLEGSKD (SEQ ID NO: 105)

pep#40b. YFYYLEGSKDALLCGFSTDSGQCPEGYTCVKIGRNPDYGY (SEQ ID NO: 106)

pep#1. KHKCFRNSLENNETLESIMNTLESEEDFRK (SEQ ID NO: 4)

pep#2. TLESEEDFRKYFYYLEGSKDALLCGFSTDS (SEQ ID NO: 5)

pep#3. ALLCGFSTDSGQCPEGYTCVKIGRNPDYGY (SEQ ID NO: 6)

pep#2a. TLESEEDFRKYFYYLEGSKD (SEQ ID NO: 103)

pep#2b. YFYYLEGSKDALLCGFSTDS (SEQ ID NO: 104)

FIG. 15A

```
DIE3IR                          3A8
        KHKCFRNSLENNETLESIMNTLESEEDFRKYFYYLEGSKDALLCGFSTDSGQCPEGYTCVKIGRNPDYGY
P40a    KHKCFRNSLENNETLESIMNTLESEEDFRKYFYYLEGSKD
P2                              TLESEEDFRKYFYYLEGSKDALLCGFSTDS
P2a                             TLESEEDFRKYFYYLEGSKD

DIE3IR                          1B6
        KHKCFRNSLENNETLESIMNTLESEEDFRKYFYYLEGSKDALLCGFSTDSGQCPEGYTCVKIGRNPDYGY
P40a    KHKCFRNSLENNETLESIMNTLESEEDFRKYFYYLEGSKD
P2                              TLESEEDFRKYFYYLEGSKDALLCGFSTDS

DIE3IR                  2G11
        KHKCFRNSLENNETLESIMNTLESEEDFRKYFYYLEGSKDALLCGFSTDSGQCPEGYTCVKIGRNPDYGY
P40a    KHKCFRNSLENNETLESIMNTLESEEDFRKYFYYLEGSKD

DIE3IR                                                      1H5
        KHKCFRNSLENNETLESIMNTLESEEDFRKYFYYLEGSKDALLCGFSTDSGQCPEGYTCVKIGRNPDYGY
P3                                              ALLCGFSTDSGQCPEGYTCVKIGRNPDYGY
```

FIG. 15J

```
EVQLQASGGGLVQAGGSLRLSCAASGFKITHYTMGWFRQAPGKEREFVSR
1       10        20        30        40        50

ITWGGDNTFYSNSVKGRFTISRDNAKNTVYLQMNSLKPEDTADYYCAAGS
        60        70        80        90        100
↓

TKHKCFRNSLENNETLESIMNTLESEEDFRKYFYYLEGSKDALLCGFSTD
        110       120       130       140       150
                           (SEQ ID NO: 108)
                              (SEQ ID NO: 107)
                    ↓(SEQ ID NO: 1)

SGQCPEGYTCVKIGRNPDYGYRVDYWGKGTQVTVSS (SEQ ID NO: 3)
        160       170       180   186
```

FIG. 16

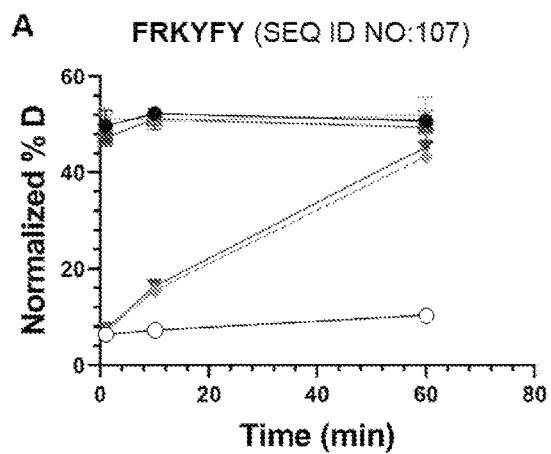
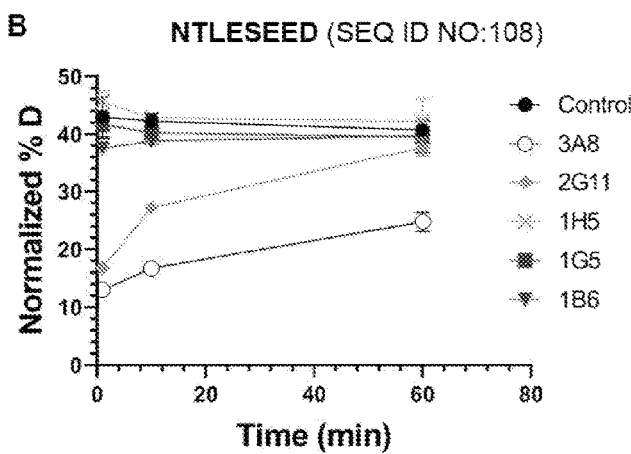
FIG. 17A  FIG. 17B
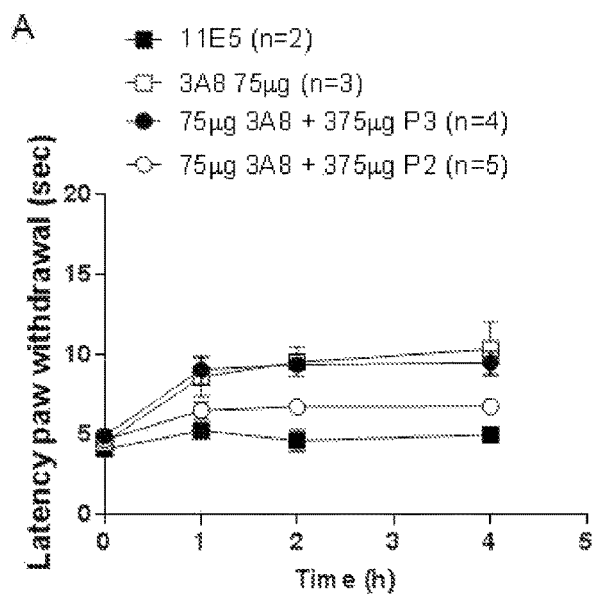
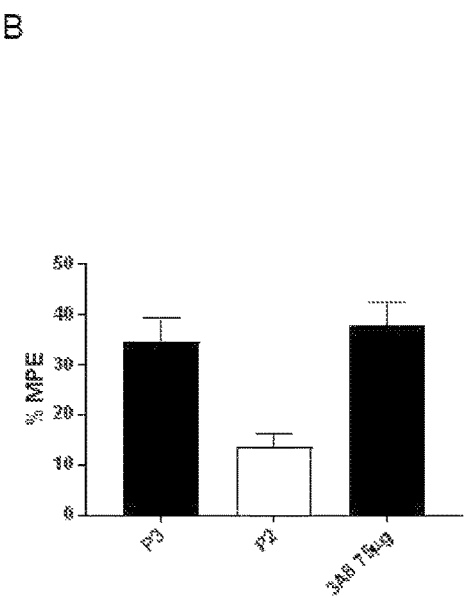
FIG. 18A  FIG. 18B

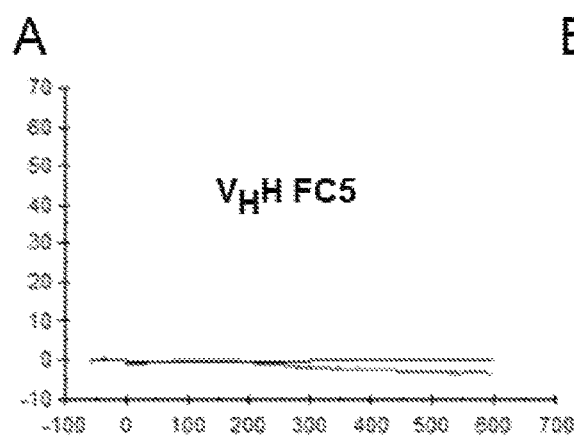
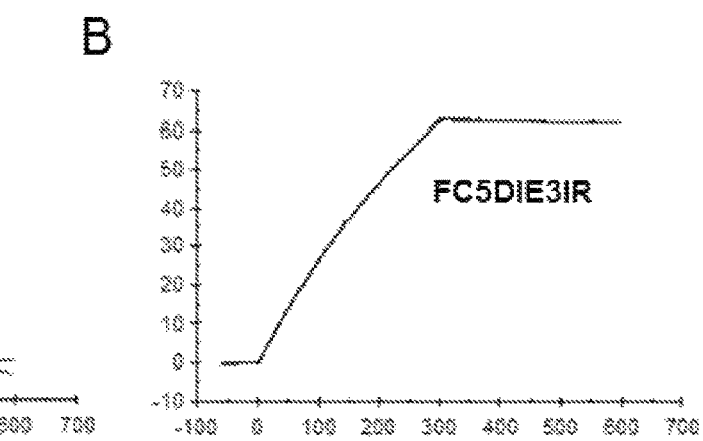
FIG. 19A     FIG. 19B

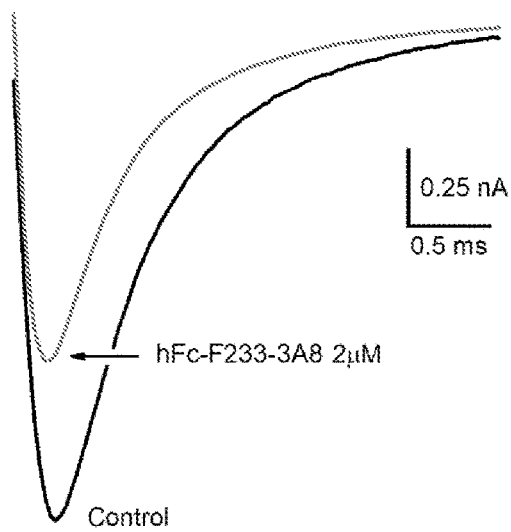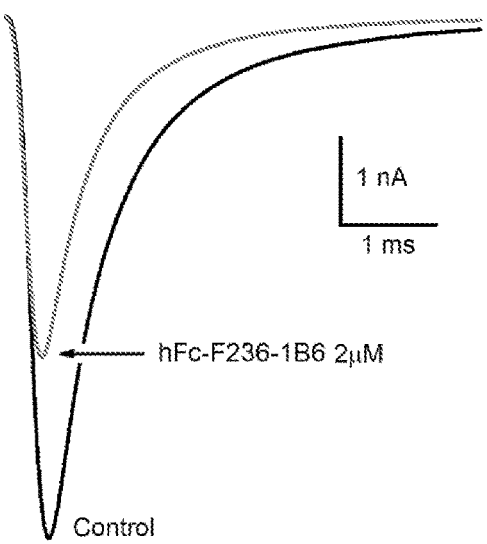
FIG. 21A  FIG. 21B
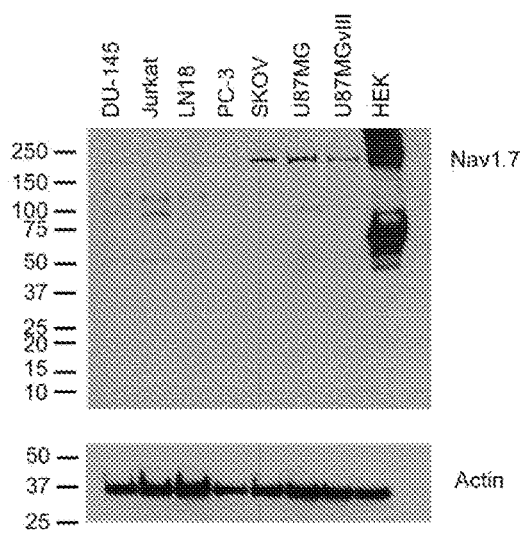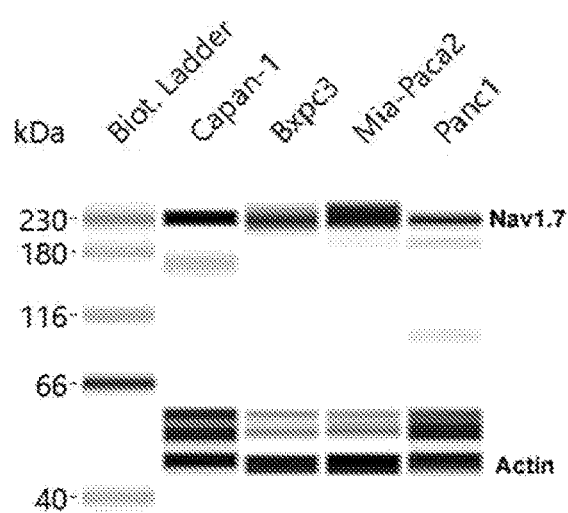
FIG. 22A  FIG. 22B

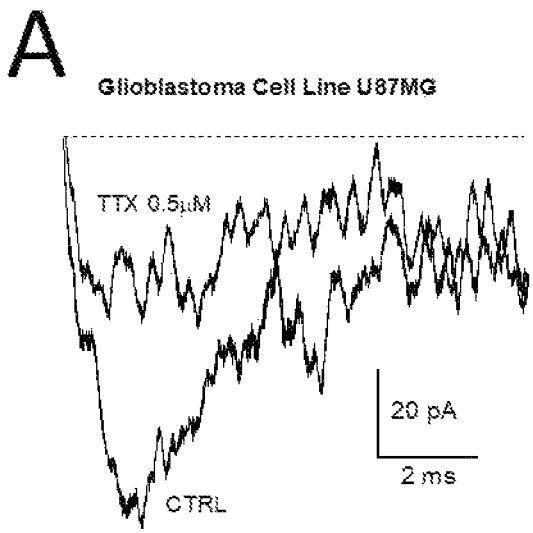
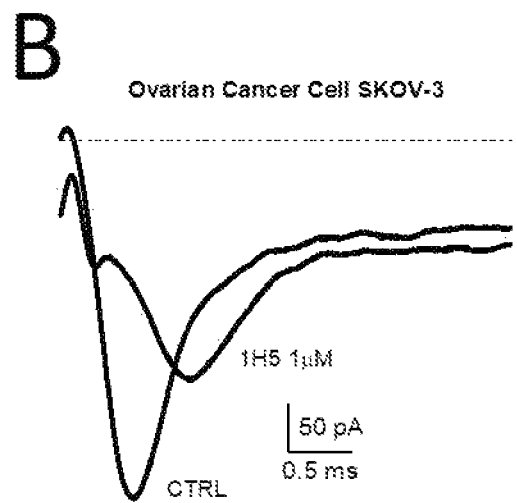
FIG. 23A    FIG. 23B
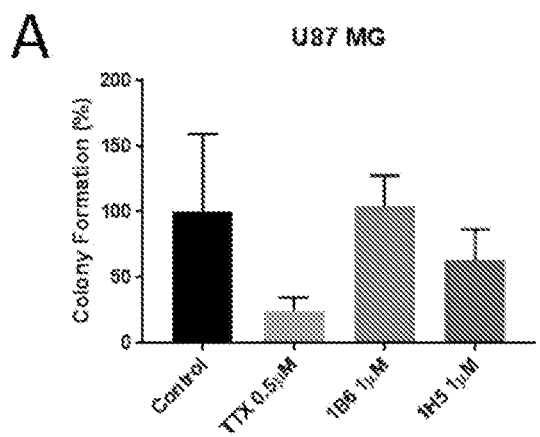
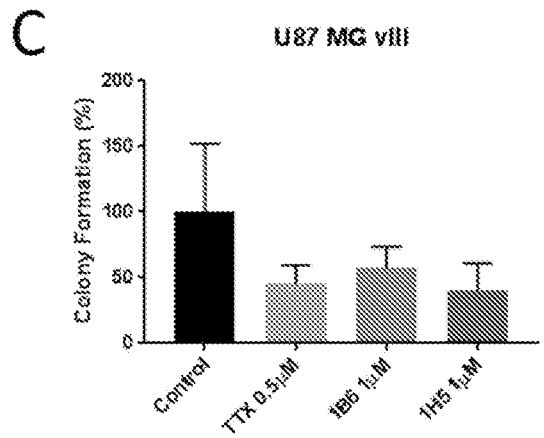
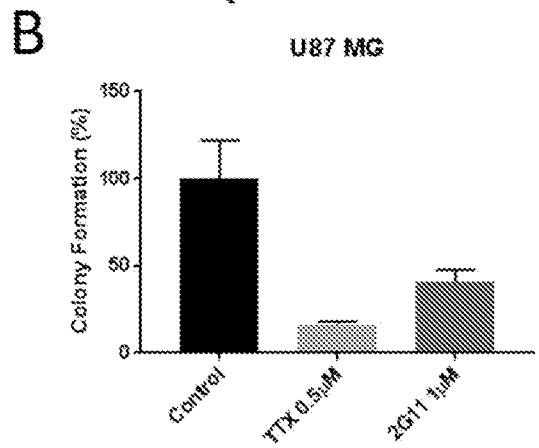
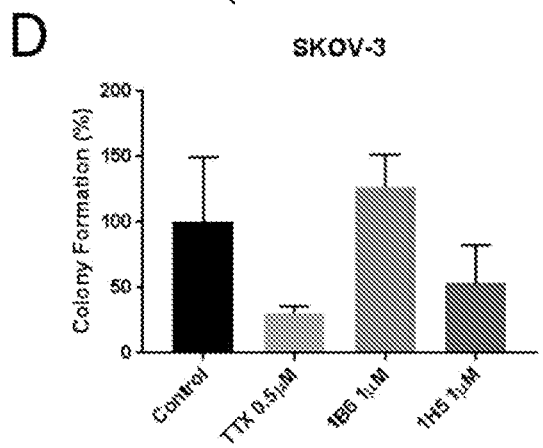
FIG. 24

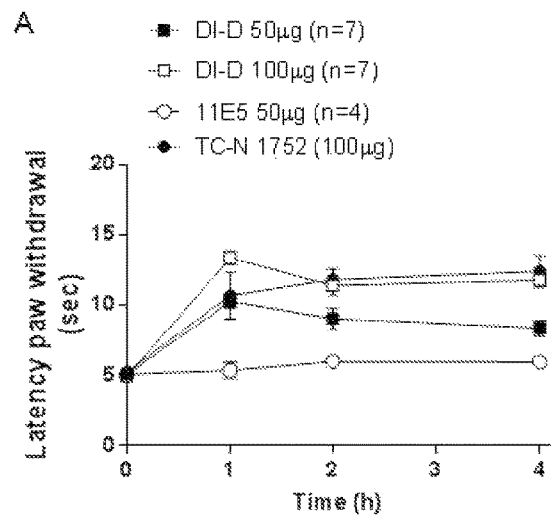
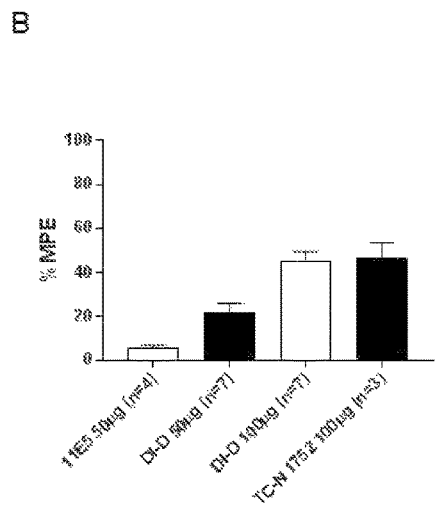
FIG. 27A  FIG. 27B
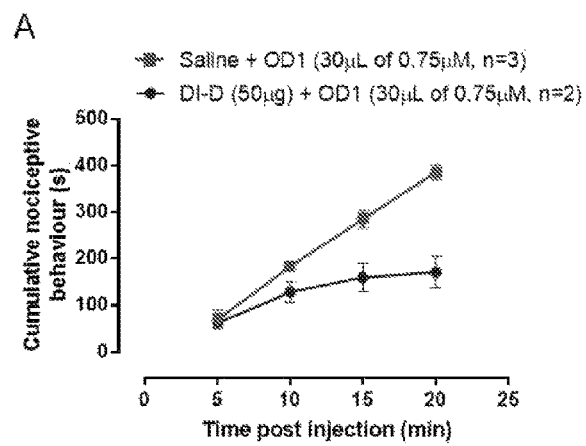
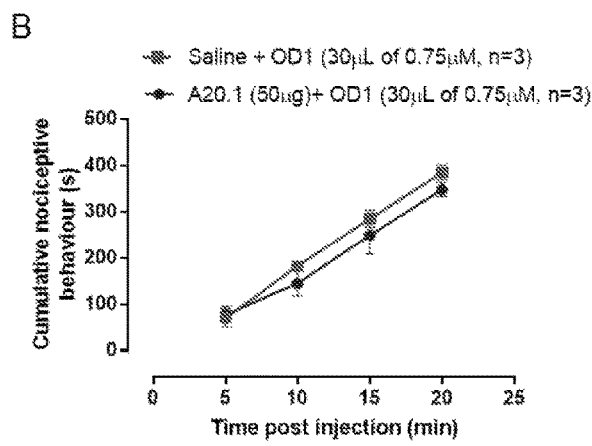
FIG. 28A  FIG. 28B

ANTIBODIES AND ANTIBODY FRAGMENTS AGAINST HNAV1.7 CHANNEL AND THEIR USE IN PAIN AND CANCER INDICATIONS

CROSS-REFERENCE TO RELATED APPLICATIONS

This application is a national stage application, filed under 35 U.S.C. § 371, of International Patent Application No. PCT/CA2019/050676, filed on May 17, 2019, which claims the benefit of U.S. Provisional Patent Application No. 62/673,210, filed May 18, 2018, which is incorporated by reference herein in its entirety.

STATEMENT REGARDING SEQUENCE LISTING

The Sequence Listing associated with this application is provided in text format in lieu of a paper copy and is hereby incorporated by reference in the specification. The name of the text file containing the Sequence Listing is USPTO_Sequence_Listing. The text fie is 126 KB, was created on Nov. 17, 2020 and is being submitted electronically via EFS-Web.

TECHNOLOGICAL FIELD

The present disclosure concerns antibodies and compositions comprising antibodies for antagonizing the human $Na_v1.7$ ($HNa_v1.7$) channel for various indications including treatment and/or alleviation of symptoms of pain and cancer.

BACKGROUND

Ion channels are proteins that form pores in cell membranes and regulate the flux of ions between the intracellular and extracellular spaces. They are involved in the control of many fundamental physiological processes in various tissues and alterations in their functions give rise to a wide range of conditions, including neurological disorders, diabetes, cancer, hypertension and arrhythmia. There are ~60 different inherited ion channel diseases, known as "channelopathies", that have been identified across cardiovascular, neuronal, neuromuscular, musculoskeletal, metabolic, and respiratory systems; and this number is destined to grow as knowledge about ion channel functions increases.

Sodium channels ($Na_v$) are involved in the control of many fundamental physiological processes in various tissues of human body. In excitable cells, they are essential for the initiation and propagation of electrical signals.

$Na_v$ has also been demonstrated to play a role in cancer. Ion channels are at the basis of the electrical variations that accompany the transitions along the different phases of cell cycle. Blocking the channels responsible for these electrical variations can inhibit the progression of cell cycle and consequently impair cell proliferation. Ion channels modify the osmotic gradients across the cell membrane and therefore induce changes in cellular volume and shape. Such changes, coordinated with polymerization/depolymerization of actin filaments underlie cell motility and, consequently, the metastatic potential of tumor cells. The degree of malignancy of various tumors also correlates with the de-novo expression of some specific ion channels. $Na_v$ are totally absent in non excitable cells, however, in various cancers (e.g. breast, prostate, lung) de-novo functional expression of $Na_v$ channels has been found and linked to malignant phenotypes (Fraser et al. 2005; Diss et al., 2001; Roger et al., 2007).

The $Na_v$ family has nine members (nine types of pore-forming a subunits), which in mammals are numerically named from $Na_v1.1$ to 1.9. These isoforms share a common overall structural motif and each $Na_v$ type has a different function and expression profile. $Na_v1.1$, $Na_v1.2$, $Na_v1.3$, and $Na_v1.6$ are mainly expressed in the central nervous system (CNS). $Na_v1.7$, $Na_v1.8$, and $Na_v1.9$ are present in the peripheral nervous system (PNS), where they are known to accumulate in the region of peripheral nerve injury and consequently may be important in chronic and neuropathic pain. $Na_v1.4$ is the muscle sodium channel and $Na_v1.5$ is the predominant cardiac myocyte channel.

The $Na_v1.7$ channel is expressed in nociceptive neurons (Dorsal Root Ganglion, DRG) of the PNS. When nociceptive stimuli (i.e., injury or inflammation) are initiated at periphery receptors, they are transduced at peripheral termini by Nays dependent action potentials. $Na_v1.7$ channels are also present in the central axonal projections of DRG neurons and their presynaptic terminals within the dorsal horn of the spinal cord where they may facilitate impulse invasion or evoked release of neurotransmitters. Homology modelling based on crystal structures of ion channels suggests an atomic-level structural basis for the altered gating of mutant $Na_v1.7$ that causes pain. Genetic, structural and functional studies have shown that $Na_v1.7$ regulates sensory neuron excitability which is a major contributor to several sensory modalities, and have established the contribution of $Na_v1.7$ to human pain disorders. In particular, genetic studies show that mutations in SCN9A gene which encode for $Na_v1.7$ produce familial pain disorders. These mutations can be described as gain of function mutations (increase activity of $Na_v1.7$) which cause paroxysmal extreme pain disorder (PEPD) or loss of function mutations (reduction of $Na_v1.7$ activity) which are linked to complete insensitivity to pain (CIP). Importantly, people totally lacking $Na_v1.7$ have minimal cognitive, cardiac, motor and sensory deficits, supporting $Na_v1.7$ as a valid and indeed attractive target for development of drug against pain.

De novo functional expression of $Na_v1.7$ has been documented in prostate, non small cell lung cancer and leukemia. The expression of $Na_v1.7$ in these cancers is reported to promote cell invasion. It has been shown that in vitro application of tetrodotoxin (TTX), a potent Nays blocker, in prostate cancer cells inhibits cancer invasion, proliferation and migration (Laniado at al., 1997; Grimes at al., 1995). Likewise, in vivo injection of TTX directly into primary tumours, to avoid systemic toxicity of TTX, in a Copenhagen rat model of prostate cancer, reduced by >40% the number of lung metastasis (Yildirim at al., 2012). Consequently, blocking the $Na_v1.7$ is a valid target to develop a drug against cancer malignancy.

The first generations of molecules developed against Nays were analgesics. These drugs were clinically effective, but, due to their non-selective $Na_v$ activity, their analgesic potential was limited by numerous side effects (dizziness, sedation, convulsions, and cardio-toxicity). For example: lidocaine (as well as other $Na_v$ blockers) is known to relieve pain but can only be used as topical jelly or ointment; other administration routes can be fatal. In the last decades a large number of programs have been put in place by pharmaceutical companies to develop a second generation of $Na_v$ inhibitors which target specific subunits with a high degree of specificity in order to develop more effective and better tolerated compounds for pain management. However, the development of a novel therapeutic selectively targeting $Na_v1.7$ represents a challenge due to the high degree of amino acid sequence homology among the different $Na_v$ subtypes. In addition, Navs are complex structures which have different dynamic states (closed, open, or inactivated). Nevertheless, large bodies of evidence concerning the sequences containing the lower homology between the subtypes of human $Na_v$ channels, regions containing mutations causing CIP and interaction regions for pore blockers (i.e., small molecules and natural toxins) are now available to help the development of new inhibitors.

Biologics such as monoclonal antibodies (mAbs) have the great advantage of being extremely selective, however, the majority of mAbs developed against ion channels so far are binders lacking functional efficacy. The difficulty to produce functional mAbs is because these targets have multiple transmembrane regions and small extracellular loops, are difficult to purify (unstable antigens) and the functional epitope is generally inside the pore. However, the tarantula toxin ProTx-II a 30 amino acid peptide which is a highly selective $Na_v1.7$ inhibitor does not bind the $Na_v1.7$ pore region, demonstrating that targeting molecular regions outside the pore could be a successful strategy in identifying subtype-selective compounds.

Data seem to suggest that $Na_v1.7$-mediated antinociception is obtained via both peripheral and central mechanisms. However, since the majority of therapeutics, biologics and small molecule, do not penetrate the blood-brain barrier (BBB) sufficiently to induce pharmacologically meaningful effects on central nervous system (CNS) targets, a successful therapeutic could be developed by increasing brain penetration.

There is need to be provided with $Na_v1.7$ inhibitors that not only bind to the $Na_v1.7$ but also lowers or inhibits its biological activity in mediating pain and halt or reduce cancer progression. In some embodiments, there is a need to be provided with $Na_v1.7$ inhibitors which are capable of penetration into the brain.

BRIEF SUMMARY

In a first aspect, the present disclosure provides an immunogen for making a specific antibody to a peptide epitope, the immunogen comprising a single-domain antibody having at least one complementary determining region (CDR), wherein the at least one CDR has been modified to include the peptide epitope. In an embodiment, the at least one CDR has been modified by deleting at least one amino acid residue. In another embodiment, the single-domain antibody comprises a first CDR, a second CDR and a third CDR. In a further embodiment, the third CDR has been modified to include the peptide epitope. In an embodiment, the antibody heavy chain is derived from a camelid antibody heavy chain. In a further embodiment, the camelid antibody heavy chain is derived from a FC5 single-domain antibody. In yet a further embodiment, the immunogen has the amino acid formula (I):

wherein SS is an optional signal sequence; FR1 has the amino acid sequence of SEQ ID NO: 60; CDR1 is the first CDR; FR2 has the amino acid sequence of SEQ ID NO: 61; CDR2 is the second CDR; FR3 has the amino acid sequence of SEQ ID NO: 62; CDR3 is the third CDR; FR4 has the amino acid sequence of SEQ ID NO: 63; and "—" is an amide bond. In an embodiment, CDR1 has the amino acid sequence of SEQ ID NO:64 or has been modified to include the peptide epitope. In yet another embodiment, CDR2 has the amino acid sequence of SEQ ID NO: 65 or has been modified to include the peptide epitope. In still a further embodiment, CDR3 has the amino acid sequence of SEQ ID NO: 66 or has been modified to include the peptide epitope. In an embodiment, the immunogen has SS which can comprise or consist essentially of, for example, amino acid sequence of SEQ ID NO: 2 or 67. In another embodiment, the immunogen lacks SS and can comprise or consist essentially of the amino acid sequence of SEQ ID NO: 3 or 68.

According to a second aspect, the present disclosure also provides an immunogen for making an antibody specific to a Nav1.7 polypeptide. The immunogen having the amino acid sequence of SEQ ID NO: 1, 2, 3, 4, 5, 6, 67 or 68, be an immunogenic variant of the amino acid sequence of SEQ ID NO: 1, 2, 3, 4, 5, 6, 67 or 68 or be an immunogenic fragment of amino acid sequence of SEQ ID NO: 1, 2, 3, 4, 5, 6, 67 or 68.

According to a third aspect, the present disclosure provides the immunogen as described herein for selecting an antibody specific for the peptide epitope as well as method using same to select an antibody specific for the peptide epitope. In some embodiments, the method comprises selecting the antibody having an affinity to the immunogen as described herein. In an embodiment, the immunogen is intended for administration or is administered to an animal and a cell producing the antibody specific for the peptide epitope is intended to be selected or is selected from an organ of the animal having received the immunogen (the spleen, the lymph node or the bone marrow for example). In another embodiment, the selected cell is intended to be fused or is fused to a cancer cell to make an hybridoma. Alternatively or in combination, the immunogen is intended for contacting or is contacted with a library of cells producing antibodies and a cell producing the antibody specific for the peptide epitope is intended to be selected or is selected from the library. In such embodiment, the library of cells producing antibodies can be intended to be obtained or can be obtained from immunizing an animal with the immunogen. In a further embodiment, the affinity and/or specificity of the selected antibody is intended to be or is characterized with an immunological assay and/or surface plasmon resonance.

According to a fourth aspect, the present disclosure provides an antibody (which can be a monoclonal antibody) specifically recognizing a $Na_v1.7$ polypeptide. The antibody of the present disclosure is specific for an epitope located on a loop 3 of a domain I (DI) of the $Na_v1.7$ polypeptide. The antibody is also capable of antagonizing the biological activity of the $Na_v1.7$ polypeptide. In an embodiment, the $Na_v1.7$ polypeptide is a human $Na_v1.7$ polypeptide and as such, the antibody specifically recognizes the human $Na_v1.7$ polypeptide. In another embodiment, the epitope is located on a first peptide comprising or consisting essentially of the following amino acid sequence:

In a further embodiment, the antibody is a monoclonal antibody which can have, for example, a dissociation constant ($K_D$) between 1 and 20 nM with the first peptide. In yet a further embodiments, the antibody is a single domain antibody, which can have, for example, a dissociation constant ($K_D$) of about 1 nM to about 1000 μM. In still another embodiment, the epitope is located on a second peptide comprising or consisting essentially of the following amino acid sequence:

TLESEEDFRKYFYYLEGSKDALLCGFSTDS. (SEQ ID NO: 5)

In still another embodiment, the epitope is located on a second peptide comprising or consisting essentially of the following amino acid sequence:

ALLCGFSTDSGQCPEGYTCVKIGRNPDYGY. (SEQ ID NO: 6)

In such embodiments, the antibody can be a monoclonal antibody, a camelid antibody or is in a multivalent display format.

In a further embodiment, the antibody can have at least one complementary determining region (CDR) comprising or consisting essentially of an amino acid sequence of: GYTFTNYW (SEQ ID NO: 7), a variant thereof or a fragment thereof; INPSNGRA (SEQ ID NO: 8), a variant thereof or a fragment thereof; ARSPYGYYDY (SEQ ID NO: 9), a variant thereof or a fragment thereof; QSLLHSNGNTY (SEQ ID NO: 13), a variant thereof or a fragment thereof; KVS (SEQ ID NO: 14), a variant thereof or a fragment thereof; and/or SQITHVPLT (SEQ ID NO: 15), a variant thereof or a fragment thereof. In another embodiment, the antibody can have a first CDR having an amino acid sequence of GYTFTNYW (SEQ ID NO: 7), the variant thereof or the fragment thereof; a second CDR having an amino acid sequence of INPSNGRA (SEQ ID NO: 8), the variant thereof or the fragment thereof; and a third CDR having an amino acid sequence of ARSPYGYYDY (SEQ ID NO: 9), the variant thereof or the fragment thereof. In still a further embodiment, the antibody of can have a heavy chain of amino acid sequence of SEQ ID NO: 12, a variant thereof or a fragment thereof. In another embodiment, the antibody can have a fourth CDR having an amino acid sequence of QSLLHSNGNTY (SEQ ID NO: 13), a variant thereof or a fragment thereof; a fifth CDR having an amino acid sequence of KVS (SEQ ID NO: 14), a variant thereof or a fragment thereof; and a sixth CDR having an amino acid sequence of SQITHVPLT (SEQ ID NO: 15), a variant thereof or a fragment thereof. In a further embodiment, the antibody can have a light chain of amino acid sequence of SEQ ID NO: 18, a variant thereof or a fragment thereof. In still another embodiment, the antibody can have the following amino acid sequences: GYTFTNYW (SEQ ID NO: 7), a variant thereof or a fragment thereof; INPSNGRA (SEQ ID NO: 8), a variant thereof or a fragment thereof; ARSPYGYYDY (SEQ ID NO: 9), a variant thereof or a fragment thereof; QSLLHSNGNTY (SEQ ID NO: 13), a variant thereof or a fragment thereof; KVS (SEQ ID NO: 14), a variant thereof or a fragment thereof; and SQITHVPLT (SEQ ID NO: 15), a variant thereof or a fragment thereof. In a further embodiment, the antibody can have a heavy chain of amino acid sequence of SEQ ID NO: 12, a variant thereof or a fragment thereof.

In still another embodiment, the antibody can have at least one a complementary determining region (CDR) comprising or consisting essentially of an amino acid sequence of: GFSLSRYN (SEQ ID NO: 75), a variant thereof or a fragment thereof; IWGGGST (SEQ ID NO: 76), a variant thereof or a fragment thereof; ARNGANWDWFAY (SEQ ID NO: 77), a variant thereof or a fragment thereof; QSL-LYSSNQKNY (SEQ ID NO: 80), a variant thereof or a fragment thereof; WAS (SEQ ID NO: 81), a variant thereof or a fragment thereof; and/or QQYYSYPFT (SEQ ID NO: 82), a variant thereof or a fragment thereof. In another embodiment, the antibody can have a first CDR having an amino acid sequence of GFSLSRYN (SEQ ID NO: 75), the variant thereof or the fragment thereof; a second CDR having an amino acid sequence of IWGGGST (SEQ ID NO: 76), the variant thereof or the fragment thereof; and a third CDR having an amino acid sequence of ARNGANWDW-FAY (SEQ ID NO: 77), the variant thereof or the fragment thereof. For example, the antibody can have a heavy chain of amino acid sequence of SEQ ID NO: 74 or 113, a variant thereof or a fragment thereof. In yet another embodiment, the antibody can have a fourth CDR having an amino acid sequence of QSLLYSSNQKNY (SEQ ID NO: 80), a variant thereof or a fragment thereof; a fifth CDR having an amino acid sequence of WAS (SEQ ID NO: 81), a variant thereof or a fragment thereof; and a sixth CDR having an amino acid sequence of QQYYSYPFT (SEQ ID NO: 82), a variant thereof or a fragment thereof. For example, the antibody can have a light chain of amino acid sequence of SEQ ID NO: 79 or 115, a variant thereof or a fragment thereof. In still another embodiment, the antibody can have the following amino acid sequences: GFSLSRYN (SEQ ID NO: 75), a variant thereof or a fragment thereof; IWGGGST (SEQ ID NO: 76), a variant thereof or a fragment thereof; ARNGANWDWFAY (SEQ ID NO: 77), a variant thereof or a fragment thereof; QSLLYSSNQKNY (SEQ ID NO: 80), a variant thereof or a fragment thereof; WAS (SEQ ID NO: 81), a variant thereof or a fragment thereof; and QQYYSYPFT (SEQ ID NO: 82), a variant thereof or a fragment thereof. In still another embodiment, the antibody can have a heavy chain of amino acid sequence of SEQ ID NO: 113, a variant thereof or a fragment thereof and a light chain of amino acid sequence of SEQ ID NO: 115, a variant thereof or a fragment thereof.

In yet another embodiment, the antibody can have at least one a complementary determining region (CDR) comprising or consisting essentially of an amino acid sequence of: GYTFTTYW (SEQ ID NO: 85), a variant thereof or a fragment thereof; INPSNGRA (SEQ ID NO: 86), a variant thereof or a fragment thereof; LRSLGYFDY (SEQ ID NO: 87), a variant thereof or a fragment thereof; QSLVHSNG-NTY (SEQ ID NO: 90), a variant thereof or a fragment thereof; KVS (SEQ ID NO: 91), a variant thereof or a fragment thereof; and/or SQSTHVPYT (SEQ ID NO: 92), a variant thereof or a fragment thereof. In some embodiments, the antibody can have a first CDR having an amino acid sequence of GYTFTTYW (SEQ ID NO: 85), the variant thereof or the fragment thereof; a second CDR having an amino acid sequence of INPSNGRA (SEQ ID NO: 86), the variant thereof or the fragment thereof; and a third CDR having an amino acid sequence of LRSLGYFDY (SEQ ID NO: 87), the variant thereof or the fragment thereof. For example, the antibody can have a heavy chain of amino acid sequence of SEQ ID NO: 84 or 117, a variant thereof or a fragment thereof. In a further embodiment, the antibody can have a fourth CDR having an amino acid sequence of QSLVHSNGNTY (SEQ ID NO: 90), a variant thereof or a fragment thereof; a fifth CDR having an amino acid sequence of KVS (SEQ ID NO: 91), a variant thereof or a fragment thereof; and a sixth CDR having an amino acid sequence of SQSTHVPYT (SEQ ID NO: 92), a variant thereof or a fragment thereof. For example, the antibody can have a light chain of amino acid sequence of SEQ ID NO: 89 or 119, a variant thereof or a fragment thereof. In another embodiment, the antibody can have the following amino acid sequences: GYTFTTYW (SEQ ID NO: 85), a variant thereof or a fragment thereof; INPSNGRA (SEQ ID NO: 86), a variant thereof or a fragment thereof; LRSLGYFDY (SEQ ID NO: 87), a variant thereof or a fragment thereof; QSLVHSNGNTY (SEQ ID NO: 90), a variant thereof or a fragment thereof; KVS (SEQ ID NO: 91), a variant thereof or a fragment thereof; and SQSTHVPYT (SEQ ID NO: 92), a variant thereof or a fragment thereof. In still a further embodiment, the antibody can have a heavy chain of amino acid sequence of SEQ ID NO: 117, a variant thereof or a fragment thereof and a light chain of amino acid sequence of SEQ ID NO: 119, a variant thereof or a fragment thereof.

In still another embodiment, the antibody can have at least one a complementary determining region (CDR) comprising or consisting essentially of an amino acid sequence of: GFTFRSYA (SEQ ID NO: 95), a variant thereof or a fragment thereof; ISSGGST (SEQ ID NO: 96), a variant thereof or a fragment thereof; ARGYDGYYERI-WYYAMDY (SEQ ID NO: 97), a variant thereof or a fragment thereof; QNVGTI (SEQ ID NO: 100), a variant thereof or a fragment thereof; SAS (SEQ ID NO: 101), a variant thereof or a fragment thereof; and/or QQYNTYPLT (SEQ ID NO: 102), a variant thereof or a fragment thereof. In some embodiments, the antibody can have a first CDR having an amino acid sequence of GFTFRSYA (SEQ ID NO: 95), the variant thereof or the fragment thereof; a second CDR having an amino acid sequence of ISSGGST (SEQ ID NO: 96), the variant thereof or the fragment thereof; and a third CDR having an amino acid sequence of ARGYDGYYERIWYYAMDY (SEQ ID NO: 97), the variant thereof or the fragment thereof. For example, the antibody can have a heavy chain of amino acid sequence of SEQ ID NO: 94 or 121, a variant thereof or a fragment thereof. In additional embodiments, the antibody can have: a fourth CDR having an amino acid sequence of QNVGTI (SEQ ID NO: 100), a variant thereof or a fragment thereof; a fifth CDR having an amino acid sequence of SAS (SEQ ID NO: 101), a variant thereof or a fragment thereof; and a sixth CDR having an amino acid sequence of QQYNTYPLT (SEQ ID NO: 102), a variant thereof or a fragment thereof. For example, the antibody can have a light chain of amino acid sequence of SEQ ID NO: 99 or 123, a variant thereof or a fragment thereof. In still another embodiment, the antibody can have the following amino acid sequences: GFTFRSYA (SEQ ID NO: 95), a variant thereof or a fragment thereof; ISSGGST (SEQ ID NO: 96), a variant thereof or a fragment thereof; ARGYDGYYERI-WYYAMDY (SEQ ID NO: 97), a variant thereof or a fragment thereof; QNVGTI (SEQ ID NO: 100), a variant thereof or a fragment thereof; SAS (SEQ ID NO: 101), a variant thereof or a fragment thereof; and QQYNTYPLT (SEQ ID NO: 102), a variant thereof or a fragment thereof. In a further embodiment, the antibody can have a heavy chain of amino acid sequence of SEQ ID NO: 121, a variant thereof or a fragment thereof and a light chain of amino acid sequence of SEQ ID NO: 123, a variant thereof or a fragment thereof.

In another embodiment, the antibody can have at least one complementary determining region (CDR) comprising or consisting of an amino acid sequence of GFAFSSAP (SEQ ID NO: 39), a variant thereof or a fragment thereof; IESDQDHTI (SEQ ID NO: 40), a variant thereof or a fragment thereof; and/or QKRGEKKT (SEQ ID NO: 41), a variant thereof or a fragment thereof. In still another embodiment, the antibody can have a first CDR having an amino acid sequence of SEQ ID NO: 39, the variant thereof or the fragment thereof; a second CDR having an amino acid sequence of SEQ ID NO: 40, the variant thereof or the fragment thereof; and a third CDR having an amino acid sequence of SEQ ID NO: 41, the variant thereof or the fragment thereof. In another embodiment, the antibody can have a heavy chain of amino acid sequence of SEQ ID NO: 38, a variant thereof or a fragment thereof. In another embodiment, the antibody can have the following amino acid sequences: GFAFSSAP (SEQ ID NO: 39), a variant thereof or a fragment thereof; IESDQDHTI (SEQ ID NO: 40), a variant thereof or a fragment thereof; and QKRGEKKT (SEQ ID NO: 41), a variant thereof or a fragment thereof. In another embodiment, the antibody can have a heavy chain of SEQ ID NO: 38.

In yet another embodiment, the biological activity of the $Na_v1.7$ polypeptide can be measured as the amplitude of current associated with the $Na_v1.7$ polypeptide and the antibody can be capable of substantially reducing the amplitude of current associated with the $Na_v1.7$ polypeptide. In a further embodiment, the biological activity of the $Na_v1.7$ polypeptide can be measured as a normalized current associated with the $Na_v1.7$ polypeptide and the antibody can be capable of substantially maintaining or reducing the normalized current associated with the $Na_v1.7$ polypeptide. In still a further embodiment, the biological activity of the $Na_v1.7$ polypeptide can be measured in an hyperalgesia animal model and the antibody can be capable of substantially increasing the latency of paw withdrawal and/or increasing the percentage of the maximal possible effect in the hyperalgesia animal model.

According to a fifth aspect, the present disclosure provides a chimeric protein comprising the antibody described herein and a moiety, preferably an antibody, capable of transmigrating the blood-brain barrier, crossing the spinal cord and/or entering the central nervous system.

According to a sixth aspect, the present disclosure provides a pharmaceutical composition comprising the antibody described herein or the chimeric protein described herein and a pharmaceutically acceptable carrier. In an embodiment, the pharmaceutical composition is formulated or intended for intravenous administration.

According to a seventh aspect, the present disclosure provides the antibody described herein, the chimeric protein described herein or the pharmaceutical composition described herein for alleviating the symptoms of pain and/or managing pain in a subject in need thereof. The present disclosure also provides the use of the antibody described herein, the chimeric protein described herein or the pharmaceutical composition described herein for alleviating the symptoms of pain and/or managing pain in a subject in need thereof. The present disclosure further provides the use of the antibody described herein, the chimeric protein described herein or the pharmaceutical composition described herein for the manufacture of a medicament for alleviating the symptoms of pain and/or managing pain in a subject in need thereof. In an embodiment, the pain is a neuropathic pain. In another embodiment, the pain is a chronic pain. In still another embodiment, the subject is a human subject. In yet another embodiment, the subject is an animal subject.

According to a eighth aspect, the present disclosure provides a method of alleviating the symptoms of pain and/or managing pain in a subject in need thereof, the method comprising administering an effective amount of the antibody described herein, the chimeric protein described herein or the pharmaceutical composition described herein to the subject under conditions so as to alleviate the symptoms of pain and/or manage pain. In an embodiment, the pain is a neuropathic pain. In another embodiment, the pain is a chronic pain. In still another embodiment, the subject is a human subject. In yet another embodiment, the subject is an animal subject.

According to a ninth aspect, the present disclosure provides an antibody defined herein, a chimeric protein defined herein or a pharmaceutical composition defined herein for treating or alleviating the symptoms of an hyperproliferative disease in a subject in need thereof. The present disclosure also provides using and antibody defined herein, a chimeric protein defined herein or a pharmaceutical composition defined herein for treating or alleviating the symptoms of an hyperproliferative disease in a subject in need thereof. The present disclosure further provides using an antibody defined herein, a chimeric protein defined herein or a pharmaceutical composition defined herein for the manufacture of a medicament for treating or alleviating the symptoms of an hyperproliferative disease in a subject in need thereof. In an embodiment, the hyperproliferative disease can be cancer. In some additional embodiments, the subject can have a cancerous tumor. In specific embodiments, the cancerous tumor comprises at least one cancerous cell expressing a $Na_v1.7$ polypeptide. In an embodiment, the the subject is a human subject. In another embodiment, the subject is an animal subject.

According to a tenth aspect, the present disclosure provides a method of treating or alleviating the symptoms of an hyperproliferative disease in a subject in need thereof. Broadly, the method comprising administering an effective amount of antibody defined herein, a chimeric protein defined herein or a pharmaceutical composition defined herein to the subject under conditions so as to treat or alleviate the symptoms of the hyperproliferative disease. In an embodiment, the hyperproliferative disease can be cancer. In some additional embodiments, the subject can have a cancerous tumor. In specific embodiments, the cancerous tumor comprises at least one cancerous cell expressing a $Na_v1.7$ polypeptide. In an embodiment, the subject is a human subject. In another embodiment, the subject is an animal subject.

BRIEF DESCRIPTION OF THE DRAWINGS

Having thus generally described the nature of the invention, reference will now be made to the accompanying drawings, showing by way of illustration, a preferred embodiment thereof, and in which:

FIG. 2A shows the molecular model of $V_HH$ FC5 lacking 6 amino-acid residues from the inner region of its CDR3. Retained segments of CDR3 are highlighted in black. The molecular model of FC5 $V_HH$ was constructed as described below.

FIG. 2B provides a modeled three-dimensional (3D) structure of DIE3 loop including two disulfide bonds (labeled).

FIG. 2C provides the 3D-location of DIE3 loop (black) relative to cell membrane (planes) shown on the cryo-EM structure (PDB ID 5XSY) of the homologous electric eel $Na_v1.4$ channel a subunit complexed with β-1 subunit (β1-IgL).

FIG. 4A shows the current-voltage relationship of the peak current amplitude (left panel) and current density (right panel) in $hNa_v1.7$-HEK293 cells (open circles) and non-transfected HEK293 cells (filled circles).

FIG. 4B shows current traces (lower trace) generated by voltage steps (from −85 to +60 mV; 5 mV increments; upper trace).

FIG. 4C shows the activation (filled circles) and inactivation (diamonds) curves for $Na^+$ currents recorded from $hNa_v1.7$-HEK293 cells. Half-maximal activation occurred at −28.82±4.33 mV (n=8). Half-maximal inactivation occurred at −63.47±3.98 mV (n=8). These values correspond to literature values for $hNa_v1.7$ channels expressed in HEK293 cells. Statistics shown as mean±SEM.

FIG. 6A Examples of $hNa_v1.7$ current recordings in $hNa_v1.7$-HEK293 cells in control and in response to the application of 3A8 (left; voltage step to −15 mV) and 1G5 (right; voltage step to −20 mV) respectively. 3A8 at concentrations of 1 μM and 2 μM reduced the $hNa_v1.7$ currents in a dose dependent manner, whereas 1G5 (1 μM) had no effect.

FIG. 6B Time course of the effect of 3A8 (1 μM; open circles) and 1G5 (1 μM; filled circles) on the $hNa_v1.7$ currents. 1G5 did not reduce $hNa_v1.7$ currents, whereas 3A8 reduced the current of approx. 13%. The onset time of the mAb effect was estimated by curve-fitting the 3A8 induced current decay with an exponential function (solid line; T=176 sec).

FIG. 6C Normalized current-voltage (I-V) relationships for $hNa_v1.7$ currents in control (open circles) and after the application of 3A8 (1 μM filled circles; 2 μM, open squares). Note the dose dependent decrease in the current amplitudes and the shift of the current onset to more hyperpolarized voltages.

FIG. 6D Activation and steady state fast inactivation curves for $hNa_v1.7$ in control (open circles; curve fitting, solid lines) and after application of 3A8 (1 μM, filled circles; curve fitting, dotted lines). Curve fitting of the experimental data to Boltzmann sigmoidal curves, allowed the estimation of half effect voltages.

FIG. 6E Summary of the effects of different mAbs on $hNa_v1.7$ currents. At the concentration of 1 μM, 3A8 was able to significantly reduce the $Na_v$ currents (8.2%±1.7; n=7), while 1G5 did not change the amplitude of the currents (0.77%±1.34, n=12). 3A8 at 2 μM reduced the $Na_v$ currents of 16.0%±2.1 (n=5).

FIG. 6F Dose-response curve of the effect of 3A8 on hNa$_v$1.7 currents. Results are provided as the percentage of Na$_v$1.7 inhibition as a function of the concentration of the antibody (in μM, logarithmic scale). The IC$_{50}$ for 3A8 was measured to be 0.9±0.2 μM.

FIG. 7A Examples of hNa$_v$1.7 current recordings in hNa$_v$1.7-HEK293 cells in control and in response to the application of 1B6 (voltage step to −15 mV). 1B6 at concentrations of 2 μM reduced the hNa$_v$1.7 currents.

FIG. 7B Time course of the effect of 1B6 (2 μM) on the hNa$_v$1.7 currents. The onset time of the mAb 1B6 effect was estimated by curve-fitting the 1B6 induced current decay with an exponential function (solid line; T=89 sec).

FIG. 7C Normalized current-voltage (l-V) relationships for hNa$_v$1.7 currents in control (filled squares) and after the application of 1B6 (1 μM filled circles; 2 μM, filled triangles).

FIG. 7D Activation and steady state fast inactivation curves for hNa$_v$1.7 in control (filled squares; curve fitting, solid lines) and after application of 1B6 (1 μM, filled circles; curve fitting, dotted lines). Curve fitting of the experimental data to Boltzmann sigmoidal curves, allowed the estimation of half effect voltages.

FIG. 7E Summary of the effects of different mAbs on hNa$_v$1.7 currents. At the concentration of 1 μM, 1B6 was able to significantly reduce the Na$_v$ currents (27.7%±2.9; n=20), while 1G5 did not change the amplitude of the currents (0.77%±1.34, n=12). 1B6 at 2 μM reduced the Na$_v$ currents of 40.3%±5.7 (n=12).

FIG. 7F Dose-response curve of the effect of 1B6 on hNa$_v$1.7 currents. Results are provided as the percentage of Na$_v$1.7 inhibition as a function of the concentration of the antibody (in μM, logarithmic scale). The IC$_{50}$ for 1B6 was measured to be 1.02±0.19 μM.

FIG. 8A Examples of hNa$_v$1.7 current recordings in hNa$_v$1.7-HEK293 cells in control and in response to the application of 2G11 (voltage step to −15 mV). 2G11 at concentrations of 2 μM reduced the hNa$_v$1.7 currents.

FIG. 8B Time course of the effect of 2G11 (2 μM) on the hNa$_v$1.7 currents. The onset time of the mAb 2G11 effect was estimated by curve-fitting the 2G11 induced current decay with an exponential function (solid line; T=57 sec).

FIG. 8C Normalized current-voltage (l-V) relationships for hNa$_v$1.7 currents in control (filled squares) and after the application of 2G11 (1 μM filled circles; 2 μM, filled triangles).

FIG. 8D Activation and steady state fast inactivation curves for hNa$_v$1.7 in control (filled squares; curve fitting, solid lines) and after application of 2G11 (1 μM, filled circles; curve fitting, dotted lines). Curve fitting of the experimental data to Boltzmann sigmoidal curves, allowed the estimation of half effect voltages.

FIG. 8E Summary of the effects of different mAbs on hNa$_v$1.7 currents. At the concentration of 1 μM, 2G11 was able to significantly reduce the Na$_v$ currents (22.8%±3.7; n=14), while 1G5 did not change the amplitude of the currents (0.77%±1.34, n=12). 2G11 at 2 μM reduced the Na$_v$ currents of 35.4%±6.1 (n=15).

FIG. 8F Dose-response curve of the effect of 2G11 on hNa$_v$1.7 currents. Results are provided as the percentage of Na$_v$1.7 inhibition as a function of the concentration of the antibody (in μM, logarithmic scale). The IC$_{50}$ for 2G11 was measured to be 1.06±0.29 μM.

FIG. 9A Examples of hNa$_v$1.7 current recordings in hNa$_v$1.7-HEK293 cells in control and in response to the application of 1H5 (voltage step to −15 mV). 1H5 at concentrations of 1 μM reduced the hNa$_v$1.7 currents.

FIG. 9B Time course of the effect of 1H5 (1 μM) on the hNa$_v$1.7 currents. The onset time of the mAb 1H5 effect was estimated by curve-fitting the 1H5 induced current decay with an exponential function (solid line; T=53 sec).

FIG. 9C Normalized current-voltage (l-V) relationships for hNa$_v$1.7 currents in control (filled squares) and after the application of 1H5 (1 μM filled circles; 2 μM, gray filled circles).

FIG. 9D Activation and steady state fast inactivation curves for hNa$_v$1.7 in control (filled squares; curve fitting, solid lines) and after application of 1H5 (1 μM, filled circles; curve fitting, dotted lines). Curve fitting of the experimental data to Boltzmann sigmoidal curves, allowed the estimation of half effect voltages.

FIG. 9E Summary of the effects of different mAbs on hNa$_v$1.7 currents. At the concentration of 1 μM, 1H5 was able to significantly reduce the Na$_v$ currents (38.4%±4.8; n=10), while 1G5 did not change the amplitude of the currents (0.77%±1.34, n=12). 1H5 at 2 μM reduced the Na$_v$ currents of 36.7%±3.2 (n=14).

FIG. 9F Dose-response curve of the effect of 1H5 on hNa$_v$1.7 currents. Results are provided as the percentage of Na$_v$1.7 inhibition as a function of the concentration of the antibody (in μM, logarithmic scale). The IC$_{50}$ for 1H5 was measured to be 0.56±0.02 μM.

FIG. 11A provides the time-course and dose-response effects of an anti-hNa$_v$1.7 mAb (3A8, 50 μg (□) and 100 (■) μg), the selective Na$_v$1.7 channel inhibitor TC-N1752 (100 μg (Δ)) or 11E5 (a negative control (•)) were tested using the Hargreaves Model of Hyperalgesia in rats. Nociceptive thermal behaviours were measured for up to 4 h post injection. Results are shown as the latency in paw withdrawal (in secs, mean±SEM of 4-6 animals per group) in function of therapeutic tested and time (in hours).

FIG. 11B provides the percentage of the effect on left paw withdrawal (% Effect) of 3A8 (50 (□) and 100 (■) μg), 11E5 (a negative control (•)) and TC-N1752 (100 μg (Δ)) Results are show as the percentage the effect (% Effect) in function of time. The maximus effect for 3A8 50 μg was 24.09±3.69 (n=5) and it was reached 2 hours after injection; for 3A8 100 μg was 40.55±2.20 (n=5) after 2 hours from injection.

FIG. 12A shows the results obtained with the 2G11 antibody.

FIG. 12B shows the results obtained with the 1H5 antibody.

FIG. 12C shows the results obtained with the 1B6 antibody.

FIG. 13A Time-course effect of mAb 3A8 (□) and a control (PBS, •) injected by intravenous route on CFA-induced thermal hyperalgesia in rats.

FIG. 13B Effect of 3A8 expressed as percentage of Maximum Possible Effect (% MPE) 4 h after intraplantar injection of test compounds. Results are shown as mean±SEM of 4 animals per group.

FIG. 14A shows the concentration-response effect of subcutaneous injection of OD1 (0.5-1 µM) into the dorsal side of the hind paw of mice. Spontaneous pain behaviours were evidenced by licking, flinching, lifting and shaking of the injected paw.

FIG. 14B shows the negative control for the results obtained in FIG. 14A.

FIG. 14C shows the results obtained with the administration of 100 µg of 3A8.

FIG. 14D shows the results obtained with the administration of 100 µg of 1H5.

FIG. 14E shows the results obtained with the administration of 100 µg of 2G11.

FIG. 14F shows the results obtained with the administration of 100 µg of 1B6.

FIGS. 15A to 15J show the mapping, as tested by ELISA, of the antigen binding domain of the anti-hNa$_v$1.7 mAbs 3A8, 1B6, 2G11 and 1H5.

FIG. 15A Seven overlapping antigen-peptides derived from DIE3IR were generated.

FIG. 15B Binding of mAbs 3A8, 1B6, 2G11 and 1H5 to peptides FC5DIE3IR, pep #40a (P40a) and pep #40b (P40b).

FIG. 15C shows the mAb 3A8 binding to peptides FC5DIE3IR, pep #1 (P1), pep #2 (P2) and pep #3 (P3).

FIG. 15D shows the mAb 3A8 binding to peptides FC5DIE3IR, pep #1 (P1), pep #2 (P2) and pep #3 (P3).

FIG. 15E shows the mAb 1B6 binding to peptides FC5DIE3IR, pep #1 (P1), pep #2 (P2) and pep #3 (P3).

FIG. 15F shows the mAb 1H5 binding to peptides FC5DIE3IR, pep #1 (P1), pep #2 (P2) and pep #3 (P3)

FIG. 15G shows the mAb 1H5 binding to peptides FC5DIE3IR, pep #1 (P1), pep #2 (P2) and pep #3 (P3).

FIG. 15H shows the binding of mAbs 3A8, 1B6 and 2G11 to pep #2a (P2a) and pep #2b (P2b), respectively.

FIG. 15I show the binding of mAbs 3A8, 1B6 and 2G11 to pep #2a (P2a) and pep #2b (P2b), respectively.

FIG. 15J shows the summary of the mAb binding properties of 3A8 (with respect to the DIE3IR peptide of SEQ ID NO: 1, the P40a peptide of SEQ ID NO: 105, the P2 peptide of SEQ ID NO: 5 and the P2a peptide of SEQ ID NO: 103), 1B6 (with respect to the DIE3IR peptide of SEQ ID NO: 1, the P40a peptide of SEQ ID NO: 105 and the P2 peptide of SEQ ID NO: 5), 2G11 (with respect to the DIE3IR peptide of SEQ ID NO: 1 and the P40a peptide of SEQ ID NO: 105) and 1H5 (with respect to the DIE3IR peptide of SEQ ID NO: 1 and the P3 peptide of SEQ ID NO: 6). The shaded area represent the peptide sequence in which the epitope resides per each mAbs.

FIG. 16 shows the position of the peptides spanning DIE3IR domain FRKYFY (SEQ ID NO:107) and NTLE-SEED (SEQ ID NO:108) on FC5DIE3IR. The rectangles represent the peptides FRKYFY (SEQ ID NO: 107) and NTLESEED (SEQ ID NO: 108). Deuteration was measured across all three time points. Arrows indicate insertion of 70 aa DIE3IR peptide (KHKCFRNSLENNETLESIMNTLE-SEEDFRKYFYYLEGSKDALLCGFSTDSGQCP-EGYTCVKIG RNPDYGY, SEQ ID NO: 1). A redundancy of 2.3 was achieved with 38 peptides covering 74% of the sequence.

FIGS. 17A and 17B display the binding kinetics for peptides spanning DIE3IR domain FRKYFY (SEQ ID NO:107) and NTLESEED (SEQ ID NO:108), respectively. Deuteration was measured in triplicate. Error bars represent ±1 SD. HDX-MS results are also shown for FC5DIE31R unbound (black circles).

FIG. 17A shows the normalized deuteration plotted as a function of time for Phe129-Tyr134 (FRKYFY; SEQ ID NO: 107).

FIG. 17B shows the normalized deuteration plotted as a function of time for residues Asn121-Asp128 (NTLESEED; SEQ ID NO: 108).

FIGS. 18A and 18B show the effects of peptide antigen fragments pep #2 (P2) and pep #3 (P3) on 3A8-mediated reversal of hyperalgesia.

FIG. 18A Peptide fragments raised against the binding epitope of the anti-hNa$_v$1.7 mAb 3A8 (P2 (○)) or against an non-related region of 3A8 (P3 (•)) were co-injected with 3A8 by intraplantar route (1:5, 3A8 to peptide ratio). Reversal of hyperalgesia was also tested with 3A8 alone (75 µg (□)), and with a negative control (11E5, 50 µg (■)). Results are shown as mean±SEM.

FIG. 18B Effect of P2 and P3 on 3A8-induced reversal of hyperalgesia expressed as percentage of maximum possible effect (% MPE) 4 hs after intraplantar injection of test compounds. Results are shown as mean±SEM of 2-5 animals per group.

FIGS. 19A and 19B show the results of Biacore T200 SPR analysis of various antibodies to captured mAb 3A8 (1 µM to captured mAb 3A8). The sensorgrams showed that 3A8 bound specifically FC5DIE3IR and did not bind FC5.

FIG. 19A shows the results obtained for FC5 (control).

FIG. 19B shows the results obtained for FC5DIE3IR.

FIG. 20A shows the results obtained with Fc-captured mAb 3A8 and $V_H$H FC5.

FIG. 20B shows the results obtained with Fc-captured mAb 3A8 and FC5DIE3IR.

FIG. 20C shows the results obtained with Fc-captured 2G11 and $V_H$H FC5.

FIG. 20D shows the results obtained with Fc-captured 2G11 and FC5DIE3IR.

FIG. 20E shows the results obtained with Fc-captured 1B6 and $V_H$H FC5.

FIG. 20F shows the results obtained with Fc-captured 1B6 and FC5DIE3IR.

FIG. 20G shows the results obtained with Fc-captured 1H5 and $V_H$H FC5.

FIG. 20H shows the results obtained with Fc-captured 1H5 and FC5DIE3IR.

FIGS. 21A and 21B show the effect of the recombinant chimeric antibodies at the concentration of 2 µM on the amplitude of the $Na_v1.7$ currents recorded at resting-closed state using patch-clamp whole-cell technique in HEK293 cells overexpressing the $hNa_v1.7$ channels.

FIG. 21A shows the results obtained for hFc-F236-1B6.

FIG. 21B shows the results obtained for hFc-F233-3A8.

FIGS. 22A and 22B show the expression of $hNa_v1.7$ in cancer cell lines.

FIG. 22A Western blot showing expression of $hNa_v1.7$ (~230 kDa) in the following human cancer cell lines: DU-145 (model of prostate cancer), Jurkat (model of leukemia, LN18 (model of glioblastoma), PC-3 (model of prostate cancer), SKOV-3 (model of ovarian cancer), U87MG (model of glioblastoma) and U87MgvIII (model of glioblastoma). HEK293 cells overexpressing $hNa_v1.7$ were used as positive control. Note that $Na_v1.7$ was absent only in the PC-3 prostate cancer cell line.

FIG. 22B Western blot showing expression of $hNa_v1.7$ (~130 kDa) in the human prostate cancer cell lines Capan-1, Bxpc3, Mia-Paca2 and Panc1. Actin was used as reference for protein expression.

FIGS. 23A and 23B show $hNa_v1.7$ currents recorded using whole cell patch clamp in glioblastoma U87MG and ovarian cancer SKOV-3 cells.

FIG. 23A Recording of $hNa_v1.7$ currents in a glioblastoma U87MG cell in control (CTRL) conditions and after block of the $Na^+$ currents by tetrodotoxin (TTX, 0.5 µM).

FIG. 23B Recording of $hNa_v1.7$ currents form an ovarian cancer SKOV-3 cell in control (CTRL) and after application of 1H5 (1 µM). MAb 1H5 reduces the current of ~50%.

FIGS. 24A to 24D provide histrograms representing quantitative analysis of the cell growth of various cancer cell lines in soft agar by cellular metabolic activity measured using Alamar Blue. Cells were subjected to either DME (Control; negative control), TTX (0.5 µM; positive control), 1B6 (1 µM), 1H5 (1 µM) or 2G11 (1 µM). Each bar represents mean fluorescence units per well±SEM; n=3.

FIG. 24A In glioblastoma U87MG cells, TTX (0.5 µM) reduced colony formation by 75%, mAb 1H5 (1 µM) by 37%, while mAb 1B6 (1 µM) did not affect colony formation.

FIG. 24B In a different experiment using U87MG cells, TTX (0.5 µM) reduced colony formation by 84% and mAb 2G11 (1 µM) by 60%.

FIG. 24C In glioblastoma U87MGvIII cells, TTX (0.5 µM) reduced colony formation of by 55%, 1B6 (1 µM) by 53% and 1H5 (1 µM) by 60%.

FIG. 24D In ovarian cancer SKOV-3 cells, TTX (0.5 µM) reduced colony formation by 70%, mAb 1H5 (1 µM) by 57%, while mAb 1B6 (1 µM) did not reduce colony formation.

FIG. 25A Phages were rescued from individual colonies, selected from the fourth round of panning and grown overnight at 37° C. Wells of a Nunc microtiter plate were coated with FC5DIE3IR and FC5 proteins at 5 µg/ml in PBS. After blocking, 100 µl of phage supernatants (from clones A-H) were added to the respective wells followed by incubation for 1 h at room temperature and addition of anti-M13-HRP conjugate. Binding was detected with TMB substrate and A450 was measured using an ELISA plate reader. As shown, six positive clones (DI-A, DI-B, DI-C, DI-D, DI-E and DI-H), having a signal of at least 3× background, were identified by phage-ELISA.

FIG. 25B The selected phage D did not bind to the $V_H$H FC5 or to another extracellular loop DIII of the $hNa_v1.7$ channels grafted to FC5 scaffold (protein FC5DIIIDIR) showing its specificity for FC5DIE3IR.

FIG. 26A $HNa_v1.7$ currents recorded in $hNa_v1.7$-HEK293 cells in control and in response to the application of the $V_H$Hs DI-D (left; voltage step to −30 mV) and DI-B (right; voltage step to −20 mV) respectively. DI-D, applied at 1 and 3 µM concentrations reduced $hNa_v1.7$ current in a dose dependent manner, whereas DI-B (1 µM) had no reducing effect.

FIG. 26B Recordings of normalized $hNa_v1.7$ currents and effect of the application of 1 µM DI-D (open circles) and 1 µM DI-B (filled circles) $V_H$Hs. In a 500 sec recording, the DI-B did not reduce $hNa_v1.7$ current, whereas DI-D reduced the current to approx. 91% of control (dashed line). Exponential curve-fitting of the DI-D induced current decay (solid line) was used to estimate the onset time of the $V_H$H effect. In this experiment, the onset value was 150 sec.

FIG. 26C Normalized current-voltage (I-V) relationships for $hNa_v1.7$ HEK293 expressing cells in control (open circles) and after application of DI-D at 1 (filled circles) and 2 (open squares) µM showing the dose dependent decrease in currents.

FIG. 26D Activation and steady state fast inactivation curves for $hNa_v1.7$ in control (open circles, solid lines) and after application of 1 µM DI-D (filled circles, dotted lines). Curve fitting of the experimental data to Boltzmann sigmoidal curves, allowed the estimation of half effect voltages.

FIG. 26E Effect of the application of $V_H$Hs on the amplitude of the $Na_v1.7$ currents recorded using patch-clamp whole-cell technique in $hNa_v1.7$-HEK293 cells. The $Na_v1.7$ currents were normalised to 100% in control (absence of $V_H$Hs). All $V_H$Hs were tested at 1 µM. At 1 µM only DI-D reduced the amplitude of the currents (11.7%±5.8, n=12). DI-D significantly reduced the currents of 15.0%±6.9 (n=4) and 24.1%±5.6 (n=7) at 2 µM and 3 µM respectively.

FIG. 26F Dose-response curve for DI-D, from this curve, the $IC_{50}$ of the effect of DI-D on the $hNa_v1.7$ current can be extrapolated to $IC_{50}$=1.48±0.25 µM.

FIGS. 27A and 27B show the effect of the $V_H$H antibody DI-D on a CFA-induced thermal hyperalgesia in rats (chronic pain model).

FIG. 27A shows the time-course of the effect of DI-D (50 µg and 100 µg), 11E5 (100 µg, negative control) and TC-N1752 (100 μg, positive control) on CFA-induced thermal hyperalgesia in rats. Nociceptive thermal behaviours were measured for up to 4 h post injection. Results are shown as the latency in paw withdrawal (in secs, mean±SEM of 4-7 animals per group) as a function of therapeutic tested and time (in hours).

FIG. 27B shows the histogram of the effect of 11E5, TC-N1752, DI-D 50 μg and DI-D 100 μg on hyperalgesia expressed as percentage of maximum possible effect (% MPE) after intraplantar injection of test compounds.

FIGS. 28A and 28B show the effects of $V_HH$ DI-D in a mouse model of $Na_v1.7$-mediated pain obtained by plantal subcutaneous injection of OD1.

FIG. 28A shows that administration of 50 μg of DI-D (•) reversed spontaneous pain behaviours evoked in mice by plantal injection of OD1 (■).

FIG. 28B shows that administration of 50 μg of a $V_HH$s not acting on the $hNa_v1.7$ (A20.1; •) did not have any effect on the spontaneous pain behaviours in mice evoked by OD1 (■). $V_HH$s were injected 60 minutes prior to OD1 injection. Results are shown as mean±SEM of 2-3 animals per group.

Figure 29A:
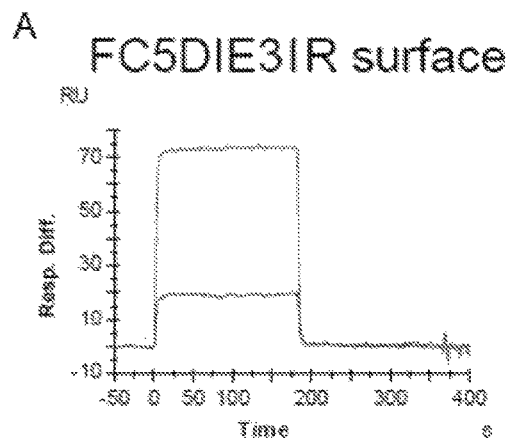
FIGS. 29A and 29B provide the results of Surface Plasmon Resonance (SPR) showing the binding of $V_HH$ DI-D to immobilized FC5 and FC5DIE3IR.

FIG. 29A Test run at 50 and 250 nM. $V_HH$ DI-D showed clear binding to immobilized FC5DIE3IR.

Figure 29B:
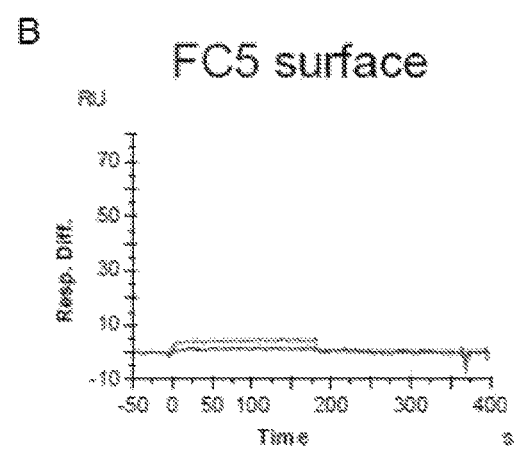

FIG. 29B Run with trace amounts of binding observed to the immobilized FC5.

Figure 30A:
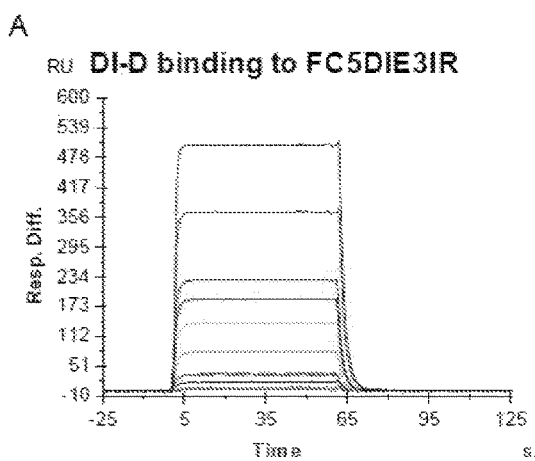
Figure 30B:
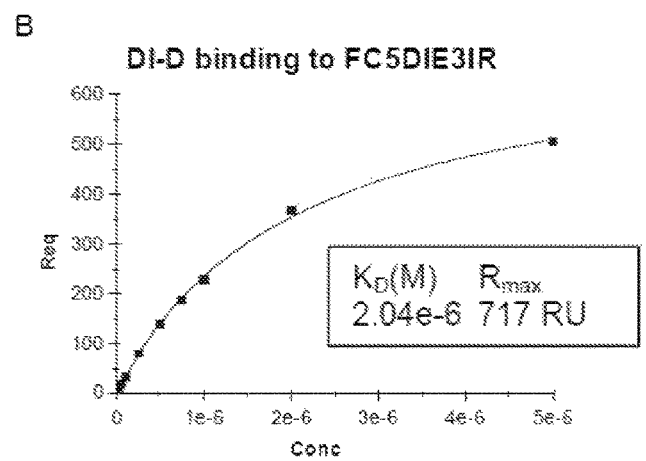

FIGS. 30A and 30B provide the results of Surface Plasmon Resonance (SPR).

FIG. 30A shows the binding affinity of $V_HH$ DI-D to immobilized FC5DIE3IR using multiple cycle kinetics (MCK).

FIG. 30B shows that $V_HH$ DI-D binds to immobilized FC5DIE3IR with a $K_D$ of approximately 2 μM and an observed $R_{max}$ of approx. 700 RU, indicating a high level of activity of immobilized FC5DIE3IR.

Figure 31:
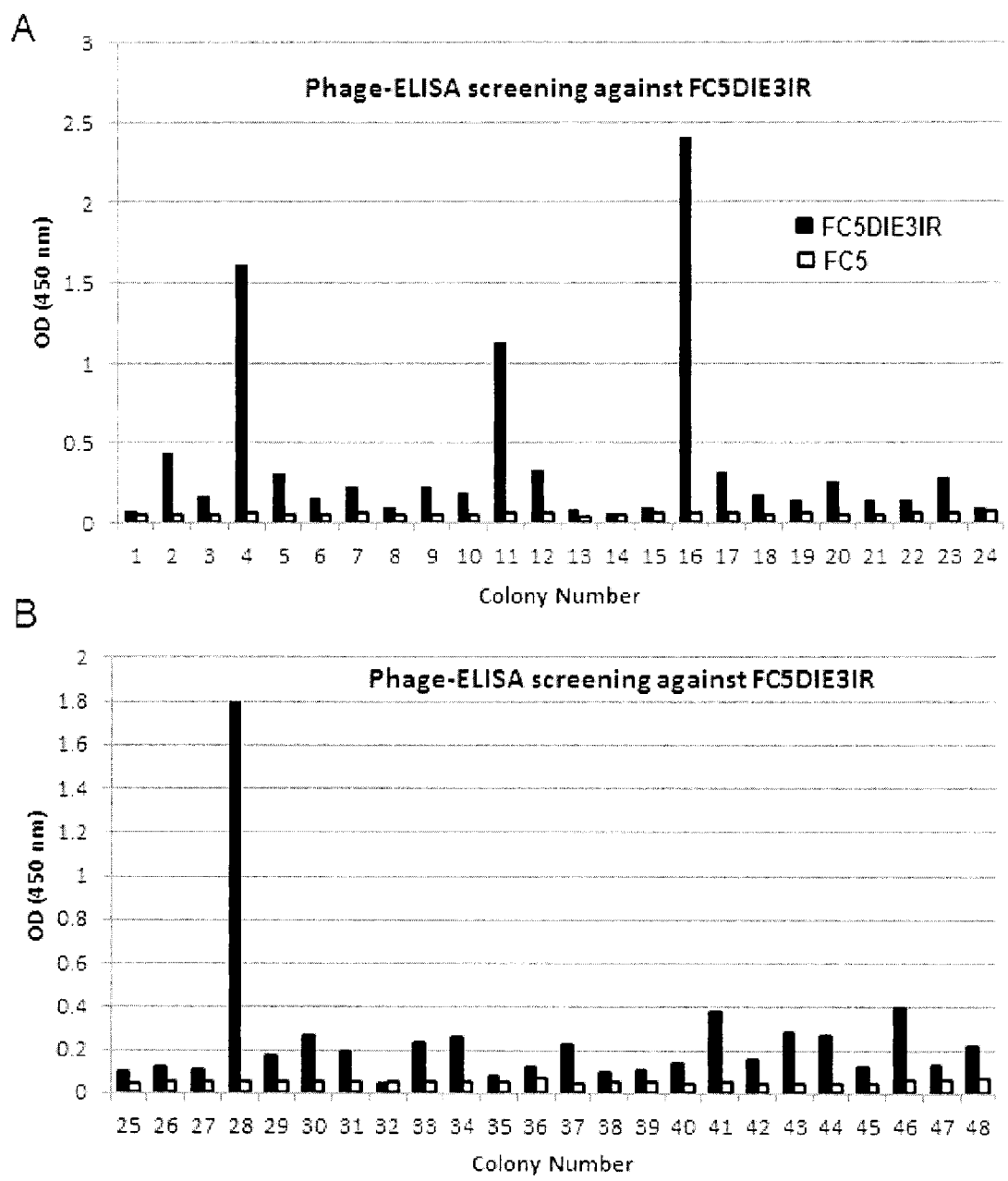

FIGS. 31A and 31B provide the results of phage ELISA screening of $V_HH$ antibodies obtained from an immunized llama. Phages were rescued from 48 individual colonies, selected from the fourth round of panning and grown overnight at 37° C. Wells of a Nunc microtiter plate were coated with FC5DIE3IR and FC5 (as a negative control) proteins at 5 μg/ml in PBS. After blocking, 100 μl of phage supernatants (from clones 1-48) were added to the respective wells (FC5 and FC5DIE31R) followed by incubation for 1 h at room temperature and addition of anti-M13-HRP conjugate. After washing the wells, binding was detected with the addition of TMB substrate and A450 was measured using an ELISA plate reader. Results are provided as OD at 450 nm in function of $V_HH$ colony number.

FIG. 31A shows the results obtained for colony numbers 1 to 24.

FIG. 31B shows the results obtained for colony numbers 25 to 48.

FIGS. 32A to 32D provide Surface Plasmon Resonance (SPR) results determined using single cycle kinetics (SCK) or steady state analysis.

Figure 32A:
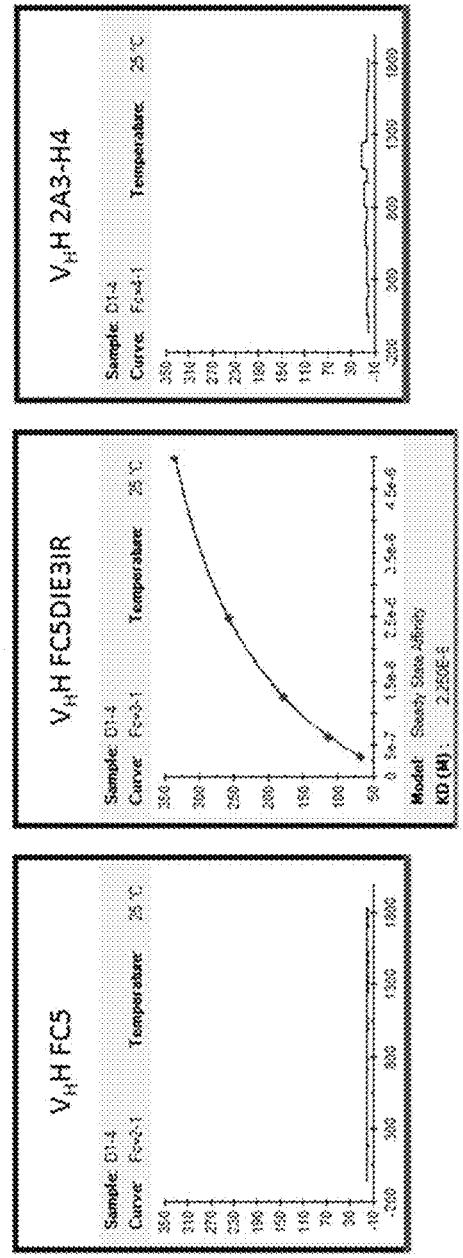

FIG. 32A shows the binding affinity of $V_HH$s DI-4 to immobilized $V_HH$ FC5 (left panel), FC5DIE3IR (center panel) and $V_HH$ 2A3-H4 (right panel).

Figure 32B:
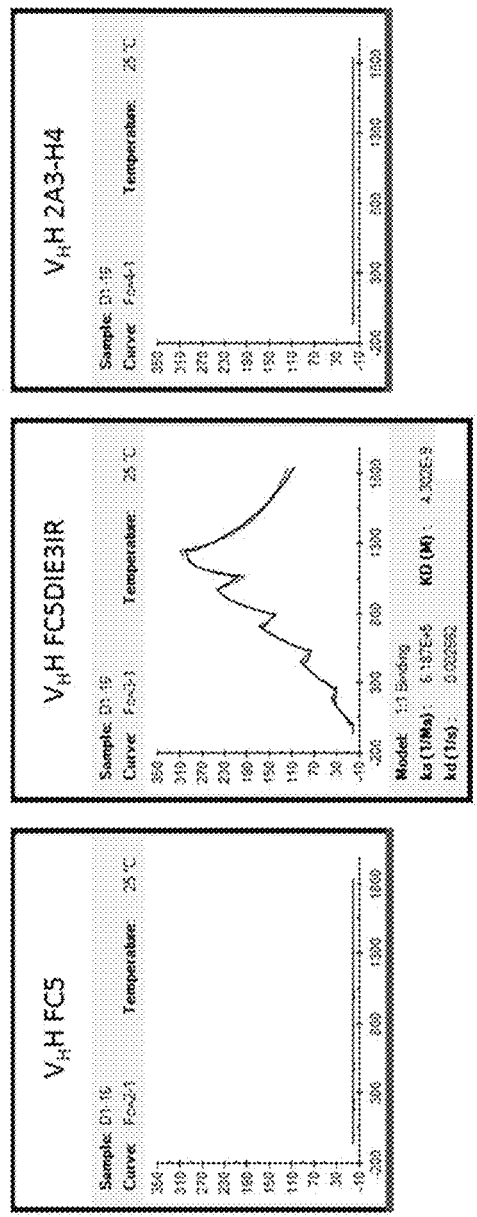

FIG. 32B shows the binding affinity of DI-16 to immobilized $V_HH$ FC5 (left panel), FC5DIE3IR (center panel) and $V_HH$ 2A3-H4 (right panel).

Figure 32C:
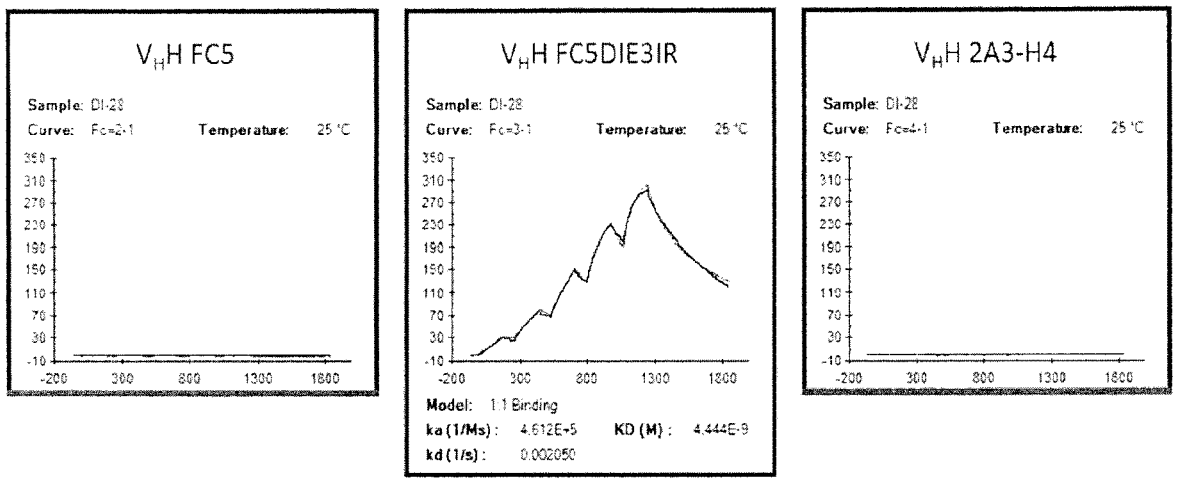

FIG. 32C shows the binding affinity of DI-28 to immobilized $V_HH$ FC5 (left panel), FC5DIE3IR (center panel) and $V_HH$ 2A3-H4 (right panel).

Figure 32D:
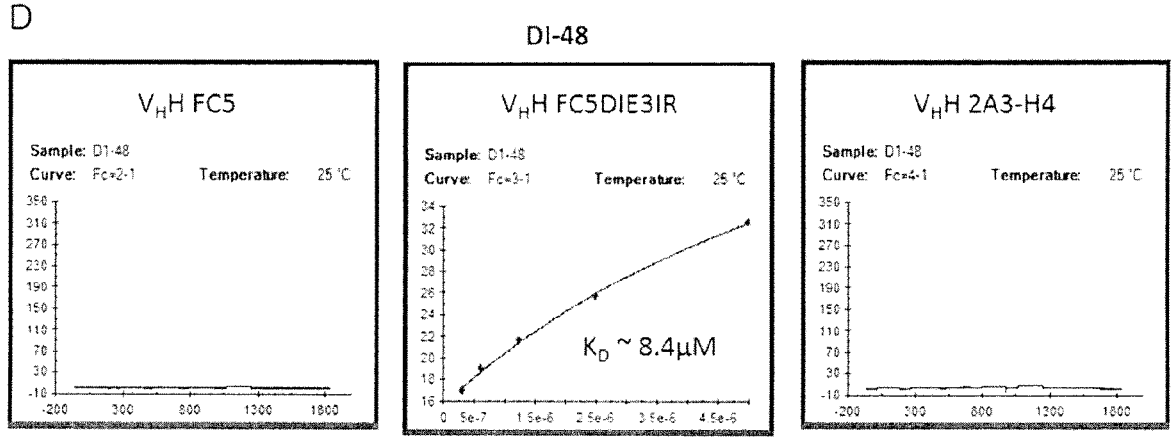

FIG. 32D shows the binding affinity of DI-48 to immobilized $V_HH$ FC5 (left panel), FC5DIE3IR (center panel) and $V_HH$ 2A3-H4 (right panel).

DETAILED DESCRIPTION

Anti-$Na_v1.7$ Antibodies

The present disclosure provides for specific antibodies against the $Na_v1.7$ polypeptide. The antibodies are considered "specific" to the $Na_v1.7$ polypeptide because their affinity for the $Na_v1.7$ polypeptide is higher than for other polypeptides (for example other polypeptides from the $Na_v$ family). The antibodies of the present disclosure can be specific for the human $Na_v1.7$ polypeptide (as described in GenBank Accession Number NP_002968 or the GeneCard ID Number GC02M166195). In an embodiment, when the antibody is a monoclonal antibody (mAb), its dissociation constant ($K_D$) with respect to the $Na_v1.7$ polypeptide is in the nanomolar range (1-1000 nM). In such embodiment, the monoclonal antibody can have a $K_D$ between about 1 and about 100 nM, between about 1 and about 50 nM, between about 1 and about 25 nM, between about 1 and about 20 nM, between about 5 and about 15 nM or between about 7 nM and 12 nM with respect to the $Na_v1.7$ polypeptide. In an embodiment, when the antibody is a single-domain antibody (sdAb), its dissociation constant ($K_D$) with respect to the $Na_v1.7$ polypeptide is in the nanomolar range (1-1000 nM) or the micromolar range (1-1000 μM). In such embodiment, the single domain antibody can have a $K_D$ between about 1 and about 100 μM, between about 1 and about 50 μM, between about 1 and about 25 μM, between about 1 and about 5 μM or about 2 μM with respect to the $Na_v1.7$ polypeptide. The present invention provides antibodies, including mAbs and sdAbs, that target the $Na_v1.7$ channel, and specifically bind a $Na_v1.7$ polypeptide, wherein said polypeptide comprises a peptide in the extracellular loop 3 of domain DI of the $Na_v1.7$ channel, having a nanomolar or micromolar affinity.

The antibodies of the present disclosure are also capable of antagonizing the biological activity of the $Na_v1.7$ polypeptide. As indicated above, the $Na_v1.7$ polypeptide is a sodium channel involved in nociception (e.g., the sensation of pain). By antagonizing its biological activity, the antibodies of the present disclosure can thus be used to alleviate the symptoms of pain and/or to treat or alleviate the symptoms of an hyperproliferative disease, such as cancer. As shown herein, some the antibodies presented in the Examples are capable of reducing the amplitude of a current associated with the $Na_v1.7$ polypeptide which in return is understood to limit or inhibit the flux of sodium ions through the $Na_v1.7$ polypeptide. As such, in an embodiment, an antibody capable of reducing the amplitude of a current associated with the $Na_v1.7$ polypeptide is considered to also be capable of antagonizing the biological activity of the $Na_v1.7$ polypeptide. In an embodiment, the antibodies have a concentration response relationship ($IC_{50}$) towards the $Na_v1.7$ polypeptide in the nanomolar range (1-1000 nM) or in the micromolar range (1-1000 μM). In another embodiment, the antibodies have a degree of maximum inhibition towards the $Na_v1.7$ polypeptide between about 5-65% (for example, between 10-20%, between 30-45%, between 45-55% or between 40-65%). In some embodiments, the antibodies have a degree of maximum inhibition towards the $Na_v1.7$ polypeptide of at least 5, 6, 7, 8, 9, 10, 11, 12, 13, 14, 15, 20, 25, 30, 35, 40, 45, 50, 55, 60 or 65%. In some embodiments, the antibodies have a degree of maximum inhibition of about 10-20%, for example 16%, 30-45%, for example 40%, 45-55%, for example 55% or 40-65%, for example 62%. As also shown herein, some of the antibodies presented in the Examples are capable of maintaining or reducing a normalized current associated with the Na$_v$1.7 polypeptide which in return is understood to limit or inhibit the flux of sodium ions through the Na$_v$1.7 polypeptide. As such, in an embodiment, an antibody capable of maintaining or reducing the normalized current associated with the Na$_v$1.7 polypeptide is considered to also be capable of antagonizing the biological activity of the Na$_v$1.7 polypeptide. As further shown herein, some of the antibodies presented in the Examples are capable of increasing the latency of paw withdrawal in an hyperalgesia animal model (for example the Rat Hargreaves Model of Hyperalgesia) when compared to control treatment or antibodies. As such, in an embodiment, an antibody capable of increasing the latency of paw withdrawal in an hyperalgesia animal model is considered to also be capable of antagonizing the biological activity of the Na$_v$1.7 polypeptide. As also shown herein, some of the antibodies presented in the Examples are capable of achieving a percentage of maximal possible effect of at least 5, 10, 15, 18, 20, 25, 30, 35, 40% or more. Consequently, in such an embodiment, an antibody capable of increasing the percentage of maximal possible effect is considered to also be capable of antagonizing the biological activity of the Na$_v$1.7 polypeptide. As shown herein, some of the antibodies of the Examples are capable of reducing the cumulative nociceptive behavior by 5, 10, 15, 20, 25, 30, 35, 40, 45, 50% or more. Consequently, in such embodiment, an antibody capable of decreasing the cumulative nociceptive behavior is also considered to be specific of antagonizing the biological activity of the Na$_v$1.7 polypeptide. As further shown herein, some of the antibodies presented in the Examples are capable of reducing colony formation of cancer cells by 5, 10, 15, 20, 25, 30, 35, 40, 45, 50% or more. Consequently, in such an embodiment, an antibody capable of decreasing colony formation of cancer cells is considered to also be capable of antagonizing the biological activity of the Na$_v$1.7 polypeptide.

An "antibody", as used in the context of the present disclosure, refers to an immunoglobulin polypeptide having at least three complementary determining regions (CDRs) and, in some embodiments, up to twelve CDRs. A "complementary determining region" refers to a region of the immunoglobulin polypeptide located in the variable parts of the polypeptide and involved in specifically binding the epitope. The combination of CDRs constitutes the paratope of the antibody.

Some naturally occurring immunoglobulins (for example mouse and human immunoglobulins) have a common core structure in which two identical light chains (about 24 kD) and two identical heavy chains (about 55 or 70 kD) form a tetramer. The amino-terminal portion of each chain is known as the variable (V) region and can be distinguished from the more conserved constant (C) regions of the remainder of each chain. Within the variable region of the light chain is a C-terminal portion known as the J region. Within the variable region of the heavy chain, there is a D region in addition to the J region. Most of the amino acid sequence variation in immunoglobulins is confined to three separate locations in the V regions known as hypervariable regions or complementarity determining regions (CDRs) which, as indicated above are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3, and FR4, respectively. The locations of CDR and FR regions and a numbering system have been defined by Kabat et al.

Antibodies of the present disclosure include monoclonal antibodies. Antibodies which are specific for a single epitope on the Na$_v$1.7 polypeptide are considered as monoclonal antibodies (also referred to as mAbs). In some embodiments, monoclonal antibodies are produced from a single clone of an immune cell. Monoclonal antibodies can be produced by techniques known in the art, such as by using cell culture by fusing a myeloma cell to a spleen cell from a subject (such as a mouse or a human) which has been immunized with an antigen comprising the epitope of the Na$_v$1.7 polypeptide (for example the FC5DIE3IR polypeptide as described in the Examples below). Monoclonal antibodies can also be obtained phage display by screening library of monoclonal antibodies using an antigen comprising the epitope of the Na$_v$1.7 polypeptide (for example the FC5DIE3IR polypeptide as described in the Examples below). Additional techniques for making monoclonal antibodies include, but are not limited to single B cell culture, single cell amplification from B cell populations. Monoclonal antibodies of the present disclosure can be from various origins (e.g., mouse or human for example) and can include two identical light chains and two identical heavy chains, wherein each chain comprises three CDRs. Monoclonal antibodies can be from any isotype, including, but not limited to immunoglobulin A (IgA), IgD, IgE, IgG (including subtypes IgG1, IgG2 or IgG3) or IgM. Monoclonocal antibodies can be, in an embodiment, from the IgG isotype.

A single-domain antibody (also referred to as a sdAb or a nanobody) is considered a monoclonal antibody as it is specific for a single epitope. Single-domain antibodies have a single heavy chain or light chain comprising three CDRs. In an embodiment, the single-domain antibody has a single heavy chain comprising three CDRs. Single domain antibodies can be found in nature, for example in camelids (V$_H$H antibodies) and in cartilaginous fishes (V$_{NAR}$ fragments). Single domain antibodies can be engineered from fragmenting IgG antibodies (of human or mouse origin for example).

Antibodies of the present disclosure further include antibody derivatives, such as, for example chimeric and humanized antibodies. The expression "chimeric antibody" refers to an immunoglobulin which comprises regions from two different species. The expression "humanized antibody" refers to an immunoglobulin that comprises both a region derived from a human antibody or immunoglobulin and a region derived from a non-human antibody or immunoglobulin. The action of humanizing an antibody consists in substituting a portion of a non-human antibody with a corresponding portion of a human antibody. For example, a humanized antibody as used herein could comprise a non-human region variable region (such as a region derived from a murine antibody) capable of specifically recognizing the Na$_v$1.7 polypeptide and a human constant region derived from a human antibody. In another example, the humanized immunoglobulin can comprise a heavy chain and a light chain, wherein the light chain comprises a complementarity determining region derived from an antibody of non-human origin which binds to the Na$_v$1.7 polypeptide and a framework region derived from a light chain of human origin, and the heavy chain comprises a complementarity determining region derived from an antibody of non-human origin which binds to the Na$_v$1.7 polypeptide and a framework region derived from a heavy chain of human origin.

Antibodies of the present disclosure also include functional antibody fragments which comprise at least three CDRs, recognize the Na$_v$1.7 polypeptide and are capable of limiting the biological activity of the Na$_v$1.7 polypeptide. As used herein, a "fragment" of an antibody (which can be, for example, a monoclonal antibody) is a portion of an antibody that is capable of specifically recognizing the same epitope as the full version of the antibody. Antibody fragments include, but are not limited to, the antibody light chain, antibody heavy chain, single chain antibodies, Fv, Fab, Fab' and F(ab')$_2$ fragments. Such fragments can be produced by enzymatic cleavage or by recombinant techniques. For instance, papain or pepsin cleavage can be used to generate Fab or F(ab')$_2$ fragments, respectively. Antibodies can also be produced in a variety of truncated forms using antibody genes in which one or more stop codons have been introduced upstream of the natural stop site. For example, a chimeric gene encoding the heavy chain of an F(ab')$_2$ fragment can be designed to include DNA sequences encoding the CH1 domain and hinge region of the heavy chain.

The antibodies of the present disclosure are specific for at least one epitope located on the 3$^{rd}$ loop of domain I of the Na$_v$1.7 polypeptide (located between amino acid residues 271 to 341 on the sequence shown in the GenBank Accession number NP_002968 or SEQ ID NO: 72). As shown on FIG. 1, the Na$_v$1.7 polypeptide comprises of four domains (DI, DII, DIII and DIV), each containing six transmembrane helices (S1-S6) and 4 extracellular loops. S4 is known to be the voltage sensor of the channels. The epitope is preferably located on solvent-accessible region of the 3rd loop of domain I of the Na$_v$1.7 polypeptide. In an embodiment, the epitope is located on the DIE3IR peptide which comprises or consists essentially of the following amino acid sequence:

(SEQ ID NO: 1)
KHKCFRNSLENNETLESIMNTLESEEDFRKYFYYLEGSKDALLCGFSTDS
GQCPEGYTCVKIGRNPDYGY.

In the context of the present disclosure, and especially when referring to the amino acid sequence of the DIE3IR peptide, the expression "consisting essentially of" indicates that the epitope is necessarily located on the amino acid sequence of SEQ ID NO: 1, but that additional, non-essential, amino acid residues can be added at the amino or the carboxyl end of the amino acid sequence of SEQ ID NO: 1 (for example when the DIE3IR peptide is used as an immunogen to identify/generate anti-Na$_v$1.7 antibodies). In an embodiment, when the antibody is a monoclonal antibody, its dissociation constant (K$_D$) with respect to the DIE3IR peptide is in the nanomolar range (1-1000 nM). In such embodiment, the monoclonal antibody can have a K$_{ID}$ between about 1 and about 100 nM, between about 1 and about 50 nM, between about 1 and about 25 nM, between about 5 and about 15 nM or between about 7 and 12 nM with respect to the DIE3IR peptide. In an embodiment, when the antibody is a single-domain antibody, its dissociation constant (K$_D$) with respect to the DIE3IR peptide is in the micromolar range (1-1000 μM). In such embodiment, the single domain antibody can have a K$_D$ between about 1 and about 100 μM, between about 1 and about 50 μM, between about 1 and about 25 μM, between about 1 and about 5 μM or about 2 μM with respect to the DIE3IR peptide.

In some embodiments, the epitope recognized by the anti-Na$_v$1.7 antibody is located on the peptide #2 which comprises or consists essentially of the following amino acid sequence:

(SEQ ID NO: 5)
TLESEEDFRKYFYYLEGSKDALLCGFSTDS.

In the context of the present disclosure, and especially when referred to the amino acid sequence of peptide #2, the expression "consisting essentially of" indicates that the epitope is necessarily located on the amino acid sequence of SEQ ID NO: 5, but that additional, non-essential, amino acid residues can be added at the amino or the carboxy end of the amino acid sequence of SEQ ID NO: 5. In an embodiment, when the antibody is a monoclonal antibody, its dissociation constant (K$_D$) with respect to peptide #2 is in the nanomolar range (1-1000 nM). In such embodiment, the monoclonal antibody can have a K$_D$ between about 1 and about 100 nM, between about 1 and about 50 nM, between about 1 and about 25 nM, between about 5 and about 15 nM or between about 7 and 12 nM with respect to peptide #2.

In other embodiments, the epitope recognized by the anti-Na$_v$1.7 antibody is located on the peptide #2a which comprises or consists essentially of the following amino acid sequence:

(SEQ ID NO: 103)
TLESEEDFRKYFYYLEGSKD.

In the context of the present disclosure, and especially when referring to the amino acid sequence of peptide #2a, the expression "consisting essentially of" indicates that the epitope is necessarily located on the amino acid sequence of SEQ ID NO: 103, but that additional, non-essential, amino acid residues can be added at the amino or the carboxy end of the amino acid sequence of SEQ ID NO: 103. In an embodiment, when the antibody is a monoclonal antibody, its dissociation constant (K$_D$) with respect to peptide #2a is in the nanomolar range (1-1000 nM). In such embodiment, the monoclonal antibody can have a K$_D$ between about 1 and about 100 nM, between about 1 and about 50 nM, between about 1 and about 25 nM or between about 5 and about 15 nM with respect to peptide #2a. In other embodiments, the epitope recognized by the anti-Na$_v$1.7 antibody is located on the peptide #2b which comprises or consists essentially of the following amino acid sequence:

(SEQ ID NO: 104)
YFYYLEGSKDALLCGFSTDS.

In the context of the present disclosure, and especially when referring to the amino acid sequence of peptide #2b, the expression "consisting essentially of" indicates that the epitope is necessarily located on the amino acid sequence of SEQ ID NO: 104, but that additional, non-essential, amino acid residues can be added at the amino or the carboxy end of the amino acid sequence of SEQ ID NO: 104. In an embodiment, when the antibody is a monoclonal antibody, its dissociation constant (K$_D$) with respect to peptide #2b is in the nanomolar range (1-1000 nM). In such embodiment, the monoclonal antibody can have a K$_D$ between about 1 and about 100 nM, between about 1 and about 50 nM, between about 1 and about 25 nM or between about 5 and about 15 nM with respect to peptide #2b.

In other embodiments, the epitope recognized by the anti-Na$_v$1.7 antibody is located on the peptide #3 which comprises or consists essentially of the following amino acid sequence:

(SEQ ID NO: 6)
ALLCGFSTDSGQCPEGYTCVKIGRNPDYGY.

In the context of the present disclosure, and especially when referring to the amino acid sequence of peptide #3, the expression "consisting essentially of" indicates that the epitope is necessarily located on the amino acid sequence of SEQ ID NO: 6, but that additional, non-essential, amino acid residues can be added at the amino or the carboxy end of the amino acid sequence of SEQ ID NO: 6. In an embodiment, when the antibody is a monoclonal antibody, its dissociation constant ($K_D$) with respect to peptide #3 is in the nanomolar range (1-1000 nM). In such embodiment, the monoclonal antibody can have a $K_D$ between about 1 and about 100 nM, between about 1 and about 50 nM, between about 1 and about 25 nM or between about 5 and about 15 nM with respect to peptide #3.

In other embodiments, the epitope recognized by the anti-Na$_v$1.7 antibody is located on the peptide #40a which comprises or consists essentially of the following amino acid sequence:

(SEQ ID NO: 105)
KHKCFRNSLENNETLESIMNTLESEEDFRKYFYYLEGSKD.

In the context of the present disclosure, and especially when referring to the amino acid sequence of peptide #40a, the expression "consisting essentially of" indicates that the epitope is necessarily located on the amino acid sequence of SEQ ID NO: 105, but that additional, non-essential, amino acid residues can be added at the amino or the carboxy end of the amino acid sequence of SEQ ID NO: 105. In an embodiment, when the antibody is a monoclonal antibody, its dissociation constant ($K_D$) with respect to peptide #40a is in the nanomolar range (1-1000 nM). In such embodiment, the monoclonal antibody can have a $K_D$ between about 1 and about 100 nM, between about 1 and about 50 nM, between about 1 and about 25 nM or between about 5 and about 15 nM with respect to peptide #40a.

In other embodiments, the epitope recognized by the anti-Na$_v$1.7 antibody is located on the peptide #40b which comprises or consists essentially of the following amino acid sequence:

(SEQ ID NO: 106)
YFYYLEGSKDALLCGFSTDSGQCPEGYTCVKIGRNPDYGY.

In the context of the present disclosure, and especially when referring to the amino acid sequence of peptide #40b, the expression "consisting essentially of" indicates that the epitope is necessarily located on the amino acid sequence of SEQ ID NO: 106, but that additional, non-essential, amino acid residues can be added at the amino or the carboxy end of the amino acid sequence of SEQ ID NO: 106. In an embodiment, when the antibody is a monoclonal antibody, its dissociation constant ($K_D$) with respect to peptide #40b is in the nanomolar range (1-1000 nM). In such embodiment, the monoclonal antibody can have a $K_D$ between about 1 and about 100 nM, between about 1 and about 50 nM, between about 1 and about 25 nM or between about 5 and about 15 nM with respect to peptide #40b.

When the antibody of the present disclosure is a monoclonal antibody, it can include both a heavy and a light chain and can, in some embodiments, comprise two identical copies of the light chain and two identical copies of the heavy chain. Each chain can comprise three CDRs, wherein each CDR is flanked at both the amino terminus and on the carboxyl terminus, by a framework region. When the antibody of the present disclosure is a single-chain antibody, it can include either a heavy or a light chain. The single-domain antibody can comprise three CDRs, wherein each CDR is flanked at both the amino terminus and on the carboxyl terminus, by a framework region.

In an embodiment, the antibody of present invention has at least one complementary determining region comprising or consisting essentially of the amino acid sequence of SEQ ID NO: 7, 8, 9, 13, 14, 15, 39, 40, 41, 75, 76, 77, 80, 81, 82, 85, 86, 87, 90, 91, 92, 95, 96, 97, 100, 101 or 102 variant thereof or fragments thereof. In the context of the present disclosure, and especially when referred to the amino acid sequence of CDR, the expression "consisting essentially of" indicates that the CDR necessarily comprises the amino acid sequence of SEQ ID NO: 7, 8, 9, 13, 14, 15, 39, 40, 41, 75, 76, 77, 80, 81, 82, 85, 86, 87, 90, 91, 92, 95, 96, 97, 100, 101 or 102, but that additional, non-essential, amino acid residues can be added at the amino or the carboxyl end of those sequences (as long as these amino acid residues do not substantially modify the affinity of the antibody for the Na$_v$1.7 polypeptide or its ability to antagonize the biological activity of the Na$_v$1.7 polypeptide).

The antibody of the present disclosure can include a functional variant of a CDR having the amino acid sequence of SEQ ID NO: 7, 8, 9, 13, 14, 15, 39, 40, 41, 75, 76, 77, 80, 81, 82, 85, 86, 87, 90, 91, 92, 95, 96, 97, 100, 101 or 102. A variant CDR comprises at least one amino acid difference when compared to the amino acid sequence of the CDR. As used herein, a variant refers to alterations in the amino acid sequence that do not adversely affect the biological functions of the antibody (e.g., providing specificity and affinity towards the Na$_v$1.7 polypeptide). In some embodiments, the overall charge, structure or hydrophobic-hydrophilic properties of the antibody can be altered without adversely affecting a biological activity. Accordingly, the amino acid sequence of the CDR can be altered, for example to render the antibody more hydrophobic or hydrophilic, without adversely affecting the biological activities of the antibody. The CDR variants have at least 50%, 55%, 60%, 65%, 70%, 75%, 80%, 85%, 90%, 95%, 96%, 97%, 98% or 99% identity to the CDRs described herein. The term "percent identity", as known in the art, is a relationship between two or more polypeptide sequences or two or more polynucleotide sequences, as determined by comparing the sequences. The level of identity can be determined conventionally using known computer programs. Identity can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The CDR variants may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group. A "variant" of the CDR can be a conservative variant or an allelic variant.

The antibody of the present disclosure can include a functional fragment of a CDR having the amino acid sequence of SEQ ID NO: 7, 8, 9, 13, 14, 15, 39, 40, 41, 75, 76, 77, 80, 81, 82, 85, 86, 87, 90, 91, 92, 95, 96, 97, 100, 101 or 102. A fragment of a CDR comprises at least one less amino acid residue compared to the amino acid sequence of the CDR. The CDR fragments comprise some consecutive amino acid residues of the CDR of amino acid sequence of SEQ ID NO: 7, 8, 9, 13, 14, 15, 39, 40, 41, 75, 76, 77, 80, 81, 82, 85, 86, 87, 90, 91, 92, 95, 96, 97, 100, 101 or 102. The CDR fragments have at least 50%, 55%, 60%, 65%, 70%, 75%, 80%, 85%, 90%, 95%, 96%, 97%, 98% or 99% identity to the CDRs described herein.

In an embodiment, the antibody of the present disclosure comprises at least one CDR comprising or consisting essentially of an amino acid sequence of SEQ ID NO: 7, 8, 9, 13, 14, 15, 75, 76, 77, 80, 81, 82, 85, 86, 87, 90, 91, 92, 95, 96, 97, 100, 101 and/or 102. In another embodiment, the antibody comprises at least two CDRs each comprising or consisting essentially of a distinct amino acid sequence from the following: SEQ ID NO: 7, 8, 9, 13, 14, 15, 75, 76, 77, 80, 81, 82, 85, 86, 87, 90, 91, 92, 95, 96, 97, 100, 101 and/or 102, functional variants thereof and functional fragments thereof. In yet another embodiment, the antibody comprises at least three CDRs each comprising or consisting essentially of a distinct amino acid sequence from the following: SEQ ID NO: 7, 8, 9, 13, 14, 15, 75, 76, 77, 80, 81, 82, 85, 86, 87, 90, 91, 92, 95, 96, 97, 100, 101 and/or 102, functional variants thereof and functional fragments thereof. In still another embodiment, the antibody comprises at least four CDRs each comprising or consisting essentially of a distinct amino acid sequence from the following: SEQ ID NO: 7, 8, 9, 13, 14, 15, 75, 76, 77, 80, 81, 82, 85, 86, 87, 90, 91, 92, 95, 96, 97, 100, 101 and/or 102. In a further embodiment, the antibody comprises at least five CDRs each comprising or consisting essentially of a distinct amino acid sequence from the following: SEQ ID NO: 7, 8, 9, 13, 14, 15, 75, 76, 77, 80, 81, 82, 85, 86, 87, 90, 91, 92, 95, 96, 97, 100, 101 and/or 102, functional variants thereof and functional fragments thereof. In still a further embodiment, the antibody comprises six CDRs each comprising or consisting essentially of a distinct amino acid sequence from the following: SEQ ID NO: 7, 8, 9, 13, 14, 15, 75, 76, 77, 80, 81, 82, 85, 86, 87, 90, 91, 92, 95, 96, 97, 100, 101 and/or 102, functional variants thereof and functional fragments thereof.

In another embodiment, the antibody comprises a heavy chain and the heavy chain comprises at least one CDR comprising or consisting essentially of an amino acid sequence of SEQ ID NO: 7, 8, 9, 75, 76, 77, 85, 86, 87, 95, 96 and/or 97, functional variants thereof and functional fragments thereof. In still another embodiment the antibody comprises a heavy chain and the heavy chain comprises at least one CDR comprising or consisting essentially of an amino acid sequence of SEQ ID NO: 7, 8, 9, 75, 76, 77, 85, 86, 87, 95, 96 and/or 97, functional variants thereof and functional fragments thereof. In a further embodiment, the heavy chain comprises at least two CDRs each comprising or consisting essentially of a distinct amino acid sequence from the following: SEQ ID NO: 7, 8, 9, 75, 76, 77, 85, 86, 87, 95, 96 or 97, functional variants thereof and functional fragments thereof. In still a further embodiment, the heavy chain comprises three CDRs each comprising or consisting essentially of a distinct amino acid sequence from the following: SEQ ID NO: 7, 8 and 9, functional variants thereof and functional fragments thereof. In another embodiment, the heavy chain comprises or consists essentially of the amino acid sequence of SEQ ID NO: 11 or 12, functional variants thereof and functional fragments thereof. In the context of the present disclosure, and especially when referred to the amino acid sequence of heavy chain, the expression "consisting essentially of" indicates that the CDR necessarily comprises the amino acid sequence of SEQ ID NO: 11 or 12, but that additional, non-essential, amino acid residues can be added at the amino or the carboxyl end of those sequences (as long as these amino acid residues do not substantially modify the affinity of the antibody for the $Na_v1.7$ polypeptide or its ability to antagonize the biological activity of the $Na_v1.7$ polypeptide). In still a further embodiment, the heavy chain comprises three CDRs each comprising or consisting essentially of a distinct amino acid sequence from the following: SEQ ID NO: 75, 76 and 77, functional variants thereof and functional fragments thereof. In another embodiment, the heavy chain comprises or consists essentially of the amino acid sequence of SEQ ID NO: 74, functional variants thereof and functional fragments thereof. In still a further embodiment, the heavy chain comprises three CDRs each comprising or consisting essentially of a distinct amino acid sequence from the following: SEQ ID NO: 85, 86 and 87, functional variants thereof and functional fragments thereof. In another embodiment, the heavy chain comprises or consists essentially of the amino acid sequence of SEQ ID NO: 84, functional variants thereof and functional fragments thereof. In still a further embodiment, the heavy chain comprises three CDRs each comprising or consisting essentially of a distinct amino acid sequence from the following: SEQ ID NO: 95, 96 and 97, functional variants thereof and functional fragments thereof. In another embodiment, the heavy chain comprises or consists essentially of the amino acid sequence of SEQ ID NO: 94, functional variants thereof and functional fragments thereof. The antibody can be a monoclonal antibody or a single-domain antibody.

In another embodiment, the antibody comprises a light chain and the light chain comprises at least one CDR comprising or consisting essentially of an amino acid sequence of SEQ ID NO: 13, 14, 15, 80, 81, 82, 90, 91, 92, 100, 101 and/or 102, functional variants thereof and functional fragments thereof. In still another embodiment the antibody comprises a light chain and the light chain comprises at least one CDR comprising or consisting essentially of an amino acid sequence of SEQ ID NO: 13, 14 and/or 15, functional variants thereof and functional fragments thereof. In a further embodiment, the light chain comprises at least two CDRs each comprising or consisting essentially of a distinct amino acid sequence from the following: SEQ ID NO: 13, 14 and/or 15, functional variants thereof and functional fragments thereof. In still a further embodiment, the light chain comprises three CDRs each comprising or consisting essentially of a distinct amino acid sequence from the following: SEQ ID NO: 13, 14 and/or 15, functional variants thereof and functional fragments thereof. In another embodiment, the light chain comprises or consists essentially of the amino acid sequence of SEQ ID NO: 17 or 18, functional variants thereof and functional fragments thereof. In the context of the present disclosure, and especially when referred to the amino acid sequence of light chain, the expression "consisting essentially of" indicates that the CDR necessarily comprises the amino acid sequence of SEQ ID NO: 17 or 18, but that additional, non-essential, amino acid residues can be added at the amino or the carboxyl end of those sequences (as long as these amino acid residues do not substantially modify the affinity of the antibody for the $Na_v1.7$ polypeptide or its ability to antagonize the biological activity of the $Na_v1.7$ polypeptide). In still a further embodiment, the light chain comprises three CDRs each comprising or consisting essentially of a distinct amino acid sequence from the following: SEQ ID NO: 80, 81 and/or 82, functional variants thereof and functional fragments thereof. In another embodiment, the light chain comprises or consists essentially of the amino acid sequence of SEQ ID NO: 79, functional variants thereof and functional fragments thereof. In still a further embodiment, the light chain comprises three CDRs each comprising or consisting essentially of a distinct amino acid sequence from the following: SEQ ID NO: 90, 91 and/or 92, functional variants thereof and functional fragments thereof. In another embodiment, the light chain comprises or consists essentially of the amino acid sequence of SEQ ID NO: 89, functional variants thereof and functional fragments thereof. In still a further embodiment, the light chain comprises three CDRs each comprising or consisting essentially of a distinct amino acid sequence from the following: SEQ ID NO: 100, 101 and/or 1022, functional variants thereof and functional fragments thereof. In another embodiment, the light chain comprises or consists essentially of the amino acid sequence of SEQ ID NO: 99, functional variants thereof and functional fragments thereof. The antibody can be a monoclonal antibody or a single-domain antibody.

In yet another embodiment, the antibody can comprise both a heavy chain and the light chain. In such embodiment, the heavy chain can comprise at least one, at least two or three CDRs each CDR comprising or consisting essentially of a distinct amino acid sequence from the following: SEQ ID NO: 7, 8 and 9, functional variants thereof and functional fragments thereof. In another embodiment, the heavy chain can comprise or consist essentially of the amino acid sequence of SEQ ID NO: 11 or 12, functional variants thereof and functional fragments thereof. In addition, the light chain can comprise at least one, at least two or three CDRs each CDR comprising or consisting essentially of a distinct amino acid sequence from the following: SEQ ID NO: 13, 14 and 15, functional variants thereof and functional fragments thereof. In some embodiment, the light chain can comprise or consist essentially of the amino acid sequence of SEQ ID NO: 17 or 18, functional variants thereof and functional fragments thereof. In some embodiments, the antibody can be a monoclonal antibody, such as, for example, from the IgG isotype and, in some embodiments, from the IgG1 subtype.

In yet another embodiment, the antibody can comprise both a heavy chain and the light chain. In such embodiment, the heavy chain can comprise at least one, at least two or three CDRs each CDR comprising or consisting essentially of a distinct amino acid sequence from the following: SEQ ID NO: 75, 76 and 77, functional variants thereof and functional fragments thereof. In another embodiment, the heavy chain can comprise or consist essentially of the amino acid sequence of SEQ ID NO: 74, functional variants thereof and functional fragments thereof. In addition, the light chain can comprise at least one, at least two or three CDRs each CDR comprising or consisting essentially of a distinct amino acid sequence from the following: SEQ ID NO: 80, 81 and 82, functional variants thereof and functional fragments thereof. In some embodiment, the light chain can comprise or consist essentially of the amino acid sequence of SEQ ID NO: 79, functional variants thereof and functional fragments thereof. In some embodiments, the antibody can be a monoclonal antibody, such as, for example, from the IgG isotype and, in some embodiments, from the IgG2a subtype.

In yet another embodiment, the antibody can comprise both a heavy chain and the light chain. In such embodiment, the heavy chain can comprise at least one, at least two or three CDRs each CDR comprising or consisting essentially of a distinct amino acid sequence from the following: SEQ ID NO: 85, 86 and 87, functional variants thereof and functional fragments thereof. In another embodiment, the heavy chain can comprise or consist essentially of the amino acid sequence of SEQ ID NO: 84, functional variants thereof and functional fragments thereof. In addition, the light chain can comprise at least one, at least two or three CDRs each CDR comprising or consisting essentially of a distinct amino acid sequence from the following: SEQ ID NO: 90, 91 and 92, functional variants thereof and functional fragments thereof. In some embodiment, the light chain can comprise or consist essentially of the amino acid sequence of SEQ ID NO: 89, functional variants thereof and functional fragments thereof. In some embodiments, the antibody can be a monoclonal antibody, such as, for example, from the IgG isotype and, in some embodiments, from the IgG1 subtype.

In yet another embodiment, the antibody can comprise both a heavy chain and the light chain. In such embodiment, the heavy chain can comprise at least one, at least two or three CDRs each CDR comprising or consisting essentially of a distinct amino acid sequence from the following: SEQ ID NO: 95, 96 and 97, functional variants thereof and functional fragments thereof. In another embodiment, the heavy chain can comprise or consist essentially of the amino acid sequence of SEQ ID NO: 94, functional variants thereof and functional fragments thereof. In addition, the light chain can comprise at least one, at least two or three CDRs each CDR comprising or consisting essentially of a distinct amino acid sequence from the following: SEQ ID NO: 100, 101 and 102, functional variants thereof and functional fragments thereof. In some embodiment, the light chain can comprise or consist essentially of the amino acid sequence of SEQ ID NO: 99, functional variants thereof and functional fragments thereof. In some embodiments, the antibody can be a monoclonal antibody, such as, for example, from the IgG isotype and, in some embodiments, from the IgG1 subtype.

In an embodiment, the antibody of the present disclosure comprises at least one CDR comprising or consisting essentially of an amino acid sequence of SEQ ID NO: 13, 14 and/or 15. In another embodiment, the antibody comprises at least two CDRs each comprising or consisting essentially of a distinct amino acid sequence from the following: SEQ ID NO: 13, 14 and/or 15, functional variants thereof and functional fragments thereof. In yet another embodiment, the antibody comprises the three CDRs each comprising or consisting essentially of a distinct amino acid sequence from the following: SEQ ID NO: 13, 14 and/or 15, functional variants thereof and functional fragments thereof. In some embodiments, the antibody can comprise or consist essentially of the amino acid sequence of SEQ ID NO: 38, functional variants thereof and functional fragments thereof. In an embodiment, the CDRs having the amino acid sequence of SEQ ID NO: 13, 14 and/or 15 can be located on a heavy chain of a single-domain antibody. In some embodiment, the single-domain antibody can be a $V_HH$ camelid antibody.

In some embodiments, the antibody of the present disclosure can include a light chain comprising or consisting essentially of the amino acid sequence of SEQ ID NO: 17, 18, 110, 79, 115, 116, 89, 119, 120, 99, 123, 124, functional variants and/or functional fragments thereof. The light chain of the antibodies of the present disclosure can include a leader sequence (such as, for example, the exemplary leader sequence shown in Table 7 or any other suitable leader sequence) to facilitate its extracellular expression.

In some embodiments, the antibody of the present disclosure can include a heavy chain comprising or consisting essentially of the amino acid sequence of SEQ ID NO: 11, 12, 109, 38, 74, 113, 114, 84, 117, 118, 94, 121, 122, functional variants and/or functional fragments thereof. The heavy chain of the antibodies of the present disclosure can include a leader sequence (such as, for example, the exemplary leader sequence shown in Table 7 or any other suitable leader sequence) to facilitate its extracellular expression.

In some embodiment, the antibodies of the present disclosure may be further designed to cross the blood-brain barrier to reach the spinal cord thereby allowing the antibody to mediate its therapeutic actions of a treated subject. In one embodiment, it is possible to link an antibody disclosed herein to another antibody or antibody fragment capable of transmigrating the blood brain barrier. For example, said another antibody or antibody fragment may be a further entity (e.g., an antibody fragment) which is capable of recognizing an epitope of a human cerebromicrovascular endothelial cell as described in U.S. Pat. No. 8,715,659 or to a blood-barrier antigen found on the surface of a mammalian cell as described in U.S. Pat. No. 8,383,107 (collectively referred to as antibody fragment allowing the migration across the blood-brain barrier). This can be achieved by providing an antibody fragment of the antibody of the present disclosure with an antibody fragment allowing the migration across the blood-brain barrier. This can also be achieved by adding an antibody fragment allowing the migration across the blood-brain barrier to the antibody (thereby forming a chimeric protein, or a fusion protein). The present disclosure thus provides a chimeric protein comprising the antibody of the present disclosure comprising an antibody fragment moiety which allows/facilitates the migration across the blood-brain barrier.

This chimeric protein can take the form of antibody-drug-conjugate (ADC) or bi-specific antibodies in which one antibody binding specificity recognizes a BBB receptor that undergoes receptor-mediated transcytosis (RMT) from the brain into the CNS, and the second binding specificity recognizes a therapeutic target i.e. $Na_v1.7$ within the CNS. The development of BBB-crossing bi-specific antibodies requires targeted antibody engineering to optimize multiple characteristics of "BBB carrier" and therapeutic arms, as well as other antibody properties impacting pharmacokinetics and effector function. It is widely recognised now that the preclinical models of chronic pain do not translate well to the clinic with many failures of compounds that had good efficacy in the animal models. The possibility to target an additional CNS site may provide the additional efficacy required to be a successful analgesic. With respect to a potential cancer indications, the development of a bi-specific Ab targeting both the tumour cells and $Na_v1.7$ could ensure concentration of the therapeutic Ab in the tumour.

If CNS access is required for efficacy in humans then a BBB-crossing mAb targeting $Na_v1.7$ may have such an advantage. With respect to a cancer indication a bi-specific Ab targeting both the tumour cell and $Na_v1.7$ may have an advantage in allowing lower systemic exposure due to concentration within the tumour and thus avoiding side-effects associated with inhibiting the normal functioning of the $Na_v1.7$ channel.

The present disclosure also provides nucleotide molecules encoding the antibodies described herein. The nucleotide molecules can be provided in an isolated form and may be derived from a variety of sources including DNA, cDNA, synthetic DNA, synthetic RNA, derivatives, mimetics or combinations thereof. Such sequences may comprise genomic DNA, which may or may not include naturally occurring introns, genic regions, nongenic regions, and regulatory regions. Moreover, such genomic DNA may be obtained in association with promoter regions or poly (A) sequences. The sequences, genomic DNA, or cDNA may be obtained in any of several ways. Genomic DNA can be extracted and purified from suitable cells by means well known in the art. Alternatively, mRNA can be isolated from a cell and used to produce cDNA by reverse transcription or other means. The nucleotide molecules described herein are used in certain embodiments of the methods of the present disclosure for production of RNA, proteins or polypeptides, through incorporation into host cells, tissues, or organisms. The nucleotide molecules can include any nucleic acid sequence described in Table 7. In an embodiment, the nucleotide molecules can be codon-optimized for expression in a particular host. The nucleotide molecules can include, in some embodiments, one or more promoter sequence and/or one or more terminator sequence. The nucleotide molecules can be included in a vector for expression in a recombinant host.

Methods of Using the Anti-$Na_v1.7$ Antibodies

Due to their high specificity towards the $Na_v1.7$ polypeptide, the antibodies of the present disclosure can be used to substantially purify the $Na_v1.7$ polypeptide from a mixture suspected of comprising the $Na_v1.7$ polypeptide. In such embodiment, the antibodies of the present disclosure can be provided in association with a solid support (e.g., a bead, a resin, a plate for example) for binding to the $Na_v1.7$ polypeptide and allowing the (partial or complete) removal of the other components of the mixture.

The antibodies of the present disclosure can be used to detect, and in some embodiments, localize or quantify the amounts of the $Na_v1.7$ polypeptide either in vitro (in immunological assays, such as, for example, ELISA, immunological staining and flow cytometry) or in vivo (in imaging techniques). In such embodiment, the antibodies of the present disclosure can be associated (coupled or physically linked) to a detectable label and used in combination with a method for detecting, localizing and/or quantifying the amount of the $Na_v1.7$ polypeptide by determining the presence, absence, location, amount of the detactable label. Examples of detectable labels include, but are not limited to, various enzymes, prosthetic groups, fluorescent materials, luminescent materials, bioluminescent materials and radio-active materials. Examples of suitable enzymes include, but are not limited to, horseradish peroxidase, alkaline phosphatase, beta-galactosidase, or acetylcholinesterase. Examples of suitable prosthetic group complexes include, but are not limited to, streptavidin/biotin and avidin/biotin. Examples of suitable fluorescent materials include, but are not limited to, umbelliferone, fluorescein, fluorescein isothiocyanate, rhodamine, dichlorotriazinylamine fluorescein, dansyl chloride or phycoerythrin. Examples of a luminescent material include, but are not limited to, luminol. Examples of bioluminescent materials include, but are not limited to, luciferase, luciferin, and aequorin. Examples of suitable radioactive materials include, but are not limited to, $^{125}I$, $^{131}I$, $^{35}S$, $^{32}P$ or $^{3}H$.

Due to their ability to antagonize the biological activity of the $Na_v1.7$ polypeptide, the antibodies of the present disclosure can also be used as a medicine for the alleviation of the symptoms of pain. As used herein, the expression "alleviation of symptoms of pain" refer to the ability of the antibody to limit the symptomology of pain in a subject in need thereof (e.g., experiencing pain). In some embodiments, the antibodies can be used to treat chronic pain. In other embodiments, the antibodies can be used to treat neuropathic pain. Symptoms associated with pain include, but are not limited to: nociception, nausea, headache, swelling, weakness, lack of energy, mood changes, trouble sleeping and/or decreased appetite. Type of pain: nociceptive, inflammatory and neuropathic. In some embodiments, the pain is a chronic pain caused by cancer, inflammation or degeneration of joints; a neuropathic pain caused by injury to nerves, phantom limbs; a pain caused by tissue injury (trauma, burns, etc.) and/or a post-surgery pain.

Because some of the embodiments of the antibodies of the present disclosure are capable of reducing colony formation of cancerous cells, the antibodies can also be used for the treatment or the alleviation of symptoms associated with an hyperproliferative disease. The expressions "treatment or alleviation of symptoms" refer to the ability of a method or an antibody to limit the development, progression and/or symptomology of an hyperproliferative disease. Broadly, the treatment and/or alleviation of symptoms can encompass the reduction of proliferation of the cells (e.g., by reducing the total number of cells in an hyperproliferative state and/or by reducing the pace of proliferation of cells). Symptoms associated with proliferation-associated disorder include, but are not limited to: local symptoms which are associated with the site of the primary cancer (such as lumps or swelling (tumor), hemorrhage, ulceration and pain), metastatic symptoms which are associated to the spread of cancer to other locations in the body. (such as enlarged lymph nodes, hepatomegaly, splenomegaly, pain, fracture of affected bones, and neurological symptoms), and systemic symptoms (such as weight loss, fatigue, excessive sweating, anemia and paraneoplastic phenomena).

Hyperproliferative diseases form a class of diseases where cells proliferate more rapidly, and usually not in an ordered fashion. The proliferation of cells cause an hyperproliferative state that may lead to biological dysfunctions, such as the formation of tumors (malignant or benign). One of the hyperproliferative disease is cancer. Also known medically as a malignant neoplasm, cancer is a term for a large group of different diseases, all involving unregulated cell growth. In cancer, cells divide and grow uncontrollably, forming malignant tumors, and invade nearby parts of the body. The cancer may also spread to more distant parts of the body through the lymphatic system or bloodstream. In another embodiment, the cancer is associated with the expression and, in some embodiments overexpression, of the $Na_v1.7$ polypeptide. In some embodiments, the antibodies can be used in combination with other chemotherapeutic agents.

As indicated above, the antibody can be provided in a chimeric form when it is intended that the antibody cross the blood brain barrier to provide its therapeutic benefits. For some therapeutic or preventive applications, the antibody of the present disclosure can also be coupled to a chemotherapeutic agent, a toxin (e.g., an enzymatically active toxin of bacterial, fungal, plant, or animal origin, or fragments thereof), a radioactive isotope (i.e., a radioconjugate). Exemplary toxins include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes.

In some embodiments, the antibodies and the chimeric proteins of the present disclosure can be provided as pharmaceutical compositions. As used herein, "pharmaceutical composition" means therapeutically effective amounts (dose) of the antibody/chimeric protein together with pharmaceutically acceptable diluents, preservatives, solubilizers, emulsifiers, adjuvants and/or carriers. Such compositions can be liquid or lyophilized or otherwise dried formulations and include diluents of various buffer content (e.g., Tris-HCl, acetate, phosphate), pH and ionic strength, additives such as albumin or gelatin to prevent absorption to surfaces, and detergents (e.g., Tween20™, Tween80™, Pluronic F68™, bile acid salts). The pharmaceutical composition can comprise pharmaceutically acceptable solubilizing agents (e.g., glycerol, polyethylene glycerol), anti-oxidants (e.g., ascorbic acid, sodium metabisulfite), preservatives (e.g., thimerosal, benzyl alcohol, parabens), bulking substances, amino acids or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines).

The antibodies of the present disclosure may be used individually or in combination. For example, a pharmaceutical composition of the present invention may comprise one or more than one antibody defined herein. For example, antibodies 3A8, 1B6, 1H5, 2G11 and DI-D may be used individually or in a combination of two or more antibodies. In some further embodiments, the antibodies can be used with other therapeutic agents for managing pain and/or cancer.

The antibodies and the chimeric proteins of the present disclosure (which can be included in a pharmaceutical composition) can be formulated or intended to be administered by various routes, although more than one route can be used to administer a particular composition, a particular route can often provide a more immediate and more effective reaction than another route. The antibodies and chimeric proteins of the present disclosure may be administered, either orally or parenterally, systemically or locally. In an embodiment, the antibodies and chimeric proteins are formulated/intended for intravenous administration, such as, by injection or infusion. The effective dosage can be chosen from the range of 0.01 mg to 100 mg per kg of body weight per administration. Alternatively, the dosage is a fixed dosage and is in the range of 1 to 1000 mg, preferably 5 to 50 mg per patient may be chosen. In some embodiments, the effective dosage can be at least 10 mg/kg and at most 100 mg/kg.

The antibodies and chimeric proteins of the present disclosure are formulated/intended to be administered at a therapeutically effective amount. A "therapeutically effective amount" as used herein refers to that amount which provides a therapeutic effect (e.g., alleviation of the symptoms of pain) for a given condition and administration regimen. The antibodies and chimeric proteins can be used alone or in combination with other therapeutic agents for the treatment of pain. When used in combination with other therapeutic agents for the treatment of pain, the antibodies and chimeric protein can be formulated/intended to be administered sequentially, subsequently or simultaneously.

The antibodies and the chimeric protein of the present disclosure can be used or administered to various subjects, including humans and non-human mammals (such as cats and dogs for example).

Single-Domain Antibody-Based Immunogen

The present disclosure also provides immunogens as well as methods for making antibodies specific to a peptide epitope with the immunogens. As shown in the Examples below, an immungen (FC5DIE31R) was used to immunize an animal and/or select an antibody from a library of antibodies in order to obtain or identify an antibody specific for a peptide epitope found on the $Na_v1.7$ polypeptide. As also shown in the Examples below, the antibodies obtained were specific for the $Na_v1.7$ polypeptide. Consequently, the present disclosure provides an immunogen for making additional antibodies, including additional anti-$Na_v1.7$ polypeptide antibodies, based on a similar approach.

As used in the context of the present disclosure, an "immunogen" is a polypeptide which is capable of either eliciting an immune reaction (e.g., production of antibodies) upon the administration in a host as well as being able to select, from a library of antibodies, antibodies specific for the epitope. The immunogen of the present disclosure is intended to be expressed in a recombinant fashion in a host, as such, the epitope it bears is constituted of a contiguous stretch of amino acid residues which form an epitope in the immunogen.

The immunogen of the present disclosure comprises or consists of a single-domain antibody (sdAb) in which the epitope is introduced in one complementary determining region (and in some embodiments, in a single complementary determining region of the sdAb). Single-domain antibodies, such a camelid $V_HH$ antibodies, usually have three CDRs (from amino to carboxyl terminus, CDR1, CDR2 and CDR3) and the peptide epitope can be introduced in any one of the three CDRs. In a specific embodiment, the peptide epitope is introduced in the CDR3 of the sdAb. Preferably, the epitope is introduced in the single-domain antibody in such a way that the overall tridimensional structure of the framework regions remains substantially similar to the overall tridimensional structure of the original single-domain antibody that does not bear the peptide epitope. This can be achieved, for example, by deleting one or more amino acid residues in one location (for example the CDR) intended to receive the peptide epitope and introducing the peptide epitope at the location of the deletion. In some embodiments, the entire CDR is removed and replaced by the peptide epitope. In other embodiments, only parts of the CDR (which may be a contiguous stretch of amino acids) is removed and replaced by the peptide epitope.

The peptide epitope that can be introduced in the CDR of the immunogen can be of any length, for example between 2 and 500 amino acid residues. In an embodiment, the peptide epitope is between 2 and 400, 2 and 300, 2 and 200, 2 and 100, 5 and 100, 10 and 100, 20 and 100, 30 and 100, 40 and 100 or 50 and 100 amino acid residues. In a specific embodiment, the peptide epitope is 70 amino acid residue-long.

The immunogen can comprise any sdAb and, in some embodiments, the immunogen is derived from a camelid $V_HH$ antibody, the FC5 antibody (as described in U.S. Pat. Nos. 8,715,659 and 8,383,107). When the immunogen is derived from the FC5 antibody, it can comprise or consist essentially of the polypeptide of formula (I):

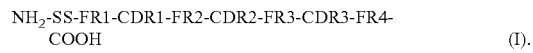

$$NH_2\text{-SS-FR1-CDR1-FR2-CDR2-FR3-CDR3-FR4-COOH} \quad (I).$$

In the polypeptides of formula (I), $NH_2$ refers to the amino terminus of the polypeptide and COOH refers to the carboxyl terminus of the polypeptide. Since the polypeptide of formula (I) are intended to be produced from a recombinant host, the moieties it comprises are comprised of stretch of contiguous amino acid residues linked to one another by an amide bond.

The moiety SS is an optional component of the polypeptide of formula (I). The abbreviation "SS" refers to a "signal sequence" which can allow targeting the polypeptide of formula (I) for secretion from the recombinant host producing the immunogen. The SS is usually absent for the secreted form of the polypeptide. As such, the SS is usually present on the polypeptides of formula (I) when they are located inside the recombinant host and usually absent on the polypeptides of formula (I) when they are secreted. When present, the carboxyl terminus of AA is bound (directly or indirectly) to the amino terminus of the FR1 moiety. If present, the SS can have or consist essentially of the amino acid sequence of SEQ ID NO: 69. However, the person skilled in the art will appreciate that other SS can be used to achieve extracellular expression of the immunogen.

The moieties FR1, FR2, FR3 and FR4 refer to the first, second, third and fourth framework regions of the sdAb, when starting from the amino terminus of the polypeptide of formula (I). The moieties CDR1, CDR2 and CDR3 refer to the first, second and third complementary determining regions of the sdAb, when starting from the amino terminus of the polypeptide of formula (i). When the SS moiety is present, the carboxyl terminus of the SS moiety is bound (directly or indirectly) to the amino terminus of the FR1 moiety. The carboxyl terminus of the FR1 moiety is bound (directly or indirectly) to the amino terminus of the CDR1 moiety. The carboxyl terminus of the CDR1 moiety is bound (directly or indirectly) to the amino terminus of the FR2 moiety. The carboxyl terminus of the FR2 moiety is bound (directly or indirectly) to the amino terminus of the CDR2 moiety. The carboxyl terminus of the CDR2 moiety is bound (directly or indirectly) to the amino terminus of the FR3 moiety. The carboxyl terminus of the FR3 moiety is bound (directly or indirectly) to the amino terminus of the CDR3 moiety. The carboxyl terminus of the CDR3 moiety is bound (directly or indirectly) to the amino terminus of the FR4 moiety.

When the immunogen is derived from the FC5 antibody, the FR1 moiety has the amino acid sequence of SEQ ID NO:

60, the FR2 moiety has the amino acid sequence of SEQ ID NO: 61, the FR3 moiety has the amino acid sequence of SEQ ID NO: 62 and the FR4 moiety has the amino acid sequence of SEQ ID NO 63.

In an embodiment, the peptide epitope is included in the CDR1 moiety. In such embodiment, the polypeptide of formula (I) can have a CDR2 moiety comprising the amino acid sequence of SEQ ID NO: 65 and a CDR3 moiety comprising the amino acid sequence of SEQ ID NO: 66.

In another embodiment, the peptide epitope is included in the CDR2 moiety. In such embodiment, the polypeptide of formula (I) can have a CDR1 moiety comprising the amino acid sequence of SEQ ID NO: 64 and a CDR3 moiety comprising the amino acid sequence of SEQ ID NO: 66.

In yet another embodiment, the peptide epitope is included in the CDR3 moiety. In such embodiment, the polypeptide of formula (I) can have a CDR1 moiety comprising the amino acid sequence of SEQ ID NO: 64 and a CDR2 moiety comprising the amino acid sequence of SEQ ID NO: 65. In such embodiment, the polypeptide of formula (I) can have the amino acid sequence of SEQ ID NO: 70 (including a signal sequence) or 71 (with no signal sequence) in which the residue identified with "Xaa" is the location of the peptide epitope. When the peptide epitope is the DIE3IR peptide, the polypeptide of formula (I) can have the amino acid sequence of SEQ ID NO: 2 or 67 (including a signal sequence) or 3 or 68 (with no signal sequence).

In an embodiment, the immunogen comprises an antibody or antibody fragment wherein the antibody comprises the peptide of SEQ ID NO: 2, 3, 67, 68, 103, 104, 105 or 106. The peptide is intended to replace a portion of the antibody, preferably a CDR region of the antibody. Wherein the antibody may comprise a peptide selected from the group consisting of SEQ ID NO: 2, 3, 67, 68, 103, 104, 105 or 106 wherein the modified immunogen is structurally equivalent to the original (unmodified) antibody. When the original antibody has been modified to comprise a peptide of SEQ ID NO: 2, 3, 67, 68, 103, 104, 105 or 106, the modified antibody can be used as immunogen capable of yielding anti-Na$_v$1.7 antibodies. An immunogen of the present invention may comprise, but is not limited to, an antibody comprising the amino acid sequence of SEQ ID NO: 2, 3, 67, 68, 103, 104, 105 or 106.

The present disclosure comprises using the immunogen for making or selecting an antibody specific to the peptide epitope. The immunogen can be used in an animal for eliciting an immune reaction and the production of antibodies which may be further screened for their ability to specifically bind to the peptide antibody or the target polypeptide comprising the peptide epitope. The immunogen can also be used to screen a library of antibodies to select those having specificity towards the peptide antibody or the target polypeptide comprising the peptide epitope. The immunogen of the present disclosure can be used in combination with another control sdAb which corresponds to the sdAb used to make the immunogen but which lacks the peptide epitope.

The present disclosure comprises a method of making/selecting an antibody (which can be, for example, a monoclonal antibody or a single-domain antibody) specific for the peptide epitope. The method comprises a step of selecting an antibody specific for the peptide epitope from a library of antibodies or a population of antibody-producing cells by contacting the immunogen with the library or the population and selecting the antibodies/cells producing antibodies which binding specifically to the immunogen. The method can comprise a step of contacting a control sdAb (which corresponds to the sdAb used to make the immunogen but which lacks the peptide epitope) with the library/population and discarding the antibodies/cells producing antibodies which bind specifically to the control sdAb. In some embodiments, the method can also comprise a step of immunizing an animal (such as, for example, a mouse or a llama) with the immunogen (alone or in combination with an adjuvant, once or multiple times) and generating antibody-producing cell lines or clones from an organ of the immunized animal. In such embodiment, the method can also comprising fusing the antibody-producing cell obtained from the animal to a cancer cell to make an hybridoma.

The affinity of the antibodies selected using the immunogen of the present disclosure for the peptide epitope or the target polypeptide comprising the peptide epitope can be determined by various techniques known in the art including an immunological assay (such as, for example, an ELISA) and/or surface plasmon resonance (SPR).

The present invention will be more readily understood by referring to the following examples which are given to illustrate the invention rather than to limit its scope.

Example I—Materials and Methods

Figure 1:
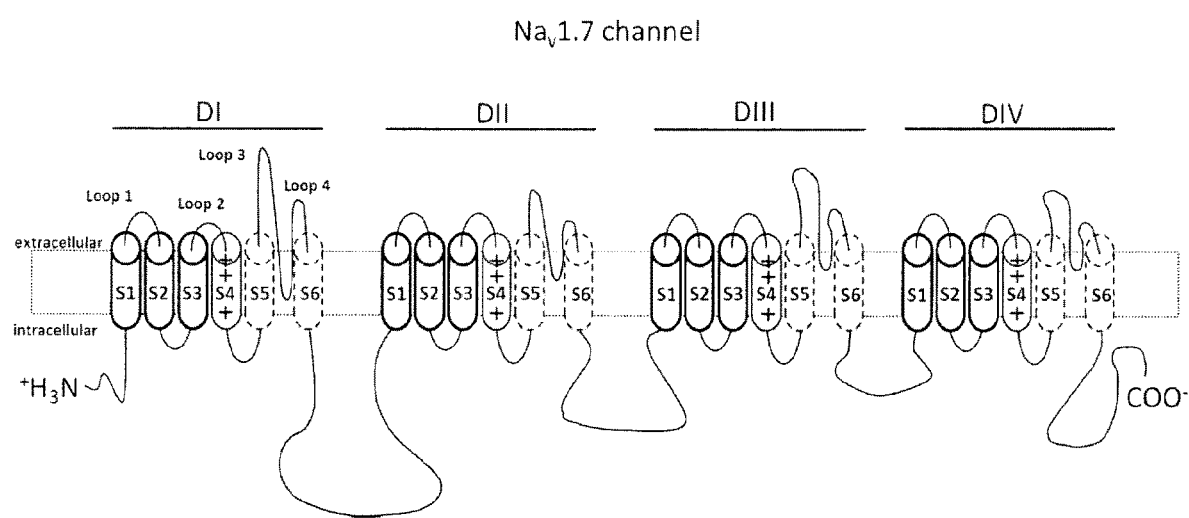
FIG. 1 provides a schematic representation of the $Na_v1.7$ channel.

Epitope selection. Na$_v$1.7 is comprised of four domains (DI, DII, DIII and DIV), each containing six transmembrane helices (S1-S6) and 4 extracellular loops (FIG. 1). S4 is the voltage sensor of the channels. Studies of mutant Na$_v$1.7 in native neuron (mutations in the gene coding for the Na$_v$1.7, SCN9, which cause a channelopathy-associated insensitivity to pain, CIP), sequence and structural homology of human Na$_v$1.7 sodium channel to the solved crystal structures of the bacterial sodium channel Na$_v$Ab (Payandeh et al., 2011) and of eukaryotic ion channel Na$_v$PaS (Shen et al., 2017) were used in order to select a solvent-accessible region of 70 amino-acid peptide (referred to as DIE3IR and provided as SEQ ID NO: 1) from the extracellular loop 3 of the domain DI of the wild-type human Na$_v$1.7, which also corresponds to the sequence that contains mutations linked to CIP. DIE3IR was then grafted within the CDR3 (Kabat definition) in the V$_H$H FC5, thus producing the recombinant protein FC5DIE3IR (corresponding to SEQ ID NO: 2 or 67 with the signal peptide and to SEQ ID NO: 3 or 68 without the signal peptide).

Figure 2A:
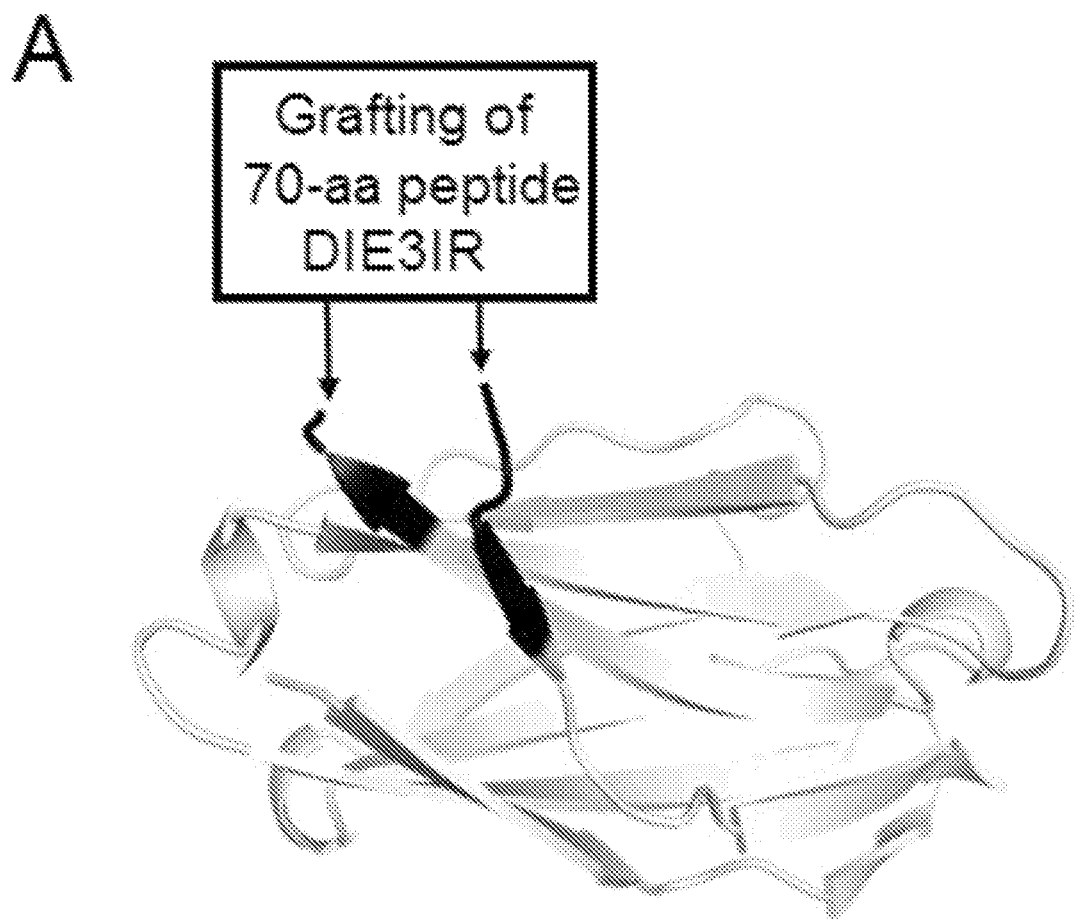
FIGS. 2A to 2C provide a 3D view of $V_HH$ FC5 lacking 6 amino-acid residues from the inner region of its CDR3.
Figures 2B, 2C:
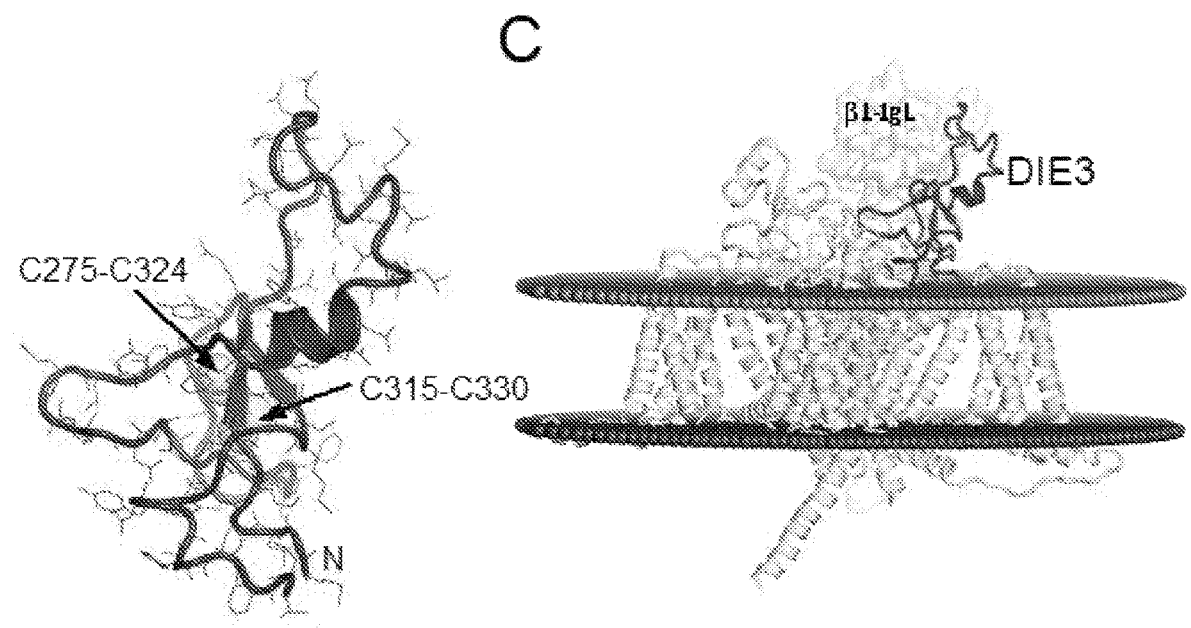

In the design of this recombinant protein construct, six amino acid residues in the middle of the CDR3 of FC5 were removed and replaced by the DIE3IR sequence of 70 amino-acid residues. Seven amino-acid residues from the original CDR3 of FC5 were retained, three on the N-terminal side and four on the C-terminal side of the grafted DIE3IR peptide, in an attempt to maximize its accessibility for antibody recognition and to minimize possible alterations of its native folding due to proximity to the FC5 structure. A molecular model of the FC5 V$_H$H with the retained regions of the CDR3 (between which the DIE3IR peptide is to be grafted) is shown in FIG. 2A. The DIE3IR extracellular segment is predicted to form a well-folded globular domain stabilized by two disulphide bonds and to have its N- and C-termini in close proximity (FIG. 2B), based on its high homology to the recent cryo-EM structures of eukaryotic sodium channels. This solvent accessible extracellular domain appears to be prone to interactions with immunoglobulin (Ig) folded structures, based on the crystal structure of eel Na$_v$1.4 complexed with the Ig-like β-1 subunit (FIG. 2C), which we found to be relevant for our immunization attempts.

FC5DIE3IR protein production. The codon-optimized sequence encoding the human DIE3IR domain engrafted within the FC5 in place of CDR3 region was synthesized (GenScript, Piscataway, N.J., USA) and cloned into the pTT5 vector. The Chinese hamster ovary cell line expressing a truncated EBNA1 protein (CHO-3E7; Raymond et al., 2015) were grown in suspension in serum-free FreeStyle™ F17 medium (Invitrogen, Carlsbad, Calif., USA) supplemented with 0.1% Kolliphor P188 (Sigma-Aldrich, St. Louis, Mo., USA) and 4 mM Glutamine (Sigma-Aldrich, St. Louis, Mo., USA). Cultures were maintained in 125 ml Erlenmeyer ventilated flasks shaken at 120 rpm in a humidified incubator at 37° C. with 5% $CO_2$. Cell density and viability were determined using the Cedex Innovatis automated cell counter Cedex Analyzer (Roche, Basel, Switzerland) based on the trypan blue exclusion method.

Linear deacylated polyethylenimine Max (PEImax) was obtained from Polysciences (Warrington, Pa., USA). Stock solution (3 mg/ml) was prepared in ultrapure water, sterilized by filtration (0.2 µm), aliquoted and stored à +4° C. Cells were diluted one day before transfection in fresh medium at $0.7 \times 10^6$ cells/ml. They were then transfected the following day with viability greater than 99% at densities between 2.0 and $2.5 \times 10^6$ cells/ml with 1 µg of plasmid DNA per ml of CHO culture. To that effect, plasmid DNA and PEImax were separately prepared in complete F17 medium. Plasmid DNA (pTT5-FC5DIE31R) was diluted at 20 µg/ml in F17 medium, and an equivalent volume of F17 medium containing 100 µg/ml of 25 kDa PEImax was added. The polyplexes mixture was immediately vortexed and incubated 5 min at room temperature prior to addition to the cells. Twenty four hours post-transfection (hpt), cells were fed with peptone TN1 (0.5% w/v final), and the culture temperature was shifted to 32° C.

Cell culture was centrifuged 20 min at 3000 g 10-12 days post-transfection (dpt) at a viability >60%. The supernatant was collected and loaded on a 5 ml MabSelect™ SuRe™ column (GE Healthcare) equilibrated in PBS. The column was washed with PBS and FC5DIE3IR was eluted with 100 mM citrate buffer pH 3.6. The fractions containing FC5DIE3IR were pooled and the citrate buffer was exchanged against PBS on Econo-Pac® 10DG columns (Bio-Rad, cat #732-2010). Purified FC5DIE3IR was concentrated on Amicon Ultra 3 kDa and sterilized by passing through 0.2 µm filters, aliquoted, and stored at −80° C.

As indicated in Examples II, III and IV, this recombinant protein has been used as antigen/immunogen to immunize mice and generate monoclonal antibodies (mAbs), isolate $V_HH$s against $hNa_v1.7$ from a phage-displayed naïve $V_HH$ library generated from llama, alpaca and camel, immunize llamas to obtain a FC5DIE3IR llama immune library, isolate $V_HH$s against $hNa_v1.7$ from a phage-displayed $V_HH$ library generated from immunizing llamas with FC5DIE3IR.

Generation of $hNa_v1.7$-HEK293 cell line. Anti-$hNa_v1.7$ mAbs and $V_HH$s were tested on $hNa_v1.7$ currents recorded with patch-clamp whole-cell technique in HEK293 cells overexpressing $hNa_v1.7$ channels ($hNa_v1.7$-HEK293 cells). HEK-293 cells (ATCC CRL1573) were transfected with human $Na_v1.7$ plasmid (SC398916; OriGene Technologies, Rockville, Md., USA) as per Lipofectamine 2000's protocol (Invitrogen Life Technologies P/N 52887). One day before transfection, HEK293 cells were seeded in 3 wells of a 6 well plate at a density of $8 \times 10^5$ cells/well in growth medium (EMEM supplemented with 10% FBS). On the morning of transfection, the growth medium was replaced and the DNA/Lipofectamine solution was prepared as follows: for each well, 125 µl of OptiMEME containing 3 µg of DNA was mixed with 125 µl of OptiMEM pre-incubated with 9 µl of Lipofectamine 2000 at room temperature for 5 minutes. The DNA/Lipofectamine solution was then incubated for 20 minutes prior to adding it to the cells. After 5 h of transfection, the growth medium was replaced. Two days post transfection, cells were combined, plated in 6 10 $cm^2$ dishes, and grown in the presence 300 µg/ml G418 sulfate, an antibiotic selective for transfected cells (400-130-IG, Wisent Bio Products, Saint-Jean-Baptiste, QC, Canada). Growth medium containing G418 sulfate was replaced every 2 days. When colonies became visible, they were selected and plated on cover slips for screening.

Figure 3:
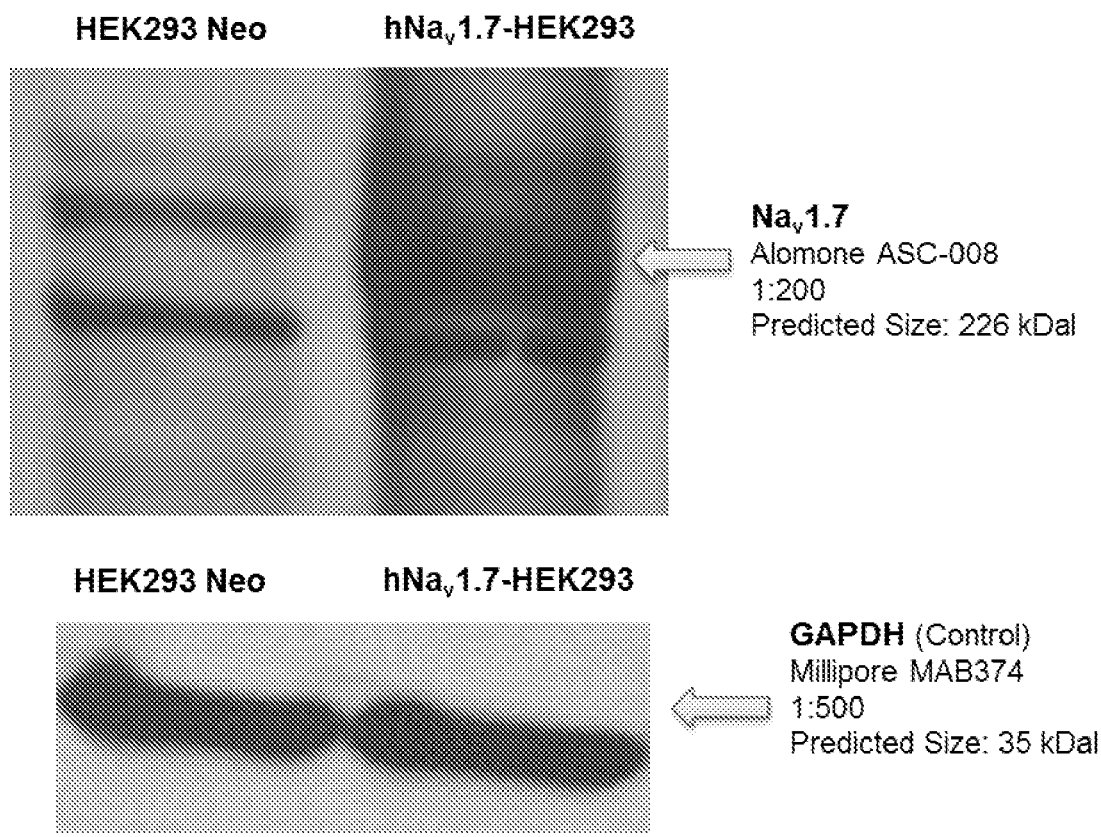
FIG. 3 provides the results of a Western blot showing the expression of $hNa_v1.7$ in transfected cells. Results are shown for control cells transfected with a control plasmid (HEK293 Neo) and cells transfected with the plasmid for $Na_v1.7$ ($hNa_v1.7$-HEK293 or SNC9) for both the $Na_v17$ polypeptide (top panel) and GADPH control polypeptide (lower panel).

Western blot. Western blot was performed to determine the expression of the $hNa_v1.7$ polypeptide in the transfected cells. Proteins (10 ng for each cell type, determined using the Bradford's reagent) were isolated, loaded and run on a precast Biorad Mini Protean TGX 4%-20% gel. The proteins of the gel were transferred to a membrane and incubated with an Alomone ACS-008 rabbit antibody (for $Na_v1.7$, expected size 226 kDa, dilution 1:200) or a Millipore MAB374 mouse antibody (for GAPDH, expected size 35 kDa, dilution 1:500). The membranes were washed and incubated with a secondary antibody labelled with horseradish peroxidase. The presence of each protein was determined using enhanced chemiluminescence. FIG. 3 shows the results of the Western Blot demonstrating a higher level of $hNa_v1.7$ protein in $hNa_v1.7$-HEK293 cells compared to non-transfected cells.

Antibody Binding Assays (Protein-ELISA). FC5DIE3IR binding of $V_HH$ monomers was assessed by direct protein ELISA. Briefly, wells of a NUNC MaxiSorp microtiter plate were coated overnight at 4° C. with 0.5 µg of the recombinant protein (FC5DIE31R) in 100 µl PBS, pH 7.4. As negative control, the parental FC5 $V_HH$ was used for immobilization as described above. After blocking with Starting block for 2 h, monomeric $V_HH$s (DI-A, DI-B, DI-C, DI-D, DI-E, DI-F, DI-G and DI-H) were added to the corresponding wells (FC5DIE3IR and FC5, respectively) and incubated for 2 h at room temperature. Wells were washed with PBST (0.05% v/v Tween-20) and further incubated with 100 µl rabbit anti-$His_6$ IgG conjugated to HRP (1:5000 in PBS) (Bethyl Laboratories) for 1 hour at room temperature. Binding was detected with TMB substrate (Kirkegaard and Perry Laboratories) and the reaction was stopped with 1M $H_3PO_4$ and A450 was measured using an ELISA plate reader as described (Hussack et al., 2012).

Cellular preparations for the patch-clamp assays. To prepare the cells for a patch-clamp whole-cell experiment, a vial of frozen $hNa_v1.7$-HEK293 cells was thawed in a 37.0° C. water bath for ~2 min or until completely thawed. Cells were then transferred to a 15 ml centrifuge tube and brought up to a volume of 5 ml with complete media (EMEM+10% FBS+G418). Cells were centrifuged at 1000 g for 3 min and the supernatant aspirated from pellet. The pellet was then re-suspended in 4 ml of complete media. The pellet was gently triturated several times with a 5 ml pipette to break the cell pellet apart and remove clumps. A complete media was added to the cell suspension to obtain a final volume of 12 ml. Cell suspension was then added to a labelled T-75 flask which was rocked back and forth a few times to ensure homogeneous cell distribution prior to placing into incubator. Cells were maintained in a 37.0° C./5% $CO_2$ incubator and fed every 2 days with complete media. Cells were split when confluency reached ~70-80%.

At time of cell splitting, a dilute cell suspension was prepared in complete media (100 µl of cells plus 2.4 ml of media). 500 µl of dilute cell suspension was added to each well of a 24 well plate containing poly-1-lysine (0.025 mg/ml; Sigma-Aldrich, St. Louis, Mo., USA) coated 13 mm plastic coverslips (Thermanox Plastic coverslips, Thermo Fisher, Waltham, Mass., USA).

Figure 4:
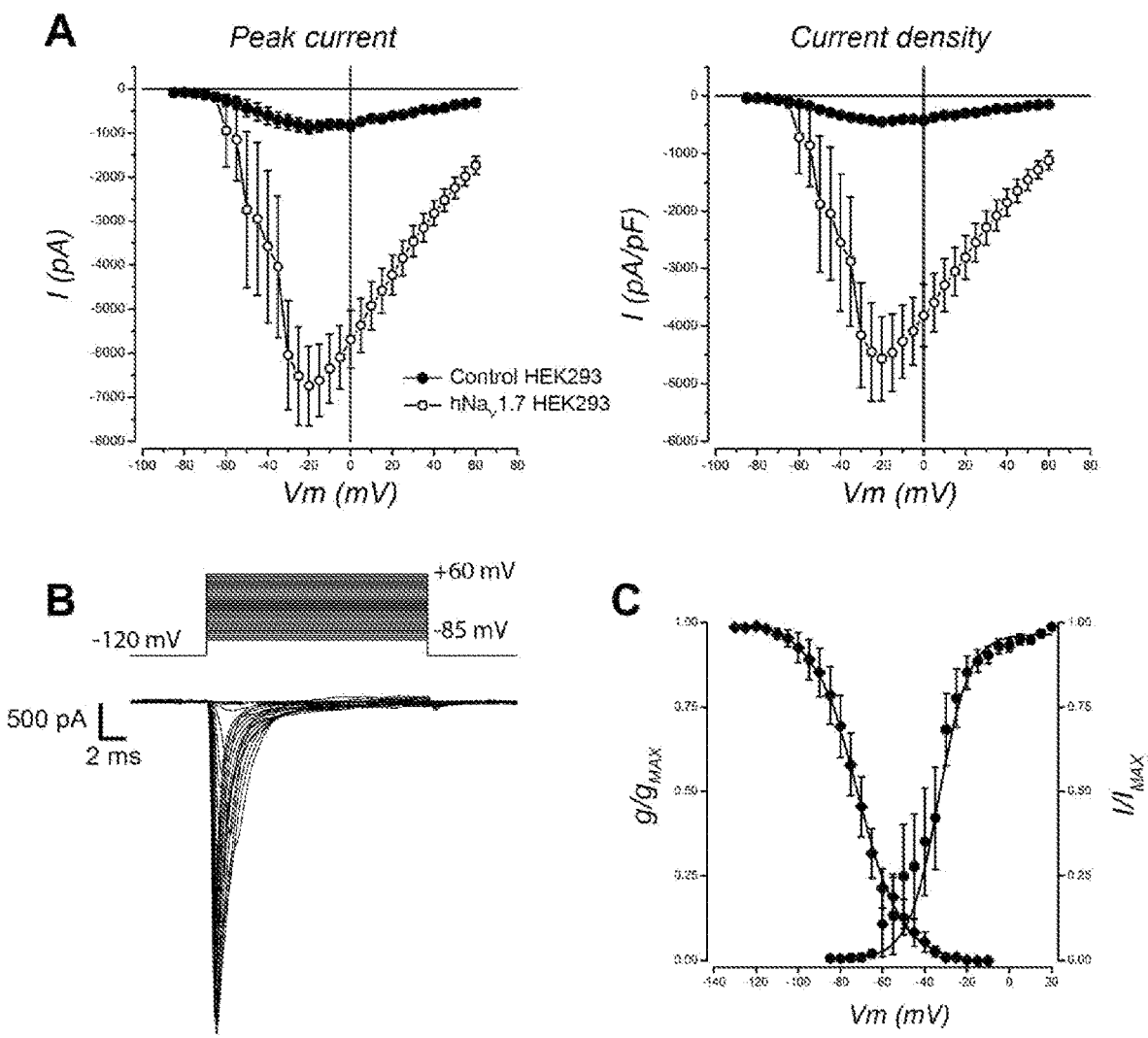
FIGS. 4A to 4C show that HEK293 cells stably transfected with the SNC9A plasmid ($hNa_v1.7$-HEK293 cells) have significantly larger $Na^+$ currents (n=8) compared to non-transfected HEK293 cells (Control HEK293 cells; n=8).

Patch-clamp whole-cell recordings. Human $Na_v1.7$-HEK293 cells were further evaluated using patch-clamp whole-cell recordings to determine the functionality of the $hNa_v1.7$ channels over-expressed in the HEK293 cells. Whole-cell patch-clamp recordings were obtained with a Multiclamp 700B amplifier (Molecular Devices, Carlsbad, Calif., USA) controlled with pClamp (v 10.2) software (Molecular Devices, Carlsbad, Calif.) used in combination with a Digidata 1440A A/D converter (Molecular Devices, Carlsbad, Calif.). Data were acquired at 20 KHz and filtered at 2 KHz. Patch-clamp experiments were conducted on transfected cells within 24-48 hours of plating. All recordings were done in the patch-clamp whole-cell configuration and voltage-clamp mode. Voltage-clamp experiments were performed with borosilicate pipettes filled with a solution (pipette solution) containing (in mM): CsF (140), NaCl (10), EGTA (1), HEPES (10), ATP (2), GTP (0.2). The pH was corrected to 7.3 using CsOH. The osmolarity of the pipette solution was adjusted to 280-290 mOsm. Recording electrodes were fire-polished with a microforge (MF-830, Narishige, Japan) and when filled with the pipette solution had a resistance of 1.5-3 MΩ. Whole-cell access resistances measured in voltage-clamp ranged from 5 to 10 MO. The access resistance was routinely monitored throughout each experiment. To record $Na^+$ currents, cells were maintained in an extracellular recording solution contained (in mM): NaCl (140), KCl (3), $CaCl_2$ (1), $MgCl_2$ (1), HEPES (10). The pH was corrected to 7.3 using NaOH, and the osmolarity adjusted to ~300 mOsm. Over-expression of $hNa_v1.7$ was analyzed by plotting current-voltage (I-V) relationships of evoked inward currents in response to step protocols (voltage steps from ~85 to +60 mV in 5 mV increments) and raw traces of inward current, and by analyzing half-maximal activation ($g/g_{MAX}$) and inactivation ($I/I_{MAX}$) potential (FIG. 4). For reference, HEK293 cells express an endogenous $Na_v1.7$ current which peaks between 200-500 pA.

Patch-clamp whole-cell assays for determining functionality of mAbs in vitro. Stock solutions of each mAb to be tested, were prepared in extracellular recording solution the day of the experiment. The concentration of the mAb was 20 times the concentration to be tested. This was done to consistently add 50 µl of mAb solution to the recording chamber containing the cells. The 50 µl of mAb solution was statically added to 650 µl of extracellular recording solution present in the recording chamber.

Whole-cell patch-clamp recordings were obtained with a Multiclamp 700B amplifier (Molecular Devices, Carlsbad, Calif., USA) controlled with a pClamp (v10.2) software (Molecular Devices, Carlsbad, Calif.) used in combination with a Digidata 1320A A/D converter (Molecular Devices). Data were acquired at 20 KHz and filtered at 2 KHz. Borosilicate pipettes had a resistance between 1.5 and 32MΩ when filled with a solution containing (mM): CsF (140), NaCl (10), $MgCl_2$ (1), HEPES (10), ATP-$Mg^{2+}$ (2), GTP-$Mg^{2+}$ (0.2). The pH was adjusted to 7.3 with CsOH. Pipettes were pulled from borosilicate glass using a P-97 Flaming-Brown type micropipette puller (Sutter Instrument, Novato, Calif., USA) and fire-polished with a microforge (MF-830; Narishige, Japan).

To record $Na^+$ currents, the cells were maintained in an extracellular solution containing (in mM): NaCl (150), CsCl (3), $CaCl_2$ (1), $MgCl_2$ (1), HEPES (10). The pH was adjusted to 7.3 with NaOH. The stimulus protocol to evoke $Na^+$ currents consisted of 1 Hz frequency, and 20 ms duration voltage steps elicited from the resting-state of $hNa_v1.7$ channels (−120 mV) to a potential that evoke maximal inward $Na^+$ current. The test potential was determined by stimulating the cell to various potential levels around the peak activation potential of $hNa_v1.7$ (from −40 mV to −20 mV). The stimulus potential that generated the greatest magnitude of inward current was used for subsequent experimental protocols. Cells were allowed to stabilize for up to 5 minutes following initial breaking of the membrane into the whole-cell configuration.

Following observation of a stable baseline, the experimental protocol was initiated. Two minutes baseline recordings were followed by recordings during mAb exposure. mAbs were applied through static bath application. The effect of the mAbs was assessed comparing the amplitudes of the currents in control and in the presence of the mAb. Analyses were performed off-line with the software IGOR (WaveMetrics Inc., Portland, Oreg., USA) and/or Origin 2016 (OriginLab Corporation, Northampton, Mass., USA). Statistical significance of the results was determined with paired Student's t-tests (two-tailed). All values are expressed as means±SEM, and a p-value of <0.05 is considered significant.

The current-voltage (I-V) relationships were obtained by plotting the amplitudes of the evoked inward currents in response to voltage steps versus the potentials of the steps (voltage steps from −85 to +60 mV in 5 mV increments). To calculate fast inactivation, the cells were held at −120 mV, 500 ms voltage steps (from −140 to −35 my; 5 mV increments) were followed by a depolarization step of the duration of 20 msec at 0 mV.

Hargreaves Model of Hyperalgesia in rats. Rats aged 4-6 weeks (weight range, 180-220 g) were used for intraplantar (ipl) administrations of various antibodies and evaluation of their efficacy in the Hargreaves model of inflammatory pain. Chronic inflammatory pain is induced by injecting a low volume (50 µl) of complete Freund's adjuvant (CFA; heat-killed M. tuberculosis—Sigma, St. Louis, Mo.—suspended in oil:saline 2:1 emulsion) into the right hind paw. The paw withdrawal latency in response to the application of a radiant stimulus onto the plantar surface of both right and left paw was measured using the plantar Analgesia Meter equipment for paw stimulation (IITC Life Science, Woodland Hills, Calif.). The time taken by the animal to respond by licking or flicking its paw is interpreted as positive response (paw withdrawal latency). After 48 h of the CFA injection, the baseline for latency paw withdrawal was measured and the mAbs tested. Test compound were injected by intraplantar route (50 µg diluted in 50 µl) with Hamilton (glass) syringe. A cut-off time (20 sec) is established at the end of which the heat source shuts off automatically to avoid tissue damage. Animals were kept (randomized) one per cage and staff performing pain experiments are blinded to the content of injectable compounds. Percentage of maximum possible effect (% MPE) was calculated using the formula % MPE= (Test Latency−Baseline Latency)×100/(Cut-off−Baseline Latency).

OD1 Mouse Pain Model. OD1 model was performed as previously described (Deuis et al., 2016) with minor modifications. CD-1 mice aged 4-6 weeks (weight range, 25-30 g) were kept under 12-h light-dark cycles and had standard rodent chow and water ad libitum. Scorpion α-toxin OD1, isolated from the venom of the Iranian yellow scorpion, is a C-terminally amidated polypeptide of 65 amino acids. It is shown to be a potent modulator of $Na_v1.7$ ($EC_{50}$ 4.5 nM), with little effect on $Na_v1.3$ and $Na_v1.5$ ($EC_{50}$>1 µM) and no effect on Na$_v$1.2 and Na$_v$1.8. OD1 (Bristol, United Kingdom) was diluted in phosphate-buffered saline/0.1% BSA and administered by shallow subcutaneous injection into the dorsal side of the left hind paw of mice in a volume of 30 µL under isoflurane anesthesia. Mice were then placed into polyvinyl boxes (10×10×10 cm), and spontaneous pain behavior (licks and flinches) was recorded and counted by blinded investigator. Test compounds were injected subcutaneous injection into the dorsal side of the left hind paw 60 minutes before OD1 injection.

Manufacturing of peptides #1-3, #2a, #20a, #40a and #40b. The peptides were custom-synthesized (Biomatik) and tested for antibody binding by ELISA. For ELISA, peptides #1-3, #20a, #20b, #40a and #40b were coated on ELISA plates at various doses (100-500 ng/well) overnight at 4° C. in PBS. The wells were blocked with 1% BSA in TBS-T for 30 min and then incubated with 1:1000 dilution of anti-hNa$_v$1.7 mAb at room temperature (RT) for one hr. Following three TBS-T washes (3×5 min), mAb binding to peptides was detected by incubating with HRP-conjugated anti-mouse Fc antibody for 90 min at RT in TBS-T. The bound antibody was detected with SureBlue™ TMB reagent kit (KPL) by colorimetric measurement at 450 nm according to manufacturer's instructions.

To verify a possible cross reactivity among members of the Na$_v$ family, the epitope sequences of the mAbs were searched in the database "non-redundant protein sequences" (nr) using Basic Local Alignment Search Tool (BLAST) 2.8.1 (protein-protein BLAST; Altschul et al., 1997). It was found that, the highest homology that pep #2 has with other members of the human Na$_v$ family is 78% homology with the structure of the hNa$_v$1.4 in complex with β1 (E value=3e-07) and 72% with the hNa$_v$1.2 (E value=1e-05), while, the pep #2a has a 78% homology with hNa$_v$1.4 (E value=4.7). The highest homology that peptide pep #3 has is 80% with the hNa$_v$1.2 (E value=8e-17). Overall this analysis suggests that the probability that 3A8, 1H5, 2G11 and 1B6 acts on others subtypes of the Na$_v$ family other than the Na$_v$1.7 is low.

Hydrogen-Deuterium Exchange Mass Spectrometry (HDX-MS). FC5DIE3IR and purified mAbs (3A8, 1H5, 2G11, 1B6, 1G5) were diluted to 40 and 20 µM, respectively, and mixed at a 1:1 ratio and kept on at 25° C. For the unbound control, FC5DIE3IR was diluted to 20 µM with PBS. Labelling reactions were initiated by adding 3 µL of IGF1R complexes to 3 µL of 90% D$_2$O at 25° C. Labelling was quenched after 1, 10, and 60 min by the addition of 39 µL ice-cold 8M urea/500 mM TCEP/200 mM Gly-HCl, pH 3.0, and samples were allowed to reduce for 2 min on ice. The sample was loaded into a 20 µL loop and manually injected in a custom valve cooler. This was followed by digestion at room temperature with a Poroszyme Immobilized Pepsin Cartridge (2.1×30 mm, Thermo Scientific) at 50 µL/min for 1.5 min, followed by washing/trapping onto a C18 PepMap100 cartridge kept at 1° C. (5 µm, 1×5 mm, Thermo Scientific) at 400 µL/min for 1 min in mobile phase A (0.23% formic acid in water). Peptides were eluted at 1° C. from a Biobasic-18 (5 µm, 0.32×50 mm, Thermo Scientific) analytical column at 10 µL/min with a 10-35% mobile phase B gradient (0.23% formic acid in acetonitrile) over 6 min. LC-MS analysis was performed with an Agilent 1260 Infinity pump coupled to a Q-Tof Ultima API mass spectrometer (Water). Peptides were identified with Mascot and validated using an unlabelled sample injection. Data was collected in triplicate and analyzed with MS studio, and mass shifts were considered significant if greater than >3 SD with a p-value of 0.05 (Rey et al., 2016).

Surface Plasmon Resonance of mAbs. FC5 and FC5DIE3IR proteins were SEC purified using a Superdex 75 column (GE Healthcare) connected to an AKTAPurifier (GE Healthcare) in HBS-EP+ running buffer (10 mM HEPES, pH 7.4, containing 150 mM NaCl, 3 mM EDTA and 0.05% P20) at a flow rate of 1 ml/min. Monomeric eluted peaks were used to flow over Fc-capture 3A8 mAb surfaces. To prepare the 3A8 mAb surfaces, approximately 6000 RUs of anti-mouse IgG (GE Healthcare) was first immobilized on CM5 Series S sensor chips (GE Healthcare) at pH 5.0, using standard amine coupling methods previously reported (Hussack et al., 2011) and according to the manufacturer's instructions (GE Healthcare). HBS-EP running buffer used for SPR experiments. The mAb 3A8 was captured on the anti-mouse IgG surface using 10 µg/ml of mAb, 30 sec contact time and flow rate of 10 µl/min. IMAC-purified DI-D V$_H$H was passed through a Superdex 75 (GE Healthcare) column for SEC purification in HBS-EP buffer (10 mM HEPES, pH 7.4, containing 150 mM NaCl, 3 mM EDTA and 0.005% P20), connected to an AKTAPurifier (GE Healthcare) at a flow rate of 1 ml/min. Test binding experiments of FC5 control and FC5DIE3IR involved flowing 1 µM concentrations of SEC-pure material over the mAb surface at a flow rate of 30 µl/min for 5 min. Surfaces could be regenerated using 10 mM glycine, pH 1.7, with a 120 sec pulse at 20 µl/min. All SPR experiments were evaluated with Biacore T200 Software v 3.0. For kinetic analysis, single cycle kinetic analysis was used by flowing a range of FC5DIE3IR concentrations (320 nM-20 nM) at a flow rate of 30 µl/min, with 600 sec contact time and 1200 sec dissociation. Regeneration conditions were the same as above. Data were fit to a 1:1 binding model and analyzed using the Biacore T200 Software v3.0.

For affinity determination, various concentrations of the antibodies (10-5000 nM) were injected over FC5DIE3IR, FC5 and 2A3-H4 surfaces, using an ethanolamine blocked surface as a reference, at a flow rate of 40 µl/min with 60 s contact time and 180 s of dissociation. Surfaces were regenerated by washing with running buffer (HBS-EP). Data were analyzed with BIAevaluation 4.1 software as described (Hussack et al., 2011) and affinities determined using the steady state binding model.

Surface Plasmon Resonance for V$_H$H antibodies. For SPR experiments, IMAC-purified V$_H$Hs DI-D, DI-4, DI-16, DI-28 and DI-48 were passed through a Superdex 75 (GE Healthcare) column for SEC purification in HBS-EP+buffer (10 mM HEPES, pH 7.4, containing 150 mM NaCl, 3 mM EDTA and 0.05% P20), connected to an AKTAPurifier (GE Healthcare) at a flow rate of 1 ml/min. Monomeric V$_H$H fractions were collected and protein concentration determined by measuring A280 measurement. Using a Biacore T200 instrument (GE Healthcare), approximately 500-1000 RUs of FC5DIE3IR, FC5 and an irrelevant V$_H$H (2A3-H4) were immobilized on a CM5 Series S sensor chip (GE Healthcare) at pH 4.0 using standard amine coupling according to the manufacturer's instructions (GE Healthcare). For affinity determination, various concentrations of the antibodies (312 nM-5000 nM for DI-4, DI-48 and DI-D; 2.5 nM-500 nM for DI-16 and DI-28) were injected over FC5DIE3IR, FC5 and 2A3-H4 surfaces, using an ethanolamine blocked surface as a reference, at a flow rate of 30 µl/min with 180 s contact time and 600 s of dissociation. Surfaces were regenerated by washing with a 120 s pulse of 10 mM glycine pH 1.5. Data were analyzed with Biacore T200 Software v 3.0 and affinities determined using steady state binding or a 1:1 binding model.

Soft Agar Assay Method. The anchorage-independent cell growth of two glioblastoma cell lines (U87MG and U87MGvIII) and an ovarian cell line (SKOV-3) was evaluated in semi-solid agar in the absence or presence of either TTX (0.5 µM) or 1B6 (1 µM), 1H5 (1 µM) or 2G11 (1 µM) as described previously (Moreno et al., 2006). Approximately 1800 cells±treatment were resuspended in 150 µl of growth medium (DMEM+10% FBS) containing either 0.6% agar (U87MG and U87MGvIII) or 0.45% agar (SKOV3) and seeded into a well of a 24-well plate previously layered with 250 µl of 0.6% agar. The solidified cell layer was covered with 50 µl of DMEM±treatment that was replaced every 3 days over a 14-day period. Phase contrast images (six fields per well) were captured using a digital video camera (Olympus U-CMT) and analyzed with Northern Eclipse v.5.0 software. To measure cell viability, at the end of the experiment, 50 µl of Alamar Blue™ (Cedarlane, Burlington, Ontario) was added to each well and fluorescence readings (530 nm excitation and 590 nm emission) were performed every 10 minutes for a period of 180 minutes.

Western Blot Method. Cell pellets from DU-145, Jurkat, LN18, PC-3, SKOV-3, U87MG, U87MG and Nav1.7-overexpressing HEK cells were lysed in RIPA buffer (BioRad) with Complete protease inhibitor cocktail (Roche) and protein concentrations determined using BioRad Reagent. Protein samples (30 µg) were prepared with loading buffer (BioRad), boiled for 5 minutes in a boiling water bath, and were loaded on a Mini-protean TGX 4-15% gel (BioRad). Proteins and Precision Plus Dual Colored Standard (BioRad) were separated at 100V then electrotransferred to nitrocellulose at 80V for 1 h. The nitrocellulose membrane was blocked for 1 h in 1×TBST with 5% Carnation skim milk. Rabbit polyclonal anti-$Na_v1.7$ (Alomone labs, ASC-008) was diluted 1:200 in the same buffer and incubated on the blots overnight at 4° C. on a rocking shaker. The blots were washed 3 times for 10 minutes with TBST, and incubated with anti-rabbit-HRP antibody (Invitrogen) at 1:5000 in TBST/milk for 1 h at room temperature. The blots were washed 3 times for 10 minutes as above, incubated for 5 minutes with Clarity ECL substrate (BioRad) and exposed to film. Film was developed on a Minolta SRX101A film developer and scanned on a Sharp MX-4111N copier. The membrane was washed for 30 minutes with TBST and incubated for 1 h with anti-βactin-HRP (Sigma). The blot was washed 3 times for 10 minutes with TBST and exposed to film. Images were analyzed using Adobe Photoshop 7.0.1.

Western Blot Method (alternative method). Cell pellets from pancreatic tumor cell lines, Capan-1, Bxpc3, MiaPaca2 and Pant were lysed in RIPA buffer (BioRad) with Complete protease inhibitor cocktail (Roche) and protein concentrations determined using the Quantipro BCA Assay Kit (Sigma). The gel was run using the 12-230 kDA separation module (ProteinSimple), and the rabbit detection module (ProteinSimple). The samples (0.8 mg/ml) were prepared by combining the Master Mix to sample in a 1:4 ratio. The samples and a biotinylated ladder were heated in a Accublock digital dry bath at 95° C. for 5 minutes. The samples were cooled to room temperature, vortexed to mix and centrifuged in a Mandel mini microfuge. The biotinylated ladder (5 µl) was loaded in the first well of row A1. The samples (4 µl) were loaded in the remaining wells of row A. An antibody diluent (10 µl) was added to row B and the first well of row C. A rabbit polyclonal anti-$Na_v1.7$ (Alomone labs, ASC-008, 1:20) and an anti-βactin-HRP (Sigma, 1:100) were combined in antibody diluent and added to the remaining wells of row C. Streptavidin-HRP (10 µl) was added to the first well of row D. Anti-rabbit secondary antibodies were added to the other wells of row D. Luminol and peroxide were mixed (200 µl of each) and 15 µl was added to each well of row E. The plate was covered with a lid and centrifuged at 1000 g for 5 minutes in a Eppendorf 5810R centrifuge. A wash buffer (500 µl) was added to three rows of wells on the plate. The foil was removed from the separation reagents and the plate and capillaries were placed in the Wes™ (automated western blot system; ProteinSimple, San Jose, Calif., USA) for analisys.

Example II—Anti-$Na_v7$ Mouse Monoclonal Antibodies

Animal immunization. Four six-week old female NJ mice (The Jackson Laboratory, Bar Harbor, Me.) were bled (preimmune serum) and injected intraperitoneally and subcutaneously with 100 µg of FC5DIE3IR antigen emulsified in Titermax adjuvant (Cedarlane Labs, Burlington, ON) at day 0 and in PBS without adjuvant at day 26. Blood was collected in microvette CB 300Z (Sarstedt, Montreal, QC) at day 33, and serum was stored at −20° C. until further use.

ELISA (serum titer determination). Pre- and post-immune sera titer of animals immunized with FC5DIE3IR antigen were assessed by ELISA. Unless otherwise stated, all incubations were performed at room temperature. Briefly, half-area 96-well plates (Costar #3690) were coated with 25 µl per well of FC5DIE3IR at 5 µg/ml in PBS and incubated overnight at 4° C. Microplates were washed three times in PBS and blocked for 30 min with PBS containing 1% bovine serum albumin (BSA, Sigma Cat #A7030). Blocking buffer was removed and 25 µl of serial dilutions of sera samples were added. After a 2 h incubation, microplates were washed 4 times with PBS-Tween 20 0.05% and 25 µl of a 1/5.000 dilution of alkaline phosphatase conjugated goat anti-mouse IgG (H+L) (#115-056-062, Jackson Immunoresearch, Cedarlane, Burlington, ON) in blocking buffer was added. After a 1 h incubation, microplates were washed 4 times and 25 µl of p-nitrophenyl phosphate (pNPP) substrate (Sigma-Aldrich Canada Co., Oakville, ON) at 1 mg/ml in carbonate buffer at pH 9.6 was added and further incubated for 30 min. Absorbance was read at 405 nm using a SpectraMax plate reader (Molecular Devices, Sunnyvale, Calif.). All pre-immune bleeds were negative and all post-immune bleeds were very strong (above 1/12800) on FC5DIE3IR. After 2-3 months, an i.p. booster injection (100 µg of FC5DIE3IR protein in PBS) was done 3/4 days prior to fusion experiment.

Fusion of the harvested spleen cells. All manipulations were done under sterile conditions. Spleen cells were harvested in Iscove's Modified Dulbecco's medium (IMDM, Gibco Cat. #31980-030) and fused to NS0 myeloma cell line using polyethylene glycol (PEG, F233) or electrofusion (F236) protocols.

Fusion with PEG. Spleen cells and myeloma cells were washed in IMDM, counted in RBC lysing buffer (Sigma, Cat #7757-100ML) and mixed together at a 5:1 ratio. Pelleted cells were fused together by adding 1 ml of a 50% solution of PEG 4000 (EMD-Millipore Cat #9727-2) in PBS preheated at 37° C. drop-wise over one minute, and incubated at 37° C. for an additional 90 sec. The reaction was stopped by addition of 30 ml of IMDM at 22° C. over a period of 2 min. After a 10 min incubation, freshly fused cells were spun at 233 g for 10 min. Cells were washed once in IMDM supplemented with 10% heat inactivated FBS (Sigma Cat #F1051).

Electrofusion protocol. Spleen cells and myeloma cells were washed separately in IMDM. Red blood cells from splenocytes preparation were lyzed with RBC lysing buffer. Cells were washed in Isoosmolar buffer (Eppendorf cat #4308070536), then in Cytofusion Medium C (BTX cat #47-0001). Myeloma and lymphocytes were mixed together at a 2:1 ratio and fused using an ECM 2001 Cell Fusion System (BTX, Harvard Bioscience Inc.) following manufacturer's instructions.

Following fusion, cells were suspended at a concentration of $2\times10^5$ input myeloma cells per ml in HAT selection medium (IMDM containing 20% heat inactivated FBS, penicillin-streptomycin (Sigma Cat #P7539), 1 ng/ml mouse IL-6 (Biolegend Cat #575706), HAT media supplement (Sigma Cat #H0262) and L-glutamine (Hy-Clone Cat #SH30034.01) and incubated at 37° C., 5% $CO_2$. The next day, hybridoma cells were washed and suspended at a concentration of $2\text{-}3\times10^5$ input myeloma cells per ml in semi-solid medium D (StemCell Technologies Cat. #03804) supplemented with 5% heat inactivated FBS, 1 ng/ml mouse IL-6 and 10 µg/ml FITC-F(ab')$_2$ Goat anti-mouse IgG (Jackson #115-096-071 for F233 or 115-096-062 for F236). The cell mixture was plated in Omnitray dish (Nunc cat #242811) and further incubated for 6-7 days at 37° C., 5% $CO_2$. Fluorescent secretor clones were then transferred using a mammalian cell clone picker (ClonepixFL, Molecular Devices) into sterile 96-w plates (Costar #3595) containing 200 µl of IMDM supplemented with 20% heat inactivated FBS, penicillin-streptomycin, 1 ng/ml mouse IL-6, HT media supplement (Sigma Cat #H0137) and L-glutamine and incubated for 2-3 days at 37° C., 5% $CO_2$.

Screening. Hybridoma supernatants were screened by ELISA to detect specific binders. To this end, 96-well half-area plates (Costar #3690) were coated with 25 µl of FC5DIE3IR or FC5-V$_H$H or FC5-hFc-1X0 at 5 µg/ml in PBS and incubated overnight at 4° C. Microplates were washed 3 times with PBS, blocked with PBS-BSA 1%, and 25 µl of hybridoma supernatants were added and incubated at 37° C., 5% $CO_2$ for 2 hours. Plates were washed 4 times with PBS-Tween 20 0.05% and incubated for one hour at 37° C., 5% $CO_2$ with 25 µl of secondary antibody alkaline phosphatase conjugated F(ab')$_2$ goat anti-mouse IgG Fc-gamma specific (Jackson Immunoresearch #115-056-071) diluted 1/3000 in blocking buffer. After 4 washes with PBS-Tween 20 0.05%, 25 µl of a 1 mg/ml pNPP substrate solution was added and further incubated for one hour at 37° C. $OD_{405\ nm}$ measurements were done using a microplate reader (Spectramax 340 PC, Molecular Devices).

From the two fusions of the mouse spleen cells, 31 mAbs specific for FC5DIE3IR were identified from which supernatant was collected and evaluated for binding to CHO expressing human Na$_v$1.7 by ELISA.

Cell-ELISA. Sterile 96-well plates (Costar #3595) were pre-treated with 50 µl/well of branched polyethyleneimine (PEI, Sigma Cat #408727) at 25 µg/ml in PBS for 30 min at room temperature. PEI was removed and CHO-3E7 or hNA$_v$1.7-CHO (ChanTest cat #CT4003) were seeded at $6\times10^5$ cells per well in FreeStyle F17 Expression Medium (Gibco Cat #A1383501) and incubated overnight at 37° C., 5% $CO_2$. Microplates were blocked with Starting block (Thermofisher Cat #37538) for 30 min at room temperature, and 50 µl of hybridoma supernatants were added and incubated at 4° C. for 3 h. Plates were washed 5 times with PBS and incubated for one hour at 4° C. with 50 µl of secondary antibody HRP-conjugated F(ab')$_2$ goat anti-mouse IgG (H+L) (Jackson Immunoresearch #115-036-062) diluted 1/5000 in blocking buffer. After 10 washes with PBS, 50 µl of TMB substrate solution (Pierce Cat #34021) was added and further incubated for 60 min at room temperature. Twenty-five µl/well of stop solution (H2SO4 1M) was added and $OD_{450\ nm}$ measurements were done using a microplate reader (Spectramax 340 PC, Molecular Devices). Summary ELISA results for the top five clones are shown in Table 1.

TABLE 1

Evaluation of the supernatant collected from mAb-producing hybridomas by ELISA

| | | ELISA on purified proteins | | ELISA on live cells (duplicates) | | | |
|---|---|---|---|---|---|---|---|
| Clone | Isotype | FC5-DIE3IR | FC5-V$_H$H | CHO-Na$_v$1.7 | | CHO-3E7 | |
| 3A8 | IgG2a, k | 0.995 | 0.029 | 0.102 | 0.183 | −0.027 | −0.018 |
| 1G5 | IgG1, k | 1.139 | 0.096 | 0.172 | 0.225 | 0.008 | ND* |
| 1H5 | IgG1, k | 1.401 | 0.042 | 0.065 | 0.126 | −0.014 | 0.029 |
| 1B6 | IgG1, k | 1.704 | 0.028 | 0.027 | ND* | −0.013 | −0.012 |
| 2G11 | IgG2a, k | 0.860 | 0.021 | 0.041 | 0.049 | −0.027 | −0.025 |

*Not determined

All mAbs were then purified using Protein G Mag Sepharose (GE Cat #28-9670-70) and desalted using Zeba-spin desalting columns (Pierce cat #89889) equilibrated in PBS. The final concentration of the antibody solutions was determined using a Nano-drop 1000 (ThermoFisher), using IgG as sample type.

Figure 5:
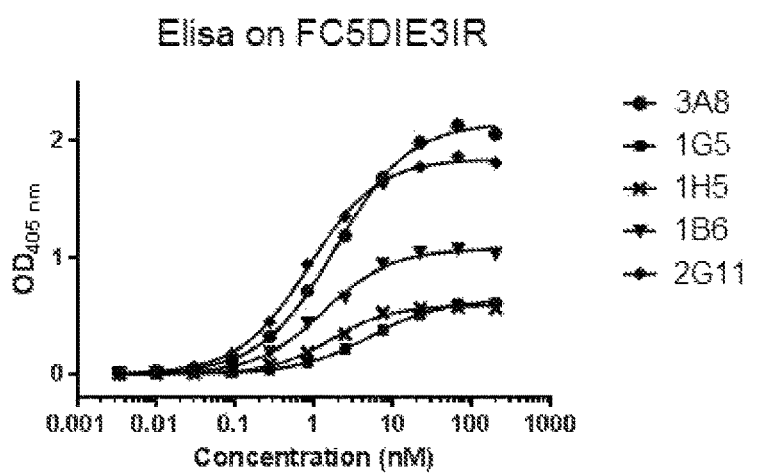
FIG. 5 provides the results of an ELISA of purified mAbs on FC5DIE3IR recombinant protein and evaluation of Bmax and apparent affinity for antibody 3A8 (•), 1G5 (■), 1H5 (✱), 1B6 (▼) and 2G11 (♦). Results are provided as the OD at 405 nm in function of the antibody concentration (provided on a logarithmic scale in nM).

Evaluation of apparent affinity in ELISA. Purified antibodies were assessed for their binding activity by ELISA in a dose-dependent binding curve. Serial 1/3 dilutions of purified mAbs starting at 120 nM were applied onto wells and ELISA was performed as described above (screening section). The data were analyzed with GraphPad Prism software using one-site specific binding-with Hill slope non-linear regression curve fit model to determine $B_{max}$ (maximum specific binding) and Kd$_{app}$ (concentration needed to achieve a half-maximum binding at equilibrium) for each mAb tested. As shown in FIG. 5, the apparent $K_D$ of the 3A8 clone (1.9 nM) is approximately 2.5 times lower than for the 1G5 clone (4.8 nM). Without wishing to be bound to theory, the difference in $B_{max}$ observed in FIG. 5 (3.2 vs 1.7) may be due to the use of polyclonal secondary antibodies that may bind more efficiently to IgG2a (3A8) vs IgG1 (1G5).

Re-cloning of hybridomas. Selected hybridomas were re-cloned by limiting dilution to ensure their monoclonality.

In vitro identification of functional monoclonal antibody (mAbs). To determine the functional effect of anti-hNa$_v$1.7 mAbs on hNa$_v$1.7 channels, Na$_v$ currents were evoked using whole-cell patch-clamp technique in hNa$_v$1.7-HEK293 cells as described in Example I. The hNa$_v$1.7-HEK293 cells were prepared from frozen vials and plated on poly-1-lysine coated 13 mm plastic coverslips. The coverslips were then mounted on a recording chamber and placed under an inverted microscope to perform the patch-clamp experiments. Recordings of Na$_v$ currents were obtained as described in Example I.

Figure 6:
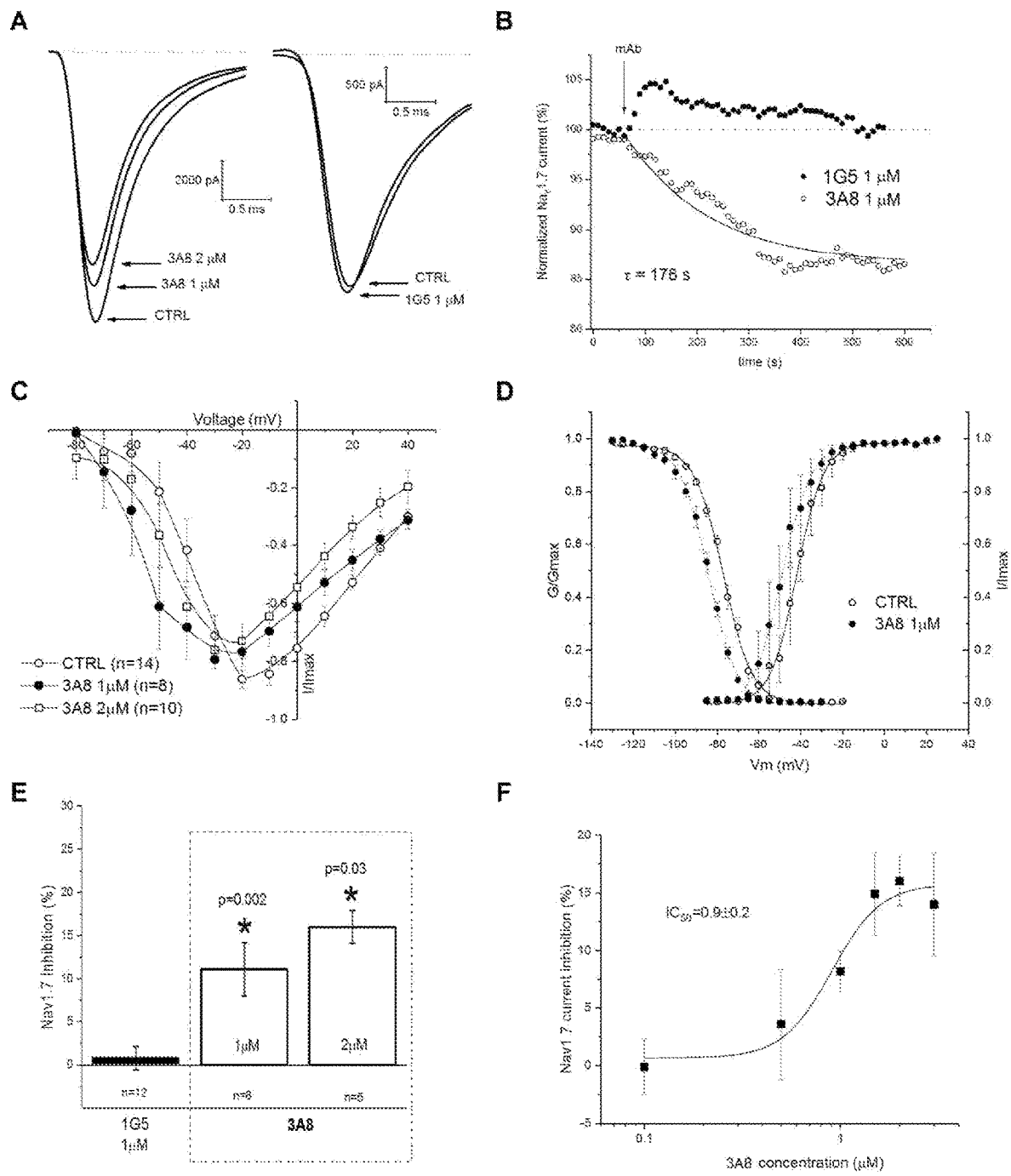
FIGS. 6A to 6F show the effect of the anti-$hNa_v1.7$ mAbs 3A8 and 1G5 on the amplitude of the $Na_v1.7$ currents recorded at resting-closed state using patch-clamp whole-cell technique in HEK293 cells overexpressing the $hNa_v1.7$ channels.

As shown in FIG. 6, the mAb 3A8 was able to reduce the amplitude of the Na$_v$ currents by 8.2%±1.7 (n=7) and 16.0%±2.1 (n=5) at the concentration of 1 µM and 2 µM, respectively, while the mAb 1G5 did not change the amplitude of the currents (0.77%±1.34, n=12 FIGS. 6A, B and E). The mAb 3A8 had an effect onset (time constants of the block of the Na$_v$1.7 currents) of 184±39 sec (n=4) when applied at the concentration 1 µM and 105±6 sec (n=2) when applied at the concentrations of 2 μM (FIG. 6B). These data suggest that 3A8 is functional in inhibiting the flux of $Na^+$ thought the $hNa_v1.7$ channels. Based upon the results presented in FIG. 6, the mAb 3A8 concentration response relationship ($IC_{50}$) and efficacy (degree of maximum inhibition) were 0.9±0.2 μM and 16.0±2.1%, respectively (FIG. 6F).

Next, it was evaluated if the anti-$hNa_v1.7$ 3 A8 mAb had an effect on the kinetics and voltage dependence properties of the $hNa_v1.7$ channels. To do this, the effect of 3A8 on the current-voltage (I-V) relationship, the voltage-dependence of activation and steady-state fast inactivation of $hNa_v1.7$ channels were examined in $hNa_v1.7$-HEK293 cells (FIGS. 6C, 6D). The mAb 3A8 shifted the voltage-dependence of activation of $Na_v1.7$ currents to more hyperpolarized membrane potentials ($V_{1/2}$ activation: Δ=–6.0±1.0 mV at 1 μM; n=7), suggesting a gating modifier activity (FIG. 6D). A minor effect was also observed on the voltage-dependence of the steady-state fast inactivation ($V_{1/2}$ inactivation: Δ=–7.1±1.7 mV at 1 μM; n=4). However, these shifts towards hyperpolarizing voltages of activation and steady-state inactivation curves may not be entirely due to mAb 3A8. In fact, it has been reported that changes in activation and inactivation of $Na_v$ channels may be caused by perturbations of the membrane-cytoskeleton interaction due to the application of the antibody. In addition, negative-shifts of the same order were observed also in control experiment in which an equivalent volume of extracellular solution containing no antibody was added instead of the antibody solution.

To further investigate the effects of 3A8 on $hNa_v1.7$ kinetics of activation and fast inactivation, the time-to-peak and the time constants of fast inactivation of $hNa_v1.7$ channels were calculated. The mAb 3A8 (1 μM) did not significantly change the times-to-peak measured at –20 mV (control, 0.91±0.06 ms; 3A8, 0.88±0.07 ms; n=7; p>0.10, paired t-Test). It also did not change the inactivation time constants at –20 mV (control 0.80±0.12 ms; 3A8 0.72±0.08 ms; p>0.10, paired t-Test).

Figure 7:
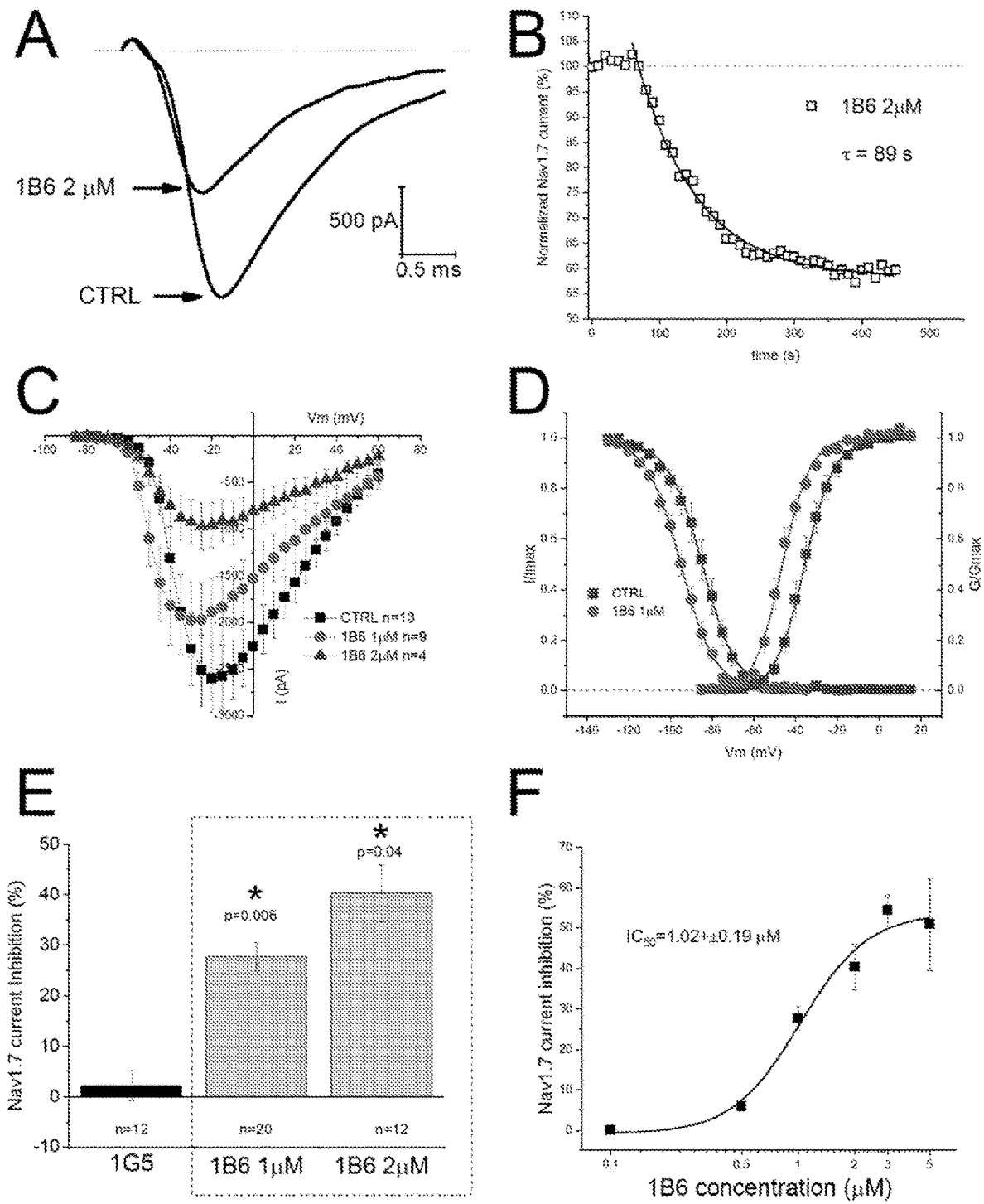
FIGS. 7A to 7F show the effect of the anti-hNa$_v$1.7 mAb 1B6 on the amplitude of the Na$_v$1.7 currents recorded at resting-closed state using patch-clamp whole-cell technique in HEK293 cells overexpressing the hNa$_v$1.7 channels.

As shown in FIG. 7, the mAb 1B6 was able to reduce the amplitude of the $Na_v$ currents by 27.7%±2.9 (n=20) and 40.3%±5.7 (n=12) at the concentration of 1 μM and 2 μM, respectively (FIGS. 7A, 7C and 7E; Table 2). The mAb 1B6 had an effect onset (time constants of the block of the $Na_v1.7$ currents) of 416±126 sec (n=5) when applied at the concentration 1 μM and 84±6 sec (n=4) when applied at the concentrations of 2 μM (FIG. 7B). 1B6 concentration response relationship ($IC_{50}$) and efficacy (degree of maximum inhibition) was 1.02±0.19 μM and 54.3%±3.7, respectively (FIG. 7F; Table 2).

Figure 8:
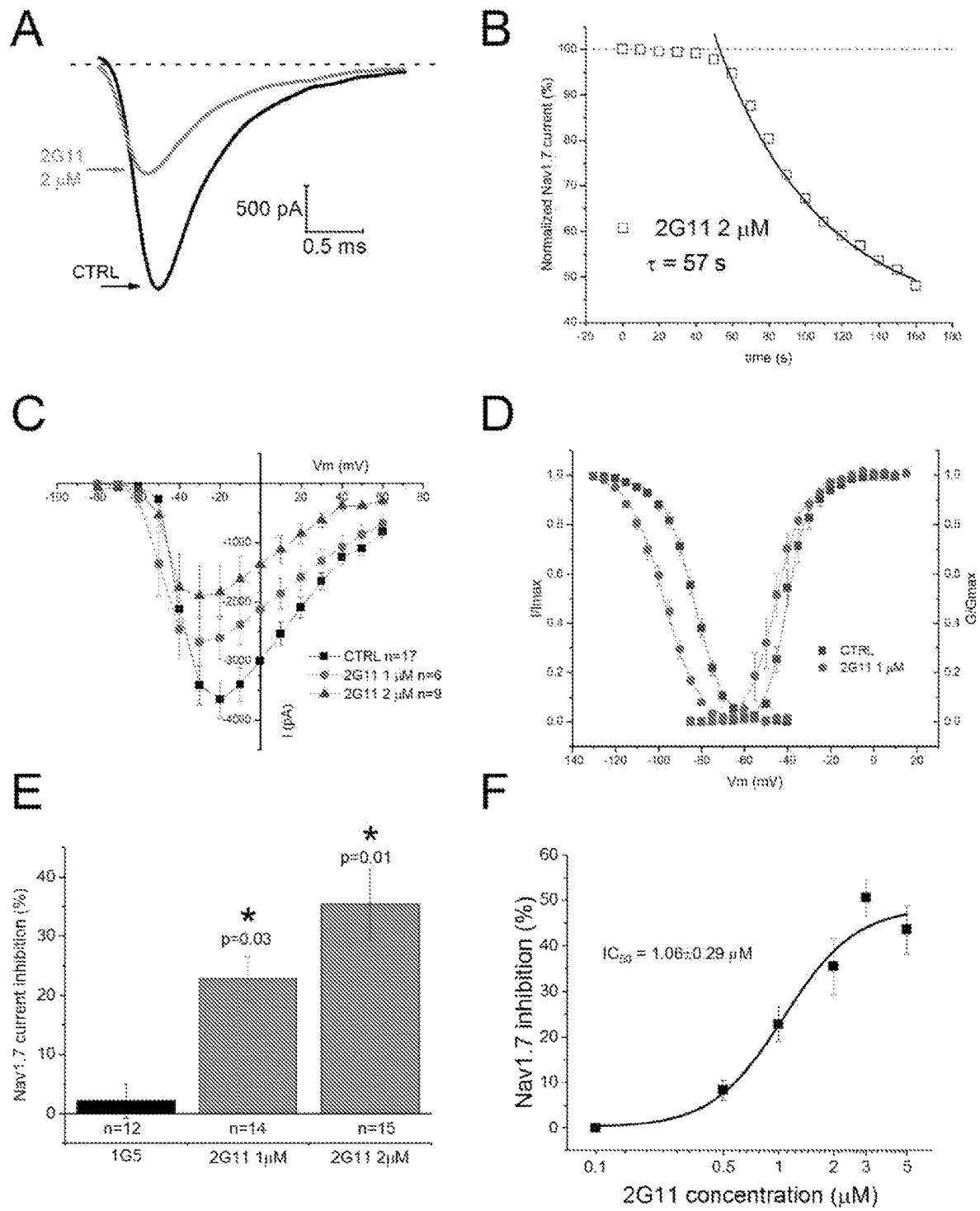
FIGS. 8A to 8F show the effect of the anti-hNa$_v$1.7 mAb 2G11 on the amplitude of the Na$_v$1.7 currents recorded at resting-closed state using patch-clamp whole-cell technique in HEK293 cells overexpressing the hNa$_v$1.7 channels.

As shown in FIG. 8, the mAb 2G11 was able to reduce the amplitude of the $Na_v$ currents by 22.8%±3.7 (n=14) and 35.4%±6.1 (n=15) at the concentration of 1 μM and 2 μM, respectively (FIGS. 8A, 8C and 8E; Table 2). The mAb 2G11 had an effect onset (time constants of the block of the $Na_v1.7$ currents) of 68.8±0.8 sec (n=2) when applied at the concentration 1 μM and 39±9 sec (n=3) when applied at the concentrations of 2 μM (FIG. 8B). 2G11 concentration response relationship ($IC_{50}$) and efficacy (degree of maximum inhibition) was 1.06±0.29 μM and 50.5%±0.03, respectively (FIG. 8F; Table 2).

Figure 9:
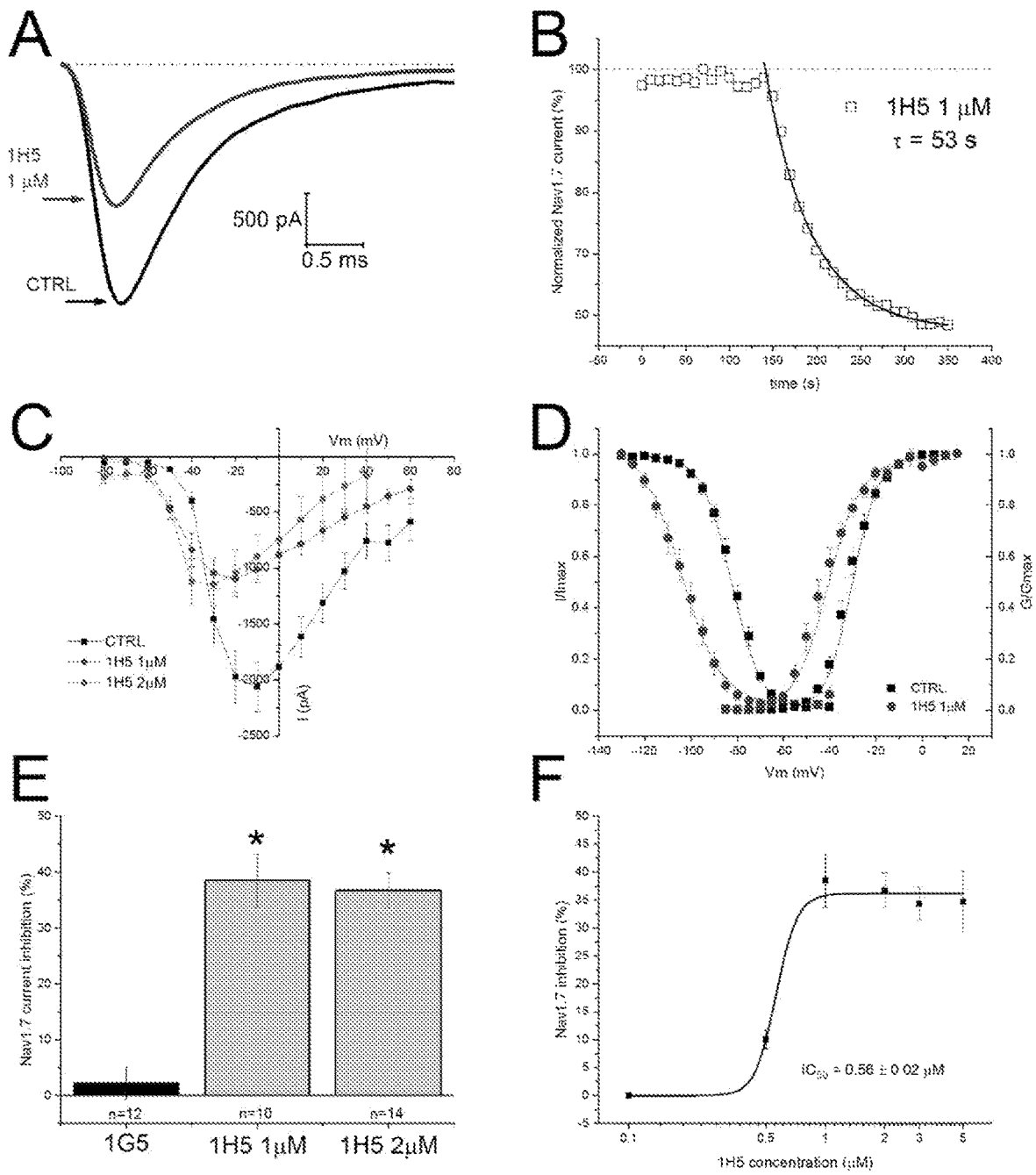
FIGS. 9A to 9F show the effect of the anti-hNa$_v$1.7 mAb 1H5 on the amplitude of the Na$_v$1.7 currents recorded at resting-closed state using patch-clamp whole-cell technique in HEK293 cells overexpressing the hNa$_v$1.7 channels.

As shown in FIG. 9, the mAb 1H5 was able to reduce the amplitude of the $Na_v$ currents by 38.4%±4.8 (n=10) and 36.7%±3.2 (n=14) at the concentration of 1 μM and 2 μM, respectively (FIGS. 9A, 9C and 9E; Table 2). The mAb 1H5 had an effect onset (time constants of the block of the $Na_v1.7$ currents) of 78±15 sec (n=4) when applied at the concentration 1 μM and 149±46 sec (n=4) when applied at the concentrations of 2 μM (FIG. 9B). 1H5 concentration response relationship ($IC_{50}$) and efficacy (degree of maximum inhibition) was 0.56±0.02 μM and 38.4%±4.4, respectively (FIG. 9F; Table 2).

These data suggest that also and 1B6, 2G11 and 1H5 are functional in inhibiting the flux of $Na^+$ thought the $hNa_v1.7$ channels. Values for the effect of anti-$hNa_v1.7$ 1B6 (FIG. 7D) 2G11 (FIG. 8D), 1H5 (FIG. 9D) on the kinetics and voltage dependence properties of the $hNa_v1.7$ channels were calculated in the same way as for 3A8 (see above) and are listed in Table 2.

Overall, these data suggest that the main functional effect of 3A8, 1B6, 2G11 and 1H5 on $Na_v1.7$ is on the $Na^+$ permeation pathway, which reduces the amplitude of the current through the channel. Table 2 below summarizes the characteristics of the monoclonal antibodies obtained.

TABLE 2

Values for the effect of anti-$hNa_v1.7$ 3A8, 1G5, 1H5, 2G11, 1B6 on the kinetics and voltage dependence properties of the $hNa_v1.7$ channels in the resting/closed state

| mAbs on $Na_v1.7$ channels in resting/closed state | 3A8 | 1G5 (negative control) | 1H5 | 2G11 | 1B6 |
|---|---|---|---|---|---|
| Concentration response relationship ($IC_{50}$) μM | 0.85 ± 0.09 | N/A | 0.56 ± 0.02 | 1.06 ± 0.29 | 1.06 ± 0.29 |
| Efficacy (degree of maximum inhibition) % | 16.0 ± 2.1 | N/A | 38.4 ± 4.4 | 50.5 ± 4.03 | 54.3 ± 3.7 |
| Reduction currents (%) | 0.5 μM, 3.6 ± 4.8 (n = 4) 1 μM, 8.2 ± 1.7 (n = 7) 1.5 μM, 15.6 ± 2.1 (n = 5) 2 μM, 16.0 ± 2.1 (n = 5) 3 μM, 15.4 ± 3.8 (n = 11) | 1 μM, 0.77 ± 1.34 (n = 12) | 0.5 μM, 10 ± 1.7 (n = 3) 1 μM, 38.4 ± 4.8 (n = 10) 2 μM, 36.7 ± 3.2 (n = 14) 3 μM, 34.3 ± 2.9 (n = 5) 5 μM, 34.8 ± 5.4 (n = 8) | 0.5 μM, 8.3 ± 2.2 (n = 4) 1 μM, 22.8 ± 3.7 (n = 14) 2 μM, 35.4 ± 6.1 (n = 15) 3 μM, 50.5 ± 4.0 (n = 10) 5 μM, 43.4 ± 5.4 (n = 7) | 0.5 μM, 5.9 ± 1.1 (n = 6) 1 μM, 27.7 ± 2.9 (n = 20) 2 μM, 40.3 ± 5.7 (n = 12) 3 μM, 54.3 ± 3.7 (n = 8) 5 μM, 50.9 ± 11.5 (n = 4) |
| Time constant of the block of the $hNa_v1.7$ currents (1 μM) | 184 ± 39 sec (n = 4) | N/A | 78 ± 15 sec (n = 4) | 68.8 ± 0.8 sec (n = 2) | 416 ± 126 sec (n = 5) |
| Time constant of the block of the $hNa_v1.7$ currents (2 μM) | 105 ± 6 sec (n = 2) | N/A | 149 ± 46 sec (n = 4) | 39 ± 9 sec (n = 3) | 84 ± 6 sec (n = 4) |
| Voltage-dependence of activation | Δ = –6.0 ± 1.0 | N/A | Δ = –9.7 ± 1.3 | Δ = –4.7 ± 1.5 | Δ = –11.6 ± 2.6 |

TABLE 2-continued

Values for the effect of anti-hNa$_v$1.7 3A8, 1G5, 1H5, 2G11, 1B6 on the kinetics and voltage dependence properties of the hNa$_v$1.7 channels in the resting/closed state

| mAbs on Na$_v$1.7 channels in resting/closed state | 3A8 | 1G5 (negative control) | 1H5 | 2G11 | 1B6 |
|---|---|---|---|---|---|
| (shift V$_{1/2}$ activation at 1 µM) | mV (n = 7) | | mV (n = 7) | mV (n = 8) | mV (n = 10) |
| Voltage-dependence of the steady-state fast inactivation (shift V$_{1/2}$ inactivation at 1 µM) | Δ = −7.1 ± 1.7 mV (n = 4) | N/A | Δ = −18.4 ± 3.4 mV (n = 6) | Δ = −13.9 ± 2.4 mV (n = 7) | Δ = −12.7 ± 2.3 mV (n = 8) |
| Time-to-peak (−20 mV) p = paired t-Test | Control, 0.91 ± 0.06 ms 3A8, 0.88 ± 0.07 ms (n = 7) p > 0.10 | N/A | Control, 0.97 ± 0.09 ms 1H5, 0.81 ± 0.10 ms (n = 6) p < 0.05 | Control, 0.91 ± 0.07 ms 2G11, 0.87 ± 0.04 ms (n = 6) p > 0.10 | Control, 0.98 ± 0.06 ms 1B6, 0.88 ± 0.04 ms (n = 9) p < 0.05 |
| Fast inactivation (time constant −20 mV) p = paired t-Test | Control, 0.80 ± 0.12 ms 3A8, 0.72 ± 0.08 ms (n = 7) p > 0.10 | N/A | Control, 1.03 ± 0.08 ms 1H5, 0.89 ± 0.07 ms (n = 6) p > 0.10 | Control, 0.75 ± 0.05 ms 2G11, 0.81 ± 0.10 ms (n = 6) p > 0.10 | Control, 1.06 ± 0.07 ms 1B6, 1.10 ± 0.14 ms (n = 9) p > 0.10 |

Figure 10:
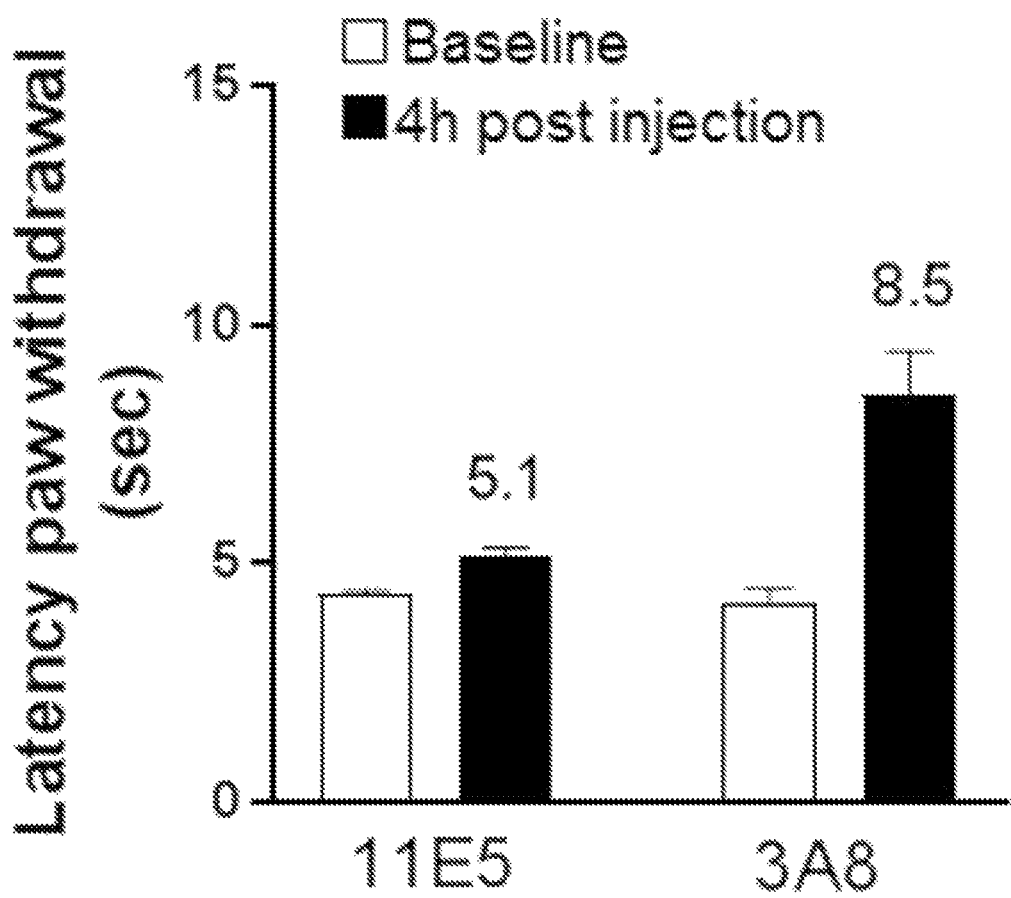
FIG. 10 shows the ability of mAbs 3A8 and 11E5 to mediate reversal of hyperalgesia in a chronic pain model. Results are shown as the latency in paw withdrawal (in secs, mean±SEM of 4-6 animals per group) in function of antibody tested and time (white bars: baseline; black bars: 4 hours after injection).

In vivo Validation of the mAb 3A8: Rat Hargreaves Model of Hyperalgesia. To evaluate if the functional in vitro effect of anti hNa$_v$1.7 mAbs translated in a functional in vivo effect against pain, the mAbs were tested in rats using a Hargreaves model of hyperalgesia. The anti-hNa$_v$1.7 mAb 3A8 was tested along with a negative control anti-GFP mAb 11E5. As previously demonstrated, CFA induced hyperalgesia to a thermal stimulus 48 h post injection. Baseline latency paw withdrawal was reduced to 4.33±0.22 sec (n=12) in ipsilateral paw versus 19.89±0.06 sec (n=12) of contralateral paw (see FIG. 10). The mAb effect on the latency paw withdrawal was measured 4 hours after administration. Intraplantar injection of 3A8 (8.50±0.94 sec, n=3) but not 11E5 (5.13±0.19 sec, n=3) significantly increased latency paw withdrawal (p<0.05 vs baseline; FIG. 10). Taken together, these results suggest that targeting Na$_v$1.7 successfully promoted the reversal of hyperalgesia in a chronic pain model.

Figure 11:
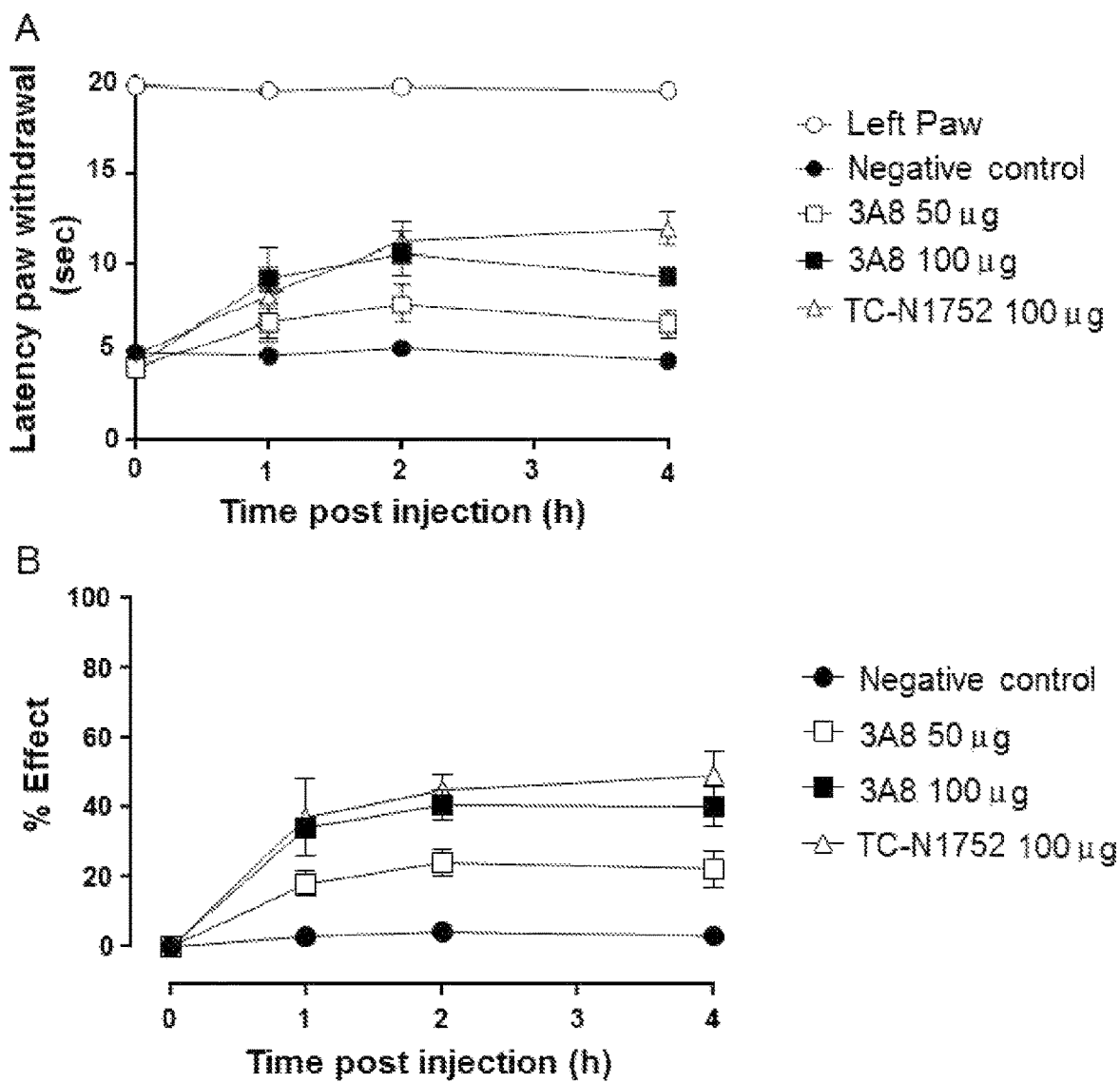
FIGS. 11A and 11B provide a time-course effect of mAb 3A8 and small molecule TC-N1752 on CFA-induced thermal hyperalgesia in rats. TC-N1752 is a selective blocker of human Na$_v$1.7 channels (IC$_{50}$ values are 0.17, 0.3, 0.4 and 1.1 μM at hNa$_v$1.7, hNa$_v$1.3, hNa$_v$1.4 and hNa$_v$1.5 respectively).

To further evaluate the effect of 3A8, a CFA-induced thermal hyperalgesia in rats was used to compared the mAb with the selective blocker for hNa$_v$1.7 channels TC-N1752 (Tocris, Bristol, United Kingdom). FIG. 11 shows the time-course effect and dose-response effects of anti-hNa$_v$1.7 mAb 3A8 at 50 µg and 100 µg, and TC-N1752 (100 µg) injected by intraplantar route. The anti-hNa$_v$1.7 mAb 3A8 was able to increase the latency paw withdrawal time when injected at 50 µg (6.08±0.70 sec, 7.38±0.67 sec, 6.79±0.50 sec at 1, 2 and 4 h respectively; n=3) and at 100 µg (9.56±0.70 sec, 10.58±0.90 sec, 10.28±1.20 sec at 1, 2 and 4 hours respectively; n=4). In addition, 3A8 at 100 µg had an effect similar to that of TC-N1752 (100 µg; 8.15±1.6 sec, 11.17±1.19 sec, 11.90±0.99 sec at 1, 2 and 4 hours respectively; n=3). The effect of 3A8 (50 and 100 µg), 11E5 (negative control) and TC-N1752 (100 µg) were also expressed as percentage of the effect on left paw withdrawal (% Effect, FIG. 11B). Table 3 below summarizes the values of % Effect for 11E5, 3A8 and TC-N1752. From these values the % MPE is extrapolated. Overall these data suggest that anti-hNa$_v$1.7 mAb 3A8 functionally mediated reversal of hyperalgesia in a chronic pain model.

TABLE 3

Values of the effect of 11E5, 3A8 and TC-N1752 expressed as percentage of the effect on left paw withdrawal.
Percentage of effect after injection

| Samples | Time (h) | Average (%) | SEM | n |
|---|---|---|---|---|
| 11E5 | 0 | 0 | 0 | 2 |
| 11E5 | 1 | 2.78 | 1.23 | 2 |
| 11E5 | 2 | 4.12 | 1.70 | 2 |
| 11E5 | 4 | 3.04 | 0.05 | 2 |
| 3A8 50 µg | 0 | 0 | 0 | 5 |
| 3A8 50 µg | 1 | 18.00 | 3.52 | 5 |
| 3A8 50 µg | 2 | 24.09 | 3.69 | 5 |
| 3A8 50 µg | 4 | 22.40 | 5.22 | 5 |
| 3A8 100 µg | 0 | 0 | 0 | 5 |
| 3A8 100 µg | 1 | 33.96 | 2.56 | 5 |
| 3A8 100 µg | 2 | 40.55 | 4.20 | 5 |
| 3A8 100 µg | 4 | 40.18 | 5.91 | 5 |
| TC-N1752 | 0 | 0 | 0 | 6 |
| TC-N1752 | 1 | 37.01 | 11.09 | 6 |
| TC-N1752 | 2 | 44.77 | 4.85 | 6 |
| TC-N1752 | 4 | 49.05 | 7.04 | 6 |

Figure 12:
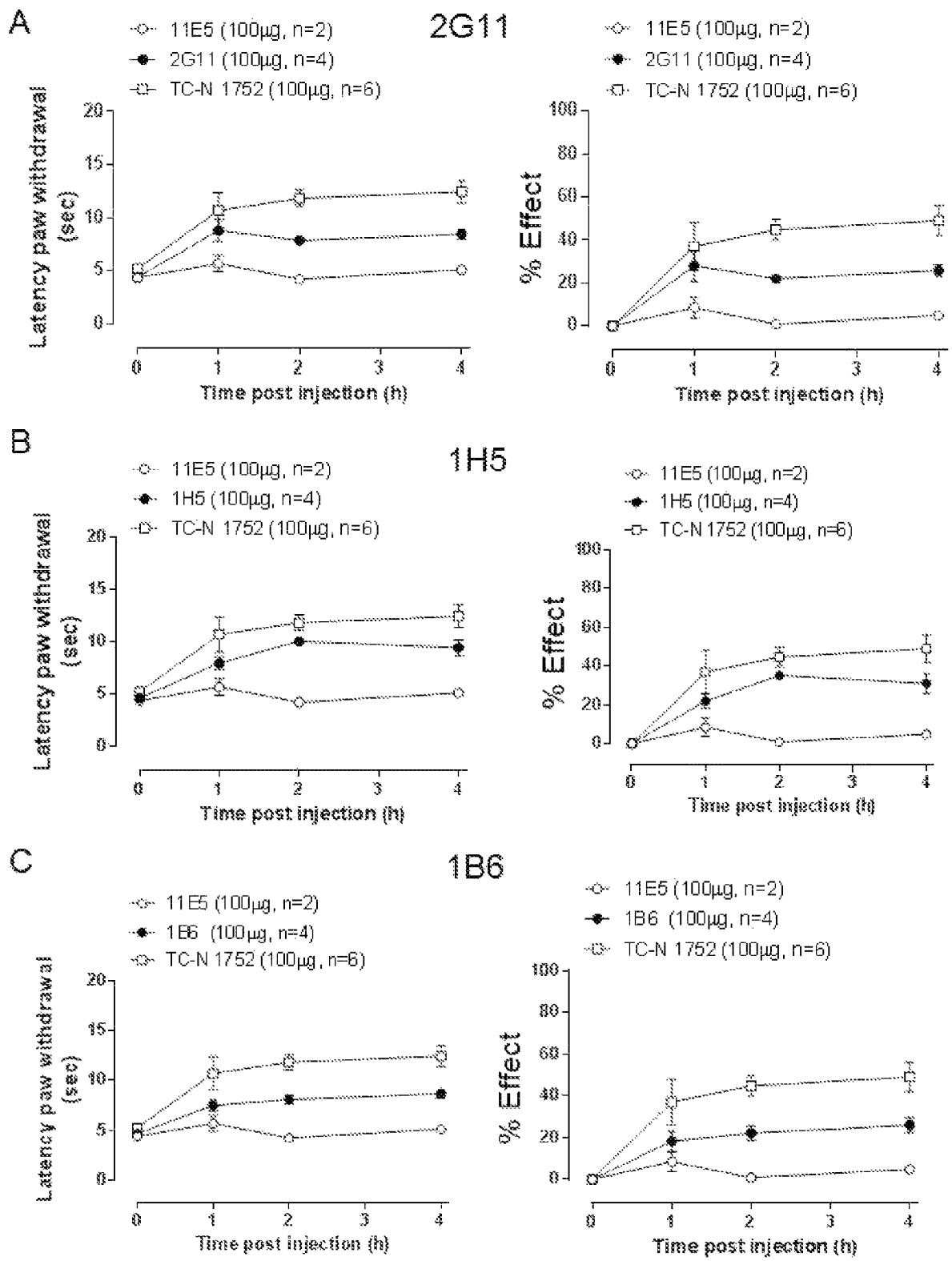
FIGS. 12A to 12C provide the time-course of the effect of various antibodies CFA-induced thermal hyperalgesia in rats. The data are plotted with those obtained with TC-N1752 (positive control) and 11E5 (negative control). On the panels on the left, results are shown as the latency in paw withdrawal (in secs, mean±SEM of 4-6 animals per group) as a function of therapeutic tested and time (in hours). On the panels on the right, results are expressed as percentage effect on left paw withdrawal (% Effect). Results are shown as mean±SEM of 4-6 animals per group. The maximum percentages of the effects (% Effect) were 27.98±7.17 for 2G11 (n=4, after 1 hour from injection), 35.23±0.88 for 1H5 (n=4, after 2 hours from injection) and 25.96±3.69 for 1B6 (n=4, after 4 hours of injection).

To further evaluate the effect of the anti-hNa$_v$1.7 mAbs 2G11, 1H5 and 1B6, and the selective blocker for hNa$_v$1.7 channels TC-N1752 (Tocris, Bristol, United Kingdom) a CFA-induced thermal hyperalgesia in rats was used. FIG. 12 shows the time-course effect and dose-response effects of anti-hNa$_v$1.7 mAbs 2G11, 1H5, 1B6 at 100 µg, and TC-N1752 (100 µg) injected by intraplantar route. Intraplantar injection of 2G11, 1H5 or 1B6 (8.45±0.44 sec, n=4; 9.43±0.72 sec, n=4; 8.66±0.45 sec, n=4) but not 11E5 (5.12±0.19 sec, n=2) significantly increased latency paw withdrawal (p<0.05 vs baseline). Taken together, these results suggest that targeting Na$_v$1.7 successfully promoted the reversal of hyperalgesia in a chronic pain model.

To further evaluate the effect of 2G11, 1B6 and 1H5, they were tested on CFA-induced thermal hyperalgesia in rats and compared it with the selective blocker for hNa$_v$1.7 channels TC-N1752 (Tocris, Bristol, United Kingdom). FIG. 12 right shows the time-course effect of anti-hNa$_v$1.7 2 G11, 1H5 and 1B6 and TC-N1752 at 100 µg injected by intraplantar route. 2G11, 1H5 and 1B6 were able to increase the latency paw withdrawal time when injected at 100 µg (2G11: 8.80±1.02 sec, n=4; 7.86±0.33 sec, n=4; 8.45±0.44 sec at 1, 2 and 4 hours respectively; n=4; 1H5: 7.97±0.61 sec, n=4; 10.03±0.11 sec, n=4; 9.43±0.72 sec at 1, 2 and 4 hours respectively; n=4; 1B6: 7.79±0.56 sec, n=4; 8.08±0.46 sec, n=4; 8.66±0.45 sec at 1, 2 and 4 hours respectively; n=4;) similar to that of TC-N1752 (8.15±1.6 sec, 11.17±1.19 sec, 11.90±0.99 sec at 1, 2 and 4 hours respectively; n=3). Overall these data suggest that each of 2G11, 1H5 and 1B6 functionally mediated reversal of hyperalgesia in a chronic pain model.

The effect of 2G11, 1H5 and 1B6 were also expressed as percentage of the effect on left paw withdrawal (% Effect). Table 4 below summarizes the values of % Effect for 1H5, 2G11 and 1B6. From these values the % MPE was extrapolated (2G11, 27.98±7.17 (n=4) after 1 hour from injection; 1H5, 35.23±0.88 (n=4) after 2 hours from injection; 1B6, 25.96±3.69 (n=4) after 4 hours of injection).

TABLE 4

Values of the effect of 1H5, 2G11 and 1B6 expressed as
percentage of the effect on left paw withdrawal.
Percentage of effect after injection

|     | 1H5             | 2G11            | 1B6             |
| --- | --------------- | --------------- | --------------- |
| 0   | 0               | 0               | 0               |
| 1 h | 21.85% ± 3.71   | 27.98% ± 7.17   | 18.28% ± 4.85   |
| 2 h | 35.23% ± 0.88   | 22.02% ± 2.08   | 22.20% ± 3.40   |
| 4 h | 31.20% ± 5.18   | 25.80% ± 2.82   | 25.96% ± 3.69   |

Figure 13A:
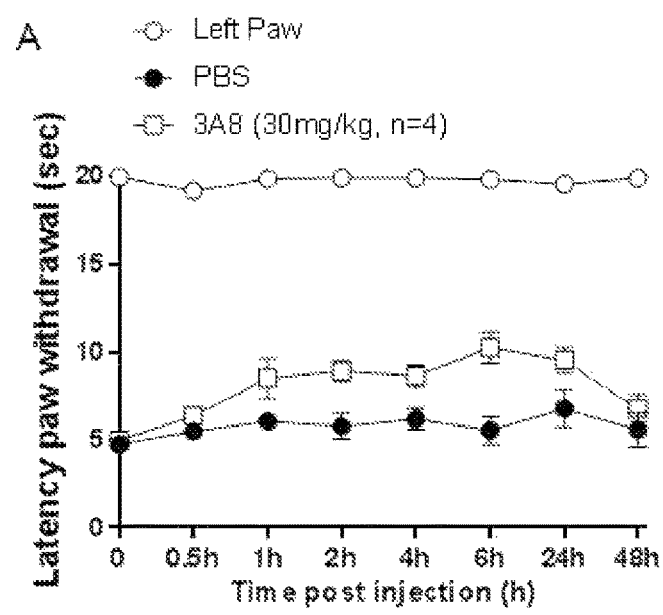
FIGS. 13A and 13B provide the in vivo effects of mAb 3A8 at a 30 mg/kg dose.
Figure 13B:
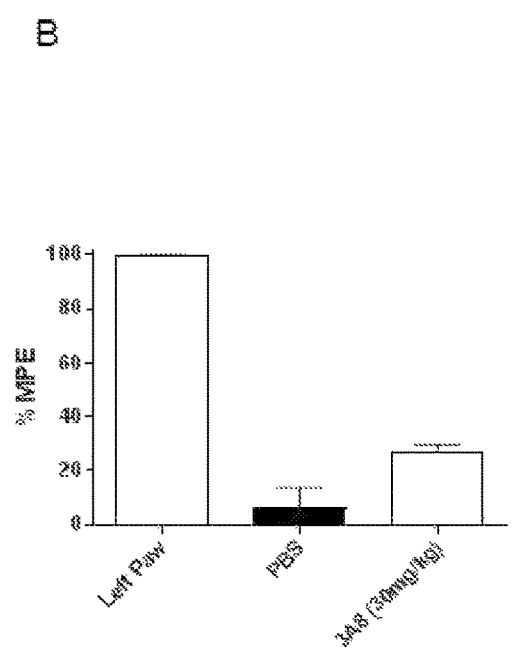

It was next evaluated the effects of 3A8 injected by intravenous route. FIG. 13A shows that 3A8 at a dose of 30 mg/kg through the tail vein was able to reverse CFA-induced hyperalgesia. Effects are observed one hour post injection and lasts for up to 24 h. FIG. 13B shows the response at 4 h expressed as percentage of the maximum possible effect (PBS, 5.50±3.4, n=3 and 3A8, 26.60±3.26, n=4).

Figure 14:
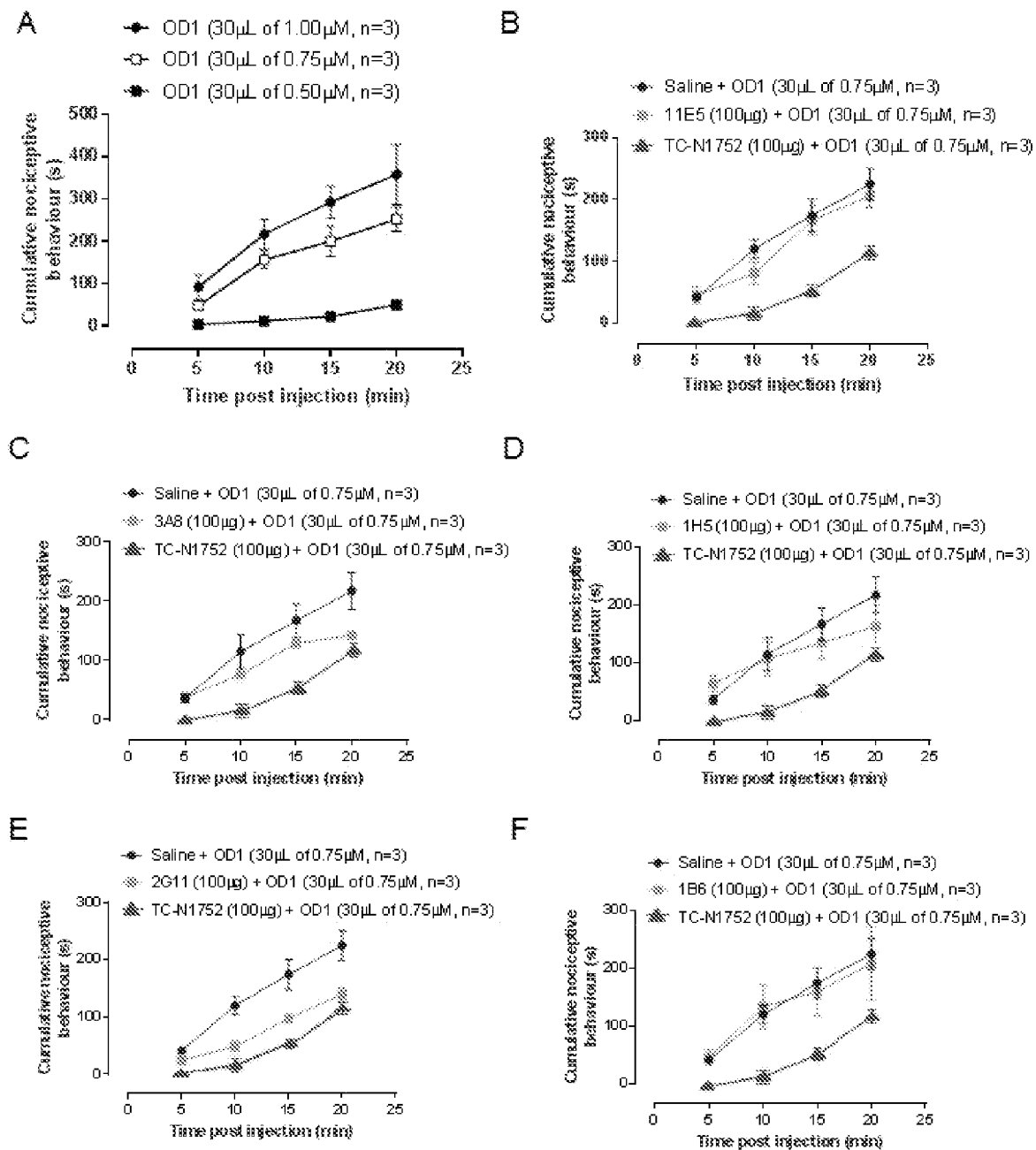
FIGS. 14A to 14F show the effects of anti-hNa$_v$1.7 mAbs in a mouse model of Na$_v$1.7-mediated pain based on subcutaneous injection of OD1. Selective Na$_v$1.7 channel inhibitor TC-N1752 (100 µg) was used as positive control. Anti-hNa$_v$1.7 mAbs and TC-N1752 were injected 60 minutes prior to OD1 injection. Results are shown as mean±SEM of 3 animals per group.

To further evaluate the functionality of the anti-Na$_v$1.7 mAbs and target engagement, they were tested on a Na$_v$1.7 pain model: OD1 pain model. The intraplantar administration of OD1 in mice induces spontaneous pain behaviors as evidenced by licking, flinching, lifting and shaking of the injected hind paw. These behaviors are dose dependent (FIG. 14A) and develop rapidly, occurring soon after injection, and persists for up to 40 min after injection. One major advantage of the intraplantar route of administration is that it delivers the peptide directly to the terminals of peripheral sensory neurons in the skin, allowing simple quantification of unilateral pain behaviors while avoiding systemic adverse effects. Different concentrations of OD1 were tested (FIG. 14A). The injection of 30 µl of OD1 at the concentration of 0.75 µM evoked a response of 200 sec after 15 minutes from the injection (FIG. 14A), similar to what reported in literature (Deuis et al., 2016). Thus this concentration was selected to test our to test the antibodies. The effect of 100 µg of mAb injection was tested and compared it with the injection of saline (saline plus OD1). The pain behavior was considered at 100%, 20 min after the injection. Twenty min after the injection, 100 µg of 3A8 (FIG. 14C), 1H5 (FIG. 14D), 2G11 (FIG. 14E) caused a significant reduction of the time spent in pain behaviors (3A8; 73.76%±5.38; 1H5, 73.84%±16.78; 2G11 63.47±4.78) whereas 1B6 (FIG. 14F; 94.13%±28.63) was not different from the negative control 11E5 (FIG. 14B; 93.40%±8.67). TC-N5172 was 51.62%±4.85.

Figure 15B:
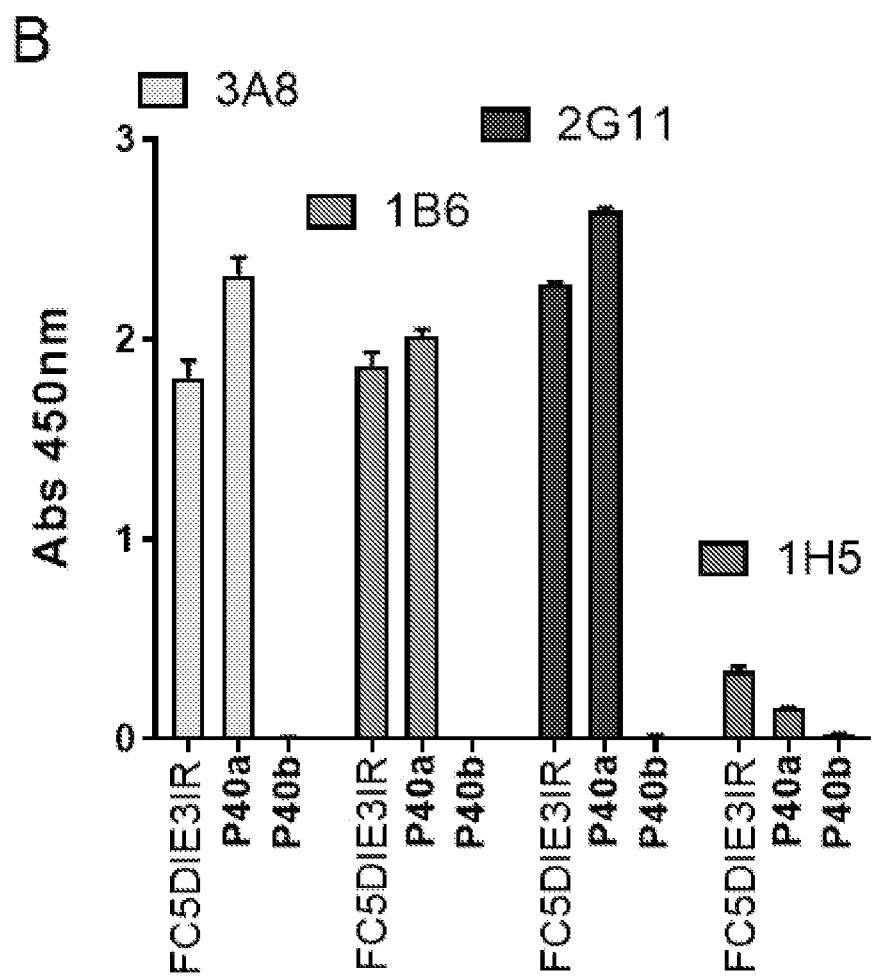
Figure 15C:
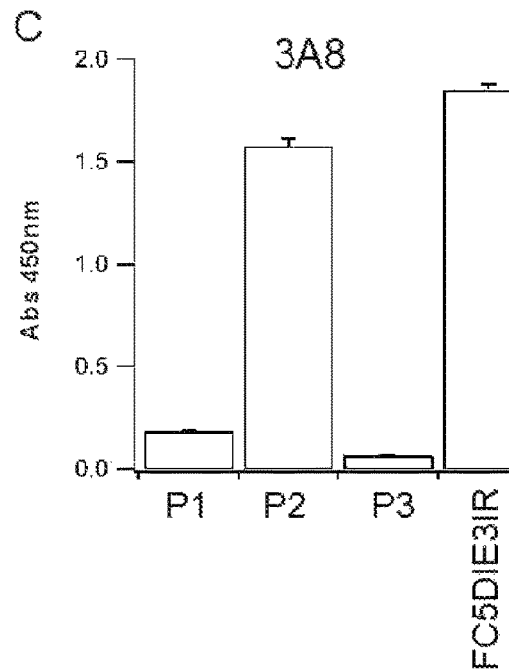
Figure 15D:
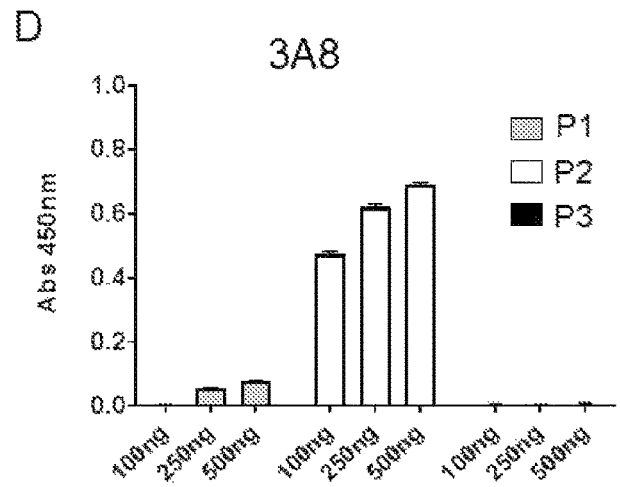
Figure 15E:
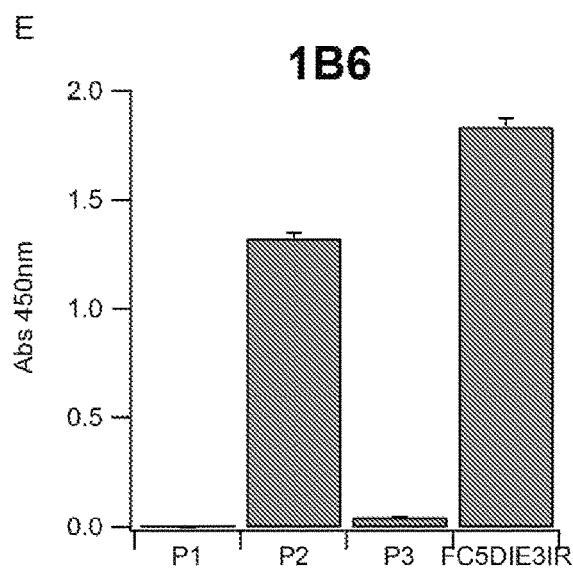
Figure 15F:
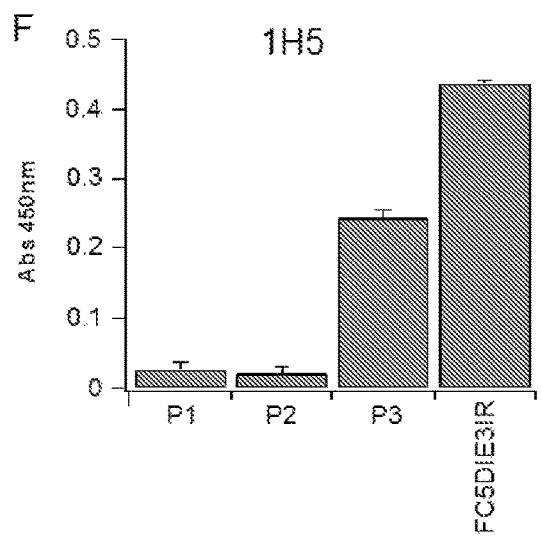
Figure 15G:
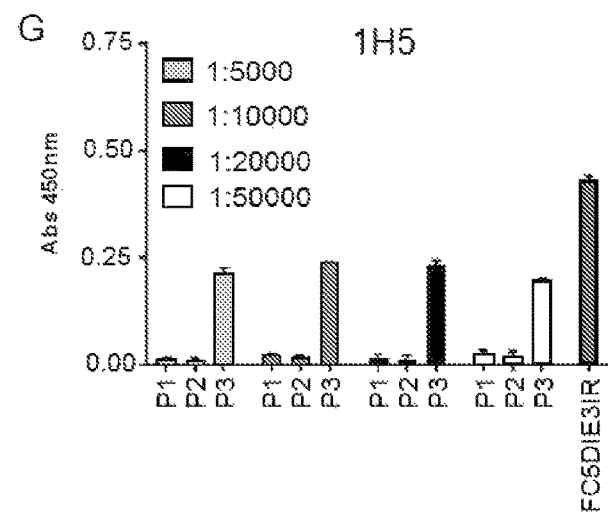
Figure 15H:
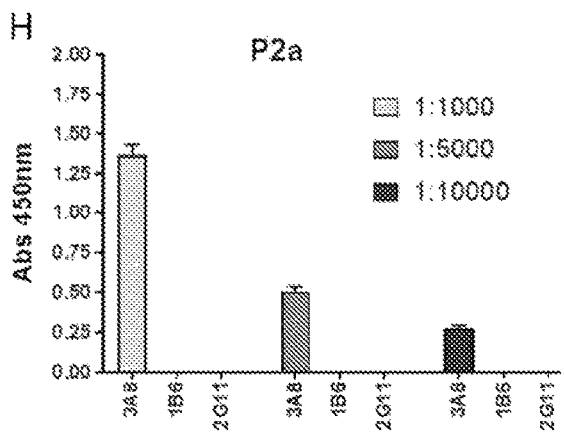
Figure 15I:
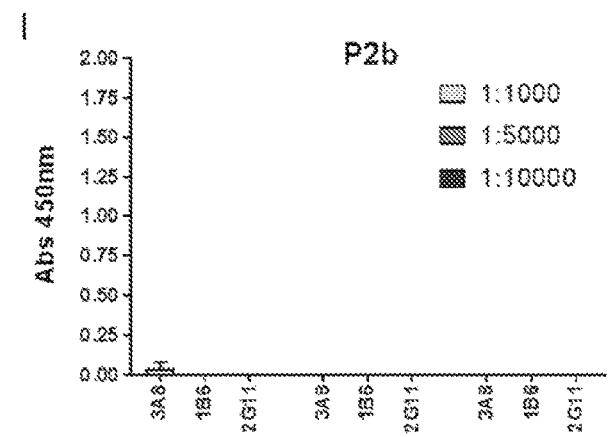

Identification of the hNa$_v$1.7 epitope for mAb 3A8, 186 and 1H5. To identify the epitope for mAb 3A8 on DIE3IR, seven overlapping antigen-peptides were generated (FIG. 15A) and an ELISA was performed to determine the binding between these peptides and the various mAb (FIGS. 15C to 15I). The maximum binding for 3A8 was observed with pep #40a (FIG. 15B), pep #2 (FIGS. 15C and 15D) and pep #2a (FIG. 15H). Similarly, the maximum binding for 1B6 was observed with pep #40a (FIG. 15B), pep #2 (FIG. 15E), but 1B6 showed no binding with pep #2a (FIG. 15F) and pep #2b (FIG. 15I). The mAb 2G11 showed binding for only the pep #40a (FIG. 15B), The mAb 1H5 showed low binding with pep #40a (FIG. 15B) and pep #3 (FIGS. 15F and 15G). FIG. 15J show a summary of the region of binding between mAbs and peptides. This clearly indicates that 3A8 and 1B6 binding motif resides in pep #2a and pep #2, respectively. The maximum binding for 1H5 was observed with Pep #3, while Pep #1 and Pep #2 showed low binding, clearly indicating that 1H5 binding motif resides in Pep #3.

Differential HDX-MS was performed to obtain a snapshot of the changes in conformational stability imparted by binding events and as a result to map antibody based-interactions (Shaolong et al., 2018). Differential HDX-MS was performed by comparing the extent of deuteration between bound and unbound forms of FC5DIE3IR. Overall, deuteration was measured for 38 peptides covering 74% of the sequence of the entire FC5-DIE3IR, including 94% coverage of the grafted DIE3IR domain (FIG. 16). Full HDX-MS kinetics plots can be found in FIG. 17. As expected, no effect on conformational stability was observed for the negative binding control, 1G5. No significant changes in deuteration were observed outside of the DIE3IR domain for any of the mAbs, demonstrating that the mAbs are only binding the grafted DIE3IR domain. Stabilization across residues Asn121-Tyr134 (NTLESEED; SEQ ID NO: 108) was observed in response to 3A8 and 2G11 binding (FIGS. 17A and 17B). Stabilization in response to 1B6 binding was located to residues Phe129-Tyr134 (FRKYFY; SEQ ID NO: 107; FIG. 17A). In each of these cases, stabilization is centered on the DIE3IR α-helix spanning residues Ser125-Lys131, providing additional evidence that the epitopes are at least partially conformational in nature. Unlike 2G11 and 1B6, the deuteration of 3A8 did not converge with that of the unbound control, particularly in residues Phe129-Tyr134. This may be a result of 3A8 inducing a stronger stabilization at the aforementioned helix, however the functional impact of this observation is unclear. Finally, no stabilization was observed in the presence of 1H5; this is likely a result of its challenging binding kinetics (Table 5).

In vivo validation of the 3A8 epitope. To verify if in the sequence of the peptide antigen fragment Pep #2 (P2) resides the binding motif of 3A8, the effect of P2 and Pep #3 (P3) on 3A8-mediated reversal of hyperalgesia was tested. P2 (375 µg) or P3 (375 µg) were co-injected with 3A8 (75 µg) by intraplantar route in rats Hargreaves model and their effect compared to the reversal of hyperalgesia caused by 3A8 (75 µg) and 11E5 (negative control, 50 µg) (FIG. 18A). When co-injected with 3A8, P2 was able to reduce (6.76±0.32 sec, n=5) the latency paw withdrawal time observed with 3A8 alone (10.59±0.87 sec, n=3), while P3 did not had any effect on 3A8 ability to reduce the latency paw withdrawal time (10.17±0.65 sec; n=4; FIG. 18B). The 3A8-induced reversal of hyperalgesia (35.35%±4.44; n=3) was significantly reduced by P2 (13.49%±2.62; n=5), while was not affected by P3 (34.63%±4.71, n=5; FIG. 18B). These data strongly support 3A8 binding motif residing in the P2 sequence.

Surface Plasmon Resonance (SPR) for monoclonal antibodies. To determine the binding affinity of 3A8, 2G11, 1B6 and 1H5 for the recombinant protein FC5DIE3IR, Surface Plasmon Resonance (SPR) analyses were performed as described in Example I. Pure monomeric fractions of target protein FC5DIE3IR and control V$_H$H FC5 were obtained using Size Exclusion Chromatography purification (SEC). To examine the binding of 3A8, 2G11, 1B6 and 1H5 to the recombinant protein FC5DIE3IR, two SPR assay orientations were used:

Fc-captured mAb 3A8, 2G11, 1B6 and 1H5, and flow of FC5DIE3IR and FC5 control, and Immobilized FC5DIE3IR and FC5 control, and flow mAb 3A8, 2G11, 1B6 and 1H5

Figure 20:
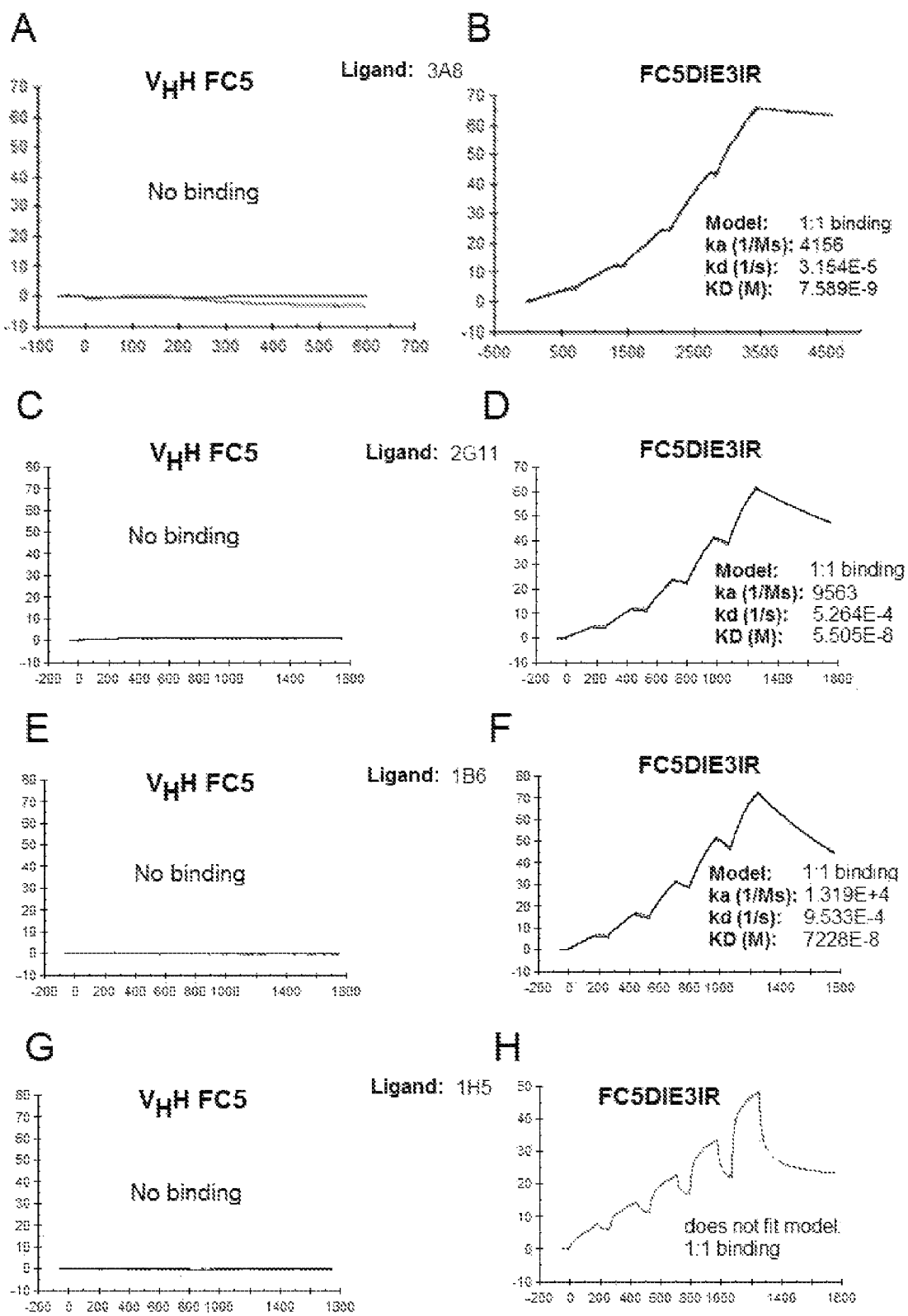
FIGS. 20A to 20H show the results of Surface Plasmon Resonance (SPR) analysis to determine the binding affinity of V$_H$H FC5 and FC5DIE3IR using Single Cycle Kinetics (SCK). Fc captured mAb 3A8, 2G11 and 1B6 showed strong and specific binding to FC5DIE3IR with K$_D$s (see values Table 5). The mAb 1H5 could not be fitted with the 1:1 model, consequently $K_D$s, on-rate (ka (1/Ms)) and Rmax values could not be calculated.

In both orientations 3A8, 2G11 and 1B6 strongly and specifically bound to FC5DIE3IR and did not bind to FC5 control (see Table 5). At 1 µM concentration of FC5 and FC5DIE3IR flowed over the captured 3A8 (FIG. 19), specific and high affinity binding of FC5DIE3IR is evident. The results also showed that 3A8 bind to the immobilized FC5DIE3IR with an extremely slow off rate. The binding affinity of FC5DIE3IR to Fc-captured 3A8. 2G211, 1B6 and 1H5 was determined using Single Cycle Kinetics (SCK; FIG. 20) analysis, using a range of FC5DIE3IR concentrations from 320 nM-20 nM. The captured 3A8, 2G11 and 1B6 showed strong and specific binding to FC5DIE3IR. Values of $K_D$s, on-rate (ka (1/Ms)) and Rmax are shown in Table 5. Rmax indicates that the captured mAbs possesses high activity (theoretical $R_{max}$~120 RU). The mAb 1H5 could not be fitted with the 1:1 model, consequently $K_D$s, on-rate (ka (1/Ms)) and Rmax values could not be calculated.

TABLE 5

Affinity and binding kinetics for mAbs 2G11, 1B6, 1H5, 3A8 and 1G5 obtained with SPR.

| mAb | Target | $k_a$ (1/Ms) | $k_d$ (1/s) | $K_D$ (M) | $R_{max}$ (RU) | Temp (° C.) | Comment |
|---|---|---|---|---|---|---|---|
| 2G11 | FC5 | | | | | 25 | No binding |
| | FC5-DIE3IR | 9.56E+03 | 5.26E−04 | 5.51E−08 | 84 | 25 | |
| IB6 | FC5 | | | | | 25 | No binding |
| | FC5-DIE3IR | 1.32E+04 | 9.53E−04 | 7.23E−08 | 93 | 25 | |
| 1H5 | FC5 | | | | | 25 | No binding |
| | FC5-DIE3IR | | | | | 25 | No fit to 1:1 model |
| 3A8 | FC5 | | | | | 25 | No binding |
| | FC5-DIE3IR | 7.05E+03 | 2.59E−04 | 3.67E−08 | 80 | 25 | |
| 1G5 | FC5 | 2.89E+05 | 1.7E−02 | 5.88E−08 | | 25 | Binding to both FC5 and DIE3IR |
| | FC5-DIE3IR | 7.29E+04 | 1.36E−02 | 1.86E−07 | | 25 | |

Recombinant Chimeric Human-Mouse mAbs. To validate the sequences of the mAbs (3A8, 1B6; Table 7), recombinant chimeric human-mouse mAbs (hFc-F233-3A8, hFc-F236-1B6) have been production and purified (for sequences see Table 7).

In vitro Validation of Recombinant Chimeric Human-Mouse mAbs. To determine if the recombinant chimeric human-mouse mAbs hFc-F233-3A8 and hFc-F236-1B6 were functional in reducing the hNa$_v$1.7 currents, Na$_v$ currents were evoked using whole-cell patch-clamp technique in hNa$_v$1.7-HEK293 cells as described in Example I. The hNa$_v$1.7-HEK293 cells were prepared from frozen vials and plated on poly-1-lysine coated 13 mm plastic coverslips. The coverslips were then mounted on a recording chamber and placed under an inverted microscope to perform the patch-clamp experiments. Recordings of Na$_v$ currents were obtained as described in Example I.

At the concentration of 2 μM, hFc-F233-3A8 and hFc-F236-1B6 were able to reduce significantly the amplitude of the Na$_v$ currents (FIGS. 21A and 21B) by 28.6%±6.0 (n=9; p=0.005) and 29.7%±5.4 (n=11; p=0.0005), respectively. These data validate the antibodies sequences.

Effect of mAbs Application on Cancer models. The four monoclonal antibodies targeting Na$_v$1.7 were tested on a number cancer cell lines expressing Na$_v$1.7. Expression of Na$_v$1.7 in these cell lines was first assessed with western blot analysis. FIGS. 22A and 22B show the results of western blot analysis performed on 11 cancer cell lines: DU-145 (model of prostate cancer), Jurkat (model of leukemia, LN18 (model of glioblastoma), PC-3 (model of prostate cancer), SKOV-3 (model of ovarian cancer), U87MG and U87MgvIII (models of glioblastoma), Capan-1, Bxpc3, Mia-Paca2 and Panc1 (all models of pancreatic cancer). Expression of the Na$_v$1.7 protein was found in all cell lines, except the prostate cancer PC-3 cells. The functionality of Na$_v$1.7 on these cell lines was also studied in electrophysiology experiments. FIGS. 23A and 23B show recordings of Na$_v$1.7 currents measured in the U87MG glioblastoma cells and the SKOV-3 ovarian cancer cells, respectively. Application of tetrodotoxin (TTX), a potent inhibitor of voltage gated sodium channels, successfully and completely blocked Na$_v$1.7 currents in these cells (FIG. 23A), and application of monoclonal antibodies provoked a partial inhibition of Na$_v$1.7 currents, which was consistent with the degree on inhibition observed in HEK293 cells overexpressing Na$_v$1.7 (FIG. 23B). Both TTX and the monoclonal antibodies were then applied in functional malignancy in vitro experiments, in which the capacity of the cancer cells lines to form colonies in a soft agar substrate was measured. TTX was used as positive control and reduced colony formation by 55% to 84%, depending of the cell line studied. The antibodies 1H5, 1B6 and 2G11 were also tested on the two glioblastoma cells lines U87MG and U87MGvIII (which differs from U87MG in a mutation on the EGF receptor) and the ovarian cancer cell line SKOV-3 (FIG. 24D). The antibody 1H5 reduced colony formation in all three cell lines (37%, 60% and 57% respectively; FIGS. 24A, 24C and 24D); 2G11 was only teset on the U87MG cells and it was efficacious in inhibiting colony formation by 60% (FIG. 24B); 1B6 had no inhibitory effect on U87MG and SKOV-3 cells (FIGS. 24A and 24D) but interestingly reduced colony formation in the mutation bearing U87MGvIII glioblastoma cell line by 53% (FIG. 24C).

Example III—Anti-Na$_v$1.7 V$_H$H Antibodies from a LAC-M Naïve Library

V$_H$Hs from a phage-displayed LAC-M nave library. The FC5DIE3IR recombinant protein (described in Example I) was used in panning experiment to isolate V$_H$Hs from a phage-displayed LAC-M naïve library (Kumaran et al., 2012). Before the panning, rescued phages were pre-incubated with FC5 protein in a blocking buffer with slow rotation overnight at 4° C. After centrifugation in a microfuge for 10 min, pre-adsorbed phages were added onto subtraction wells coated with FC5 V$_H$H protein and a blocking buffer to remove/reduce the phage population binding to the parental FC5 V$_H$H protein and plastic surface/blocking buffer. Thereafter, the pre-adsorbed phages were exposed to the target well(s) coated with FC5DIE3IR recombinant protein. Panning was performed for a total of four rounds against the FC5DIE3IR antigen. 5×10$^{10}$ cells of LAC-M library were grown in 500 ml of 2YT-Tet (12.5

μg/ml) at 220 rpm, 30° C. overnight. The culture was then centrifuged at 5,000 rpm, 4° C. for 15 min and filtered through 0.2 μm filter unit. The phage supernatant was precipitated with 1/5 volume of PEG-NaCl (500 ml+100 ml), incubated on ice for 1 h and then centrifuged at 10,000 rpm, 4° C., for 15 min. The pellet was re-suspended in 1 ml PBS and a serial dilution was done to determine the phage titer. To start the panning, 100 μl of 0.2-1 mg FC5DIE3IR/ml PBS was added to one well of a NUNC MaxiSorp™ ELISA plate (eBioscience, San Diego, Calif.). Another well (Blank) was coated with the same amount of FC5 $V_HH$ protein. The wells were sealed with parafilm and incubated overnight at 4° C. The rescued phages (from LAC-M library) were also pre-incubated with FC5 $V_HH$+Starting-Block (Thermo Scinetific, USA) (1:1 ratio) with slow rotation overnight at 4° C. On Day 2, the wells were rinsed twice and blocked with 200 μl of StartingBlock at room temperature (RT) for 1-2 h. After one hour, 100 μl of pre-adsorb phage ($10^{12}$) was added to the blank well and continued the incubation for another hour. This step will further pre-adsorb undesired phage binders. Subsequently, 100 μl of pre-adsorbed phages were transferred from the Blank well to the DIE3IR-coated well and incubated for 2 h at RT. The supernatant containing the unbound phages was discarded and the wells were rinsed 5 times with PBS—0.1% (v/v) Tween and 5 times with PBS (the washing times were increased to 7 times, 10 times, and 12 times on the $2^{nd}$, $3^{rd}$ and $4^{th}$ rounds of panning, respectively). The bound phages were eluted by adding 100 μl/well of 100 mM trimethylamine (TEA) and incubated at RT for exactly 10 min. The content of the well (100 μl) were transferred into a microcentrifuge tube containing 50 μl of 1M Tris-HCl (pH 7.4) and vortexed to neutralize the TEA. TG1 cells were infected with the neutralized phages and incubated at 37° C. for 15-30 min. A serial dilution ($10^{-1}$, $10^{-2}$ and $10^{-3}$) was prepared with 10 μl of the infected cells in 150 μl of TG1 cells. The cells were then plated on 2YT-Tet plates and Incubated at 37° C. O/N. The remaining infected TG1 cells were spun at 3500 rpm for 3-5 min at 4° C. The pellet was suspended in 200 μl of 2YT-Tet, spread on a large 2YT-Tet plate, and incubated at 37° C. O/N. On day 3, the bacterial cells were scraped off from the large plate using 50 ml of 2YT-Tet 5 ml of the cells were diluted with 5 ml of fresh 2YT-Tet broth and the culture were grown at 30° C. at 220 rpm for 5 h. The culture was then centrifuged at 4100 rpm at 4° C. for 30 min and the phage supernatant was filtered through 0.2 μm filter unit. The phage supernatant was precipitated as described above and the phage pellet was re-suspended in 200 μl starting block. The phage concentration (at $10^{-2}$ dilution) was measured on Nanovue and the physical phage titer was determined using the following formula:

$$pfu/ml = A_{260} \times 10^{10} \times 100 \times 22.14.$$

Figure 25:
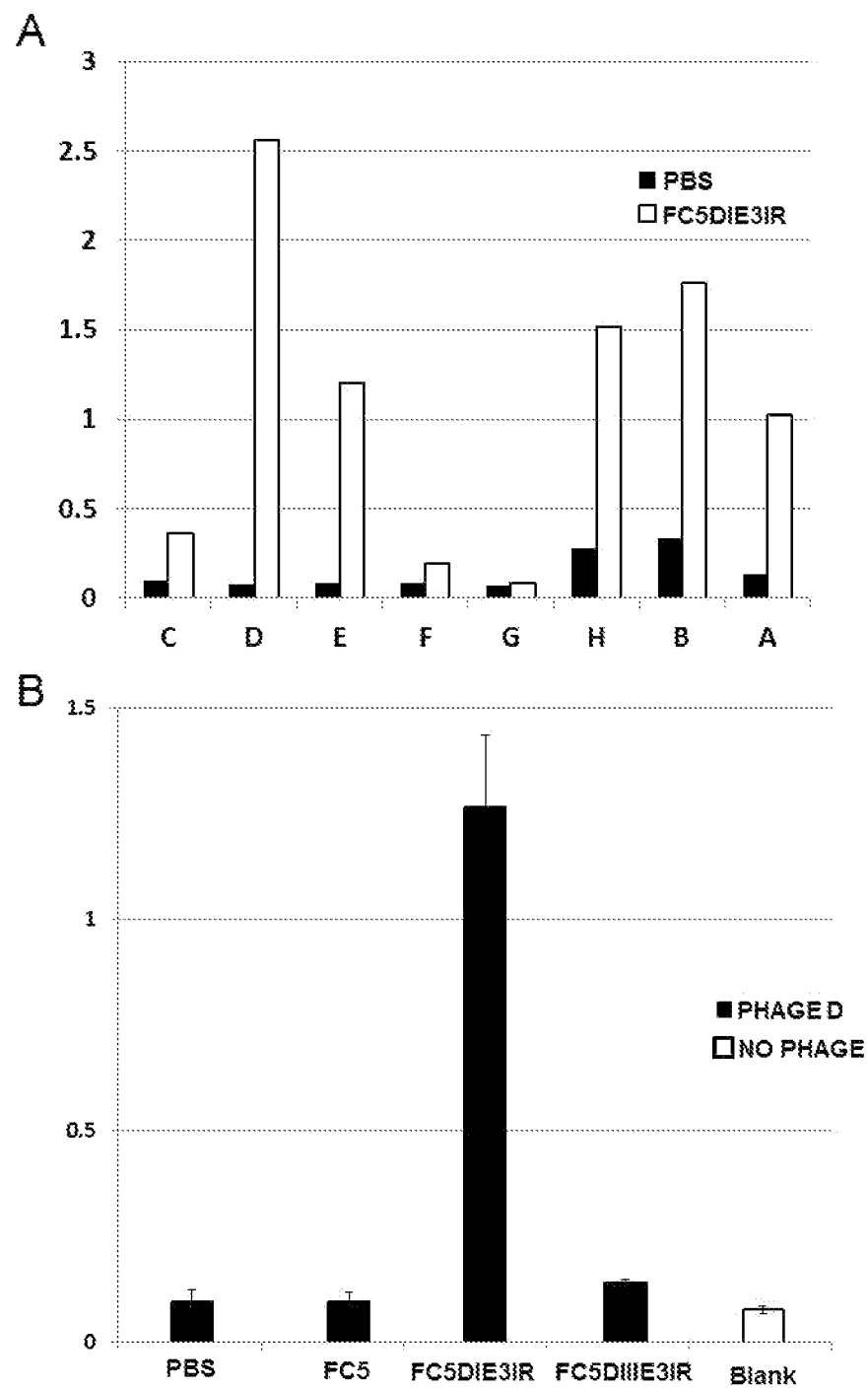
FIGS. 25A and 25B provide the result of a phage ELISA of $V_H$H colonies obtained from a non-immunized llama.

Additional rounds (up to 3) of panning were performed by coating the ELISA plate with the same proteins and using the amplified phages after each round of panning as described above. After four rounds of panning, 77 randomly picked colonies were grown and subjected to monoclonal phage ELISA screening as described previously (Arbabi-Ghahroudi et al., 2009) except that 5 μg/ml of FC5DIE3IR and FC5 $V_HH$ (the negative control) were coated onto a microtiter plate. All positive clones specifically binding to FC5DIE3IR were sequenced and unique $V_HH$ sequences were selected for sub-cloning, large-scale expression, and purification. A total of 6 $V_HH$s specific to FC5DIE3IR were isolated. Six $V_HH$ clones specific to FC5DIE3R (DI-A, DI-B, DI-C, DI-D, DI-E and DI-H) were identified by phage ELISA using FC5 parental FC5 $V_HH$ protein as negative control (FIGS. 25A and B). The sequencing data revealed 2 enriched and 4 unique $V_HH$ sequences (Table 7).

Expression and Purification of Soluble Monomeric $V_HH$s. DNA constructs (see Table 7 for a description of the nucleotide sequence) encoding the isolated $V_HH$s were synthesized commercially by GeneArt (Life Technologies, Carlsbad, Calif.) as described (Baral et al., 2013). 6×His- and c-Myc-tagged $V_HH$ monomers were expressed in E. coli TG1, extracted from periplasmic space by osmotic shock and purified by immobilized metal affinity chromatography (IMAC) using a HisTrap HP column (GE Healthcare, Piscataway, N.J.) as described in Baral et al., 2013 and Arbabi-Ghahroudi et al., 2009. The integrity and aggregation status of soluble $V_HH$ monomers were assessed by sodium dodecyl sulfate polyacrylamide gel electrophoresis (SDS-PAGE), Western blotting and size exclusion chromatography (SEC) as described in Baral et al., 2013 and Arbabi-Ghahroudi et al., 2009.

It was determined, by performing an protein-ELISA assay that all $V_HH$ antibodies showed specific binding to the FC5DIE3R protein with little or no cross-reactivity to FC5 $V_HH$ (data not shown).

Figure 26:
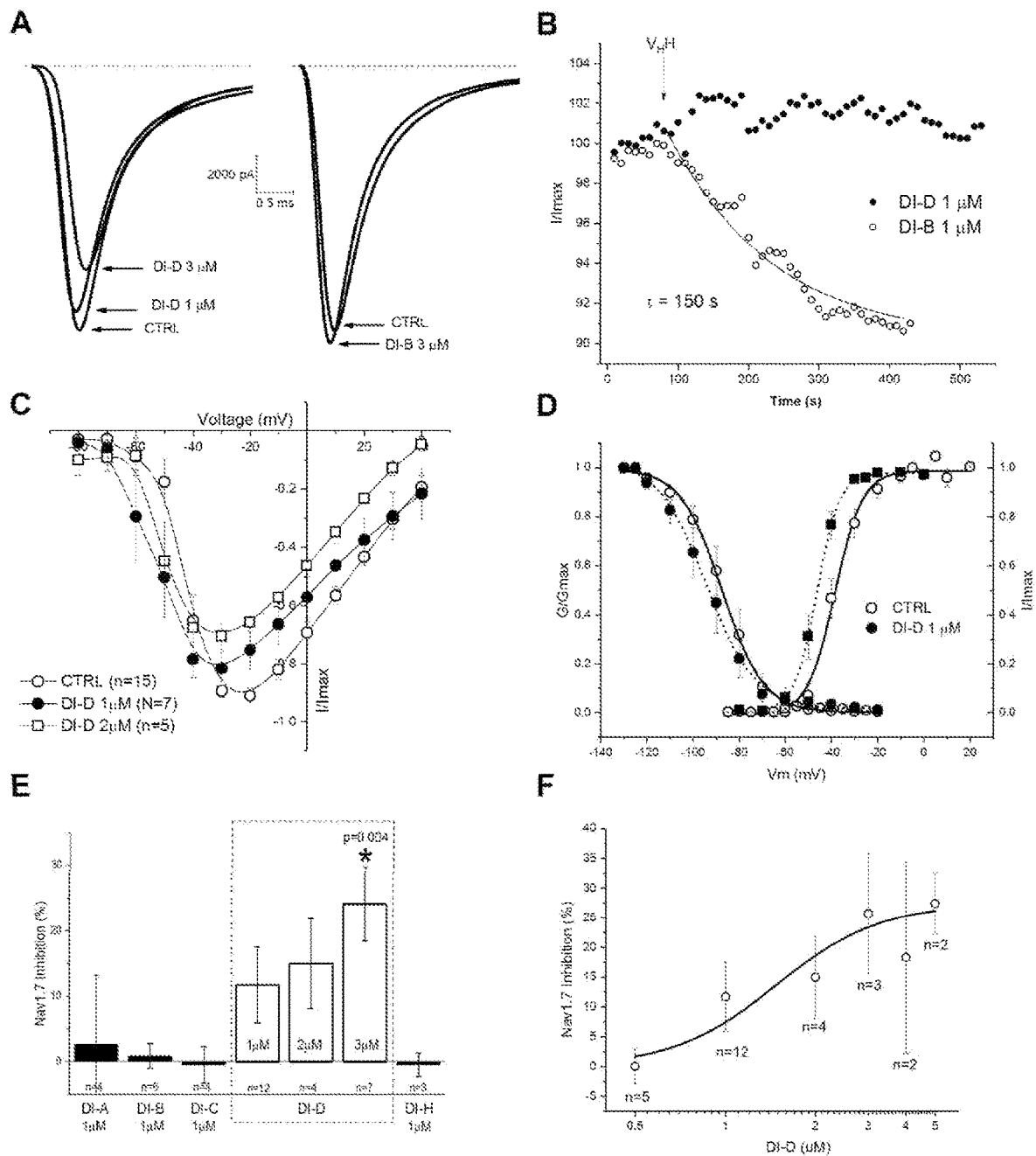
FIGS. 26A to 26F show the effect of the application of $V_H$Hs on the amplitude of the $Na_v1.7$ currents recorded using patch-clamp whole-cell technique in HEK293 cells overexpressing the $hNa_v1.7$ channels.

In vitro Identification of Functional $V_HH$s. To determine the functional effect of the isolated $V_HH$s on hNa$_v$1.7 channels, Na$_v$ currents were evoked using the whole-cell patch-clamp technique in hNa$_v$1.7-HEK293 cells as described in Example I. Five $V_HH$s (DI-A, DI-B, DI-C, DI-D, and DI-H) were tested using patch-clamp whole-cell. The $V_HH$ DI-E protein was not stable and consequently not tested. $V_HH$s were tested at an initial concentration of 1 μM. At this concentration, DI-D reduced the amplitude of the Na$_v$1.7 currents of 11.7%±5.8 (n=12), while DI-A, DI-B, DI-C, DI-H had no effect (DI-A, 2.73%±10.52, n=4; DI-B, 1.73%±1.96, n=6; DI-C, 0.46%±2.07, n=4; DI-H, 1.72%±1.32, n=3; FIG. 26E). At 2 μM and 3 μM, DI-D significantly reduced the currents by 15.0%±6.9 (n=4) and 24.1%±5.6 (n=7), respectively (FIGS. 26A, E and F). The $V_HH$ DI-D had a slow onset of effect, with time constants of block of 113±11 sec (n=4), and 200±45 sec (n=4) for concentrations of 1 μM and 2 μM, respectively (FIG. 26B). These data suggest that DI-D is functional in inhibiting the flux of Na$^+$ thought the hNa$_v$1.7 channels. Based upon the results presented in FIG. 26F, the DI-D concentration response relationship (IC$_{50}$) and efficacy (degree of maximum inhibition) were 1.48±0.25 μM and 27.4±5.% inhibition, respectively.

Next, it was evaluated if the $V_HH$ DI-D had an effect on the kinetics and voltage dependence properties of the hNa$_v$1.7 channels. To do this, the effect of DI-D on the current-voltage (I-V) relationship as well as the voltage-dependence of activation and steady-state fast inactivation of hNa$_v$1.7 channels in hNa$_v$1.7-HEK293 cells were examined (FIGS. 26C and D). The DI-D shifted the voltage-dependence of activation to more hyperpolarized membrane potentials (V$_{1/2}$ activation: Δ=−6.1±1.0 mV at 1 μM; n=5), suggesting a gating modifier activity (FIG. 26C). Minor effect was observed for DI-D on the voltage-dependence of steady-state fast inactivation for Na$_v$1.7 (V$_{1/2}$ inactivation: Δ=−6.8±1.5 mV at 1 μM; n=5). However, like in the case of mAbs, these shifts towards hyperpolarizing voltages of activation and steady-state inactivation curves may be not significant. In fact, it has been previously reported in literature that these changes in activation and inactivation of voltage gated sodium channels may derive from perturbations of the cellular membrane resulting from the application of the V$_H$H. In addition, negative-shifts of the same order were observed also in control experiment in which an equivalent volume of extracellular solution containing no V$_H$H was added to the patch-clamp chamber. In order to further investigate the effects of DI-D on hNa$_v$1.7 kinetics of activation and fast inactivation, time-to-peak and the time constants of fast inactivation of hNa$_v$1.7 were measured. The V$_H$H DI-D (1 μM) did not significantly change the times-to-peak which were 1.76±0.28 ms and 1.64±0.37 ms (measured at −20 mV, n=4) in control and after DI-D application respectively (p>0.10, paired t-Test). It also did not change the inactivation time constants which were 1.32±0.33 ms and 1.29±0.30 ms (measured at −20 mV, n=4) in control and with 1 μM DI-D, respectively (p>0.10, paired t-Test). These data suggest that the main functional effect of DI-D on the activity of Na$_v$1.7 is on the sodium ion permeation pathway, which reduces the amplitude of the current through the channel, and that the observed effects on Na$_v$1.7 kinetic properties likely derive from the perturbation to the membrane-cytoskeleton interactions provoked by the V$_H$H application.

In vivo validation of the V$_H$H: rat Hargreaves model of hyperalgesia. To evaluate if the functional in vitro effect of the V$_H$H DI-D translated in a functional in vivo effect against pain, DI-D was tested on CFA-induced thermal hyperalgesia in rats and compared it with the selective blocker for hNa$_v$1.7 channels TC-N1752 (Tocris, Bristol, United Kingdom). The V$_H$H DI-D was tested also along with a negative control anti-GFP mAb 11E5. As previously demonstrated, CFA induced hyperalgesia to a thermal stimulus 48 h post injection (Webster et al., 2016). Baseline latency paw withdrawal was reduced to 4.98±0.15 sec (n=18) in ipsilateral paw versus 19.98±0.19 sec (n=18) of contralateral paw (see FIG. 7). The DI-D effect on the latency paw withdrawal was measured 4 h after administration. Intraplantar injection of 50 μg of DI-D (8.36±0.53 sec, n=7), 100 μg of DI-D (11.78±0.50 sec, n=7) and but not 11E5 (5.92±0.14 sec, n=4) significantly increased latency paw withdrawal (p<0.05 vs baseline; FIG. 27A). In addition, DI-D at 100 μg (13.35±0.44 sec, 11.40±0.69 sec, 11.78±0.50 sec at 1, 2 and 4 hours respectively; n=7) had an effect similar to that of TC-N1752 (100 μg; 8.15±2.60 sec, 11.17±1.19 sec, 11.90±0.99 sec at 1, 2 and 4 hours respectively; n=3). FIG. 27B shows a histogram of the effect of 11E5 (5.78%±1.08, n=4), TC-N1752 (46.47%±7.14, n=3), DI-D 50 μg (21.59%±4.05, n=7) and DI-D 100 μg (45.19%±4.40, n=7) on hyperalgesia expressed as percentage of maximum possible effect (% MPE) 4 h after intraplantar injection of test compounds.

To further evaluate the functionality of the V$_H$H DI-D and target engagement, the V$_H$H was tested on the OD1 pain model. The intraplantar administration of OD1 in mice induces spontaneous pain behaviors as evidenced by licking, flinching, lifting and shaking of the injected hind paw. These behaviors are dose dependent (FIG. 14A) and develop rapidly, occurring soon after injection, and persists for up to 40 min after injection. The effect of 50 μg of VHH injection was tested and compared it with the injection of saline (saline plus OD1 30 μl). The pain behavior was considered at 100%, 20 min after the injection. Twenty min after the injection, 50 μg of V$_H$H DI-D (FIG. 28A), but not V$_H$H A20.1 (FIG. 28B) significantly reduced the time spent in pain behaviors (DI-D; 44.33%±8.8; n=2). Surface Plasmon Resonance (SPR). To determine the binding affinity of the V$_H$H DI-D with the recombinant protein FC5DIE3IR used to isolate the V$_H$H, SPR binding assays were used as provided in Example I. Before starting, pure monomeric fractions of the V$_H$Hs DI-D and FC5 control, and FC5DIE3IR target protein were obtained using SEC. To determine the binding the V$_H$H DI-D with the recombinant protein FC5DIE3IR, FC5DIE3IR and FC5 surfaces were prepared. SPR analysis showed that DI-D binds specifically to FC5DIE3IR (FIGS. 29A and 29B) with a K$_D$ of 2 μM (FIGS. 30A and 30B) and an observed R$_{max}$ of approx. 700 RU, indicating a high level of activity of immobilized FC5DIE3IR. Weak/residual binding to FC5 was observed by DI-D, although an affinity could not be determined (data not shown).

Example IV—Anti-Na$_v$1.7 V$_H$H Antibodies from a LAC-M Naïve Library

V$_H$Hs from a FC5DIE3IR llama immune library. The FC5DIE3IR recombinant protein (100 μg, described in Example I) was used to subcutaneously immunize a young male llama five times at two-week intervals. Briefly, a male llama (*Lama glama*) was immunized five times subcutaneously with 100 μg of FC5DIE3IR protein mixed with an equal volume of either complete (day 1) or incomplete (days 14, 28, 42, 49) Freund's adjuvant (Sigma). Pre-immune blood (15-20 ml) was collected before the first injection and on days 35 and 56. The specific immune responses were analyzed by ELISA using total pre-immune and immune sera. Briefly, microtitre plates (Maxisorp™ plates) (Nalge Nunc International, Rochester, N.Y.) were coated overnight at 4° C. with 5 μg/ml of FC5DIE3IR antigen in PBS. As negative control, FC5 protein was coated on each second row on the same plate. Wells were rinsed and blocked with 200 μl of 1% casein. Serially diluted pre-immune and immune sera were added to the wells and incubated at room temperature for 1.5 h. Wells were washed with PBST (0.05% v/v Tween-20), and incubated with goat anti-llama IgG-HRP (H+L) (1:1,000 in PBS) (Bethyl Laboratories, Montgomery, Tex.). Signal was detected by adding 100 μl/well TMB peroxidase substrate (Kirkegaard and Perry Laboratories, Gaithersburg, Md., USA). Reactions were stopped by adding 100 μl of 1M phosphoric acid and A450 was measured using a standard ELISA plate reader.

The V$_H$H library was constructed as described previously (Baral et al., 2013). In brief, total RNA was isolated from approximately 1×10$^7$ lymphocytes collected on day 56 post-immunization using QIAamp™ RNA blood mini kit (Qiagen, Mississauga, Ontario, Canada). First-strand cDNA was synthesized with oligo (dT) primer using 5 μg total RNA as template according to manufacturer's recommendations (GE Healthcare). Variable and part of the constant domains DNAs were amplified using oligonucleotides MJ1-3 (sense) and two CH2 domain antisense primers CH2 and CH2b3 (for primer sequences see (Baral et al., 2013) and heavy chain fragments (550-650 bp in length) were gel-purified using QIA quick gel extraction kit (Qiagene). The variable regions of heavy chain antibodies (IgG2 and IgG3) were re-amplified in a second PCR reaction using MJ7 and MJ8 primers (for primer sequences see Baral et al., 2013). The amplified PCR products were purified with a QIAquick PCR purification kit (Qiagene), digested with Sfil (New England BioLabs, Pickering, Ontario, Canada), and re-purified using the same kit. Twelve micrograms of digested V$_H$H fragments were ligated with 40 μg (3:1 molar ratio, respectively) Sfi-digested pMED1 phagemid vector using LigaFast Rapid DNA ligation system and its protocol (Promega, Madison, Wis.), transformed into commercial electrocompetent TG1 *E. coli* cells (Stratagene, La Jolla, Calif.) as described previously (Baral et al., 2013) and a library size of 5×10$^7$ transformants was obtained. The $V_HH$ fragments from 30 colonies were PCR-amplified and sequenced to analyze the complexity of the library; all clones had inserts of expected sizes and were different from each other at their CDR regions as determined by sequencing of their encoding $V_HH$ fragments. The library was grown for 3-4 h at 37° C., 250 rpm in 2×YT/Amp-Glucose (2% w/v) medium. The bacterial cells were pelleted, resuspended in the same medium and stored as glycerol stock at −80° C. as described previously (Baral et al., 2013).

Panning experiments was essentially performed as described in Baral et al., 2013. Panning was performed for a total of four rounds against the FC5DIE3IR antigen. Two milliliters of the library stock (5×10$^{10}$ cells) was grown in for 1-2 hours at 37° C., 250 rpm in 2×YT/Amp-Glucose (2% w/v) medium ($A_{600}$=0.4-0.5), infected with M13KO7 helperphage (New England Biolobas) for 1 h at 37° C. After centrifugation of the culture at 4° C., the infected cell pellets were re-suspended in 200 ml of 2×YT/Amp with 50 μg/ml kanamycin and incubated overnight at 37° C. and 250 rpm. The phage particles in culture supernatant were PEG-precipitated as described previously (Baral et al., 2013) and the phage pellets were re-suspended in 2 ml of sterile PBS and the phage titration was determined. During the panning process, rescued phages from the library were first incubated with FC5 protein in a blocking buffer overnight at 4° C. on a rotating shaker. The phage solution was centrifuged at top speed for 10 min and the phage supernatant was added onto subtraction wells coated with FC5 $V_HH$ protein and a blocking buffer to remove/reduce the phage population binding to the parental FC5 $V_HH$ protein and plastic surface/blocking buffer. Thereafter, the pre-adsorbed phages were exposed to the target well(s) coated with FC5DIE3IR recombinant protein. Panning was performed for a total of four rounds against the FC5DIE3IR antigen. To start the panning, 100 μl of 0.4 mg/ml of FC5DIE3IR in PBS was added to one well of a NUNC MaxiSorp™ ELISA plate (eBioscience, San Diego, Calif.). Another well (blank) was coated with the same amount of FC5 $V_HH$ protein. The wells were sealed with parafilm and incubated overnight at 4° C. The rescued phages (from immune library) were also pre-incubated with FC5 $V_HH$+StartingBlock (Thermo Scinetific, USA) (1:1 ratio) with slow rotation overnight at 4° C. On Day 2, the wells were rinsed twice and blocked with 200 μl of StartingBlock at room temperature (RT) for 1-2 h. After one hour, 100 μl of pre-adsorb phage (10$^{12}$) was added to the blank well and continued the incubation for another hour. This step will further pre-adsorb undesired phage binders. Subsequently, 100 μl of pre-adsorbed phages were transferred from the blank well to the FC5DIE31R-coated well and incubated for 2 h at room temperature. The supernatant containing the unbound phages was discarded and the wells were rinsed 5 times with PBS—0.1% (v/v) Tween and 5 times with PBS (the washing times were increased to 7 times, 10 times, and 12 times on the 2$^{nd}$, 3$^{rd}$ and 4$^{th}$ rounds of panning, respectively). The bound phages were eluted with 0.1 M triethylamine, neutralized with 1M Tris-HCL, PH 7.4 and incubated with exponentially growing TG1 cells. After 30 min incubation at 37° C., the cells were superinfected with M13KO7 for additional 15 min and grown in 2×YT-Amp-Kan overnight at 37° C. Panning was continued for three more rounds following the same conditions except that antigen concentration was reduced to 20, 15, and 10 μg/well and washing was increased 7, 10 and 12× with PBS-T and PBS for the second, third and fourth rounds of panning, respectively. After four rounds of panning, 48 randomly picked colonies were grown and subjected to phage ELISA screening as described previously (Baral et al., 2013) except that 5 μg/ml of FC5DIE3IR and FC5 were coated, respectively, onto each row of the microtiter plates as positive and negative antigens.

In total, four rounds of solid-phase panning were performed and 48 colonies were screened by phage-ELISA as described previously (Arbabi-Ghahroudi et al., 2009) except that 5 μg/ml of FC5DIE3IR and FC5 $V_HH$ (the negative control) were coated onto a microtiter plate. Four $V_HH$ clones specific to FC5DIE3IR (DI-4, DI-16, DI-28, DI-48) were identified by phage ELISA using FC5 parental $V_HH$ protein as negative control (FIGS. 31A and 31B). Additional phage-ELISA screening (on 48 colonies) and sequencing revealed that in total four unique $V_HH$ sequences, DI-4, DI-16, DI-28, and DI-48, were enriched 3×, 3×, 21×, 5×, respectively (Table 7). Unique $V_HH$ sequences were gene-synthesized and cloned into the pSJF2 expression vector for large-scale expression, and purification.

Expression and Purification of Soluble Monomeric $V_H$Hs. DNA constructs encoding the isolated $V_H$Hs (DI-4, D116, DI-28 and DI-48; Table 7) were synthesized and cloned into the pSJF2H expression vector commercially by GeneArt (Life Technologies, Carlsbad, Calif.) as described (Baral et al., 2013). The final construct included an OmpA leader sequence for secretion of sdAb proteins to the periplasmic space of *E. coli*, and a cmyc and His$_6$ tags for ease of purification, at the C-terminus of the sdAb. Large-scale protein expression and purification was performed essentially as previously described (Baral et al., 2013). Briefly, individual colonies were grown (25 ml LB-Amp overnight at 37° C. The pre-culture was used to seed 1 liter 2×YT-Amp culture and grown at 37° C. with vigorous shaking. At OD$_{600}$=0.8, the cultures were induced by the addition of IPTG to a final concentration of 1 mM. The culture was grown overnight at 32° C. The bacteria were pelleted by centrifuging at 6,000 rpm for 12 min, and then submitted to cold osmotic shock to extract sdAb from the periplasmic space. The pellet was re-suspended in 30 ml of cold TES buffer (0.2M Tris-CI pH 8.0, 20% sucrose, 0.5 mM EDTA). The suspension was incubated on ice and vortexed every 10 min for 1 h. Then 40 ml of cold TES (1/8 volume of total volume) was added and immediately vortexed for 1 min and for 15 sec every 10 min thereafter for 1 h to extract the protein from the periplasm. The periplasmic extracts containing $V_H$Hs were dialyzed overnight against buffer (20 mM phosphate buffer (pH 7.4), 0.5M NaCl, 10 mM imidazole) at 4° C. then filtered through a 0.45 μm membrane (EMD Millipore, Canada). Filtered supernatant was loaded onto nickel-charged 5 ml HisTrap™ FF column (GE Healthcare, Canada) and fractionation was performed on an ÄKTA FPLC purification system (GE Healthcare). The $V_H$Hs were eluted using gradient elution (buffer containing 500 mM imidazole); the fractions were pooled and dialyzed against PBS. $V_H$H concentrations were determined by absorbance measurements at 280 nm using theoretical MW and extinction coefficients calculated with the ExPASy ProtParam Tool (expasy.org/tools/protparam.html).

Antibody Binding Assays (Protein-ELISA). A phage ELISA assay was performed and four positive clones (DI-4, DI-11, DI-16, DI-28) (having a signal of at least 3× background) were identified and further characterized. Sequencing data showed that clones DI-11 and DI-16 have identical sequences and the difference in ELISA signal could be due to lower phage titer for clone DI-11. Additional rounds of screening (data not shown) identified a new $V_H$H clone, named DI-48.

Surface Plasmon Resonance (SPR). To determine the binding affinity of the V$_H$Hs DI-4, DI-16, DI-28 and DI-48 with the recombinant protein FC5DIE3IR used to isolate the V$_H$Hs, SPR binding assays were performed. Before starting, pure monomeric fractions of the V$_H$Hs DI-4, DI-16, DI-28, DI-48, FC5 control, and FC5DIE3IR target protein were obtained using SEC (data not shown). To determine the binding affinity of DI-4, DI-16, DI-28 and DI-48 for recombinant FC5DIE3IR, FC5DIE3IR, FC5 (negative control) and V$_H$H 2A3-H4 (negative control) surfaces were prepared.

As shown in Table 6, SPR analysis showed that DI-4, DI-16, DI-28 and DI-48 bind specifically to FC5DIE3IR (FIGS. 32A to 32D) with a K$_{ID}$ of 2.25 µM, 4.3 nM, 4.4 nM and 8.4 µM, with observed R$_{max}$s ranging from 318-470 RUs (Table 6). These results indicate a high level of activity of immobilized FC5DIE3IR and V$_H$Hs. No binding to FC5 and to 2A3-H4 was observed for any of the V$_H$Hs tested. DI-4 and DI-48 had similar affinities for FC5DIE3IR as DI-D (K$_D$~2 µM), while DI-16 and DI-48 had affinities 1000 times lower.

TABLE 6

Affinity and binding kinetics for DI-4, DI-16, DI-28, DI-48 and DI-D obtained with SPR

| Sample | SEC Fraction | Target | ka (1/Ms) | kd (1/s) | KD (M) | Rmax (RU) | Temp (C.) | Comment |
|---|---|---|---|---|---|---|---|---|
| DI-4 | 32 | FC5 | | | | | 25 | No binding |
| | 32 | FC5DIE3IR | | | 2.25E−06 | 469.2 | 25 | Steady State fit |
| | 32 | 2A3-H4 | | | | | 25 | Very low non-specific binding |
| DI-16 | 28 | FC5 | | | | | 25 | No binding |
| | 28 | FC5DIE3IR | 6.19E+05 | 2.66E−03 | 4.30E−09 | 317.9 | 25 | |
| | 28 | 2A3-H4 | | | | | 25 | No binding |
| DI-28 | 28 | FC5 | | | | | 25 | No binding |
| | 28 | FC5DIE3IR | 4.61E+05 | 2.05E−03 | 4.44E−09 | 318.3 | 25 | |
| | 28 | 2A3-H4 | | | | | 25 | No binding |
| DI-48 | 29 | FC5 | | | | | 25 | No binding |
| | 29 | FC5DIE3IR | | | | 8.40E−06 | 25 | Low affinity, approximately 8.4 µM with steady-state fit |
| | 29 | 2A3-H4 | | | | | 25 | Very low non-specific binding |
| DI-D | 25 | FC5 | | | | | 25 | Weak binding; no curvature when tested at 5 µM |
| | 25 | FC5DIE3IR | | | 1.93E−06 | 496.9 | 25 | Steady State fit |
| | 25 | 2A3-H4 | | | | | 25 | No binding |

TABLE 7

Nucleotide and amino acid sequences. CDR determination were done using the IMGT website.

| SEQ ID NO # | Sequence | Description |
|---|---|---|
| 1 | KHKCFRNSLENNETLESIMNTLESEEDFRKYFYYLEGSKDALLCGF STDSGQCPEGYTCVKIGRNPDYGY | DIE3IR 70aa |
| 2 | MEFGLSWLFLVAILKGVQCEVQLQASGGGLVQAGGSLRLSCAASG FKITHYTMGWFRQAPGKEREFVSRITWGGDNTFYSNSVKGRFTISR DNAKNTVYLQMNSLKPEDTADYYCAAGSTKHKCFRNSLENNETLE SIMNTLESEEDFRKYFYYLEGSKDALLCGFSTDSGQCPEGYTCVKI GRNPDYGYRVDYWGKGTQVTVSS | FC5DIE3IR |
| 3 | EVQLQASGGGLVQAGGSLRLSCAASGFKITHYTMGWFRQAPGKE REFVSRITWGGDNTFYSNSVKGRFTISRDNAKNTVYLQMNSLKPED TADYYCAAGSTKHKCFRNSLENNETLESIMNTLESEEDFRKYFYYL EGSKDALLCGFSTDSGQCPEGYTCVKIGRNPDYGYRVDYWGKGT QVTVSS | FC5DIE3IR without signal peptide |
| 4 | KHKCFRNSLENNETLESIMNTLESEEDFRK | peptide#1 30aa |
| 5 | TLESEEDFRKYFYYLEGSKDALLCGFSTDS | peptide#2 30aa |
| 6 | ALLCGFSTDSGQCPEGYTCVKIGRNPDYGY | peptide#3 30aa |
| 7 | GYTFTNYW | 3A8 CDR1-H |
| 8 | INPSNGRA | 3A8 CDR2-H |
| 9 | ARSPYGYYDY | 3A8 CDR3-H |

TABLE 7-continued

Nucleotide and amino acid sequences. CDR determination were done using the IMGT website.

| SEQ ID NO # | Sequence | Description |
|---|---|---|
| 10 | TTTTTGGTAGCAACAGCTACAGATGTCCACTCCCAGGTCCAACT GCAGCAGCCTGGGGCTGAACTGGTGAAGCCTGGGGCTTCAGT GAAGCTGTCCTGCAAGGCTTCTGGCTACACCTTCACCAACTAC TGGATGCACTGGGTGAAGCAGAGGCCTGGACAAGGCCTTGAG TGGATTGGAGAGATTAATCCTAGCAACGGTCGTGCTAACTACA ATGAGAAGTTCAAGAGCAAGGCCACACTGACTGTAGACAAATC CTCCAGCACAGCCTACATGCAACTCAGCAGCCTGACATCTGAG GACTCTGCGGTCTATTACTGTGCAAGATCCCCTTATGGTTACTA CGACTACTGGGGCCAAGGCACCACTCTCACAGTCTCCTCAGCC AAAACAACAGCCCCATCGGTCTATCCCCTGGCCCCT | 3A8 DNA-H variable region is in bold |
| 11 | FLVATATDVHSQVQLQQPGAELVKPGASVKLSCKASGYTFTNYWM HWVKQRPGQGLEWIGEINPSNGRANYNEKFKSKATLTVDKSSSTA YMQLSSLTSEDSAVYY<u>CARSPYGYY</u>DYWGQGTTLTVSSAKTTAPS VYPLAP | 3A8 Heavy chain with examplary leader sequence (CDR underlined) |
| 12 | QVQLQQPGAELVKPGASVKLSCKASGYTFTNYWMHWVKQRPGQ GLEWIGEINPSNGRANYNEKFKSKATLTVDKSSSTAYMQLSSLTSE DSAVYYCARSPYGYYDYWGQGTTLTVSSAKTTAPSVYPLAP | 3A8 Heavy chain without leader sequence |
| 109 | QVQLQQPGAELVKPGASVKLSCKASGYTFTNYWMHWVKQRPGQ GLEWIGEINPSNGRANYNEKFKSKATLTVDKSSSTAYMQLSSLTSE DSAVYYCARSPYGYYDYWGQGTTLTVSS | 3A8 VH |
| 13 | QSLLHSNGNTY | 3A8 CDR1-L |
| 14 | KVS | 3A8 CDR2-L |
| 15 | SQITHVPLT | 3A8 CDR3-L |
| 16 | CTGATGAAGTTGCCTGTTAGGCTGTTGGTGCTGATGTTCTGGAT TCCTGCTTCCAGCAGTGATGTTTTGATGACCCAAACTCCACTCT CCCTGCCTGTCAGTCTTGGAGATCAAGCCTCCATCTCTTGCAG ATCTAGTCAGAGCCTTTTACACAGTAATGGAAACACCTATTTCC ATTGGTACCTGCAGAAGCCAGGCCAGTCTCCAAAGCTCCTGAT CTACAAAGTTTCCAACCGATTTTTTGGGGTCCCAGACAGGTTCA GTGGCAGTGGATCAGGGACAGATTTCACACTCAAGATCAGCA GAGTGGAGGCTGAGGATCTGGGAGTTTATTTCTGCTCTCAAAT TACACATGTTCCGCTCACGTTCGGTGCTGGGACCAAGCTGGAG CTGAAACGGGCTGATGCTGCACCAACTGTATCCATCTTCCCACC ATCCAGT | 3A8 DNA-L variable region is in bold |
| 17 | LMKLPVRLLVLMFWIPASSSDVLMTQTPLSLPVSLGDQASISCRSS <u>QSLLHSNGNTY</u>FHWYLQKPGQSPKLLIYKVSNRFFGVPDRFSGSG SGTDFTLKISRVEAEDLGVYFC<u>SQITHVPLT</u>FGAGTKLELKRADAAP TVSIFPPSS | 3A8 Light chain with examplary leader sequence (CDR underlined) |
| 18 | DVLMTQTPLSLPVSLGDQASISCRSSQSLLHSNGNTYFHWYLQKP GQSPKLLIYKVSNRFFGVPDRFSGSGSGTDFTLKISRVEAEDLGVY FCSQITHVPLTFGAGTKLELKRADAAPTVSIFPPSS | 3A8 Light chain without leader sequence |
| 110 | DVLMTQTPLSLPVSLGDQASISCRSSQSLLHSNGNTYFHWYLQKP GQSPKLLIYKVSNRFFGVPDRFSGSGSGTDFTLKISRVEAEDLGVY FCSQITHVPLTFGAGTKLELK | 3A8 VL |
| 19 | TTTTTGGTAGCTGCAGCTACAGGTGTCCACTCCAGGTCCAACT GCAGCAGCCTGGGGCTGAGCTTGTGAAGCCTGGGGCTTCAGT GAAGCTGTCCTGCAAGGCTTCTGGCTACACTTTCACCAGCTAC TGGATAAACTGGGTGAAGCAGAGGCCTGGACAAGGCCTTGAG TGGATTGGAAATATTTATCCTGGTAATAGTAATACTAACTACAA TGAGAAGTTCAAGAGCAAGGCCACACTGACTGTAGACAAATCC TCCAGCACAGCCTACATGCAGCTCAGCAGCCTGACATCTGAGG ACTCTGCGGTCTATTATTGTGCAAGACGGTACTACTATGATTAC GACGATGCTATGGACTACTGGGGTCAAGGAACCTCAGTCACC GTCTCCTCAGCCAAAACGACACCCCCATCGTCTATCCCCTGGC CCCT | 1G5 DNA-H variable region is in bold |

TABLE 7-continued

Nucleotide and amino acid sequences. CDR determination were done using the IMGT website.

| SEQ ID NO # | Sequence | Description |
|---|---|---|
| 20 | FLVAAATGVHSQVQLQQPGAELVKPGASVKLSCKASGYTFTSYWI NWVKQRPGQGLEWIGNIYPGNSNTNYNEKFKSKATLTVDKSSSTA YMQLSSLTSEDSAVYYCARRYYYDYDDAMDYWGQGTSVTVSSAK TTPPSVYPLAP | 1G5 (and 1G9) Heavy chain with exemplary leader sequence (CDR underlined) |
| 21 | QVQLQQPGAELVKPGASVKLSCKASGYTFTSYWINWVKQRPGQG LEWIGNIYPGNSNTNYNEKFKSKATLTVDKSSSTAYMQLSSLTSED SAVYYCARRYYYDYDDAMDYWGQGTSVTVSSAKTTPPSVYPLAP | 1G5 (and 1G9) Heavy chain without leader sequence |
| 111 | QVQLQQPGAELVKPGASVKLSCKASGYTFTSYWINWVKQRPGQG LEWIGNIYPGNSNTNYNEKFKSKATLTVDKSSSTAYMQLSSLTSED SAVYYCARRYYYDYDDAMDYWGQGTSVTVSS | 1G5 (and 1G9) VH |
| 22 | GYTFTSYW | 1G5 (and 1G9) CDR1-H |
| 23 | IYPGNSNT | 1G5 (and 1G9) CDR2-H |
| 24 | ARRYYYDYDDAMDY | 1G5 (and 1G9) CDR3-H |
| 25 | CTTATGTTGCTGCTGCTATGGGTTCCAGGTTCCACAGGTGACAT TGTGCTGACCCAATCTCCAGCTTCTTTGGCTGTGTCTCTAGGGC AGAGGGCCACCATATCCTGCAGAGCCAGTGAAAGTGTTGATA GTTATGGCAATGGTTTTATGCACTGGTACCAGCAGAAACCAGG ACAGCCACCCAAACTCCTCATCTATCGTGCATCCAACCTAGAA TCTGGGATCCCTGCCAGGGTCAGTGGCAGTGGGTCTAGGACA GACTTCACCCTCACCATTAATCCTGTGGAGGCTGATGATGTTG CAACCTATTACTGTCAGCAAAGTAATGAGGATCCGTGGACGTT CGGTGGAGGCACCAAGCTGGAAATCAAACGGGCTGATGCTGC ACCAACTGTATCCATCTTCCCACCATCCAGT | 1G5 (and 1G9) DNA -L variable region is in bold |
| 26 | LMLLLLWVPGSTGDIVLTQSPASLAVSLGQRATISCRASESVDSYG NGFMHWYQQKPGQPPKLLIYRASNLESGIPARVSGSGSRTDFTLTI NPVEADDVATYYCQQSNEDPWTFGGGTKLEIKRADAAPTVSIFPPSS | 1G5 (and 1G9) Light chain with exemplary leader sequence (CDR underlined) |
| 27 | DIVLTQSPASLAVSLGQRATISCRASESVDSYGNGFMHWYQQKPG QPPKLLIYRASNLESGIPARVSGSGSRTDFTLTINPVEADDVATYYC QQSNEDPWTFGGGTKLEIKRADAAPTVSIFPPSS | 1G5 (and 1G9) Light chain without leader sequence |
| 112 | DIVLTQSPASLAVSLGQRATISCRASESVDSYGNGFMHWYQQKPG QPPKLLIYRASNLESGIPARVSGSGSRTDFTLTINPVEADDVATYYC QQSNEDPWTFGGGTKLEIK | 1G5 (and 1G9) VL |
| 28 | ESVDSYGNGF | 1G5 CDR1-L |
| 29 | RAS | 1G5 CDR2-L |
| 30 | QQSNEDPWT | 1G5 CDR3-L |
| 31 | CAGGCTCAGGTACAGCTGGTGGAGTCTGGGGGAGGATTGGTGC AGCCTGGGGGCTCTCTGAGACTCTCCTGTGCAGCCTCTGGACG CACCATCAGTAGCTTTACCATGGGCTGGTTCCGCCAGGCTCCAG GGGCGGAGCGTGAGTTTGTAGCAGCTATTAGTCGGAGTGGTAG TAGTACAGTCTATGCAGGCTCCGTGAAGGGCCGATTCACCATCT CCAGAGACAACGCCAAGAACACGGTGTATCTGCAAATGAACAGC CTGAAACCTGAGGACACGGCCGTCTATTACTGTAATGCAGTTAT TACCGAACCCCTCTACAAAACGGACGATAGTTACTGGGGCCAG GGGACCCAGGTCACCGTCTCCTCA | DI-A DNA |
| 32 | QAQVQLVESGGGLVQPGGSLRLSCAASGRTISSFTMGWFRQAPG AEREFVAAISRSGSSTVYAGSVKGRFTISRDNAKNTVYLQMNSLKP EDTAVYYCNAVITEPLYKTDDSYWGQGTQVTVSS | DI-A $V_HH$ |

TABLE 7-continued

Nucleotide and amino acid sequences. CDR determination were done using the IMGT website.

| SEQ ID NO # | Sequence | Description |
|---|---|---|
| 33 | CAGGTAAAGCTGGAGGAGTCTGGGGGAGGCTTGGTGCCGCCT GGGGAGTCTCTGAGGCTCACCTGTGCGGCCACTGGACAAACCG CTAGTGTATATGAAATGGCCTGGTTCCGCCGCGCTCCAGAGAAG GAGCAAGTATATGTGGCATCTATTAACTGGCGGGATGGTGACAC ACAATATCATAACTCCGTGAAGGGCCGATTCATCATCTCTAGAG ACAATGCCAAGAACACGGTATTTCTCCAAATGAACAGTTTAACAC CTGAGGACACGGCCATCTATTACTGCGCAGCGCGAAAAGAATTG GCGGGGTATGACTACTGGGGCCAAGGGACCCAGGTCACCGTCT CCTCA | DI-B DNA |
| 34 | QVKLEESGGGLVPPGESLRLTCAATGQTASVYEMAWFRRAPEKE QVYVASINWRDGDTQYHNSVKGRFIISRDNAKNTVFLQMNSLTPED TAIYYCAARKELAGYDYWGQGTQVTVSS | DI-B V$_H$H |
| 35 | CAGGTAAAGCTGGAGGAGTCTGGGGGAGGCTTGGTGCAGCCTG GGGAGTCTCTGAGACTCTCGTGTGTAGGTTCTGGATTCAACTTC AGGATCCAGGCCATGGCCTGGTTCCGCCAGGCTCCAGGGAAGG AGCGTGAATTTGTCGCCAGTATTAGCGGGAGCGGTGCTACCAC CGACCATGCAGACTCCGTGAAGGGCCGATTCGCCATCTCCAAA GACAACGCCAGGGACACAATGTATTTGCAAATGAACAACCTGAA ACCGGAGGACACGGCCGTCTATTACTGCTATGCAATTAGTCAAC ATGTACCGCCGTATCACTACTGGGGCCAGGGGACCCAGGTCAC CGTCTCCTCA | DI-C DNA |
| 36 | QVKLEESGGGLVQPGESLRLSCVGSGFNFRIQAMAWFRQAPGKE REFVASISGSGATTDHADSVKGRFAISKDNARDTMYLQMNNLKPED TAVYYCYAISQHVPPYHYWGQGTQVTVSS | DI-C V$_H$H |
| 37 | CAGGTAAAGCTGGAGGAGTCTGGGGGGGGCTTGGTACAGCCC GGGGGGTCTCTGAAACTCTCGTGTGTAGCCTCTGGATTCGCCTT CAGCTCCGCTCCAATGGACTGGGTCCGTAAGGCTCCAGGGAAG GACGTTGAGTGGCTCTCAACTATTGAAAGTGACCAAGACCACAC CATATATTATGCAAACTCCGTGAAGGGCCGATTCACTATTTCCCG AGATGATGTCCAGAACATCTTGTATCTGCAAATGAACGACCTGA AAATTGAGGACACGGCCACATATTACTGTCAGAAACGTGGAGAG AAGAAAACCCGGGGCCAGGGGACCCAGGTCACCGTCTCCTCA | DI-D DNA |
| 38 | QVKLEESGGGLVQPGGSLKLSCVASGFAFSSAPMDWVRKAPGKD VEWLSTIESDQDHTIYYANSVKGRFTISRDDVQNILYLQMNDLKIED TATYYCQKRGEKKTRGQGTQVTVSS | DI-D V$_H$H |
| 39 | GFAFSSAP | DI-D CDR1 |
| 40 | IESDQDHTI | DI-D CDR2 |
| 41 | QKRGEKKT | DI-D CDR3 |
| 42 | CAGGTAAAGCTGGAGGAGTCTGGGGGAGGCTTGGTGCAGCCTG GGGGGTCTCTGAGACTCTCCTGTGCAGCCTCTGAATTCACCTTC AGTAGCTCCTGGGGCATTGGGTCCGTCAGGCTCCAGGGAAGG GGCTCAAGTGGGTCTCAAGTATTAATTCTGGTGGCGAAGGCACA TACTATGCAGACTCCGTGAAGGGCCGATTCACCATCTCCAGAGA CAACGGCAAGAACACGCTGTATCTGGAAATGAACAGTCTGAAAT CTGAAGACACGGCCGTGTATTACTGCACATCAGCCTCCGGGGC GTGGGGCCAGGGGATCCAGGTCACCGTCTCCTCA | DI-E DNA |
| 43 | QVKLEESGGGLVQPGGSLRLSCAASEFTFSSSWGHWVRQAPGKG LKWVSSINSGGEGTYYADSVKGRFTISRDNGKNTLYLEMNSLKSED TAVYYCTSASGAWGQGIQVTVSS | DI-E V$_H$H |
| 44 | CAGGTAAAGCTGGAGGAGTCTGGGGGAGGCTTGGTGCAGGCT GGGGAGTCTCTGAGACTCTCCTGTGTAAATTCTGGAAGTACCTT CAGTATCTATGCCATGGGCTGGTACCGCCAGGCTCCAGGGAAG CAGCGCGAGTTGGTCGCAGCCATTAGTAGTGTTGGTAGGACAA ACTATGCAGACTCCGTGAAGGGCCGATTCACCATCTCCAGAGCC GGAGCCAAGAACACAGTCTATCTTCATATGAACAACCTTAAACC CGAGGACACGGCCGTCTATTCGTGTATAACGTACTACCAGAACG CAATGTATTTTGGCCAGGGCACCCAGGTCACCGTCTCCTCA | DI-H DNA |
| 45 | QVKLEESGGGLVQAGESLRLSCVNSGSTFSIYAMGWYRQAPGKQ RELVAAISSVGRTNYADSVKGRFTISRAGAKNTVYLHMNNLKPEDT AVYSCITYYQNAMYFGQGTQVTVSS | DI-H V$_H$H |

TABLE 7-continued

Nucleotide and amino acid sequences. CDR determination were done using the IMGT website.

| SEQ ID NO # | Sequence | Description |
| --- | --- | --- |
| 46 | CAGGTGCAGCTGGTGGAGTCTGGGGGAGGCTTGGTGCAGCCT GGGGGGTCTCTGAGACTCTCCTGTGCAGCCTCTGGATTCACCTT CAGTAACTACTGGATGTATTGGGTCCGACAGGCTCCAGGGAAG GGGCTCGAGCGGGTCTCATCCATTTATATCAGTGGTGGTAATAC ATACTATGCAGACTCCGTGAAGGGCCGATTCACCATCTCCAGAG ACAACGCCAAGAACACGCTGTATCTGCAAATGAATAGTCTGAAA TCTGAGGACACGGCCGTGTATTACTGTGTAAAAGGGGATACTTT TGGCGGCATGGACTATTGGGGCAAAGGGACCCAGGTCACCGTC TCCTCA | DI-4 DNA |
| 47 | QVQLVESGGGLVQPGGSLRLSCAASGFTFSNYWMYWVRQAPGK GLERVSSIYISGGNTYYADSVKGRFTISRDNAKNTLYLQMNSLKSED TAVYYCVKGDTFGGMDYWGKGTQVTVSS | DI-4 V$_H$H |
| 48 | CAGGCTCAGGTACAGCTGGTGGAGTCTGGGGGAGGATTGGTGC AGGCTGGGGGCTCTCTGAGACTCTCCTGTGCAGCCTCTGGACG CACCGTCAGTAGCTATACCATGGGCTGGTTCCGCCAGGCTCCA GGGAAGGAGCGTAGATTCGTAGCGACTGTTAATTCTAGTGGTAG AGGAACTCATTATGCAGACTCCGTGAAGGGCCGATTCACCATCT CCAGAGACAACGCCAAGAACACGGTGTATCTGCAAATGAACAGC CTGAAACCTGAGGACACGGCCGTTTATTACTGTGCAGCAGCTCC GTATCCCGACGGATCGCTGGGACCGGGATATGACTACTGGGGC CAGGGGACCCAGGTCACCGTCTCCTCA | DI-16 DNA |
| 49 | QAQVQLVESGGGLVQAGGSLRLSCAASGRTVSSYTMGWFRQAPG KERRFVATVNSSGRGTHYADSVKGRFTISRDNAKNTVYLQMNSLK PEDTAVYYCAAAPYPDGSLGPGYDYWGQGTQVTVSS | DI-16 V$_H$H |
| 50 | GRTVSSYT | DI-16 CDR1 |
| 51 | VNSSGRGT | DI-16 CDR2 |
| 52 | AAAPYPDGSLGPGYDY | DI-16 CDR3 |
| 53 | CAGGCTCAGGTACAGCTGGTGGAGTCTGGGGGAGGCTTGGTGC AGGCTGGGGGCTCTCTGAGACTCTCCTGTGCAGCCTCTGGACG CACGTTCAGTAGTTCTGGCATGGGCTGGTTCCGCCAGGCTCCA GGGAAGGACCGTGAACTTGTAGCAGGTATTAGTTGGAGTGGTG ATAGCGCATACTATGCAAACTCCGTGGCGGGCCGATTCACCATC TCCAGAGACAACATCAACAACACGGTGTATCTGCAAATGAATAG CCTGAAACCTGAGGACACGGCCGTTTATTACTGTGCAGCCCGAC AAGGTGGTCGTAACTACGCAACAAGTCCGCGAGAATATGACTAC TGGGGCCAGGGGACCCAGGTCACCGTCTCCTCA | DI-28 DNA |
| 54 | QAQVQLVESGGGLVQAGGSLRLSCAASGRTFSSSGMGWFRQAP GKDRELVAGISWSGDSAYYANSVAGRFTISRDNINNTVYLQMNSLK PEDTAVYYCAARQGGRNYATSPREYDYWGQGTQVTVSS | DI-28 V$_H$H |
| 55 | GRTFSSSG | DI-28 CDR1 |
| 56 | ISWSGDSA | DI-28 CDR2 |
| 57 | AARQGGRNYATSPREYDY | DI-28 CDR3 |
| 58 | CAGGCTCAGGTACAGCTGGTGGAGTCTGGGGGAGGATTGGTGC AGGCTGGGGGCTCTCTGAGACTCTCCTGTGCAGCCTCTGGACG CACCTTCAGTACCTATGTCATGGGCTGGTTCCGCCAGACTCCAG GGAAGGAGCGTGAGTTTGTAGCAGGTTTTAGTTGGAGTGGCGA TTACGCAATCTATGTCAACTCCGTGAAGGGCCGATTCACCATCT CCAGAGACAACGCCAAGAACACGGTGTATCTGCAAATGAACAGT CTGAGACCTGAGGACACGGCCGTTTATTACTGCGCAGCACGCC AACGAGGGGGCTATAGTGGTAGATCCTATTACACCGGGCGAAAT GACTATGAGTACTGGGGCCAGGGGACCCAGGTCACCGTCTCCT CA | DI-48 DNA |
| 59 | QAQVQLVESGGGLVQAGGSLRLSCAASGRTFSTYVMGWFRQTPG KEREFVAGFSWSGDYAIYVNSVKGRFTISRDNAKNTVYLQMNSLRP EDTAVYYCAARQRGGYSGRSYYTGRNDYEYWGQGTQVTVSS | DI-48 V$_H$H |
| 60 | EVQLQASGGGLVQAGGSLRLSCAASG | FR1 FC5 |
| 61 | MGWFRQAPGKEREFVSR | FR2 FC5 |
| 62 | FYSNSVKGRFTISRDNAKNTVYLQMNSLKPEDTADYYC | FR3 FC5 |

TABLE 7-continued

Nucleotide and amino acid sequences. CDR determination were done using the IMGT website.

| SEQ ID NO # | Sequence | Description |
|---|---|---|
| 63 | WGKGTQVTVSS | FR4 FC5 |
| 64 | GFKITHYT | CDR1 FC5 |
| 65 | ITWGGDNT | CDR2 FC5 |
| 66 | AAGSTSTATPLRVDY | CDR3 FC5 |
| 67 | MEFGLSWLFLVAILKGVQCEVQLQASGGGLVQAGGSLRLSCAASG FKITHYTMGWFRQAPGKEREFVSRITWGGDNTFYSNSVKGRFTISR DNAKNTVYLQMNSLKPEDTADYYCAAGSTKHKCFRNSLENNETLE SIMNTLESEEDFRKYFYYLEGSKDALLCGFSTDSGQCPEGYTCVKI GRNPDYGYRVDYWGKGTQVTVSS | FC5DIE3IR with examplary signal sequence |
| 68 | EVQLQASGGGLVQAGGSLRLSCAASGFKITHYTMGWFRQAPGKE REFVSRITWGGDNTFYSNSVKGRFTISRDNAKNTVYLQMNSLKPED TADYYCAAGSTKHKCFRNSLENNETLESIMNTLESEEDFRKYFYYL EGSKDALLCGFSTDSGQCPEGYTCVKIGRNPDYGYRVDYWGKGT QVTVSS | FC5DIE3IR without signal sequence |
| 69 | MEFGLSWLFLVAILKGVQC | signal sequence of FC5DIE3IR |
| 70 | MEFGLSWLFLVAILKGVQCEVQLQASGGGLVQAGGSLRLSCAASG FKITHYTMGWFRQAPGKEREFVSRITWGGDNTFYSNSVKGRFTISR DNAKNTVYLQMNSLKPEDTADYYCAAGSTXRVDYWGKGTQVTVS SAS | Immunogen with no epitope with exemplary signal sequence |
| 71 | EVQLQASGGGLVQAGGSLRLSCAASGFKITHYTMGWFRQAPGKE REFVSRITWGGDNTFYSNSVKGRFTISRDNAKNTVYLQMNSLKPED TADYYCAAGSTXRVDYWGKGTQVTVSSAS | Immunogen with no epitope without signal sequence |
| 72 | mamlpppgpq sfvhftkqsl alieqriaer kskepkeekk dddeeapkps sdleagkqlpfiygdippgm vsepledldp yyadkktfiv lnkgktifrf natpalymls pfsplrrisikilvhslfsm limctiltnc ifmtmnnppd wtknveytft giytfeslvk ilargfcvgeftflrdpwnw Idfvvivfay ltefvnlgnv salrtfrvlr alktisvipg lktivgaliqsvkklsdvmi ltvfclsvfa liglqlfmgn lkhkcfrnsl ennetlesim ntleseedfrkyfyylegsk dallcgfstd sgqcpegytc vkigrnpdyg ytsfdtfswa flalfrlmtqdywenlyqqt lraagktymi ffvvviflgs fylinlilav vamayeeqnq anieeakqkelefqqmldrl kkeqeeaeai aaaaaeytsi rrsrimglse sssetsklss ksakerrnrrkkknqkklss geekgdaekl sksesedsir rksfhlgveg hrrahekrls tpnqsplsirgslfsarrss rtslfsfkgr grdigsetef addehsifgd nesrrgslfv phrpqerrssnisqasrspp mlpvngkmhs avdcngvvsl vdgrsalmlp ngqilpegtt nqihkkrrcssyllsedmln dpnlrqrams rasiltntve eleesrqkcp pwwyrfahkf liwncspywikfkkciyfiv mdpfvdlait icivlntlfm amehhpmtee fknvlaignl vftgifaaemvlkliamdpy eyfqvgwnif dslivtlslv elfladvegl svlrsfrllr vfklakswptlnmlikiign svgalgnltl vlaiivfifa vvgmqlfgks ykecvckind dctlprwhmndffhsflivf rvlcgewiet mwdcmevagq amclivymmv mvignlwln lflalllssfssdnltaiee dpdannlqia vtrikkginy vkqtlrefil kafskkpkis reirqaedlntkkenyisnh tlaemskghn flkekdkisg fgssvdkhlm edsdgqsfih npsltvtvpiapgesdlenm naeelssdsd seyskvrlnr ssssecstvd nplpgegeea eaepmnsdepeacftdgcvr rfsccqvnie sgkgkiwwni rktcykiveh swfesfivlm illsssgalafediyierkkt ikiileyadk iftyifilem llkwiaygyk tyftnawcwl dflivdvslvtlvantlgys dlgpikslrt lralrplral srfegmrvvv naligaipsi mnvllvclifwlifsimgvn lfagkfyeci nttdgsrfpa sqvpnrsecf almnvsqnvr wknlkvnfdnvglgylsllq vatfkgwtii myaavdsvnv dkqpkyeysl ymyiyfvvfi ifgsffltlnlfigviidnfn qqkkklggqk ifmteeqkky ynamkklgsk kpqkpiprpg nkiqgcifdlvtnqafdisi mvliclnmvt mmvekegqsq hmtevlywin vvfiiltlge cvlklislrhyyftvgwnif dfvvviisiv gmfladliet yfvsptlfrv irlarigril rlvkgakgirtlllfalmmsl palfniglll flvmfiyaif gmsnfayvkk edgindmfnf etfgnsmiclfqittsagwd gllapilnsk ppdcdpkkvh pgssvegdcg npsvgifyfv syiiisflvvvnmyiavile nfsvateest eplseddfem fyevwekfdp datqfiefsk lsdfaaaldppliiakpnkv qliamdlpmv sgdrihcldi lfaftkrvlg esgemdslrs qmeerfmsanpskvsyepit ttlkrkqedv satviqrayr ryrlrqnvkn issiyikdgd rdddllnkkdmafdnvnens spektdatss ttsppsydsv tkpdkekyeq drtekedkgk dskeskk | Homo sapiens NP_002968 |

TABLE 7-continued

Nucleotide and amino acid sequences. CDR determination were done using the IMGT website.

| SEQ ID NO # | Sequence | Description |
|---|---|---|
| 73 | TGCCTGGTGACGTTCCCAAGCTGTGTCCTGTCCCAGGTGCAGC TGAAGGAGTCAGGACCTGGCCTGGTGGCACCCTCACAGAGCC TGTCCATCACATGCACTGTCTCTGGGTTCTCATTATCCAGATAT AATGTACACTGGGTTCGCCAGCCTCCAGGAAAGGGTCTGGAGT GGCTGGGAATGATATGGGGTGGTGGAAGCACAGACTATAATTC AGCTCTCAAATCCAGACTTAGCATCAGCAAGGACAACTCCAAG AGCCAAGTTTTCTTAAAAATGAACAGTCTGCAAACTGATGACA CAGCCATGTACTACTGTGCCAGAAATGGAGCTAACTGGGACTG GTTTGCTTACTGGGGCCAAGGGACTCTGGTCACTGTCTCTGCA GCCAAAACGACACCCCCATCTGTCTAT | 1B6 DNA-H variable region is in bold |
| 74 | CLVTFPSCVLSQVQLKESGPGLVAPSQSLSITCTVS<u>GFSLSRYNVH</u> WVRQPPGKGLEWLGM<u>IWGGGST</u>DYNSALKSRLSISKDNSKSQVFL KMNSLQTDDTAMYYC<u>ARNGANWDWFAY</u>WGQGTLVTVSAAKTTP PSVY | 1B6 Heavy chain with examplary leader sequence (CDR underlined) |
| 113 | QVQLKESGPGLVAPSQSLSITCTVSGFSLSRYNVHWVRQPPGKGL EWLGMIWGGGSTDYNSALKSRLSISKDNSKSQVFLKMNSLQTDDT AMYYCARNGANWDWFAYWGQGTLVTVSAAKTTPPSVY | 1B6 Heavy chain without leader sequence |
| 114 | QVQLKESGPGLVAPSQSLSITCTVSGFSLSRYNVHWVRQPPGKGL EWLGMIWGGGSTDYNSALKSRLSISKDNSKSQVFLKMNSLQTDDT AMYYCARNGANWDWFAYWGQGTLVTVSA | 1B6 VH |
| 75 | GFSLSRYN | 1B6 CDR1-H |
| 76 | IWGGGST | 1B6 CDR2-H |
| 77 | ARNGANWDWFAY | 1B6 CDR3-H |
| 78 | CTGCTATGGGTATCTGGTACCTGTGGGGACATTGTGATGTCACA GTCTCCATCCTCCCTACCTGTGTCAGTTGGAGAGAAGGTTACT ATGAGCTGCAAGTCCAGTCAGAGCCTTTTATATAGTAGCAATC AAAAGAACTACTTGGCCTGGTACCAGCAGAAACCAGGGCAGT CTCCTAAACTGCTGATTTACTGGGCATCCACTAGGGAATCTGG GGTCCCTGATCGCTTCACAGGCAGTGGATCTGGGACAGATTTC ACTCTCACCATCAGCAGTGTGAAGGCTGAAGACCTGGCAGTTT ATTACTGTCAGCAATATTATAGCTATCCATTCACGTTCGGCTCG GGGACAAAGTTGGAAATAAAACGGGCTGATGCTGCACCAACTG TATCCATCTTCCCACCATCCAGTGTC | 1B6 DNA-L variable region is in bold |
| 79 | LLWVSGTCGDIVMSQSPSSLPVSVGEKVTMSCKSS<u>QSLLYSSNQK NY</u>LAWYQQKPGQSPKLLIY<u>WAS</u>TRESGVPDRFTGSGSGTDFTLTIS SVKAEDLAVYYC<u>QQYYSYPFT</u>FGSGTKLEIKRADAAPTVSIFPPSSV | 1B6 Light chain with examplary leader sequence (CDR underlined) |
| 115 | DIVMSQSPSSLPVSVGEKVTMSCKSS<u>QSLLYSSNQKNY</u>LAWYQQK PGQSPKLLIY<u>WAS</u>TRESGVPDRFTGSGSGTDFTLTISSVKAEDLAV YYC<u>QQYYSYPFT</u>FGSGTKLEIKRADAAPTVSIFPPSSV | 1B6 Light chain without leader sequence (CDR underlined) |
| 116 | DIVMSQSPSSLPVSVGEKVTMSCKSSQSLLYSSNQKNYLAWYQQK PGQSPKLLIYWASTRESGVPDRFTGSGSGTDFTLTISSVKAEDLAV YYCQQYYSYPFTFGSGTKLEIK | 1B6 VL |
| 80 | QSLLYSSNQKNY | 1B6 CDR1-L |
| 81 | WAS | 1B6 CDR2-L |
| 82 | QQYYSYPFT | 1B6 CDR3-L |
| 83 | TTTTTGGTAGCAACAGCTACAGATGTCCACTCCCCAGGTCCAACT GCAGCAGCCTGGGGCTGAACTGGTGAAGCCTGGGGCTTCAGT GAAGCTGTCCTGCAAGGCTTCTGGCTACACCTTCACCACCTAC TGGATGCACTGGGTGAAGCAGAGGCCTGGACAAGGCCTTGAG TGGATTGGAGAGATTAATCCTAGCAACGGTCGTGCTAACTACA ATGAGAAGTTCAAGAGCAAGGCCACACTGACTGTAGACAAATC | 2G11 DNA-H variable region is in bold |

TABLE 7-continued

Nucleotide and amino acid sequences. CDR determination were done using the IMGT website.

| SEQ ID NO # | Sequence | Description |
| --- | --- | --- |
| | CTCCAGCACAGCCTACATGCAACTCAGCAGCCTGACATCTGAG<br>GACTCTGCGGTCTATTACTGTTTAAGATCACTAGGCTACTTTGA<br>CTACTGGGGCCAAGGCACCACTCTCACAGTCTCCTCAGCCAAA<br>ACAACAGCCCCATCGGTCTATCCACTGGCCCCTGGG | |
| 84 | FLVATATDVHSQVQLQQPGAELVKPGASVKLSCKASGYTFTTYWM<br>HWVKQRPGQGLEWIGEINPSNGRANYNEKFKSKATLTVDKSSSTA<br>YMQLSSLTSEDSAVYYCLRSLGYFDYWGQGTTLTVSSAKTTAPSV<br>YPLAPG | 2G11 Heavy chain with examplary leader sequence (CDR underlined) |
| 117 | QVQLQQPGAELVKPGASVKLSCKASGYTFTTYWMHWWKQRPGQ<br>GLEWIGEINPSNGRANYNEKFKSKATLTVDKSSSTAYMQLSSLTSE<br>DSAVYYCLRSLGYFDYWGQGTTLTVSSAKTTAPSVYPLAPG | 2G11 Heavy chain without leader sequence |
| 118 | QVQLQQPGAELVKPGASVKLSCKASGYTFTTYWMHWVKQRPGQ<br>GLEWIGEINPSNGRANYNEKFKSKATLTVDKSSSTAYMQLSSLTSE<br>DSAVYYCLRSLGYFDYWGQGTTLTVSS | 2G11 VH |
| 85 | GYTFTTYW | 2G11 CDR1-H |
| 86 | INPSNGRA | 2G11 CDR2-H |
| 87 | LRSLGYFDY | 2G11 CDR3-H |
| 88 | AAGTTGCCTGTTAGGCTGTTGGTGCTGATGTTCTGGATTCCTGC<br>TTCCAGCAGTGATGTTGTGATGACCCAAAGTCCACTCTCCCTGC<br>CTGTCAGTCTTGGAGATCAAGCCTCCATCTCTTGCAGATCTAGT<br>CAGAGCCTTGTACACAGTAATGGAAACACCTATTTACATTGGT<br>ACCTGCAGAAGGCAGGCCAGTCTCCAAAGTTCCTGATCTACAA<br>AGTTTCCAACCGATTTTCTGGGGTCCCAGACAGGTTCAGTGGC<br>AGTGGATCAGGGACAGATTTCACACTCAAGATCAGCAGAGTG<br>GAGGCTGAGGATCTGGGAGTTTATTTCTGCTCTCAAAGTACAC<br>ATGTTCCGTACACGTTCGGAGGGGGGACCAAGCTGGAAATAA<br>AACGGGCTGATGCTGCACCAACTGTATCCATCTTCCCACCATCC<br>AGT | 2G11 DNA-L variable region is in bold |
| 89 | KLPVRLLVLMFWIPASSSDVVMTQSPLSLPVSLGDQASISCRSSQS<br>LVHSNGNTYLHWYLQKAGQSPKFLIYKVSNRFSGVPDRFSGSGSG<br>TDFTLKISRVEAEDLGVYFCSQSTHVPYTFGGGTKLEIKRADAAPTV<br>SIFPPSS | 2G11 Light chain with examplary leader sequence (CDR underlined) |
| 119 | DVVMTQSPLSLPVSLGDQASISCRSSQSLVHSNGNTYLHWYLQKA<br>GQSPKFLIYKVSNRFSGVPDRFSGSGSGTDFTLKISRVEAEDLGVY<br>FCSQSTHVPYTFGGGTKLEIKRADAAPTVSIFPPSS | 2G11 Light chain without leader sequence |
| 120 | DVVMTQSPLSLPVSLGDQASISCRSSQSLVHSNGNTYLHWYLQKA<br>GQSPKFLIYKVSNRFSGVPDRFSGSGSGTDFTLKISRVEAEDLGVY<br>FCSQSTHVPYTFGGGTKLEIK | 2G11 VL |
| 90 | QSLVHSNGNTY | 2G11 CDR1-L |
| 91 | KVS | 2G11 CDR2-L |
| 92 | SQSTHVPYT | 2G11 CDR3-L |
| 93 | AGCTTGATTTTCCTTGTCCTTGTTTTAAAAGGTGTCCAGTGTGAG<br>GTGAAGCTGGTGGAGTCTGGGGGAGGCTTAGTGAAGCCTGGA<br>GGGTCCCTGAAACTCTCCTGTGCAGCCTCTGGATTCACTTTCA<br>GAAGTTATGCCATGTCTTGGGTTCGCCAGACTCCAGAAAAGGG<br>GCTGGAGTGGGTCGCATCCATTAGTAGTGGTGGTAGCACCTAC<br>TATCCAGACAGTGTGAAGGGCCGATTCACCATCTCCAGAGATA<br>ATGCCGGGAACATCCTGTACCTGCAAATGAGCAGTCTGAGGTC<br>TGAGGACACGGCCATGTATTACTGTGCAAGAGGCTATGATGGT<br>TACTACGAGAGGATATGGTACTATGCTATGGACTATTGGGGTC<br>AAGGAACCTCAGTCACCGTCTCCTCAGCCAAAACGACACCCCC<br>ATCTGTCTAT | 1H5 DNA-H variable region is in bold |

TABLE 7-continued

Nucleotide and amino acid sequences. CDR determination were done using the IMGT website.

| SEQ ID NO # | Sequence | Description |
|---|---|---|
| 94 | SLIFLVLVLKGVQCEVKLVESGGGLVKPGGSLKLSCAASG<u>FTFRSY</u><br><u>AMS</u>WVRQTPEKGLEWVAS<u>ISSGGST</u>YYPDSVKGRFTISR<u>DNAGNIL</u><br><u>YLQMSSLRSEDTAMYYC</u><u>ARGYDGYYERIWYYAMDY</u>WGQGTSVTV<br>SSAKTTPPSVY | 1H5 Heavy chain with examplary leader sequence (CDR underlined) |
| 121 | EVKLVESGGGLVKPGGSLKLSCAASGFTFRSYAMSWVRQTPEKGL<br>EWVASISSGGSTYYPDSVKGRFTISRDNAGNILYLQMSSLRSEDTA<br>MYYCARGYDGYYERIWYYAMDYWGQGTSVTVSSAKTTPPSVY | 1H5 Heavy chain without leader sequence |
| 122 | EVKLVESGGGLVKPGGSLKLSCAASGFTFRSYAMSWVRQTPEKGL<br>EWVASISSGGSTYYPDSVKGRFTISRDNAGNILYLQMSSLRSEDTA<br>MYYCARGYDGYYERIWYYAMDYWGQGTSVTVSS | 1H5 VH |
| 95 | GFTFRSYA | 1H5 CDR1-H |
| 96 | ISSGGST | 1H5 CDR2-H |
| 97 | ARGYDGYYERIWYYAMDY | 1H5 CDR3-H |
| 98 | CAGGTCTTTGTATACATGTTGCTGTGGTTGTCTGGTGTTGATGG<br>AGACATTGTGATGACCCAGTCTCAAAAATTCATGTCCACATCA<br>GTAGGAGACAGGGTCACTGTCTCCTGCAAGGCCAGTCAGAAT<br>GTGGGTACTATTGTAGCCTGGTATCAACAAAAACCAGGTCAAT<br>CTCCTAAAGCACTGATTTACTCGGCATCCTACCGGTTCAGTGG<br>AGTCCCTGATCGCTTCACAGGCAGTGGATCTGGGACAGATTTC<br>ACTCTCACCATCAGCAATGTGCAGTCTGAAGACTTGGCAGAGT<br>ATTTCTGTCAGCAATATAACACCTATCCTCTCACGTTCGGCTCG<br>GGGACAAAGTTGGAAATAAAACGGGCTGATGCTGCACCAACTG<br>TATCCATCTTCCCACCATCCAGT | 1H5 DNA-L variable region is in bold |
| 99 | QVFVYMLLWLSGVDGDIVMTQSQKFMSTSVGDRVTVSCKAS<u>QNV</u><br><u>GTIVA</u>WYQQKPGQSPKALIY<u>SAS</u>YRFSGVPDRFTGSGSGTDFTLTI<br>SNVQSEDLAEYFC<u>QQYNTYPLT</u>FGSGTKLEIKRADAAPTVSIFPPSS | 1H5 Light chain with examplary leader sequence (CDR underlined) |
| 123 | DIVMTQSQKFMSTSVGDRVTVSCKASQNVGTIVAWYQQKPGQSPK<br>ALIYSASYRFSGVPDRFTGSGSGTDFTLTISNVQSEDLAEYFCQQY<br>NTYPLTFGSGTKLEIKRADAAPTVSIFPPSS | 1H5 Light chain without leader sequence |
| 124 | DIVMTQSQKFMSTSVGDRVTVSCKASQNVGTIVAWYQQKPGQSPK<br>ALIYSASYRFSGVPDRFTGSGSGTDFTLTISNVQSEDLAEYFCQQY<br>NTYPLTFGSGTKLEIK | 1H5 VL |
| 100 | QNVGTI | 1H5 CDR1-L |
| 101 | SAS | 1H5 CDR2-L |
| 102 | QQYNTYPLT | 1H5 CDR3-L |
| 103 | TLESEEDFRKYFYYLEGSKD | peptide#2a 20aa |
| 104 | YFYYLEGSKDALLCGFSTDS | peptide#2b 20aa |
| 105 | KHKCFRNSLENNETLESIMNTLESEEDFRKYFYYLEGSKD | peptide#40a 40aa |
| 106 | YFYYLEGSKDALLCGFSTDSGQCPEGYTCVKIGRNPDYGY | peptide#40b 40aa |
| 107 | FRKYFY | residues Phe129-Tyr134 of FC5DIE3IR |

TABLE 7-continued

Nucleotide and amino acid sequences. CDR determination were done using the IMGT website.

| SEQ ID NO # | Sequence | Description |
| --- | --- | --- |
| 108 | NTLESEED | residues Asn121-Asp128 of FC5DIE3IR |
| 125 | ATGCCTCTGCTGCTGCTGCTGCCTCTGCTGTGGGCCGGGGCTC<br>TGGCTCAGGTCCAGCTGCAGCAGCCTGGTGCCGAACTGGTCAA<br>GCCAGGCGCCAGCGTGAAGCTGTCTTGCAAGGCTTCCGGCTAC<br>ACCTTCACAAACTATTGGATGCACTGGGTGAAGCAGAGGCCCG<br>GACAGGGCCTGGAGTGGATCGGAGAGATCAACCCTAGCAATGG<br>CCGGGCCAACTACAATGAGAAGTTTAAGTCTAAGGCTACCCTGA<br>CAGTGGACAAGTCCAGCTCTACCGCCTATATGCAGCTGTCCAGC<br>CTGACATCTGAGGATTCCGCCGTGTACATTGTGCTAGGTCTCC<br>ATACGGTTACTACGACTATTGGGGCAGGGGACAACTCTGACTG<br>TGAGCAGCGCTAGCACAAAAGGGCCATCCGTGTTTCCTCTGGCT<br>CCATCCTCAAAATCAACTTCTGGGGGACTGCTGCTCTGGGCTG<br>CCTGGTGAAGGACTACTTCCCAGAGCCCGTCACCGTGTCATGG<br>AACAGCGGAGCACTGACTAGCGGAGTCCACACCTTTCCAGCAG<br>TGCTGCAGAGCTCCGGACTGTACTCCCTGTCTAGTGTGGTCACA<br>GTGCCTTCAAGCTCCCTGGGGACTCAGACCTATATCTGCAACGT<br>GAATCACAAGCCCTCCAATACTAAGGTCGACAAACGAGTGGAGC<br>CTAAGTCTTGTGATAAAACACATACTTGCCCCCCTTGTCCTGCAC<br>CAGAACTGCTGGGAGGACCTAGCGTGTTCCTGTTTCCACCCAAG<br>CCAAAAGACACCCTGATGATTAGTAGAACCCCTGAGGTCACATG<br>CGTGGTCGTGGACGTGAGCCACGAGGACCCCGAAGTCAAGTTC<br>AACTGGTACGTGGATGGCGTCGAAGTGCATAATGCTAAGACAAA<br>ACCCCGGGAGGAACAGTACAACAGTACCTATAGAGTCGTGTCA<br>GTCCTGACAGTGCTGCATCAGGATTGGCTGAACGGGAAAGAGT<br>ATAAGTGCAAAGTGTCCAATAAGGCCCTGCCCGCTCCTATCGAG<br>AAAACTATTTCTAAGGCTAAAGGCCAGCCAAGGGAACCCCAGGT<br>GTACACCCTGCCTCCATCACGCGAGGAAATGACAAAGAACCAG<br>GTCAGCCTGACTTGTCTGGTGAAAGGGTTCTATCCATCTGACAT<br>CGCAGTGGAGTGGGAAAGTAATGGACAGCCCGAAAACAATTAC<br>AAGACCACACCCCCTGTGCTGGACTCCGATGGATCTTTCTTTCT<br>GTATAGCAAGCTGACCGTGGATAAATCCCGGTGGCAGCAGGGC<br>AATGTCTTTTCTTGTAGTGTGATGCACGAAGCCCTGCATAACCAT<br>TACACCCAGAAAAGCCTGAGCCTGTCCCCCGGCAAG | hFc-F233-3A8 DNA-H |
| 126 | MPLLLLLPLLWAGALAQVQLQQPGAELVKPGASVKLSCKASGYTF<br>TNYWMHWVKQRPGQGLEWIGEINPSNGRANYNEKFKSKATLTVD<br>KSSSTAYMQLSSLTSEDSAVYYCARSPYGYYDYWGQGTTLTVSSA<br>STKGPSVFPLAPSSKSTSGGTAALGCLVKDYFPEPVTVSWNSGALT<br>SGVHTFPAVLQSSGLYSLSSVVTVPSSSLGTQTYICNVNHKPSNTK<br>VDKRVEPKSCDKTHTCPPCPAPELLGGPSVFLFPPKPKDTLMISRT<br>PEVTCVVVDVSHEDPEVKFNWYVDGVEVHNAKTKPREEQYNSTY<br>RVVSVLTVLHQDWLNGKEYKCKVSNKALPAPIEKTISKAKGQPREP<br>QVYTLPPSREEMTKNQVSLTCLVKGFYPSDIAVEWESNGQPENNY<br>KTTPPVLDSDGSFFLYSKLTVDKSRWQQGNVFSCSVMHEALHNHY<br>TQKSLSLSPGK | hFc-F233-3A8 AA-H with examplary signal peptide in bold |
| 127 | ATGCGGCTGCCTGCTCAGCTGCTGGGCCTGCTGATGCTGTGGG<br>TGTCCGGCTCCTCTGGGGATGTGCTGATGACTCAGACTCCTCTG<br>AGCCTGCCAGTGTCTCTGGGCGACCAGGCCTCTATCTCCTGCA<br>GATCCAGCCAGTCCCTGCTGCACAGCAACGGCAATACCTACTTC<br>CATTGGTATCTGCAGAAGCCCGGCCAGTCTCCTAAGCTGCTGAT<br>CTACAAGGTGTCCAACAGGTTCTTTGGCGTGCCCGACCGGTTCA<br>GCGGATCTGGATCCGGCACCGACTTCACCCTGAAGATCAGCCG<br>CGTGGAGGCTGAAGACCTGGGCGTGTATTTTGTTCACAGATTA<br>CTCATGTCCCCCTGACCTTTGGTGCCGGTACCAAAGTGGAGATC<br>AAGCGAACTGTGGCCGCTCCAAGTGTCTTCATTTTTCCACCCTC<br>CGACGAACAGCTGAAGAGCGGAACAGCATCTGTGGTCTGTCTG<br>CTGAACAATTTCTACCCCAGGGAAGCTAAAGTGCAGTGGAAGGT<br>CGATAACGCACTGCAGTCTGGCAATAGTCAGGAGTCAGTGACA<br>GAACAGGACTCCAAAGATAGCACTTATTCTCTGTCTAGTACCCT<br>GACACTGTCTAAGGCCGACTACGAGAAGCATAAAGTGTATGCTT<br>GTGAAGTCACTCATCAGGGGCTGTCTTCTCCAGTGACCAAGTCC<br>TTCAATAGGGGCGAATGT | hFc-F233-3A8 DNA-L |
| 128 | MRLPAQLLGLLMLWVSGSSGDVLMTQTPLSLPVSLGDQASISCRS<br>SQSLLHSNGNTYFHWYLQKPGQSPKLLIYKVSNRFFGVPDRFSGS<br>GSGTDFTLKISRVEAEDLGVYFCSQITHVPLTFGAGTKVEIKRTVAA<br>PSVFIFPPSDEQLKSGTASVVCLLNNFYPREAKVQWKVDNALQSG<br>NSQESVTEQDSKDSTYSLSSTLTLSKADYEKHKVYACEVTHQGLSS<br>PVTKSFNRGEC | hFc-F233-3A8 AA-L with examplary signal peptide in bold |

TABLE 7-continued

Nucleotide and amino acid sequences. CDR determination were done using the IMGT website.

| SEQ ID NO # | Sequence | Description |
|---|---|---|
| 129 | ATGCCTCTGCTGCTGCTGCTGCCTCTGCTGTGGGCTGGGGCTC<br>TGGCTCAGGTCCAGCTGAAAGAAAGCGGTCCCGGTCTGGTCGC<br>CCCATCCCAGAGCCTGTCTATCACCTGCACAGTGAGCGGCTTCT<br>CCCTGAGCAGGTACAACGTGCACTGGGTGCGGCAGCCACCTGG<br>CAAGGGCCTGGAGTGGCTGGGAATGATCTGGGGAGGAGGCTCT<br>ACCGACTATAATTCCGCCCTGAAGAGCAGACTGTCTATCTCCAA<br>GGATAACAGCAAGTCTCAGGTGTTTCTGAAGATGAACTCCCTGC<br>AGACCGACGATACAGCCATGTACTATTGTGCTCGCAACGGTGCC<br>AACTGGGACTGGTTTGCCTACTGGGGTCAGGGAACTCTGGTCA<br>CTGTCAGCAGCGCTAGCACAAAAGGGCCATCCGTGTTCCTCTG<br>GCTCCATCCTCAAAATCAACTTCTGGGGGACTGCTGCTCTGGG<br>CTGCCTGGTGAAGGACTACTTCCCAGAGCCCGTCACCGTGTCAT<br>GGAACAGCGGAGCACTGACTAGCGGAGTCCACACCTTTCCAGC<br>AGTGCTGCAGAGCTCCGGACTGTACTCCCTGTCTAGTGTGGTCA<br>CAGTGCCTTCAAGCTCCCTGGGGACTCAGACCTATATCTGCAAC<br>GTGAATCACAAGCCCTCCAATACTAAGGTCGACAAACGAGTGGA<br>GCCTAAGTCTTGTGATAAAACACATACTTGCCCCCCTTGTCCTG<br>CACCAGAACTGCTGGGAGGACCTAGCGTGTTCCTGTTTCCACCC<br>AAGCCAAAAGACACCCTGATGATTAGTAGAACCCCTGAGGTCAC<br>ATGCGTGGTCGTGGACGTGAGCCACGAGGACCCCGAAGTCAAG<br>TTCAACTGGTACGTGGATGGCGTCGAAGTGCATAATGCTAAGAC<br>AAAACCCCGGGAGGAACAGTACAACAGTACCTATAGAGTCGTGT<br>CAGTCCTGACAGTGCTGCATCAGGATTGGCTGAACGGGAAAGA<br>GTATAAGTGCAAAGTGTCCAATAAGGCCCTGCCCGCTCCTATCG<br>AGAAAACTATTTCTAAGGCTAAAGGCCAGCCAAGGGAACCCCAG<br>GTGTACACCCTGCCTCCATCACGCGAGGAAATGACAAAGAACCA<br>GGTCAGCCTGACTTGTCTGGTGAAAGGGTTCTATCCATCTGACA<br>TCGCAGTGGAGTGGGAAAGTAATGGACAGCCCGAAAACAATTAC<br>AAGACCACACCCCCTGTGCTGGACTCCGATGGATCTTTCTTTCT<br>GTATAGCAAGCTGACCGTGGATAAATCCCGGTGGCAGCAGGGC<br>AATGTCTTTTCTTGTAGTGTGATGCACGAAGCCCTGCATAACCAT<br>TACACCCAGAAAAGCCTGAGCCTGTCCCCGGCAAG | hFc-F236-1B6<br>DNA-H |
| 130 | MPLLLLLPLLWAGALAQVQLKESGPGLVAPSQSLSITCTVSGFSLS<br>RYNVHWVRQPPGKGLEWLGMIWGGGSTDYNSALKSRLSISKDNS<br>KSQVFLKMNSLQTDDTAMYYCARNGANWDWFAYWGQGTLVTVS<br>SASTKGPSVFPLAPSSKSTSGGTAALGCLVKDYFPEPVTVSWNSG<br>ALTSGVHTFPAVLQSSGLYSLSSVVTVPSSSLGTQTYICNVNHKPS<br>NTKVDKRVEPKSCDKTHTCPPCPAPELLGGPSVFLFPPKPKDTLMI<br>SRTPEVTCVVVDVSHEDPEVKFNWYVDGVEVHNAKTKPREEQYN<br>STYRVVSVLTVLHQDWLNGKEYKCKVSNKALPAPIEKTISKAKGQP<br>REPQVYTLPPSREEMTKNQVSLTCLVKGFYPSDIAVEWESNGQPE<br>NNYKTTPPVLDSDGSFFLYSKLTVDKSRWQQGNVFSCSVMHEALH<br>NHYTQKSLSLSPGK | hFc-F236-1B6<br>AA-H with<br>examplary<br>signal peptide<br>in bold |
| 131 | ATGCGCCTGCCTGCTCAGCTGCTGGGCCTGCTGATGCTGTGGG<br>TCTCTGGGTCCTCTGGGGATATTGTCATGTCTCAGTCACCAAGC<br>TCTCTGCCAGTGTCCGTGGGCGAGAAGGTGACCATGTCCTGCA<br>AGTCCAGCCAGAGCCTGCTGTACTCTTCCAACCAGAAGAATTAC<br>CTGGCCTGGTATCAGCAGAAGCCCGGCCAGTCTCCTAAGCTGC<br>TGATCTATTGGGCTAGCACAAGGGAGTCTGGCGTGCCCGACCG<br>GTTCACCGGATCCGGAAGCGGCACAGACTTCACCCTGACAATC<br>AGCTCTGTGAAGGCCGAGGACCTGGCAGTCTATTATTGTCAGCA<br>GTATTACAGCTATCCATTCACTTTTGGCAGCGGTACCAAAGTGG<br>AGATCAAGCGAACTGTGGCCGCTCCAAGTGTCTTCATTTTTCCA<br>CCCTCCGACGAGCAGCTGAAGAGCGGAACAGCATCTGTGGTCT<br>GTCTGCTGAACAATTTCTACCCCAGGGAAGCTAAAGTGCAGTGG<br>AAGGTCGATAACGCACTGCAGTCTGGCAATAGTCAGGAGTCAGT<br>GACAGAACAGGACTCCAAAGATAGCACTTATTCTCTGTCTAGTA<br>CCCTGACACTGTCTAAGGCCGACTACGAGAAGCATAAAGTGTAT<br>GCTTGTGAAGTCACTCATCAGGGGCTGTCTTCTCCAGTGACCAA<br>GTCCTTCAATAGGGGCGAATGT | hFc-F236-1B6<br>DNA-L |
| 132 | MRLPAQLLGLLMLWVSGSSGDIVMSQSPSSLPVSVGEKVTMSCK<br>SSQSLLYSSNQKNYLAWYQQKPGQSPKLLIYWASTRESGVPDRFT<br>GSGSGTDFTLTISSVKAEDLAVYYCQQYYSYPFTFGSGTKVEIKRTV<br>AAPSVFIFPPSDEQLKSGTASVVCLLNNFYPREAKVQWKVDNALQS<br>GNSQESVTEQDSKDSTYSLSSTLTLSKADYEKHKVYACEVTHQGL<br>SSPVTKSFNRGEC | hFc-F236-1B6<br>AA-L with<br>examplary<br>signal peptide<br>in bold |

While the invention has been described in connection with specific embodiments thereof, it will be understood that the scope of the claims should not be limited by the preferred embodiments set forth in the examples, but should be given the broadest interpretation consistent with the description as a whole.

REFERENCES

Arbabi-Ghahroudi M, Tanha J, MacKenzie R (2009). Isolation of monoclonal antibody fragments from phage display libraries. Methods Mol Biol 502: 341-364.

Altschul S F, Madden T L, Schaffer A A, Zhang J, Zhang Z, Miller W, Lipman D J (1997). Gapped BLAST and PSI-BLAST: a new generation of protein database search programs. Nucleic Acids Res 25: 3389-3402.

Baral T N, MacKenzie R, Arbabi Ghahroudi M (2013). Single-domain antibodies and their utility. Curr Protoc Immunol 103: Unit 2 17.

Diss J K J, Archer S N, Hirano J, Fraser S P, Djamgoz M B A (2001). Expression profiles of voltage-gated Na channel a-subunit genes in rat and human prostate cancer cell lines. Prostate 48: 1-14. doi:10.1002/pros.1095.

Deuis J R, Wingerd J S, Winter Z, Durek T, Dekan Z, Sousa S R, Zimmermann K, Hoffmann T, Weidner C, Nassar M A, Alewood P F, Lewis R J and Vetter 1 (2016). Analgesic effects of GpTx-1, PF-04856264 and CNV1014802 in a mouse model of $Na_v1.7$-mediated main. Toxins 8, 78. doi:10.3390/toxins8030078

Fraser S P, Diss J K, Chioni A M, Mycielska M E, Pan H, Yamaci R F, Pani F, Siwy Z, Krasowska M, Grzywna Z, Brackenbury W J, Theodorou D, Koyuturk M, Kaya H, Battaloglu E, De Bella M T, Slade M J, Tolhurst R, Palmieri C, Jiang J, Latchman D S, Coombes R C, Djamgoz M B (2005). Voltage-gated sodium channel expression and potentiation of human breast cancer metastasis. Clin Cancer Res 11: 5381-5389. doi:10.1158/1078-0432.

Grimes J A, Fraser S P, Stephens G J, Downing J E, Laniado M E, Foster C S, Abel P D and Djamgoz M B (1995). Differential expression of voltage-activated $Na^+$ currents in two prostatic tumour cell lines: contribution to invasiveness in vitro. FEBS Lett 369, 290-294.

Hussack G, Arbabi-Ghahroudi M, van Faassen H, Songer J G, Ng K K, MacKenzie R, Tanha J (2011). Neutralization of *Clostridium difficile* toxin A with single-domain antibodies targeting the cell receptor binding domain. J Biol Chem 286: 8961-8976. doi: 10.1074/jbc.M110.198754.

Hussack G, Arbabi-Ghahroudi M, Mackenzie C R, Tanha J (2012). Isolation and characterization of *Clostridium difficile* toxin-specific single-domain antibodies. Methods Mol Biol 911:211-39.

Kabat, E. A. et al., Sequences of Proteins of Immunological Interest, Fifth Edition, U.S. Department of Health and Human Services, U.S. Government Printing Office (1991)

Kumaran J, Mackenzie C R, Arbabi-Ghahroudi M (2012). Semi-automated panning of naive camelidae libraries and selection of single-domain antibodies against peptide antigens. Methods Mol Biol 911:105-124. doi: 10.1007/978-1-61779-968-6_7.

Laniado M E, Lalani E N, Fraser S P, Grimes J A, Bhangal G, Djamgoz M B and Abel P D (1997). Expression and functional analysis of voltage-activated $Na^+$ channels in human prostate cancer cell lines and their contribution to invasion in vitro. Am J of Path 150, 1213-1221.

Moreno M J, Ball M, Andrade M F, McDermid A, and Stanimirovic D B (2006). Insulin-like growth factor binding protein-4 (IGFBP-4) is a novel anti-angiogenic and anti-tumorigenic mediator secreted by dibutyryl cyclic AMP (dB-cAMP)-differentiated glioblastoma cells. Glia 53, 845-857.

Payandeh J, Scheuer T, Zheng N, Catterall W A (2011). The crystal structure of a voltage-gated sodium channel. Nature 475, 353-358.

Raymond C, Robotham A, Spearman M, Butler M, Kelly J, Durocher Y (2015). Production of α2,6-sialylated IgG1 in CHO cells. MAbs 7(3):571-83. doi: 10.1080/19420862.2015.1029215.

Rey M, Sarpe V, Burns K M, Buse J, Baker C A, van Dijk M, Worderman L, Bonvin A M, Schriemer D C (2016). Mass Spec Studio for integrative structural biology. Structure 22(10):1538-48.

Roger S, Rollin J, Barascu A, Besson P, Raynal P I, Iochmann S, Lei M, Bougnoux P, Gruel Y, Le Guennec J Y (2007). Voltage-gated sodium channels potentiate the invasive capacities of human non-small-cell lung cancer cell lines. Int J Biochem Cell Biol 39: 774-786. doi: 10.1016/j.biocel. 2006.12.007.

Shaolong Z, Liuini P, Ettore L, Chen T, Szeto J, Carpick B, James, D. A., Wilson, D. J. (2018) Hydrogen-deuterium exchange epitope mapping reveals distinct neutralizing mechanisms for two monoclonal antibodies against diphtheria toxin. Biochemistry, 58(6): 646-56.

Shen H, Zhou Q, Pan X, Li Z, Wu J, Yan N (2017) Structure of a eukaryotic voltage-gated sodium channel at near-atomic resolution. Science 355, eaa14326; DOI: 10.1126/science.aa14326. U.S. Pat. No. 8,383,107.

U.S. Pat. No. 8,715,659.

Webster C I, Caram-Salas N, Haqqani A S, Thom G, Brown L, Rennie K, Yogi A, Costain W, Brunette E, Stanimirovic D B (2016). Brain penetration, target engagement, and disposition of the blood-brain barrier-crossing bispecific antibody antagonist of metabotropic glutamate receptor type 1. FASEB J 30(5), 1927-1940.

Yildirim S, Altun S, Gumushan H, Patel A and Djamgoz MBA (2012). Voltage-gated sodium channel activity promotes prostate cancer metastasis in vivo. Cancer Lett 323, 58-61.

What is claimed is:

1. An antibody or antigen-binding fragment that binds specifically to loop 3 of a domain I (DI) of a $Na_v$ 1.7 polypeptide, and which inhibits the flux of $Na^+$ through an $hNA_v$ 1.7 channel, wherein the antibody comprises three variable heavy domain complementarity determining regions (CDR) (CDR H1, H2 and H3), and three variable light domain CDR (CDR L1, L2 and L3), said CDR H1, H2, H3, L1, L2, and L3 comprising the amino acid sequences:

CDR H1: GYTFTNYW (SEQ ID NO:7),
CDR H2: INPSNGRA (SEQ ID NO:8),
CDR H3: ARSPYGYYDY (SEQ ID NO:9),
CDR L1: QSLLHSNGNTY (SEQ ID NO:13),
CDR L2: KVS (SEQ ID NO:14), and
CDR L3: SQITHVPLT (SEQ ID NO:15); respectively;

or

CDR H1: GFSLSRYN (SEQ ID NO:75),
CDR H2: IWGGGST (SEQ ID NO:76),
CDR H3: ARNGANWDWFAY (SEQ ID NO:77),
CDR L1: QSLLYSSNQKNY (SEQ ID NO:80),
CDR L2: WAS (SEQ ID NO:81), and
CDR L3: QQYYSYPFT (SEQ ID NO:82), respectively;

or

CDR H1: GYTFTTYW (SEQ ID NO: 85),
CDR H2: INPSNGRA (SEQ ID NO:86),
CDR H3: LRSLGYFDY (SEQ ID NO:87),
CDR L1: QSLVHSNGNTY (SEQ ID NO:90),
CDR L2: KVS (SEQ ID NO:91), and
CDR L3: SQSTHVPYT (SEQ ID NO:92), respectively;

or

CDR H1: GFTFRSYA (SEQ ID NO:95),
CDR H2: ISSGGST (SEQ ID NO:96),
CDR H3: ARGYDGYYERIWYYAMDY (SEQ ID NO:97),
CDR L1: QNVGTI (SEQ ID NO:100),
CDR L2: SAS (SEQ ID NO:101), and
CDR L3: QQYNTYPLT (SEQ ID NO:102), respectively;

and wherein said antigen-binding fragment comprises three variable domain complementarity determining regions (CDR)(CDR 1, 2 and 3), comprising the amino acid sequences CDR 1: GFAFSSAP (SEQ ID NO:39),
CDR 2: IESDQDHTI (SEQ ID NO:40), and
CDR 3: QKRGEKKT (SEQ ID NO:41), respectively.

2. The antibody or antigen-binding fragment of claim 1, wherein said antibody comprises a variable heavy domain ($V_H$) comprising the amino acid sequence:

```
                                                   (SEQ ID NO: 109)
QVQLQQPGAELVKPGASVKLSCKASGYTFTNYWMHWVKQRPGQGLEWIGE

INPSNGRANYNEKFKSKATLTVDKSSSTAYMQLSSLTSEDSAVYYCARSP

YGYYDYWGQGTTLTVSS
``` and a variable light domain ($V_L$) comprising the amino acid sequence:

```
                                                   (SEQ ID NO: 110)
DVLMTQTPLSLPVSLGDQASISCRSSQSLLHSNGNTYFHWYLQKPGQSPK

LLIYKVSNRFFGVPDRFSGSGSGTDFTLKISRVEAEDLGVYFCSQITHVP

LTFGAGTKLELK.
```

3. The antibody or antigen-binding fragment of claim 1, wherein said antibody comprises a variable heavy domain ($V_H$) comprising the amino acid sequence:

```
                                                   (SEQ ID NO: 114)
QVQLKESGPGLVAPSQSLSITCTVSGFSLSRYNVHWVRQPPGKGLEWLGM

IWGGGSTDYNSALKSRLSISKDNSKSQVFLKMNSLQTDDTAMYYCARNGA

NWDWFAYWGQGTLVTVSA
``` and a variable light domain ($V_L$) comprising the amino acid sequence:

```
                                                   (SEQ ID NO: 116)
DIVMSQSPSSLPVSVGEKVTMSCKSSQSLLYSSNQKNYLAWYQQKPGQSP

KLLIYWASTRESGVPDRFTGSGSGTDFTLTISSVKAEDLAVYYCQQYYSY

PFTFGSGTKLEIK.
```

4. The antibody or antigen-binding fragment of claim 1, wherein said antibody comprises a variable heavy domain ($V_H$) comprising the amino acid sequence:

(SEQ ID NO: 118)
QVQLQQPGAELVKPGASVKLSCKASGYTFTTYWMHWVKQRPGQGLEWIGE

INPSNGRANYNEKFKSKATLTVDKSSSTAYMQLSSLTSEDSAVYYCLRSL

GYFDYWGQGTTLTVSS and a variable light domain (V$_L$) comprising the amino acid sequence:

(SEQ ID NO: 120)
DVVMTQSPLSLPVSLGDQASISCRSSQSLVHSNGNTYLHWYLQKAGQSPK

FLIYKVSNRFSGVPDRFSGSGSGTDFTLKISRVEAEDLGVYFCSQSTHVP

YTFGGGTKLEIK.

5. The antibody or antigen-binding fragment of claim 1, wherein said antibody comprises a variable heavy domain (V$_H$) comprising the amino acid sequence:

(SEQ ID NO: 122)
EVKLVESGGGLVKPGGSLKLSCAASGFTFRSYAMSWVRQTPEKGLEWVAS

ISSGGSTYYPDSVKGRFTISRDNAGNILYLQMSSLRSEDTAMYYCARGYD

GYYERIWYYAMDYWGQGTSVTVSS and a variable light domain (V$_L$) comprising the amino acid sequence:

(SEQ ID NO: 124)
DIVMTQSQKFMSTSVGDRVTVSCKASQNVGTIVAWYQQKPGQSPKALIYS

ASYRFSGVPDRFTGSGSGTDFTLTISNVQSEDLAEYFCQQYNTYPLTFGS

GTKLEIK.

6. The antibody or antigen-binding fragment of claim 1, wherein said antigen-binding fragment comprises the amino acid sequence:

(SEQ ID NO: 38)
QVKLEESGGGLVQPGGSLKLSCVASGFAFSSAPMDWVRKAPGKDVEWLST

IESDQDHTIYYANSVKGRFTISRDDVQNILYLQMNDLKIEDTATYYCQKR

GEKKTRGQGTQVTVSS.

7. The antibody or antigen-binding fragment of claim 1, wherein said antibody is a monoclonal antibody.

8. The antibody or antigen-binding fragment of claim 1, wherein said antibody is an IgA, IgD, IgE, IgG, or IgM.

9. The antibody or antigen-binding fragment of claim 1, wherein said antigen-binding fragment is a single-domain antibody (sdAb) or a single-chain variable fragment (scFv).

10. The antibody or antigen-binding fragment of claim 9, wherein said sdAb is a camelid antibody.

11. The antibody or antigen-binding fragment of claim 1, wherein said antibody or antigen-binding fragment is in a multivalent display format.

12. The antibody or antigen-binding fragment of claim 1, wherein said antibody or an antigen-binding fragment is humanized.

13. A V$_H$H camelid single domain antibody that binds specifically to loop 3 of a domain I (DI) of a Na$_v$ 1.7 polypeptide, and which inhibits the flux of Na$^+$ through an hNA$_v$ 1.7 channel,
wherein said V$_H$H antibody comprises three variable domain complementarity determining regions (CDR) (CDR 1, 2 and 3), comprising the amino acid sequences:
CDR 1: GFAFSSAP (SEQ ID NO:39),
CDR 2: IESDQDHTI (SEQ ID NO:40), and
CDR 3: QKRGEKKT (SEQ ID NO:41), respectively.

14. A chimeric protein comprising the V$_H$H camelid single domain antibody of claim 13 linked to an antibody operable to transmigrate the blood-brain barrier, crossing the spinal cord and/or entering the central nervous system.

15. A pharmaceutical composition comprising the V$_H$H camelid single domain antibody of claim 13 and a pharmaceutically acceptable diluent, carrier or excipient.

16. The pharmaceutical composition of claim 14, formulated for intravenous administration.

17. A method of alleviating the symptoms of pain, or managing pain of a subject in need thereof, the method comprising administering an effective amount of the antibody or antigen-binding fragment of claim 1 to said subject.

18. A method of alleviating the symptoms of pain, or managing pain of a subject in need thereof, the method comprising administering an effective amount of the V$_H$H camelid single domain antibody of claim 13 to said subject.

* * * * *

UNITED STATES PATENT AND TRADEMARK OFFICE
CERTIFICATE OF CORRECTION

PATENT NO. : 11,945,858 B2  
APPLICATION NO. : 17/056243  
DATED : April 2, 2024  
INVENTOR(S) : Martina et al.

Page 1 of 1

It is certified that error appears in the above-identified patent and that said Letters Patent is hereby corrected as shown below:

On the Title Page

Item (72) Please add inventor as follows:  
Hong LIU, Ottawa (CA)

Signed and Sealed this  
Ninth Day of September, 2025

Coke Morgan Stewart  
*Acting Director of the United States Patent and Trademark Office*

SEQUENCE LISTING

```
<160> NUMBER OF SEQ ID NOS: 132

<210> SEQ ID NO 1
<211> LENGTH: 70
<212> TYPE: PRT
<213> ORGANISM: Artificial Sequence
```

```
<220> FEATURE:
<223> OTHER INFORMATION: DIE3IR = 70 amino acid sequence located on
      loop3 of the D1 domain of the Nav1.7 polypeptide

<400> SEQUENCE: 1

Lys His Lys Cys Phe Arg Asn Ser Leu Glu Asn Asn Glu Thr Leu Glu
1               5                   10                  15

Ser Ile Met Asn Thr Leu Glu Ser Glu Glu Asp Phe Arg Lys Tyr Phe
            20                  25                  30

Tyr Tyr Leu Glu Gly Ser Lys Asp Ala Leu Leu Cys Gly Phe Ser Thr
            35                  40                  45

Asp Ser Gly Gln Cys Pro Glu Gly Tyr Thr Cys Val Lys Ile Gly Arg
    50                  55                  60

Asn Pro Asp Tyr Gly Tyr
65                  70

<210> SEQ ID NO 2
<211> LENGTH: 205
<212> TYPE: PRT
<213> ORGANISM: Artificial Sequence
<220> FEATURE:
<223> OTHER INFORMATION: Chimeric FC5DIE3IR protein with signal peptide

<400> SEQUENCE: 2

Met Glu Phe Gly Leu Ser Trp Leu Phe Leu Val Ala Ile Leu Lys Gly
1               5                   10                  15

Val Gln Cys Glu Val Gln Leu Gln Ala Ser Gly Gly Gly Leu Val Gln
            20                  25                  30

Ala Gly Gly Ser Leu Arg Leu Ser Cys Ala Ala Ser Gly Phe Lys Ile
            35                  40                  45

Thr His Tyr Thr Met Gly Trp Phe Arg Gln Ala Pro Gly Lys Glu Arg
            50                  55                  60

Glu Phe Val Ser Arg Ile Thr Trp Gly Gly Asp Asn Thr Phe Tyr Ser
65                  70                  75                  80

Asn Ser Val Lys Gly Arg Phe Thr Ile Ser Arg Asp Asn Ala Lys Asn
                85                  90                  95

Thr Val Tyr Leu Gln Met Asn Ser Leu Lys Pro Glu Asp Thr Ala Asp
            100                 105                 110

Tyr Tyr Cys Ala Ala Gly Ser Thr Lys His Lys Cys Phe Arg Asn Ser
        115                 120                 125

Leu Glu Asn Asn Glu Thr Leu Glu Ser Ile Met Asn Thr Leu Glu Ser
    130                 135                 140

Glu Glu Asp Phe Arg Lys Tyr Phe Tyr Tyr Leu Glu Gly Ser Lys Asp
145                 150                 155                 160

Ala Leu Leu Cys Gly Phe Ser Thr Asp Ser Gly Gln Cys Pro Glu Gly
                165                 170                 175

Tyr Thr Cys Val Lys Ile Gly Arg Asn Pro Asp Tyr Gly Tyr Arg Val
            180                 185                 190

Asp Tyr Trp Gly Lys Gly Thr Gln Val Thr Val Ser Ser
        195                 200                 205

<210> SEQ ID NO 3
<211> LENGTH: 186
<212> TYPE: PRT
<213> ORGANISM: Artificial Sequence
<220> FEATURE:
<223> OTHER INFORMATION: Chimeric FC5DIE3IR protein without signal
      peptide
```

-continued

<400> SEQUENCE: 3

Glu Val Gln Leu Gln Ala Ser Gly Gly Gly Leu Val Gln Ala Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Asp Tyr Tyr Cys
                85                  90                  95

Ala Ala Gly Ser Thr Lys His Lys Cys Phe Arg Asn Ser Leu Glu Asn
            100                 105                 110

Asn Glu Thr Leu Glu Ser Ile Met Asn Thr Leu Glu Ser Glu Glu Asp
        115                 120                 125

Phe Arg Lys Tyr Phe Tyr Leu Glu Gly Ser Lys Asp Ala Leu Leu
    130                 135                 140

Cys Gly Phe Ser Thr Asp Ser Gly Gln Cys Pro Glu Gly Tyr Thr Cys
145                 150                 155                 160

Val Lys Ile Gly Arg Asn Pro Asp Tyr Gly Tyr Arg Val Asp Tyr Trp
                165                 170                 175

Gly Lys Gly Thr Gln Val Thr Val Ser Ser
            180                 185

<210> SEQ ID NO 4
<211> LENGTH: 30
<212> TYPE: PRT
<213> ORGANISM: Artificial Sequence
<220> FEATURE:
<223> OTHER INFORMATION: Peptide #1 = 30 amino acid sequence located on
      loop3 of the D1 domain of the Nav1.7 polypeptide

<400> SEQUENCE: 4

Lys His Lys Cys Phe Arg Asn Ser Leu Glu Asn Asn Glu Thr Leu Glu
1               5                   10                  15

Ser Ile Met Asn Thr Leu Glu Ser Glu Glu Asp Phe Arg Lys
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Peptide #2 = 30 amino acid sequence located on
      loop3 of the D1 domain of the Nav1.7 polypeptide

<400> SEQUENCE: 5

Thr Leu Glu Ser Glu Glu Asp Phe Arg Lys Tyr Phe Tyr Tyr Leu Glu
1               5                   10                  15

Gly Ser Lys Asp Ala Leu Leu Cys Gly Phe Ser Thr Asp Ser
            20                  25                  30

<210> SEQ ID NO 6
<211> LENGTH: 30
<212> TYPE: PRT
<213> ORGANISM: Artificial Sequence

```
<220> FEATURE:
<223> OTHER INFORMATION: Peptide #3 = 30 amino acid sequence located on
      loop3 of the D1 domain of the Nav1.7 polypeptide

<400> SEQUENCE: 6

Ala Leu Leu Cys Gly Phe Ser Thr Asp Ser Gly Gln Cys Pro Glu Gly
1               5                   10                  15

Tyr Thr Cys Val Lys Ile Gly Arg Asn Pro Asp Tyr Gly Tyr
            20                  25                  30

<210> SEQ ID NO 7
<211> LENGTH: 8
<212> TYPE: PRT
<213> ORGANISM: Artificial Sequence
<220> FEATURE:
<223> OTHER INFORMATION: Heavy chain CDR1 of the 3A8 antibody

<400> SEQUENCE: 7

Gly Tyr Thr Phe Thr Asn Tyr Trp
1               5

<210> SEQ ID NO 8
<211> LENGTH: 8
<212> TYPE: PRT
<213> ORGANISM: Artificial Sequence
<220> FEATURE:
<223> OTHER INFORMATION: Heavy chain CDR2 of the 3A8 antibody

<400> SEQUENCE: 8

Ile Asn Pro Ser Asn Gly Arg Ala
1               5

<210> SEQ ID NO 9
<211> LENGTH: 10
<212> TYPE: PRT
<213> ORGANISM: Artificial Sequence
<220> FEATURE:
<223> OTHER INFORMATION: Heavy chain CDR3 of the 3A8 antibody

<400> SEQUENCE: 9

Ala Arg Ser Pro Tyr Gly Tyr Tyr Asp Tyr
1               5                   10

<210> SEQ ID NO 10
<211> LENGTH: 423
<212> TYPE: PRT
<213> ORGANISM: Artificial Sequence
<220> FEATURE:
<223> OTHER INFORMATION: Nucleotide sequence encoding the heavy chain of
      the 3A8 antibody

<400> SEQUENCE: 10

Thr Thr Thr Thr Thr Gly Gly Thr Ala Gly Cys Ala Ala Cys Ala Gly
1               5                   10                  15

Cys Thr Ala Cys Ala Gly Ala Thr Gly Thr Cys Cys Ala Cys Thr Cys
            20                  25                  30

Cys Cys Ala Gly Gly Thr Cys Cys Ala Ala Cys Thr Gly Cys Ala Gly
            35                  40                  45

Cys Ala Gly Cys Cys Thr Gly Gly Gly Cys Thr Gly Ala Ala Cys
        50                  55                  60

Thr Gly Gly Thr Gly Ala Ala Gly Cys Cys Thr Gly Gly Gly Gly Cys
65                  70                  75                  80

Thr Thr Cys Ala Gly Thr Gly Ala Ala Gly Cys Thr Gly Thr Cys Cys
                85                  90                  95
```

Thr Gly Cys Ala Ala Gly Gly Cys Thr Thr Cys Thr Gly Gly Cys Thr
            100                 105                 110

Ala Cys Ala Cys Cys Thr Thr Cys Ala Cys Cys Ala Ala Cys Thr Ala
            115                 120                 125

Cys Thr Gly Gly Ala Thr Gly Cys Ala Cys Thr Gly Gly Gly Thr Gly
            130                 135                 140

Ala Ala Gly Cys Ala Gly Ala Gly Gly Cys Cys Thr Gly Gly Ala Cys
145                 150                 155                 160

Ala Ala Gly Gly Cys Cys Thr Thr Gly Ala Gly Thr Gly Gly Ala Thr
                165                 170                 175

Thr Gly Gly Ala Gly Ala Gly Ala Thr Thr Ala Ala Thr Cys Cys Thr
            180                 185                 190

Ala Gly Cys Ala Ala Cys Gly Gly Thr Cys Gly Thr Gly Cys Thr Ala
            195                 200                 205

Ala Cys Thr Ala Cys Ala Ala Thr Gly Ala Gly Ala Ala Gly Thr Thr
            210                 215                 220

Cys Ala Ala Gly Ala Gly Cys Ala Ala Gly Gly Cys Cys Ala Cys Ala
225                 230                 235                 240

Cys Thr Gly Ala Cys Thr Gly Thr Ala Gly Ala Cys Ala Ala Ala Thr
                245                 250                 255

Cys Cys Thr Cys Cys Ala Gly Cys Ala Cys Ala Gly Cys Cys Thr Ala
            260                 265                 270

Cys Ala Thr Gly Cys Ala Ala Cys Thr Cys Ala Gly Cys Ala Gly Cys
            275                 280                 285

Cys Thr Gly Ala Cys Ala Thr Cys Thr Gly Ala Gly Gly Ala Cys Thr
            290                 295                 300

Cys Thr Gly Cys Gly Gly Thr Cys Thr Ala Thr Thr Ala Cys Thr Gly
305                 310                 315                 320

Thr Gly Cys Ala Ala Gly Ala Thr Cys Cys Cys Thr Thr Ala Cys Thr
                325                 330                 335

Gly Gly Thr Thr Ala Cys Thr Ala Cys Gly Ala Cys Thr Ala Cys Thr
            340                 345                 350

Gly Gly Gly Gly Cys Cys Ala Ala Gly Gly Cys Ala Cys Cys Ala Cys
            355                 360                 365

Thr Cys Thr Cys Ala Cys Ala Gly Thr Cys Thr Cys Cys Thr Cys Ala
            370                 375                 380

Gly Cys Cys Ala Ala Ala Ala Cys Ala Ala Cys Ala Gly Cys Cys Cys
385                 390                 395                 400

Cys Ala Thr Cys Gly Gly Thr Cys Thr Ala Thr Cys Cys Cys Cys Thr
                405                 410                 415

Gly Gly Cys Cys Cys Cys Thr
            420

<210> SEQ ID NO 11
<211> LENGTH: 141
<212> TYPE: PRT
<213> ORGANISM: Artificial Sequence
<220> FEATURE:
<223> OTHER INFORMATION: Heavy chain of the 3A8 antibody with leader
      sequence

<400> SEQUENCE: 11

Phe Leu Val Ala Thr Ala Thr Asp Val His Ser Gln Val Gln Leu Gln
1               5                   10                  15

Gln Pro Gly Ala Glu Leu Val Lys Pro Gly Ala Ser Val Lys Leu Ser
            20                  25                  30

```
Cys Lys Ala Ser Gly Tyr Thr Phe Thr Asn Tyr Trp Met His Trp Val
            35                  40                  45

Lys Gln Arg Pro Gly Gln Gly Leu Glu Trp Ile Gly Glu Ile Asn Pro
 50                  55                  60

Ser Asn Gly Arg Ala Asn Tyr Asn Glu Lys Phe Lys Ser Lys Ala Thr
 65                  70                  75                  80

Leu Thr Val Asp Lys Ser Ser Thr Ala Tyr Met Gln Leu Ser Ser
                85                  90                  95

Leu Thr Ser Glu Asp Ser Ala Val Tyr Tyr Cys Ala Arg Ser Pro Tyr
                100                 105                 110

Gly Tyr Tyr Asp Tyr Trp Gly Gln Gly Thr Thr Leu Thr Val Ser Ser
            115                 120                 125

Ala Lys Thr Thr Ala Pro Ser Val Tyr Pro Leu Ala Pro
        130                 135                 140

<210> SEQ ID NO 12
<211> LENGTH: 130
<212> TYPE: PRT
<213> ORGANISM: Artificial Sequence
<220> FEATURE:
<223> OTHER INFORMATION: Heavy chain of the 3A8 antibody without leader
      sequence

<400> SEQUENCE: 12

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Asn Tyr
                20                  25                  30

Trp Met His Trp Val Lys Gln Arg Pro Gly Gln Gly Leu Glu Trp Ile
            35                  40                  45

Gly Glu Ile Asn Pro Ser Asn Gly Arg Ala Asn Tyr Asn Glu Lys Phe
 50                  55                  60

Lys Ser Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Ser Pro Tyr Gly Tyr Tyr Asp Tyr Trp Gly Gln Gly Thr Thr
                100                 105                 110

Leu Thr Val Ser Ser Ala Lys Thr Thr Ala Pro Ser Val Tyr Pro Leu
            115                 120                 125

Ala Pro
    130

<210> SEQ ID NO 13
<211> LENGTH: 11
<212> TYPE: PRT
<213> ORGANISM: Artificial Sequence
<220> FEATURE:
<223> OTHER INFORMATION: Light chain CDR1 of the 3A8 antibody

<400> SEQUENCE: 13

Gln Ser Leu Leu His Ser Asn Gly Asn Thr Tyr
 1               5                  10

<210> SEQ ID NO 14
<211> LENGTH: 3
<212> TYPE: PRT
<213> ORGANISM: Artificial Sequence
```

```
<220> FEATURE:
<223> OTHER INFORMATION: Light chain CDR2 of the 3A8 antibody

<400> SEQUENCE: 14

Lys Val Ser
1

<210> SEQ ID NO 15
<211> LENGTH: 9
<212> TYPE: PRT
<213> ORGANISM: Artificial Sequence
<220> FEATURE:
<223> OTHER INFORMATION: Light chain CDR3 of the 3A8 antibody

<400> SEQUENCE: 15

Ser Gln Ile Thr His Val Pro Leu Thr
1               5

<210> SEQ ID NO 16
<211> LENGTH: 441
<212> TYPE: DNA
<213> ORGANISM: Artificial Sequence
<220> FEATURE:
<223> OTHER INFORMATION: Nucleotide sequence encoding the light chain of
      the 3A8 antibody

<400> SEQUENCE: 16
ctgatgaagt tgcctgttag gctgttggtg ctgatgttct ggattcctgc ttccagcagt      60
gatgttttga tgacccaaac tccactctcc ctgcctgtca gtcttggaga tcaagcctcc     120
atctcttgca gatctagtca gagccttta cacagtaatg aaacacctta tttccattgg     180
tacctgcaga agccaggcca gtctccaaag ctcctgatct acaaagtttc caaccgattt     240
tttggggtcc cagacaggtt cagtggcagt ggatcaggga cagatttcac actcaagatc     300
agcagagtgg aggctgagga tctgggagtt tatttctgct ctcaaattac acatgttccg     360
ctcacgttcg gtgctgggac caagctggag ctgaaacggg ctgatgctgc accaactgta     420
tccatcttcc caccatccag t                                              441

<210> SEQ ID NO 17
<211> LENGTH: 147
<212> TYPE: PRT
<213> ORGANISM: Artificial Sequence
<220> FEATURE:
<223> OTHER INFORMATION: Light chain of the 3A8 antibody with leader
      sequence

<400> SEQUENCE: 17

Leu Met Lys Leu Pro Val Arg Leu Leu Val Leu Met Phe Trp Ile Pro
1               5                  10                  15

Ala Ser Ser Ser Asp Val Leu Met Thr Gln Thr Pro Leu Ser Leu Pro
            20                  25                  30

Val Ser Leu Gly Asp Gln Ala Ser Ile Ser Cys Arg Ser Ser Gln Ser
        35                  40                  45

Leu Leu His Ser Asn Gly Asn Thr Tyr Phe His Trp Tyr Leu Gln Lys
    50                  55                  60

Pro Gly Gln Ser Pro Lys Leu Leu Ile Tyr Lys Val Ser Asn Arg Phe
65                  70                  75                  80

Phe Gly Val Pro Asp Arg Phe Ser Gly Ser Gly Ser Gly Thr Asp Phe
                85                  90                  95

Thr Leu Lys Ile Ser Arg Val Glu Ala Glu Asp Leu Gly Val Tyr Phe
            100                 105                 110
```

Cys Ser Gln Ile Thr His Val Pro Leu Thr Phe Gly Ala Gly Thr Lys
        115                 120                 125

Leu Glu Leu Lys Arg Ala Asp Ala Ala Pro Thr Val Ser Ile Phe Pro
    130                 135                 140

Pro Ser Ser
145

<210> SEQ ID NO 18
<211> LENGTH: 127
<212> TYPE: PRT
<213> ORGANISM: Artificial Sequence
<220> FEATURE:
<223> OTHER INFORMATION: Light chain of the 3A8 antibody without leader
      sequence

<400> SEQUENCE: 18

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Phe His Trp Tyr Leu Gln Lys Pro Gly Gln Ser
        35                  40                  45

Pro Lys Leu Leu Ile Tyr Lys Val Ser Asn Arg Phe Phe Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ile
                85                  90                  95

Thr His Val Pro Leu Thr Phe Gly Ala Gly Thr Lys Leu Glu Leu Lys
            100                 105                 110

Arg Ala Asp Ala Ala Pro Thr Val Ser Ile Phe Pro Pro Ser Ser
        115                 120                 125

<210> SEQ ID NO 19
<211> LENGTH: 435
<212> TYPE: DNA
<213> ORGANISM: Artificial Sequence
<220> FEATURE:
<223> OTHER INFORMATION: Nucleotide sequence encoding the heavy chain of
      the 1G5 and 1G9 antibodies

<400> SEQUENCE: 19 ttttggtag ctgcagctac aggtgtccac tcccaggtcc aactgcagca gcctggggct      60
gagcttgtga agcctggggc ttcagtgaag ctgtcctgca aggcttctgg ctacactttc    120
accagctact ggataaactg ggtgaagcag aggcctggac aaggccttga gtggattgga    180
aatatttatc ctggtaatag taatactaac tacaatgaga agttcaagag caaggccaca    240
ctgactgtag acaaatcctc cagcacagcc tacatgcagc tcagcagcct gacatctgag    300
gactctgcgg tctattattg tgcaagacgg tactactatg attacgacga tgctatggac    360
tactggggtc aaggaacctc agtcaccgtc tcctcagcca aaacgacacc cccatctgtc    420 tatccccctgg cccct                                                    435

<210> SEQ ID NO 20
<211> LENGTH: 145
<212> TYPE: PRT
<213> ORGANISM: Artificial Sequence
<220> FEATURE:
<223> OTHER INFORMATION: Heavy chain of the 1G5 and 1G9 antibodies with
      leader sequence

<400> SEQUENCE: 20

```
Phe Leu Val Ala Ala Ala Thr Gly Val His Ser Gln Val Gln Leu Gln
1               5                   10                  15
Gln Pro Gly Ala Glu Leu Val Lys Pro Gly Ala Ser Val Lys Leu Ser
            20                  25                  30
Cys Lys Ala Ser Gly Tyr Thr Phe Thr Ser Tyr Trp Ile Asn Trp Val
        35                  40                  45
Lys Gln Arg Pro Gly Gln Gly Leu Glu Trp Ile Gly Asn Ile Tyr Pro
50                  55                  60
Gly Asn Ser Asn Thr Asn Tyr Asn Glu Lys Phe Lys Ser Lys Ala Thr
65                  70                  75                  80
Leu Thr Val Asp Lys Ser Ser Thr Ala Tyr Met Gln Leu Ser Ser
                85                  90                  95
Leu Thr Ser Glu Asp Ser Ala Val Tyr Tyr Cys Ala Arg Arg Tyr Tyr
            100                 105                 110
Tyr Asp Tyr Asp Asp Ala Met Asp Tyr Trp Gly Gln Gly Thr Ser Val
            115                 120                 125
Thr Val Ser Ser Ala Lys Thr Thr Pro Pro Ser Val Tyr Pro Leu Ala
        130                 135                 140
Pro
145
```

<210> SEQ ID NO 21
<211> LENGTH: 134
<212> TYPE: PRT
<213> ORGANISM: Artificial Sequence
<220> FEATURE:
<223> OTHER INFORMATION: Heavy chain of the 1G5 and 1G9 antibodies
    without leader sequence

<400> SEQUENCE: 21

```
Gln Val Gln Leu Gln Gln Pro Gly Ala Glu Leu Val Lys Pro Gly Ala
1               5                   10                  15
Ser Val Lys Leu Ser Cys Lys Ala Ser Gly Tyr Thr Phe Thr Ser Tyr
            20                  25                  30
Trp Ile Asn Trp Val Lys Gln Arg Pro Gly Gln Gly Leu Glu Trp Ile
        35                  40                  45
Gly Asn Ile Tyr Pro Gly Asn Ser Asn Thr Asn Tyr Asn Glu Lys Phe
50                  55                  60
Lys Ser Lys Ala Thr Leu Thr Val Asp Lys Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Arg Tyr Tyr Tyr Asp Tyr Asp Asp Ala Met Asp Tyr Trp Gly
            100                 105                 110
Gln Gly Thr Ser Val Thr Val Ser Ser Ala Lys Thr Thr Pro Pro Ser
            115                 120                 125
Val Tyr Pro Leu Ala Pro
        130
```

<210> SEQ ID NO 22
<211> LENGTH: 8
<212> TYPE: PRT
<213> ORGANISM: Artificial Sequence
<220> FEATURE:
<223> OTHER INFORMATION: Heavy chain CDR1 of the 1G5 and 1G9 antibodies

<400> SEQUENCE: 22

Gly Tyr Thr Phe Thr Ser Tyr Trp
1               5

<210> SEQ ID NO 23
<211> LENGTH: 8
<212> TYPE: PRT
<213> ORGANISM: Artificial Sequence
<220> FEATURE:
<223> OTHER INFORMATION: Heavy chain CDR2 of the 1G5 and the 1G9
      antibodies

<400> SEQUENCE: 23

Ile Tyr Pro Gly Asn Ser Asn Thr
1               5

<210> SEQ ID NO 24
<211> LENGTH: 14
<212> TYPE: PRT
<213> ORGANISM: Artificial Sequence
<220> FEATURE:
<223> OTHER INFORMATION: Heavy chain CDR3 of the 1G5 and 1G9 antibodies

<400> SEQUENCE: 24

Ala Arg Arg Tyr Tyr Tyr Asp Tyr Asp Asp Ala Met Asp Tyr
1               5                   10

<210> SEQ ID NO 25
<211> LENGTH: 417
<212> TYPE: DNA
<213> ORGANISM: Artificial Sequence
<220> FEATURE:
<223> OTHER INFORMATION: Nucleotide sequence encoding the light chain of
      the 1G5 and 1G9 antibodies

<400> SEQUENCE: 25
cttatgttgc tgctgctatg ggttccaggt tccacaggtg acattgtgct gacccaatct      60
ccagcttctt tggctgtgtc tctagggcag agggccacca tatcctgcag agccagtgaa     120
agtgttgata gttatggcaa tggttttatg cactggtacc agcagaaacc aggacagcca     180
cccaaactcc tcatctatcg tgcatccaac ctagaatctg ggatccctgc cagggtcagt     240
ggcagtgggt ctaggacaga cttcaccctc accattaatc ctgtggaggc tgatgatgtt     300
gcaacctatt actgtcagca agtaatgag atccgtgga cgttcggtgg aggcaccaag      360
ctggaaatca aacgggctga tgctgcacca actgtatcca tcttcccacc atccagt        417

<210> SEQ ID NO 26
<211> LENGTH: 139
<212> TYPE: PRT
<213> ORGANISM: Artificial Sequence
<220> FEATURE:
<223> OTHER INFORMATION: Light chain of the 1G5 and the 1G9 antibodies
      with leader sequence

<400> SEQUENCE: 26

Leu Met Leu Leu Leu Leu Trp Val Pro Gly Ser Thr Gly Asp Ile Val
1               5                   10                  15

Leu Thr Gln Ser Pro Ala Ser Leu Ala Val Ser Leu Gly Gln Arg Ala
            20                  25                  30

Thr Ile Ser Cys Arg Ala Ser Glu Ser Val Asp Ser Tyr Gly Asn Gly
        35                  40                  45

Phe Met His Trp Tyr Gln Gln Lys Pro Gly Gln Pro Pro Lys Leu Leu
    50                  55                  60

```
Ile Tyr Arg Ala Ser Asn Leu Glu Ser Gly Ile Pro Ala Arg Val Ser
 65                 70                  75                  80

Gly Ser Gly Ser Arg Thr Asp Phe Thr Leu Thr Ile Asn Pro Val Glu
                 85                  90                  95

Ala Asp Asp Val Ala Thr Tyr Tyr Cys Gln Gln Ser Asn Glu Asp Pro
            100                 105                 110

Trp Thr Phe Gly Gly Gly Thr Lys Leu Glu Ile Lys Arg Ala Asp Ala
        115                 120                 125

Ala Pro Thr Val Ser Ile Phe Pro Pro Ser Ser
    130                 135

<210> SEQ ID NO 27
<211> LENGTH: 126
<212> TYPE: PRT
<213> ORGANISM: Artificial Sequence
<220> FEATURE:
<223> OTHER INFORMATION: Light chain of the 1G5 and 1G9 antibodies
      without leader sequence

<400> SEQUENCE: 27

Asp Ile Val Leu Thr Gln Ser Pro Ala Ser Leu Ala Val Ser Leu Gly
  1               5                  10                  15

Gln Arg Ala Thr Ile Ser Cys Arg Ala Ser Glu Ser Val Asp Ser Tyr
             20                  25                  30

Gly Asn Gly Phe Met His Trp Tyr Gln Gln Lys Pro Gly Gln Pro Pro
         35                  40                  45

Lys Leu Leu Ile Tyr Arg Ala Ser Asn Leu Glu Ser Gly Ile Pro Ala
 50                  55                  60

Arg Val Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                 85                  90                  95

Glu Asp Pro Trp Thr Phe Gly Gly Gly Thr Lys Leu Glu Ile Lys Arg
            100                 105                 110

Ala Asp Ala Ala Pro Thr Val Ser Ile Phe Pro Pro Ser Ser
        115                 120                 125

<210> SEQ ID NO 28
<211> LENGTH: 10
<212> TYPE: PRT
<213> ORGANISM: Artificial Sequence
<220> FEATURE:
<223> OTHER INFORMATION: Light chain CDR1 of the 1G5 and the 1G9
      antibodies

<400> SEQUENCE: 28

Glu Ser Val Asp Ser Tyr Gly Asn Gly Phe
  1               5                  10

<210> SEQ ID NO 29
<211> LENGTH: 3
<212> TYPE: PRT
<213> ORGANISM: Artificial Sequence
<220> FEATURE:
<223> OTHER INFORMATION: Light chain CDR2 of the 1G5 and 1G9 antibodies

<400> SEQUENCE: 29

Arg Ala Ser
  1
```

<210> SEQ ID NO 30
<211> LENGTH: 9
<212> TYPE: PRT
<213> ORGANISM: Artificial Sequence
<220> FEATURE:
<223> OTHER INFORMATION: Light chain CDR3 of the 1G5 antibodies

<400> SEQUENCE: 30

Gln Gln Ser Asn Glu Asp Pro Trp Thr
1               5

<210> SEQ ID NO 31
<211> LENGTH: 372
<212> TYPE: DNA
<213> ORGANISM: Artificial Sequence
<220> FEATURE:
<223> OTHER INFORMATION: Nucleotide sequence encoding DI-A

<400> SEQUENCE: 31
caggctcagg tacagctggt ggagtctggg ggaggattgg tgcagcctgg gggctctctg      60
agactctcct gtgcagcctc tggacgcacc atcagtagct ttaccatggg ctggttccgc     120
caggctccag gggcggagcg tgagtttgta gcagctatta gtcggagtgg tagtagtaca     180
gtctatgcag gctccgtgaa gggccgattc accatctcca gagacaacgc caagaacacg     240
gtgtatctgc aaatgaacag cctgaaacct gaggacacgg ccgtctatta ctgtaatgca     300
gttattaccg aacccctcta caaaacggac gatagttact ggggccaggg gacccaggtc     360
accgtctcct ca                                                          372

<210> SEQ ID NO 32
<211> LENGTH: 124
<212> TYPE: PRT
<213> ORGANISM: Artificial Sequence
<220> FEATURE:
<223> OTHER INFORMATION: DI-A

<400> SEQUENCE: 32

Gln Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Arg Thr Ile Ser
            20                  25                  30

Ser Phe Thr Met Gly Trp Phe Arg Gln Ala Pro Gly Ala Glu Arg Glu
        35                  40                  45

Phe Val Ala Ala Ile Ser Arg Ser Gly Ser Ser Thr Val Tyr Ala Gly
    50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Lys Pro Glu Asp Thr Ala Val Tyr
                85                  90                  95

Tyr Cys Asn Ala Val Ile Thr Glu Pro Leu Tyr Lys Thr Asp Asp Ser
            100                 105                 110

Tyr Trp Gly Gln Gly Thr Gln Val Thr Val Ser Ser
        115                 120

<210> SEQ ID NO 33
<211> LENGTH: 354
<212> TYPE: DNA
<213> ORGANISM: Artificial Sequence
<220> FEATURE:
<223> OTHER INFORMATION: Nucleotide sequence encoding DI-B

<400> SEQUENCE: 33

```
caggtaaagc tggaggagtc tgggggaggc ttggtgccgc ctggggagtc tctgaggctc    60
acctgtgcgg ccactggaca aaccgctagt gtatatgaaa tggcctggtt ccgccgcgct   120
ccagagaagg agcaagtata tgtggcatct attaactggc gggatggtga cacacaatat   180
cataactccg tgaagggccg attcatcatc tctagagaca atgccaagaa cacggtattt   240
ctccaaatga acagtttaac acctgaggac acggccatct attactgcgc agcgcgaaaa   300
gaattggcgg ggtatgacta ctgggggccaa gggacccagg tcaccgtctc ctca        354
```

<210> SEQ ID NO 34
<211> LENGTH: 118
<212> TYPE: PRT
<213> ORGANISM: Artificial Sequence
<220> FEATURE:
<223> OTHER INFORMATION: DI-B

<400> SEQUENCE: 34

```
Gln Val Lys Leu Glu Glu Ser Gly Gly Gly Leu Val Pro Pro Gly Glu
1               5                   10                  15

Ser Leu Arg Leu Thr Cys Ala Ala Thr Gly Gln Thr Ala Ser Val Tyr
            20                  25                  30

Glu Met Ala Trp Phe Arg Arg Ala Pro Glu Lys Glu Gln Val Tyr Val
        35                  40                  45

Ala Ser Ile Asn Trp Arg Asp Gly Asp Thr Gln Tyr His Asn Ser Val
    50                  55                  60

Lys Gly Arg Phe Ile Ile Ser Arg Asp Asn Ala Lys Asn Thr Val Phe
65                  70                  75                  80

Leu Gln Met Asn Ser Leu Thr Pro Glu Asp Thr Ala Ile Tyr Tyr Cys
                85                  90                  95

Ala Ala Arg Lys Glu Leu Ala Gly Tyr Asp Tyr Trp Gly Gln Gly Thr
            100                 105                 110

Gln Val Thr Val Ser Ser
        115
```

<210> SEQ ID NO 35
<211> LENGTH: 357
<212> TYPE: PRT
<213> ORGANISM: Artificial Sequence
<220> FEATURE:
<223> OTHER INFORMATION: Nucleotide sequence encoding DI-C

<400> SEQUENCE: 35

```
Cys Ala Gly Gly Thr Ala Ala Gly Cys Thr Gly Gly Ala Gly Gly
1               5                   10                  15

Ala Gly Thr Cys Thr Gly Gly Gly Gly Ala Gly Gly Cys Thr Thr
            20                  25                  30

Gly Gly Thr Gly Cys Ala Gly Cys Cys Thr Gly Gly Gly Ala Gly
        35                  40                  45

Thr Cys Thr Cys Thr Gly Ala Gly Ala Cys Thr Cys Thr Cys Gly Thr
    50                  55                  60

Gly Thr Gly Thr Ala Gly Gly Thr Thr Cys Gly Gly Ala Thr Thr
65                  70                  75                  80

Cys Ala Ala Cys Thr Thr Cys Ala Gly Gly Ala Thr Cys Cys Ala Gly
                85                  90                  95

Gly Cys Cys Ala Thr Gly Gly Cys Cys Thr Gly Gly Thr Cys Cys
            100                 105                 110
```

Gly Cys Cys Ala Gly Cys Thr Cys Ala Gly Gly Ala Ala
            115                 120                 125

Gly Gly Ala Gly Cys Gly Thr Gly Ala Ala Thr Thr Thr Gly Thr Cys
        130                 135                 140

Gly Cys Cys Ala Gly Thr Ala Thr Thr Ala Gly Cys Gly Gly Gly Ala
145                 150                 155                 160

Gly Cys Gly Gly Thr Gly Cys Thr Ala Cys Cys Ala Cys Cys Gly Ala
                165                 170                 175

Cys Cys Ala Thr Gly Cys Ala Gly Ala Cys Thr Cys Cys Gly Thr Gly
            180                 185                 190

Ala Ala Gly Gly Cys Cys Gly Ala Thr Thr Cys Gly Cys Cys Ala
            195                 200                 205

Thr Cys Thr Cys Cys Ala Ala Ala Gly Ala Cys Ala Ala Cys Gly Cys
        210                 215                 220

Cys Ala Gly Gly Gly Ala Cys Ala Cys Ala Ala Thr Gly Thr Ala Thr
225                 230                 235                 240

Thr Thr Gly Cys Ala Ala Ala Thr Gly Ala Ala Cys Ala Ala Cys Cys
                245                 250                 255

Thr Gly Ala Ala Ala Cys Cys Gly Gly Ala Gly Gly Ala Cys Ala Cys
            260                 265                 270

Gly Gly Cys Cys Gly Thr Cys Thr Ala Thr Thr Ala Cys Thr Gly Cys
            275                 280                 285

Thr Ala Thr Gly Cys Ala Ala Thr Thr Ala Gly Thr Cys Ala Ala Cys
        290                 295                 300

Ala Thr Gly Thr Ala Cys Cys Gly Cys Cys Gly Thr Ala Thr Cys Ala
305                 310                 315                 320

Cys Thr Ala Cys Thr Gly Gly Gly Gly Cys Cys Ala Gly Gly Gly Gly
                325                 330                 335

Ala Cys Cys Cys Ala Gly Gly Thr Cys Ala Cys Cys Gly Thr Cys Thr
            340                 345                 350

Cys Cys Thr Cys Ala
        355

<210> SEQ ID NO 36
<211> LENGTH: 119
<212> TYPE: PRT
<213> ORGANISM: Artificial Sequence
<220> FEATURE:
<223> OTHER INFORMATION: DI-C

<400> SEQUENCE: 36

Gln Val Lys Leu Glu Glu Ser Gly Gly Gly Leu Val Gln Pro Gly Glu
1               5                   10                  15

Ser Leu Arg Leu Ser Cys Val Gly Ser Gly Phe Asn Phe Arg Ile Gln
            20                  25                  30

Ala Met Ala Trp Phe Arg Gln Ala Pro Gly Lys Glu Arg Glu Phe Val
        35                  40                  45

Ala Ser Ile Ser Gly Ser Gly Ala Thr Thr Asp His Ala Asp Ser Val
    50                  55                  60

Lys Gly Arg Phe Ala Ile Ser Lys Asp Asn Ala Arg Asp Thr Met Tyr
65                  70                  75                  80

Leu Gln Met Asn Asn Leu Lys Pro Glu Asp Thr Ala Val Tyr Tyr Cys
                85                  90                  95

Tyr Ala Ile Ser Gln His Val Pro Pro Tyr His Tyr Trp Gly Gln Gly
            100                 105                 110

Thr Gln Val Thr Val Ser Ser
        115

<210> SEQ ID NO 37
<211> LENGTH: 348
<212> TYPE: DNA
<213> ORGANISM: Artificial Sequence
<220> FEATURE:
<223> OTHER INFORMATION: Nucleotide sequence encoding DI-D

<400> SEQUENCE: 37
caggtaaagc tggaggagtc tgggggggc ttggtacagc cggggggtc tctgaaactc      60 tcgtgtgtag cctctggatt cgccttcagc tccgctccaa tggactgggt ccgtaaggct     120
ccagggaagg acgttgagtg gctctcaact attgaaagtg accaagacca caccatatat    180
tatgcaaact ccgtgaaggg ccgattcact atttcccgag atgatgtcca gaacatcttg    240
tatctgcaaa tgaacgacct gaaaattgag gacacggcca catattactg tcagaaacgt    300
ggagagaaga aaacccgggg ccaggggacc caggtcaccg tctcctca                 348

<210> SEQ ID NO 38
<211> LENGTH: 116
<212> TYPE: PRT
<213> ORGANISM: Artificial Sequence
<220> FEATURE:
<223> OTHER INFORMATION: DI-D

<400> SEQUENCE: 38

Gln Val Lys Leu Glu Glu Ser Gly Gly Gly Leu Val Gln Pro Gly Gly
1               5                   10                  15

Ser Leu Lys Leu Ser Cys Val Ala Ser Gly Phe Ala Phe Ser Ser Ala
            20                  25                  30

Pro Met Asp Trp Val Arg Lys Ala Pro Gly Lys Asp Val Glu Trp Leu
        35                  40                  45

Ser Thr Ile Glu Ser Asp Gln Asp His Thr Ile Tyr Tyr Ala Asn Ser
    50                  55                  60

Val Lys Gly Arg Phe Thr Ile Ser Arg Asp Asp Val Gln Asn Ile Leu
65                  70                  75                  80

Tyr Leu Gln Met Asn Asp Leu Lys Ile Glu Asp Thr Ala Thr Tyr Tyr
                85                  90                  95

Cys Gln Lys Arg Gly Glu Lys Lys Thr Arg Gly Gln Gly Thr Gln Val
            100                 105                 110

Thr Val Ser Ser
        115

<210> SEQ ID NO 39
<211> LENGTH: 8
<212> TYPE: PRT
<213> ORGANISM: Artificial Sequence
<220> FEATURE:
<223> OTHER INFORMATION: Heavy chain CDR1 of DI-D

<400> SEQUENCE: 39

Gly Phe Ala Phe Ser Ser Ala Pro
1               5

<210> SEQ ID NO 40
<211> LENGTH: 9
<212> TYPE: PRT

<210> SEQ ID NO 40
<211> LENGTH: 8
<212> TYPE: PRT
<213> ORGANISM: Artificial Sequence
<220> FEATURE:
<223> OTHER INFORMATION: Heavy chain CDR2 of DI-D

<400> SEQUENCE: 40

Ile Glu Ser Asp Gln Asp His Thr Ile
1               5

<210> SEQ ID NO 41
<211> LENGTH: 8
<212> TYPE: PRT
<213> ORGANISM: Artificial Sequence
<220> FEATURE:
<223> OTHER INFORMATION: Heavy chain CDR3 of DI-D

<400> SEQUENCE: 41

Gln Lys Arg Gly Glu Lys Lys Thr
1               5

<210> SEQ ID NO 42
<211> LENGTH: 339
<212> TYPE: DNA
<213> ORGANISM: Artificial Sequence
<220> FEATURE:
<223> OTHER INFORMATION: Nucleotide sequence encoding DI-E

<400> SEQUENCE: 42
caggtaaagc tggaggagtc tgggggaggc ttggtgcagc ctggggggtc tctgagactc      60
tcctgtgcag cctctgaatt caccttcagt agctcctggg gcattgggt ccgtcaggct     120 ccagggaagg ggctcaagtg gtctcaagt attaattctg gtggcgaagg cacatactat     180
gcagactccg tgaagggccg attcaccatc tccagagaca acggcaagaa cacgctgtat     240
ctggaaatga acagtctgaa atctgaagac acggccgtgt attactgcac atcagcctcc     300
ggggcgtggg gccagggga tccaggtcacc gtctcctca                            339

<210> SEQ ID NO 43
<211> LENGTH: 113
<212> TYPE: PRT
<213> ORGANISM: Artificial Sequence
<220> FEATURE:
<223> OTHER INFORMATION: DI-E

<400> SEQUENCE: 43

Gln Val Lys Leu Glu Glu Ser Gly Gly Gly Leu Val Gln Pro Gly Gly
1               5                   10                  15

Ser Leu Arg Leu Ser Cys Ala Ala Ser Glu Phe Thr Phe Ser Ser Ser
            20                  25                  30

Trp Gly Ile Gly Trp Val Arg Gln Ala Pro Gly Lys Gly Leu Lys Trp Val
        35                  40                  45

Ser Ser Ile Asn Ser Gly Gly Glu Gly Thr Tyr Tyr Ala Asp Ser Val
    50                  55                  60

Lys Gly Arg Phe Thr Ile Ser Arg Asp Asn Gly Lys Asn Thr Leu Tyr
65                  70                  75                  80

Leu Glu Met Asn Ser Leu Lys Ser Glu Asp Thr Ala Val Tyr Tyr Cys
                85                  90                  95

Thr Ser Ala Ser Gly Ala Trp Gly Gln Gly Ile Gln Val Thr Val Ser
            100                 105                 110

Ser

```
<210> SEQ ID NO 44
<211> LENGTH: 345
<212> TYPE: DNA
<213> ORGANISM: Artificial Sequence
<220> FEATURE:
<223> OTHER INFORMATION: Nucleotide sequence encoding DI-H

<400> SEQUENCE: 44
caggtaaagc tggaggagtc tggggggaggc ttggtgcagg ctggggagtc tctgagactc      60
tcctgtgtaa attctggaag taccttcagt atctatgcca tgggctggta ccgccaggct     120
ccagggaagc agcgcgagtt ggtcgcagcc attagtagtg ttggtaggac aaactatgca     180
gactccgtga agggccgatt caccatctcc agagccggag ccaagaacac agtctatctt     240
catatgaaca accttaaacc cgaggacacg gccgtctatt cgtgtataac gtactaccag     300
aacgcaatgt attttggcca gggcacccag gtcaccgtct cctca                    345

<210> SEQ ID NO 45
<211> LENGTH: 115
<212> TYPE: PRT
<213> ORGANISM: Artificial Sequence
<220> FEATURE:
<223> OTHER INFORMATION: DI-H

<400> SEQUENCE: 45

Gln Val Lys Leu Glu Glu Ser Gly Gly Gly Leu Val Gln Ala Gly Glu
1               5                   10                  15

Ser Leu Arg Leu Ser Cys Val Asn Ser Gly Ser Thr Phe Ser Ile Tyr
            20                  25                  30

Ala Met Gly Trp Tyr Arg Gln Ala Pro Gly Lys Gln Arg Glu Leu Val
        35                  40                  45

Ala Ala Ile Ser Ser Val Gly Arg Thr Asn Tyr Ala Asp Ser Val Lys
    50                  55                  60

Gly Arg Phe Thr Ile Ser Arg Ala Gly Ala Lys Asn Thr Val Tyr Leu
65                  70                  75                  80

His Met Asn Asn Leu Lys Pro Glu Asp Thr Ala Val Tyr Ser Cys Ile
                85                  90                  95

Thr Tyr Tyr Gln Asn Ala Met Tyr Phe Gly Gln Gly Thr Gln Val Thr
            100                 105                 110

Val Ser Ser
        115

<210> SEQ ID NO 46
<211> LENGTH: 354
<212> TYPE: DNA
<213> ORGANISM: Artificial Sequence
<220> FEATURE:
<223> OTHER INFORMATION: Nucleotide sequence encoding DI-4

<400> SEQUENCE: 46
caggtgcagc tggtggagtc tggggggaggc ttggtgcagc ctggggggtc tctgagactc      60
tcctgtgcag cctctggatt caccttcagt aactactgga tgtattgggt ccgacaggct     120
ccagggaagg ggctcgagcg ggtctcatcc atttatatca gtggtggtaa tacatactat     180
gcagactccg tgaagggccg attcaccatc tccagagaca acgccaagaa cacgctgtat     240
ctgcaaatga acagtctgaa atctgaggac acggccgtgt attactgtgt aaaagggggat     300 acttttggcg gcatggacta ttggggcaaa gggacccagg tcaccgtctc ctca           354
```

<210> SEQ ID NO 47
<211> LENGTH: 118
<212> TYPE: PRT
<213> ORGANISM: Artificial Sequence
<220> FEATURE:
<223> OTHER INFORMATION: DI-4

<400> SEQUENCE: 47

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Leu Glu Arg Val
        35                  40                  45

Ser Ser Ile Tyr Ile Ser Gly Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Val Lys Gly Asp Thr Phe Gly Gly Met Asp Tyr Trp Gly Lys Gly Thr
            100                 105                 110

Gln Val Thr Val Ser Ser
        115
```

<210> SEQ ID NO 48
<211> LENGTH: 375
<212> TYPE: DNA
<213> ORGANISM: Artificial Sequence
<220> FEATURE:
<223> OTHER INFORMATION: Artificial sequence encoding DI-16

<400> SEQUENCE: 48

```
caggctcagg tacagctggt ggagtctggg ggaggattgg tgcaggctgg gggctctctg     60
agactctcct gtgcagcctc tggacgcacc gtcagtagct ataccatggg ctggttccgc    120
caggctccag ggaaggagcg tagattcgta gcgactgtta attctagtgg tagaggaact    180
cattatgcag actccgtgaa gggccgattc accatctcca gagacaacgc caagaacacg    240
gtgtatctgc aaatgaacag cctgaaacct gaggacacgg ccgtttatta ctgtgcagca    300
gctccgtatc ccgacggatc gctgggaccg ggatatgact actggggcca ggggacccag    360
gtcaccgtct cctca                                                     375
```

<210> SEQ ID NO 49
<211> LENGTH: 125
<212> TYPE: PRT
<213> ORGANISM: Artificial Sequence
<220> FEATURE:
<223> OTHER INFORMATION: DI-16

<400> SEQUENCE: 49

```
Gln Ala Gln Val Gln Leu Val Glu Ser Gly Gly Gly Leu Val Gln Ala
1               5                   10                  15

Gly Gly Ser Leu Arg Leu Ser Cys Ala Ala Ser Gly Arg Thr Val Ser
            20                  25                  30

Ser Tyr Thr Met Gly Trp Phe Arg Gln Ala Pro Gly Lys Glu Arg Arg
        35                  40                  45

Phe Val Ala Thr Val Asn Ser Ser Gly Arg Gly Thr His Tyr Ala Asp
    50                  55                  60
```

```
Ser Val Lys Gly Arg Phe Thr Ile Ser Arg Asp Asn Ala Lys Asn Thr
 65                  70                  75                  80

Val Tyr Leu Gln Met Asn Ser Leu Lys Pro Glu Asp Thr Ala Val Tyr
                 85                  90                  95

Tyr Cys Ala Ala Ala Pro Tyr Pro Asp Gly Ser Leu Gly Pro Gly Tyr
            100                 105                 110

Asp Tyr Trp Gly Gln Gly Thr Gln Val Thr Val Ser Ser
        115                 120                 125

<210> SEQ ID NO 50
<211> LENGTH: 8
<212> TYPE: PRT
<213> ORGANISM: Artificial Sequence
<220> FEATURE:
<223> OTHER INFORMATION: Heavy chain CDR1 of DI-16

<400> SEQUENCE: 50

Gly Arg Thr Val Ser Ser Tyr Thr
1               5

<210> SEQ ID NO 51
<211> LENGTH: 8
<212> TYPE: PRT
<213> ORGANISM: Artificial Sequence
<220> FEATURE:
<223> OTHER INFORMATION: Heavy chain CDR2 of DI-16

<400> SEQUENCE: 51

Val Asn Ser Ser Gly Arg Gly Thr
1               5

<210> SEQ ID NO 52
<211> LENGTH: 16
<212> TYPE: PRT
<213> ORGANISM: Artificial Sequence
<220> FEATURE:
<223> OTHER INFORMATION: Heavy chain CDR3 of DI-16

<400> SEQUENCE: 52

Ala Ala Ala Pro Tyr Pro Asp Gly Ser Leu Gly Pro Gly Tyr Asp Tyr
1               5                   10                  15

<210> SEQ ID NO 53
<211> LENGTH: 381
<212> TYPE: DNA
<213> ORGANISM: Artificial Sequence
<220> FEATURE:
<223> OTHER INFORMATION: Nucleotide sequence encoding DI-28

<400> SEQUENCE: 53
caggctcagg tacagctggt ggagtctggg ggaggcttgg tgcaggctgg gggctctctg      60
agactctcct gtgcagcctc tggacgcacg ttcagtagtt ctggcatggg ctggttccgc     120
caggctccag ggaaggaccg tgaacttgta gcaggtatta gttggagtgg tgatagcgca     180
tactatgcaa actccgtggc gggccgattc accatctcca gagacaacat caacaacacg     240
gtgtatctgc aaatgaatag cctgaaacct gaggacacgg ccgtttatta ctgtgcagcc     300
cgacaaggtg gtcgtaacta cgcaacaagt ccgcgagaat atgactactg gggccagggg     360
acccaggtca ccgtctcctc a                                               381

<210> SEQ ID NO 54
<211> LENGTH: 127
<212> TYPE: PRT
```

<213> ORGANISM: Artificial Sequence
<220> FEATURE:
<223> OTHER INFORMATION: DI-28

<400> SEQUENCE: 54

Gln Ala Gln Val Gln Leu Val Glu Ser Gly Gly Leu Val Gln Ala
1               5                   10                  15

Gly Gly Ser Leu Arg Leu Ser Cys Ala Ala Ser Gly Arg Thr Phe Ser
            20                  25                  30

Ser Ser Gly Met Gly Trp Phe Arg Gln Ala Pro Gly Lys Asp Arg Glu
            35                  40                  45

Leu Val Ala Gly Ile Ser Trp Ser Gly Asp Ser Ala Tyr Tyr Ala Asn
    50                  55                  60

Ser Val Ala Gly Arg Phe Thr Ile Ser Arg Asp Asn Ile Asn Asn Thr
65                  70                  75                  80

Val Tyr Leu Gln Met Asn Ser Leu Lys Pro Glu Asp Thr Ala Val Tyr
                85                  90                  95

Tyr Cys Ala Ala Arg Gln Gly Gly Arg Asn Tyr Ala Thr Ser Pro Arg
            100                 105                 110

Glu Tyr Asp Tyr Trp Gly Gln Gly Thr Gln Val Thr Val Ser Ser
        115                 120                 125

<210> SEQ ID NO 55
<211> LENGTH: 8
<212> TYPE: PRT
<213> ORGANISM: Artificial Sequence
<220> FEATURE:
<223> OTHER INFORMATION: Heavy chain CDR1 of DI-28

<400> SEQUENCE: 55

Gly Arg Thr Phe Ser Ser Ser Gly
1               5

<210> SEQ ID NO 56
<211> LENGTH: 8
<212> TYPE: PRT
<213> ORGANISM: Artificial Sequence
<220> FEATURE:
<223> OTHER INFORMATION: Heavy chain CDR2 of DI-28

<400> SEQUENCE: 56

Ile Ser Trp Ser Gly Asp Ser Ala
1               5

<210> SEQ ID NO 57
<211> LENGTH: 18
<212> TYPE: PRT
<213> ORGANISM: Artificial Sequence
<220> FEATURE:
<223> OTHER INFORMATION: Heavy chain CDR3 of DI-28

<400> SEQUENCE: 57

Ala Ala Arg Gln Gly Gly Arg Asn Tyr Ala Thr Ser Pro Arg Glu Tyr
1               5                   10                  15

Asp Tyr

<210> SEQ ID NO 58
<211> LENGTH: 393
<212> TYPE: DNA
<213> ORGANISM: Artificial Sequence
<220> FEATURE:
<223> OTHER INFORMATION: Nucleotide sequence encoding DI-48

<400> SEQUENCE: 58

```
caggctcagg tacagctggt ggagtctggg ggaggattgg tgcaggctgg gggctctctg      60
agactctcct gtgcagcctc tggacgcacc ttcagtacct atgtcatggg ctggttccgc     120
cagactccag gaaggagcg tgagtttgta gcaggtttta gttggagtgg cgattacgca     180
atctatgtca actccgtgaa gggccgattc accatctcca gagacaacgc caagaacacg     240
gtgtatctgc aaatgaacag tctgagacct gaggacacgg ccgtttatta ctgcgcagca     300
cgccaacgag gggctatag tggtagatcc tattacaccg ggcgaaatga ctatgagtac     360
tggggccagg ggacccaggt caccgtctcc tca                                  393
```

<210> SEQ ID NO 59
<211> LENGTH: 131
<212> TYPE: PRT
<213> ORGANISM: Artificial Sequence
<220> FEATURE:
<223> OTHER INFORMATION: DI-48

<400> SEQUENCE: 59

Gln Ala Gln Val Gln Leu Val Glu Ser Gly Gly Gly Leu Val Gln Ala
1               5                   10                  15

Gly Gly Ser Leu Arg Leu Ser Cys Ala Ala Ser Gly Arg Thr Phe Ser
            20                  25                  30

Thr Tyr Val Met Gly Trp Phe Arg Gln Thr Pro Gly Lys Glu Arg Glu
        35                  40                  45

Phe Val Ala Gly Phe Ser Trp Ser Gly Asp Tyr Ala Ile Tyr Val Asn
    50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Arg Pro Glu Asp Thr Ala Val Tyr
                85                  90                  95

Tyr Cys Ala Ala Arg Gln Arg Gly Gly Tyr Ser Gly Arg Ser Tyr Tyr
            100                 105                 110

Thr Gly Arg Asn Asp Tyr Glu Tyr Trp Gly Gln Gly Thr Gln Val Thr
        115                 120                 125

Val Ser Ser
    130

<210> SEQ ID NO 60
<211> LENGTH: 26
<212> TYPE: PRT
<213> ORGANISM: Artificial Sequence
<220> FEATURE:
<223> OTHER INFORMATION: FR1 of the framework of FC5

<400> SEQUENCE: 60

Glu Val Gln Leu Gln Ala Ser Gly Gly Gly Leu Val Gln Ala Gly Gly
1               5                   10                  15

Ser Leu Arg Leu Ser Cys Ala Ala Ser Gly
            20                  25

<210> SEQ ID NO 61
<211> LENGTH: 17
<212> TYPE: PRT
<213> ORGANISM: Artificial Sequence
<220> FEATURE:
<223> OTHER INFORMATION: FR2 of the framework of FC5

```
<400> SEQUENCE: 61

Met Gly Trp Phe Arg Gln Ala Pro Gly Lys Glu Arg Glu Phe Val Ser
1               5                   10                  15
Arg

<210> SEQ ID NO 62
<211> LENGTH: 38
<212> TYPE: PRT
<213> ORGANISM: Artificial Sequence
<220> FEATURE:
<223> OTHER INFORMATION: FR3 of the framework of FC5

<400> SEQUENCE: 62

Phe Tyr Ser Asn Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Asp Tyr Tyr Cys
            35

<210> SEQ ID NO 63
<211> LENGTH: 11
<212> TYPE: PRT
<213> ORGANISM: Artificial Sequence
<220> FEATURE:
<223> OTHER INFORMATION: FR4 of the framework of FC5

<400> SEQUENCE: 63

Trp Gly Lys Gly Thr Gln Val Thr Val Ser Ser
1               5                   10

<210> SEQ ID NO 64
<211> LENGTH: 8
<212> TYPE: PRT
<213> ORGANISM: Artificial Sequence
<220> FEATURE:
<223> OTHER INFORMATION: Heavy chain CDR1 of FC5

<400> SEQUENCE: 64

Gly Phe Lys Ile Thr His Tyr Thr
1               5

<210> SEQ ID NO 65
<211> LENGTH: 8
<212> TYPE: PRT
<213> ORGANISM: Artificial Sequence
<220> FEATURE:
<223> OTHER INFORMATION: Heavy chain CDR2 of FC5

<400> SEQUENCE: 65

Ile Thr Trp Gly Gly Asp Asn Thr
1               5

<210> SEQ ID NO 66
<211> LENGTH: 15
<212> TYPE: PRT
<213> ORGANISM: Artificial Sequence
<220> FEATURE:
<223> OTHER INFORMATION: Heavy chain CDR3 of FC5
```

<400> SEQUENCE: 66

Ala Ala Gly Ser Thr Ser Thr Ala Thr Pro Leu Arg Val Asp Tyr
1               5                   10                  15

<210> SEQ ID NO 67
<211> LENGTH: 205
<212> TYPE: PRT
<213> ORGANISM: Artificial Sequence
<220> FEATURE:
<223> OTHER INFORMATION: FC5DIE3IR with signal sequence

<400> SEQUENCE: 67

Met Glu Phe Gly Leu Ser Trp Leu Phe Leu Val Ala Ile Leu Lys Gly
1               5                   10                  15

Val Gln Cys Glu Val Gln Leu Gln Ala Ser Gly Gly Gly Leu Val Gln
                20                  25                  30

Ala Gly Gly Ser Leu Arg Leu Ser Cys Ala Ala Ser Gly Phe Lys Ile
            35                  40                  45

Thr His Tyr Thr Met Gly Trp Phe Arg Gln Ala Pro Gly Lys Glu Arg
    50                  55                  60

Glu Phe Val Ser Arg Ile Thr Trp Gly Gly Asp Asn Thr Phe Tyr Ser
65                  70                  75                  80

Asn Ser Val Lys Gly Arg Phe Thr Ile Ser Arg Asp Asn Ala Lys Asn
                85                  90                  95

Thr Val Tyr Leu Gln Met Asn Ser Leu Lys Pro Glu Asp Thr Ala Asp
            100                 105                 110

Tyr Tyr Cys Ala Ala Gly Ser Thr Lys His Lys Cys Phe Arg Asn Ser
        115                 120                 125

Leu Glu Asn Asn Glu Thr Leu Glu Ser Ile Met Asn Thr Leu Glu Ser
    130                 135                 140

Glu Glu Asp Phe Arg Lys Tyr Phe Tyr Tyr Leu Glu Gly Ser Lys Asp
145                 150                 155                 160

Ala Leu Leu Cys Gly Phe Ser Thr Asp Ser Gly Gln Cys Pro Glu Gly
                165                 170                 175

Tyr Thr Cys Val Lys Ile Gly Arg Asn Pro Asp Tyr Gly Tyr Arg Val
            180                 185                 190

Asp Tyr Trp Gly Lys Gly Thr Gln Val Thr Val Ser Ser
        195                 200                 205

<210> SEQ ID NO 68
<211> LENGTH: 186
<212> TYPE: PRT
<213> ORGANISM: Artificial Sequence
<220> FEATURE:
<223> OTHER INFORMATION: FC5DIE3IR without signal sequence

<400> SEQUENCE: 68

Glu Val Gln Leu Gln Ala Ser Gly Gly Gly Leu Val Gln Ala Gly Gly
1               5                   10                  15

Ser Leu Arg Leu Ser Cys Ala Ala Ser Gly Phe Lys Ile Thr His Tyr
                20                  25                  30

Thr Met Gly Trp Phe Arg Gln Ala Pro Gly Lys Glu Arg Glu Phe Val
            35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ala Lys Asn Thr Val Tyr
65                  70                  75                  80

```
Leu Gln Met Asn Ser Leu Lys Pro Glu Asp Thr Ala Asp Tyr Tyr Cys
                85                  90                  95

Ala Ala Gly Ser Thr Lys His Lys Cys Phe Arg Asn Ser Leu Glu Asn
            100                 105                 110

Asn Glu Thr Leu Glu Ser Ile Met Asn Thr Leu Glu Ser Glu Glu Asp
        115                 120                 125

Phe Arg Lys Tyr Phe Tyr Leu Glu Gly Ser Lys Asp Ala Leu Leu
    130                 135                 140

Cys Gly Phe Ser Thr Asp Ser Gly Gln Cys Pro Glu Gly Tyr Thr Cys
145                 150                 155                 160

Val Lys Ile Gly Arg Asn Pro Asp Tyr Gly Tyr Arg Val Asp Tyr Trp
                165                 170                 175

Gly Lys Gly Thr Gln Val Thr Val Ser Ser
            180                 185

<210> SEQ ID NO 69
<211> LENGTH: 19
<212> TYPE: PRT
<213> ORGANISM: Artificial Sequence
<220> FEATURE:
<223> OTHER INFORMATION: Signal sequence of FC5DIE3IR

<400> SEQUENCE: 69

Met Glu Phe Gly Leu Ser Trp Leu Phe Leu Val Ala Ile Leu Lys Gly
1               5                   10                  15

Val Gln Cys

<210> SEQ ID NO 70
<211> LENGTH: 138
<212> TYPE: PRT
<213> ORGANISM: Artificial Sequence
<220> FEATURE:
<223> OTHER INFORMATION: Immunogen with no epitope with signal sequence
<220> FEATURE:
<221> NAME/KEY: VARIANT
<222> LOCATION: (121)..(121)
<223> OTHER INFORMATION: Xaa is any amino acid residue

<400> SEQUENCE: 70

Met Glu Phe Gly Leu Ser Trp Leu Phe Leu Val Ala Ile Leu Lys Gly
1               5                   10                  15

Val Gln Cys Glu Val Gln Leu Gln Ala Ser Gly Gly Gly Leu Val Gln
            20                  25                  30

Ala Gly Gly Ser Leu Arg Leu Ser Cys Ala Ala Ser Gly Phe Lys Ile
        35                  40                  45

Thr His Tyr Thr Met Gly Trp Phe Arg Gln Ala Pro Gly Lys Glu Arg
    50                  55                  60

Glu Phe Val Ser Arg Ile Thr Trp Gly Gly Asp Asn Thr Phe Tyr Ser
65                  70                  75                  80

Asn Ser Val Lys Gly Arg Phe Thr Ile Ser Arg Asp Asn Ala Lys Asn
                85                  90                  95

Thr Val Tyr Leu Gln Met Asn Ser Leu Lys Pro Glu Asp Thr Ala Asp
            100                 105                 110

Tyr Tyr Cys Ala Ala Gly Ser Thr Xaa Arg Val Asp Tyr Trp Gly Lys
        115                 120                 125

Gly Thr Gln Val Thr Val Ser Ser Ala Ser
    130                 135
```

-continued

```
<210> SEQ ID NO 71
<211> LENGTH: 119
<212> TYPE: PRT
<213> ORGANISM: Artificial Sequence
<220> FEATURE:
<223> OTHER INFORMATION: Immunogen with no epitope without signal
      sequence
<220> FEATURE:
<221> NAME/KEY: VARIANT
<222> LOCATION: (102)..(102)
<223> OTHER INFORMATION: Xaa is any amino acid residue

<400> SEQUENCE: 71

Glu Val Gln Leu Gln Ala Ser Gly Gly Leu Val Gln Ala Gly Gly
1               5                   10                  15

Ser Leu Arg Leu Ser Cys Ala Ala Ser Gly Phe Lys Ile Thr His Tyr
                20                  25                  30

Thr Met Gly Trp Phe Arg Gln Ala Pro Gly Lys Glu Arg Glu Phe Val
            35                  40                  45

Ser Arg Ile Thr Trp Gly Gly Asp Asn Thr Phe Tyr Ser Asn Ser Val
    50                  55                      60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Asp Tyr Tyr Cys
                85                  90                  95

Ala Ala Gly Ser Thr Xaa Arg Val Asp Tyr Trp Gly Lys Gly Thr Gln
            100                 105                 110

Val Thr Val Ser Ser Ala Ser
        115

<210> SEQ ID NO 72
<211> LENGTH: 1977
<212> TYPE: PRT
<213> ORGANISM: Homo sapiens

<400> SEQUENCE: 72

Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
                20                  25                  30

Lys Glu Pro Lys Glu Glu Lys Lys Asp Asp Asp Glu Glu Ala Pro Lys
            35                  40                  45

Pro Ser Ser Asp Leu Glu Ala Gly Lys Gln Leu Pro Phe Ile Tyr Gly
    50                  55                      60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                     140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175
```

```
Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
            245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
            275                 280                 285

Ile Met Asn Thr Leu Glu Ser Glu Glu Asp Phe Arg Lys Tyr Phe Tyr
            290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
            325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
            355                 360                 365

Gln Thr Leu Arg Ala Ala Gly Lys Thr Tyr Met Ile Phe Phe Val Val
            370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Glu Tyr Thr
            435                 440                 445

Ser Ile Arg Arg Ser Arg Ile Met Gly Leu Ser Glu Ser Ser Ser Glu
450                 455                 460

Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
            485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
            515                 520                 525

Leu Ser Thr Pro Asn Gln Ser Pro Leu Ser Ile Arg Gly Ser Leu Phe
            530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
            565                 570                 575

Ile Phe Gly Asp Asn Glu Ser Arg Arg Gly Ser Leu Phe Val Pro His
            580                 585                 590
```

```
Arg Pro Gln Glu Arg Arg Ser Ser Asn Ile Ser Gln Ala Ser Arg Ser
        595                 600                 605

Pro Pro Met Leu Pro Val Asn Gly Lys Met His Ser Ala Val Asp Cys
610                 615                 620

Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
                645                 650                 655

Arg Arg Cys Ser Ser Tyr Leu Leu Ser Glu Asp Met Leu Asn Asp Pro
                660                 665                 670

Asn Leu Arg Gln Arg Ala Met Ser Arg Ala Ser Ile Leu Thr Asn Thr
            675                 680                 685

Val Glu Glu Leu Glu Glu Ser Arg Gln Lys Cys Pro Pro Trp Trp Tyr
        690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
                740                 745                 750

Glu His His Pro Met Thr Glu Glu Phe Lys Asn Val Leu Ala Ile Gly
            755                 760                 765

Asn Leu Val Phe Thr Gly Ile Phe Ala Ala Glu Met Val Leu Lys Leu
        770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
        835                 840                 845

Gly Asn Ser Val Gly Ala Leu Gly Asn Leu Thr Leu Val Leu Ala Ile
        850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
                900                 905                 910

Leu Cys Gly Glu Trp Ile Glu Thr Met Trp Asp Cys Met Glu Val Ala
            915                 920                 925

Gly Gln Ala Met Cys Leu Ile Val Tyr Met Met Val Met Val Ile Gly
        930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
                965                 970                 975

Leu Gln Ile Ala Val Thr Arg Ile Lys Lys Gly Ile Asn Tyr Val Lys
            980                 985                 990

Gln Thr Leu Arg Glu Phe Ile Leu  Lys Ala Phe Ser Lys  Lys Pro Lys
        995                 1000                 1005
```

```
Ile Ser Arg Glu Ile Arg Gln Ala Glu Asp Leu Asn Thr Lys Lys
1010                1015                1020

Glu Asn Tyr Ile Ser Asn His Thr Leu Ala Glu Met Ser Lys Gly
1025                1030                1035

His Asn Phe Leu Lys Glu Lys Asp Lys Ile Ser Gly Phe Gly Ser
1040                1045                1050

Ser Val Asp Lys His Leu Met Glu Asp Ser Asp Gly Gln Ser Phe
1055                1060                1065

Ile His Asn Pro Ser Leu Thr Val Thr Val Pro Ile Ala Pro Gly
1070                1075                1080

Glu Ser Asp Leu Glu Asn Met Asn Ala Glu Glu Leu Ser Ser Asp
1085                1090                1095

Ser Asp Ser Glu Tyr Ser Lys Val Arg Leu Asn Arg Ser Ser Ser
1100                1105                1110

Ser Glu Cys Ser Thr Val Asp Asn Pro Leu Pro Gly Glu Gly Glu
1115                1120                1125

Glu Ala Glu Ala Glu Pro Met Asn Ser Asp Glu Pro Glu Ala Cys
1130                1135                1140

Phe Thr Asp Gly Cys Val Arg Arg Phe Ser Cys Cys Gln Val Asn
1145                1150                1155

Ile Glu Ser Gly Lys Gly Lys Ile Trp Trp Asn Ile Arg Lys Thr
1160                1165                1170

Cys Tyr Lys Ile Val Glu His Ser Trp Phe Glu Ser Phe Ile Val
1175                1180                1185

Leu Met Ile Leu Leu Ser Ser Gly Ala Leu Ala Phe Glu Asp Ile
1190                1195                1200

Tyr Ile Glu Arg Lys Lys Thr Ile Lys Ile Ile Leu Glu Tyr Ala
1205                1210                1215

Asp Lys Ile Phe Thr Tyr Ile Phe Ile Leu Glu Met Leu Leu Lys
1220                1225                1230

Trp Ile Ala Tyr Gly Tyr Lys Thr Tyr Phe Thr Asn Ala Trp Cys
1235                1240                1245

Trp Leu Asp Phe Leu Ile Val Asp Val Ser Leu Val Thr Leu Val
1250                1255                1260

Ala Asn Thr Leu Gly Tyr Ser Asp Leu Gly Pro Ile Lys Ser Leu
1265                1270                1275

Arg Thr Leu Arg Ala Leu Arg Pro Leu Arg Ala Leu Ser Arg Phe
1280                1285                1290

Glu Gly Met Arg Val Val Val Asn Ala Leu Ile Gly Ala Ile Pro
1295                1300                1305

Ser Ile Met Asn Val Leu Leu Val Cys Leu Ile Phe Trp Leu Ile
1310                1315                1320

Phe Ser Ile Met Gly Val Asn Leu Phe Ala Gly Lys Phe Tyr Glu
1325                1330                1335

Cys Ile Asn Thr Thr Asp Gly Ser Arg Phe Pro Ala Ser Gln Val
1340                1345                1350

Pro Asn Arg Ser Glu Cys Phe Ala Leu Met Asn Val Ser Gln Asn
1355                1360                1365

Val Arg Trp Lys Asn Leu Lys Val Asn Phe Asp Asn Val Gly Leu
1370                1375                1380

Gly Tyr Leu Ser Leu Leu Gln Val Ala Thr Phe Lys Gly Trp Thr
1385                1390                1395
```

```
Ile  Ile  Met  Tyr  Ala  Ala  Val  Asp  Ser  Val  Asn  Val  Asp  Lys  Gln
1400                 1405                     1410

Pro  Lys  Tyr  Glu  Tyr  Ser  Leu  Tyr  Met  Tyr  Ile  Tyr  Phe  Val  Val
1415                 1420                     1425

Phe  Ile  Ile  Phe  Gly  Ser  Phe  Phe  Thr  Leu  Asn  Leu  Phe  Ile  Gly
1430                 1435                     1440

Val  Ile  Ile  Asp  Asn  Phe  Asn  Gln  Gln  Lys  Lys  Lys  Leu  Gly  Gly
1445                 1450                     1455

Gln  Asp  Ile  Phe  Met  Thr  Glu  Glu  Gln  Lys  Lys  Tyr  Tyr  Asn  Ala
1460                 1465                     1470

Met  Lys  Lys  Leu  Gly  Ser  Lys  Lys  Pro  Gln  Lys  Pro  Ile  Pro  Arg
1475                 1480                     1485

Pro  Gly  Asn  Lys  Ile  Gln  Gly  Cys  Ile  Phe  Asp  Leu  Val  Thr  Asn
1490                 1495                     1500

Gln  Ala  Phe  Asp  Ile  Ser  Ile  Met  Val  Leu  Ile  Cys  Leu  Asn  Met
1505                 1510                     1515

Val  Thr  Met  Met  Val  Glu  Lys  Glu  Gly  Gln  Ser  Gln  His  Met  Thr
1520                 1525                     1530

Glu  Val  Leu  Tyr  Trp  Ile  Asn  Val  Val  Phe  Ile  Ile  Leu  Phe  Thr
1535                 1540                     1545

Gly  Glu  Cys  Val  Leu  Lys  Leu  Ile  Ser  Leu  Arg  His  Tyr  Tyr  Phe
1550                 1555                     1560

Thr  Val  Gly  Trp  Asn  Ile  Phe  Asp  Phe  Val  Val  Ile  Ile  Ser
1565                 1570                     1575

Ile  Val  Gly  Met  Phe  Leu  Ala  Asp  Leu  Ile  Glu  Thr  Tyr  Phe  Val
1580                 1585                     1590

Ser  Pro  Thr  Leu  Phe  Arg  Val  Ile  Arg  Leu  Ala  Arg  Ile  Gly  Arg
1595                 1600                     1605

Ile  Leu  Arg  Leu  Val  Lys  Gly  Ala  Lys  Gly  Ile  Arg  Thr  Leu  Leu
1610                 1615                     1620

Phe  Ala  Leu  Met  Met  Ser  Leu  Pro  Ala  Leu  Phe  Asn  Ile  Gly  Leu
1625                 1630                     1635

Leu  Leu  Phe  Leu  Val  Met  Phe  Ile  Tyr  Ala  Ile  Phe  Gly  Met  Ser
1640                 1645                     1650

Asn  Phe  Ala  Tyr  Val  Lys  Lys  Glu  Asp  Gly  Ile  Asn  Asp  Met  Phe
1655                 1660                     1665

Asn  Phe  Glu  Thr  Phe  Gly  Asn  Ser  Met  Ile  Cys  Leu  Phe  Gln  Ile
1670                 1675                     1680

Thr  Thr  Ser  Ala  Gly  Trp  Asp  Gly  Leu  Leu  Ala  Pro  Ile  Leu  Asn
1685                 1690                     1695

Ser  Lys  Pro  Pro  Asp  Cys  Asp  Pro  Lys  Lys  Val  His  Pro  Gly  Ser
1700                 1705                     1710

Ser  Val  Glu  Gly  Asp  Cys  Gly  Asn  Pro  Ser  Val  Gly  Ile  Phe  Tyr
1715                 1720                     1725

Phe  Val  Ser  Tyr  Ile  Ile  Ile  Ser  Phe  Leu  Val  Val  Val  Asn  Met
1730                 1735                     1740

Tyr  Ile  Ala  Val  Ile  Leu  Glu  Asn  Phe  Ser  Val  Ala  Thr  Glu  Glu
1745                 1750                     1755

Ser  Thr  Glu  Pro  Leu  Ser  Glu  Asp  Asp  Phe  Glu  Met  Phe  Tyr  Glu
1760                 1765                     1770

Val  Trp  Glu  Lys  Phe  Asp  Pro  Asp  Ala  Thr  Gln  Phe  Ile  Glu  Phe
1775                 1780                     1785
```

| | | | | | | | | | | |
|---|---|---|---|---|---|---|---|---|---|---|
|Ser|Lys<br>1790|Leu|Ser|Asp|Phe<br>1795|Ala|Ala|Leu|Asp<br>1800|Pro Pro Leu Leu|

Ile Ala Lys Pro Asn Lys Val Gln Leu Ile Ala Met Asp Leu Pro
   1805                1810                1815

Met Val Ser Gly Asp Arg Ile His Cys Leu Asp Ile Leu Phe Ala
   1820                1825                1830

Phe Thr Lys Arg Val Leu Gly Glu Ser Gly Glu Met Asp Ser Leu
   1835                1840                1845

Arg Ser Gln Met Glu Glu Arg Phe Met Ser Ala Asn Pro Ser Lys
   1850                1855                1860

Val Ser Tyr Glu Pro Ile Thr Thr Thr Leu Lys Arg Lys Gln Glu
   1865                1870                1875

Asp Val Ser Ala Thr Val Ile Gln Arg Ala Tyr Arg Arg Tyr Arg
   1880                1885                1890

Leu Arg Gln Asn Val Lys Asn Ile Ser Ser Ile Tyr Ile Lys Asp
   1895                1900                1905

Gly Asp Arg Asp Asp Asp Leu Leu Asn Lys Lys Asp Met Ala Phe
   1910                1915                1920

Asp Asn Val Asn Glu Asn Ser Ser Pro Glu Lys Thr Asp Ala Thr
   1925                1930                1935

Ser Ser Thr Thr Ser Pro Pro Ser Tyr Asp Ser Val Thr Lys Pro
   1940                1945                1950

Asp Lys Glu Lys Tyr Glu Gln Asp Arg Thr Glu Lys Glu Asp Lys
   1955                1960                1965

Gly Lys Asp Ser Lys Glu Ser Lys Lys
   1970                1975

<210> SEQ ID NO 73
<211> LENGTH: 414
<212> TYPE: DNA
<213> ORGANISM: Artificial Sequence
<220> FEATURE:
<223> OTHER INFORMATION: Nucleotide sequence encoding the heavy chain of
      the 1B6 antibody

<400> SEQUENCE: 73
tgcctggtga cgttcccaag ctgtgtcctg tcccaggtgc agctgaagga gtcaggacct    60
ggcctggtgg caccctcaca gagcctgtcc atcacatgca ctgtctctgg gttctcatta   120
tccagatata atgtacactg ggttcgccag cctccaggaa agggtctgga gtggctggga   180
atgatatggg gtggtggaag cacagactat aattcagctc tcaaatccag acttagcatc   240
agcaaggaca actccaagag ccaagttttc ttaaaaatga acagtctgca aactgatgac   300
acagccatgt actactgtgc cagaaatgga gctaactggg actggtttgc ttactggggc   360
caagggactc tggtcactgt ctctgcagcc aaaacgacac cccatctgt ctat          414

<210> SEQ ID NO 74
<211> LENGTH: 138
<212> TYPE: PRT
<213> ORGANISM: Artificial Sequence
<220> FEATURE:
<223> OTHER INFORMATION: Heavy chain of the 1B6 antibody

<400> SEQUENCE: 74

Cys Leu Val Thr Phe Pro Ser Cys Val Leu Ser Gln Val Gln Leu Lys
1               5                  10                  15

Glu Ser Gly Pro Gly Leu Val Ala Pro Ser Gln Ser Leu Ser Ile Thr
            20                  25                  30

```
Cys Thr Val Ser Gly Phe Ser Leu Ser Arg Tyr Asn Val His Trp Val
            35                  40                  45

Arg Gln Pro Pro Gly Lys Gly Leu Glu Trp Leu Gly Met Ile Trp Gly
    50                  55                  60

Gly Gly Ser Thr Asp Tyr Asn Ser Ala Leu Lys Ser Arg Leu Ser Ile
65                  70                  75                  80

Ser Lys Asp Asn Ser Lys Ser Gln Val Phe Leu Lys Met Asn Ser Leu
                85                  90                  95

Gln Thr Asp Asp Thr Ala Met Tyr Tyr Cys Ala Arg Asn Gly Ala Asn
            100                 105                 110

Trp Asp Trp Phe Ala Tyr Trp Gly Gln Gly Thr Leu Val Thr Val Ser
        115                 120                 125

Ala Ala Lys Thr Thr Pro Pro Ser Val Tyr
    130                 135

<210> SEQ ID NO 75
<211> LENGTH: 8
<212> TYPE: PRT
<213> ORGANISM: Artificial Sequence
<220> FEATURE:
<223> OTHER INFORMATION: Heavy chain CDR1 of the 1B6 antibody

<400> SEQUENCE: 75

Gly Phe Ser Leu Ser Arg Tyr Asn
1               5

<210> SEQ ID NO 76
<211> LENGTH: 7
<212> TYPE: PRT
<213> ORGANISM: Artificial Sequence
<220> FEATURE:
<223> OTHER INFORMATION: Heavy chain CDR2 of the 1B6 antibody

<400> SEQUENCE: 76

Ile Trp Gly Gly Gly Ser Thr
1               5

<210> SEQ ID NO 77
<211> LENGTH: 12
<212> TYPE: PRT
<213> ORGANISM: Artificial Sequence
<220> FEATURE:
<223> OTHER INFORMATION: Heavy chain CDR3 of the 1B6 antibody

<400> SEQUENCE: 77

Ala Arg Asn Gly Ala Asn Trp Asp Trp Phe Ala Tyr
1               5                   10

<210> SEQ ID NO 78
<211> LENGTH: 414
<212> TYPE: DNA
<213> ORGANISM: Artificial Sequence
<220> FEATURE:
<223> OTHER INFORMATION: Nucleotide sequence encoding the light chain of
      the 1B6 antibody

<400> SEQUENCE: 78
ctgctatggg tatctggtac ctgtggggac attgtgatgt cacagtctcc atcctcccta      60
cctgtgtcag ttggagagaa ggttactatg agctgcaagt ccagtcagag ccttttatat    120
agtagcaatc aaaagaacta cttggcctgg taccagcaga accaggca gtctcctaaa      180 ctgctgattt actgggcatc cactagggaa tctggggtcc ctgatcgctt cacaggcagt   240
```

```
ggatctggga cagatttcac tctcaccatc agcagtgtga aggctgaaga cctggcagtt    300
tattactgtc agcaatatta tagctatcca ttcacgttcg gctcggggac aaagttggaa    360
ataaaacggg ctgatgctgc accaactgta tccatcttcc caccatccag tgtc          414
```

<210> SEQ ID NO 79
<211> LENGTH: 138
<212> TYPE: PRT
<213> ORGANISM: Artificial Sequence
<220> FEATURE:
<223> OTHER INFORMATION: Light chain of the 1B6 antibody

<400> SEQUENCE: 79

Leu Leu Trp Val Ser Gly Thr Cys Gly Asp Ile Val Met Ser Gln Ser
1               5                   10                  15

Pro Ser Ser Leu Pro Val Ser Val Gly Glu Lys Val Thr Met Ser Cys
            20                  25                  30

Lys Ser Ser Gln Ser Leu Leu Tyr Ser Ser Asn Gln Lys Asn Tyr Leu
        35                  40                  45

Ala Trp Tyr Gln Gln Lys Pro Gly Gln Ser Pro Lys Leu Leu Ile Tyr
    50                  55                  60

Trp Ala Ser Thr Arg Glu Ser Gly Val Pro Asp Arg Phe Thr Gly Ser
65                  70                  75                  80

Gly Ser Gly Thr Asp Phe Thr Leu Thr Ile Ser Ser Val Lys Ala Glu
                85                  90                  95

Asp Leu Ala Val Tyr Tyr Cys Gln Gln Tyr Tyr Ser Tyr Pro Phe Thr
            100                 105                 110

Phe Gly Ser Gly Thr Lys Leu Glu Ile Lys Arg Ala Asp Ala Ala Pro
        115                 120                 125

Thr Val Ser Ile Phe Pro Pro Ser Val
    130                 135

<210> SEQ ID NO 80
<211> LENGTH: 12
<212> TYPE: PRT
<213> ORGANISM: Artificial Sequence
<220> FEATURE:
<223> OTHER INFORMATION: Light chain CDR1 of the 1B6 antibody

<400> SEQUENCE: 80

Gln Ser Leu Leu Tyr Ser Ser Asn Gln Lys Asn Tyr
1               5                   10

<210> SEQ ID NO 81
<211> LENGTH: 3
<212> TYPE: PRT
<213> ORGANISM: Artificial Sequence
<220> FEATURE:
<223> OTHER INFORMATION: Light chain CDR2 of the 1B6 antibody

<400> SEQUENCE: 81

Trp Ala Ser
1

<210> SEQ ID NO 82
<211> LENGTH: 9
<212> TYPE: PRT
<213> ORGANISM: Artificial Sequence
<220> FEATURE:
<223> OTHER INFORMATION: Light chain CDR3 of the 1B6 antibody

<400> SEQUENCE: 82

Gln Gln Tyr Tyr Ser Tyr Pro Phe Thr
1               5

<210> SEQ ID NO 83
<211> LENGTH: 423
<212> TYPE: DNA
<213> ORGANISM: Artificial Sequence
<220> FEATURE:
<223> OTHER INFORMATION: Nucleotide sequence of the heavy chain of the
      2G11 antibody

<400> SEQUENCE: 83

```
tttttggtag caacagctac agatgtccac tcccaggtcc aactgcagca gcctggggct    60
gaactggtga agcctggggc ttcagtgaag ctgtcctgca aggcttctgg ctacaccttc   120
accacctact ggatgcactg ggtgaagcag aggcctggac aaggccttga gtggattgga   180
gagattaatc ctagcaacgg tcgtgctaac tacaatgaga agttcaagag caaggccaca   240
ctgactgtag acaaatcctc cagcacagcc tacatgcaac tcagcagcct gacatctgag   300
gactctgcgg tctattactg tttaagatca ctaggctact tgactactgg ggccaaggc    360 accactctca cagtctcctc agccaaaaca acagcccat cggtctatcc actggcccct    420
ggg                                                                 423
```

<210> SEQ ID NO 84
<211> LENGTH: 141
<212> TYPE: PRT
<213> ORGANISM: Artificial Sequence
<220> FEATURE:
<223> OTHER INFORMATION: Heavy chain of the 2G11 antibody

<400> SEQUENCE: 84

Phe Leu Val Ala Thr Ala Thr Asp Val His Ser Gln Val Gln Leu Gln
1               5                   10                  15

Gln Pro Gly Ala Glu Leu Val Lys Pro Gly Ala Ser Val Lys Leu Ser
            20                  25                  30

Cys Lys Ala Ser Gly Tyr Thr Phe Thr Thr Tyr Trp Met His Trp Val
        35                  40                  45

Lys Gln Arg Pro Gly Gln Gly Leu Glu Trp Ile Gly Glu Ile Asn Pro
    50                  55                  60

Ser Asn Gly Arg Ala Asn Tyr Asn Glu Lys Phe Lys Ser Lys Ala Thr
65                  70                  75                  80

Leu Thr Val Asp Lys Ser Ser Ser Thr Ala Tyr Met Gln Leu Ser Ser
                85                  90                  95

Leu Thr Ser Glu Asp Ser Ala Val Tyr Tyr Cys Leu Arg Ser Leu Gly
            100                 105                 110

Tyr Phe Asp Tyr Trp Gly Gln Gly Thr Thr Leu Thr Val Ser Ser Ala
        115                 120                 125

Lys Thr Thr Ala Pro Ser Val Tyr Pro Leu Ala Pro Gly
    130                 135                 140

<210> SEQ ID NO 85
<211> LENGTH: 8
<212> TYPE: PRT
<213> ORGANISM: Artificial Sequence
<220> FEATURE:
<223> OTHER INFORMATION: Heavy chain CDR1 of the 2G11 antibody

<400> SEQUENCE: 85

Gly Tyr Thr Phe Thr Thr Tyr Trp
1               5

<210> SEQ ID NO 86
<211> LENGTH: 8
<212> TYPE: PRT
<213> ORGANISM: Artificial Sequence
<220> FEATURE:
<223> OTHER INFORMATION: Heavy chain CDR2 of the 2G11 antibody

<400> SEQUENCE: 86

Ile Asn Pro Ser Asn Gly Arg Ala
1               5

<210> SEQ ID NO 87
<211> LENGTH: 9
<212> TYPE: PRT
<213> ORGANISM: Artificial Sequence
<220> FEATURE:
<223> OTHER INFORMATION: Heavy chain CDR3 of the 2G11 antibody

<400> SEQUENCE: 87

Leu Arg Ser Leu Gly Tyr Phe Asp Tyr
1               5

<210> SEQ ID NO 88
<211> LENGTH: 435
<212> TYPE: DNA
<213> ORGANISM: Artificial Sequence
<220> FEATURE:
<223> OTHER INFORMATION: Nucleotide sequence encoding the light chain of
      the 2G11 antibody

<400> SEQUENCE: 88
aagttgcctg ttaggctgtt ggtgctgatg ttctggattc ctgcttccag cagtgatgtt      60
gtgatgaccc aaagtccact ctccctgcct gtcagtcttg agatcaagc ctccatctct     120 tgcagatcta gtcagagcct tgtacacagt aatggaaaca cctatttaca ttggtacctg     180
cagaaggcag gccagtctcc aaagttcctg atctacaaag tttccaaccg attttctggg     240
gtcccagaca ggttcagtgg cagtggatca gggacagatt tcacactcaa gatcagcaga     300
gtggaggctg aggatctggg agtttatttc tgctctcaaa gtacacatgt tccgtacacg     360
ttcggagggg ggaccaagct ggaaataaaa cgggctgatg ctgcaccaac tgtatccatc     420
ttcccaccat ccagt                                                     435

<210> SEQ ID NO 89
<211> LENGTH: 145
<212> TYPE: PRT
<213> ORGANISM: Artificial Sequence
<220> FEATURE:
<223> OTHER INFORMATION: Light chain of the 2G11 antibody

<400> SEQUENCE: 89

Lys Leu Pro Val Arg Leu Val Leu Met Phe Trp Ile Pro Ala Ser
1               5                   10                  15

Ser Ser Asp Val Val Met Thr Gln Ser Pro Leu Ser Leu Pro Val Ser
                20                  25                  30

Leu Gly Asp Gln Ala Ser Ile Ser Cys Arg Ser Ser Gln Ser Leu Val
        35                  40                  45

His Ser Asn Gly Asn Thr Tyr Leu His Trp Tyr Leu Gln Lys Ala Gly
    50                  55                  60

```
Gln Ser Pro Lys Phe Leu Ile Tyr Lys Val Ser Asn Arg Phe Ser Gly
 65                  70                  75                  80

Val Pro Asp Arg Phe Ser Gly Ser Gly Ser Gly Thr Asp Phe Thr Leu
                 85                  90                  95

Lys Ile Ser Arg Val Glu Ala Glu Asp Leu Gly Val Tyr Phe Cys Ser
            100                 105                 110

Gln Ser Thr His Val Pro Tyr Thr Phe Gly Gly Gly Thr Lys Leu Glu
        115                 120                 125

Ile Lys Arg Ala Asp Ala Ala Pro Thr Val Ser Ile Phe Pro Pro Ser
    130                 135                 140

Ser
145

<210> SEQ ID NO 90
<211> LENGTH: 11
<212> TYPE: PRT
<213> ORGANISM: Artificial Sequence
<220> FEATURE:
<223> OTHER INFORMATION: Light chain CDR1 of the 2G11 antibody

<400> SEQUENCE: 90

Gln Ser Leu Val His Ser Asn Gly Asn Thr Tyr
 1               5                  10

<210> SEQ ID NO 91
<211> LENGTH: 3
<212> TYPE: PRT
<213> ORGANISM: Artificial Sequence
<220> FEATURE:
<223> OTHER INFORMATION: Light chain CDR2 of the 2G11 antibody

<400> SEQUENCE: 91

Lys Val Ser
 1

<210> SEQ ID NO 92
<211> LENGTH: 9
<212> TYPE: PRT
<213> ORGANISM: Artificial Sequence
<220> FEATURE:
<223> OTHER INFORMATION: Light chain CDR3 of the 2G11 antibody

<400> SEQUENCE: 92

Ser Gln Ser Thr His Val Pro Tyr Thr
 1               5

<210> SEQ ID NO 93
<211> LENGTH: 441
<212> TYPE: DNA
<213> ORGANISM: Artificial Sequence
<220> FEATURE:
<223> OTHER INFORMATION: Nucleotide sequence encoding the heavy chain of
      the 1H5 antibody

<400> SEQUENCE: 93
agcttgattt tccttgtcct tgttttaaaa ggtgtccagt gtgaggtgaa gctggtggag      60
tctgggggag gcttagtgaa gcctggaggg tccctgaaac tctcctgtgc agcctctgga    120
ttcactttca gaagttatgc catgtcttgg gttcgccaga ctccagaaaa ggggctggag    180
tgggtcgcat ccattagtag tggtggtagc acctactatc agacagtgt gaagggccga     240 ttcaccatct ccagagataa tgccgggaac atcctgtacc tgcaaatgag cagtctgagg    300
tctgaggaca cggccatgta ttactgtgca agaggctatg atggttacta cgagaggata    360
```

```
tggtactatg ctatggacta ttggggtcaa ggaacctcag tcaccgtctc ctcagccaaa    420
acgacacccc catctgtcta t                                              441
```

<210> SEQ ID NO 94
<211> LENGTH: 147
<212> TYPE: PRT
<213> ORGANISM: Artificial Sequence
<220> FEATURE:
<223> OTHER INFORMATION: Heavy chain of the 1H5 antibody

<400> SEQUENCE: 94

```
Ser Leu Ile Phe Leu Val Leu Val Leu Lys Gly Val Gln Cys Glu Val
1               5                   10                  15

Lys Leu Val Glu Ser Gly Gly Gly Leu Val Lys Pro Gly Gly Ser Leu
            20                  25                  30

Lys Leu Ser Cys Ala Ala Ser Gly Phe Thr Phe Arg Ser Tyr Ala Met
        35                  40                  45

Ser Trp Val Arg Gln Thr Pro Glu Lys Gly Leu Glu Trp Val Ala Ser
50                  55                  60

Ile Ser Ser Gly Gly Ser Thr Tyr Tyr Pro Asp Ser Val Lys Gly Arg
65                  70                  75                  80

Phe Thr Ile Ser Arg Asp Asn Ala Gly Asn Ile Leu Tyr Leu Gln Met
                85                  90                  95

Ser Ser Leu Arg Ser Glu Asp Thr Ala Met Tyr Tyr Cys Ala Arg Gly
            100                 105                 110

Tyr Asp Gly Tyr Tyr Glu Arg Ile Trp Tyr Tyr Ala Met Asp Tyr Trp
        115                 120                 125

Gly Gln Gly Thr Ser Val Thr Val Ser Ser Ala Lys Thr Thr Pro Pro
130                 135                 140

Ser Val Tyr
145
```

<210> SEQ ID NO 95
<211> LENGTH: 8
<212> TYPE: PRT
<213> ORGANISM: Artificial Sequence
<220> FEATURE:
<223> OTHER INFORMATION: Heavy chain CDR1 of the 1H5 antibody

<400> SEQUENCE: 95

```
Gly Phe Thr Phe Arg Ser Tyr Ala
1               5
```

<210> SEQ ID NO 96
<211> LENGTH: 7
<212> TYPE: PRT
<213> ORGANISM: Artificial Sequence
<220> FEATURE:
<223> OTHER INFORMATION: Heavy chain CDR2 of the 1H5 antibody

<400> SEQUENCE: 96

```
Ile Ser Ser Gly Gly Ser Thr
1               5
```

<210> SEQ ID NO 97
<211> LENGTH: 18
<212> TYPE: PRT
<213> ORGANISM: Artificial Sequence
<220> FEATURE:
<223> OTHER INFORMATION: Heavy chain CDR3 of the 1H5 antibody

<400> SEQUENCE: 97

Ala Arg Gly Tyr Asp Gly Tyr Tyr Glu Arg Ile Trp Tyr Tyr Ala Met
1               5                   10                  15

Asp Tyr

<210> SEQ ID NO 98
<211> LENGTH: 411
<212> TYPE: DNA
<213> ORGANISM: Artificial Sequence
<220> FEATURE:
<223> OTHER INFORMATION: Nucleotide sequence encoding the light chain of
      the 1H5 antibody

<400> SEQUENCE: 98
caggtctttg tatacatgtt gctgtggttg tctggtgttg atggagacat tgtgatgacc      60
cagtctcaaa aattcatgtc cacatcagta ggagacaggg tcactgtctc ctgcaaggcc     120
agtcagaatg tgggtactat tgtagcctgg tatcaacaaa aaccaggtca atctcctaaa     180
gcactgattt actcggcatc ctaccggttc agtggagtcc ctgatcgctt cacaggcagt     240
ggatctggga cagatttcac tctcaccatc agcaatgtgc agtctgaaga cttggcagag     300
tatttctgtc agcaatataa cacctatcct ctcacgttcg gctcggggac aaagttggaa     360
ataaaacggg ctgatgctgc accaactgta tccatcttcc caccatccag t              411

<210> SEQ ID NO 99
<211> LENGTH: 137
<212> TYPE: PRT
<213> ORGANISM: Artificial Sequence
<220> FEATURE:
<223> OTHER INFORMATION: Light chain of the 1H5 antibody

<400> SEQUENCE: 99

Gln Val Phe Val Tyr Met Leu Leu Trp Leu Ser Gly Val Asp Gly Asp
1               5                   10                  15

Ile Val Met Thr Gln Ser Gln Lys Phe Met Ser Thr Ser Val Gly Asp
                20                  25                  30

Arg Val Thr Val Ser Cys Lys Ala Ser Gln Asn Val Gly Thr Ile Val
            35                  40                  45

Ala Trp Tyr Gln Gln Lys Pro Gly Gln Ser Pro Lys Ala Leu Ile Tyr
        50                  55                  60

Ser Ala Ser Tyr Arg Phe Ser Gly Val Pro Asp Arg Phe Thr Gly Ser
65                  70                  75                  80

Gly Ser Gly Thr Asp Phe Thr Leu Thr Ile Ser Asn Val Gln Ser Glu
                85                  90                  95

Asp Leu Ala Glu Tyr Phe Cys Gln Gln Tyr Asn Thr Tyr Pro Leu Thr
                100                 105                 110

Phe Gly Ser Gly Thr Lys Leu Glu Ile Lys Arg Ala Asp Ala Ala Pro
            115                 120                 125

Thr Val Ser Ile Phe Pro Pro Ser Ser
        130                 135

<210> SEQ ID NO 100
<211> LENGTH: 6
<212> TYPE: PRT
<213> ORGANISM: Artificial Sequence
<220> FEATURE:
<223> OTHER INFORMATION: Light chain CDR1 of the 1H5 antibody

```
<400> SEQUENCE: 100

Gln Asn Val Gly Thr Ile
1               5

<210> SEQ ID NO 101
<211> LENGTH: 3
<212> TYPE: PRT
<213> ORGANISM: Artificial Sequence
<220> FEATURE:
<223> OTHER INFORMATION: Light chain CDR2 of the 1H5 antibody

<400> SEQUENCE: 101

Ser Ala Ser
1

<210> SEQ ID NO 102
<211> LENGTH: 9
<212> TYPE: PRT
<213> ORGANISM: Artificial Sequence
<220> FEATURE:
<223> OTHER INFORMATION: Light chain CDR3 of the 1H5 antibody

<400> SEQUENCE: 102

Gln Gln Tyr Asn Thr Tyr Pro Leu Thr
1               5

<210> SEQ ID NO 103
<211> LENGTH: 20
<212> TYPE: PRT
<213> ORGANISM: Artificial Sequence
<220> FEATURE:
<223> OTHER INFORMATION: Peptide #2a

<400> SEQUENCE: 103

Thr Leu Glu Ser Glu Glu Asp Phe Arg Lys Tyr Phe Tyr Tyr Leu Glu
1               5                   10                  15

Gly Ser Lys Asp
            20

<210> SEQ ID NO 104
<211> LENGTH: 20
<212> TYPE: PRT
<213> ORGANISM: Artificial Sequence
<220> FEATURE:
<223> OTHER INFORMATION: Peptide #2b

<400> SEQUENCE: 104

Tyr Phe Tyr Tyr Leu Glu Gly Ser Lys Asp Ala Leu Leu Cys Gly Phe
1               5                   10                  15

Ser Thr Asp Ser
            20

<210> SEQ ID NO 105
<211> LENGTH: 40
<212> TYPE: PRT
<213> ORGANISM: Artificial Sequence
<220> FEATURE:
<223> OTHER INFORMATION: Peptide #40a
```

```
<400> SEQUENCE: 105

Lys His Lys Cys Phe Arg Asn Ser Leu Glu Asn Asn Glu Thr Leu Glu
1               5                   10                  15

Ser Ile Met Asn Thr Leu Glu Ser Glu Glu Asp Phe Arg Lys Tyr Phe
            20                  25                  30

Tyr Tyr Leu Glu Gly Ser Lys Asp
        35                  40

<210> SEQ ID NO 106
<211> LENGTH: 40
<212> TYPE: PRT
<213> ORGANISM: Artificial Sequence
<220> FEATURE:
<223> OTHER INFORMATION: Peptide #40b

<400> SEQUENCE: 106

Tyr Phe Tyr Tyr Leu Glu Gly Ser Lys Asp Ala Leu Leu Cys Gly Phe
1               5                   10                  15

Ser Thr Asp Ser Gly Gln Cys Pro Glu Gly Tyr Thr Cys Val Lys Ile
            20                  25                  30

Gly Arg Asn Pro Asp Tyr Gly Tyr
        35                  40

<210> SEQ ID NO 107
<211> LENGTH: 6
<212> TYPE: PRT
<213> ORGANISM: Artificial Sequence
<220> FEATURE:
<223> OTHER INFORMATION: Peptide corresponding to residues Phe129-Tyr134
      of FC5DIE3IR

<400> SEQUENCE: 107

Phe Arg Lys Tyr Phe Tyr
1               5

<210> SEQ ID NO 108
<211> LENGTH: 8
<212> TYPE: PRT
<213> ORGANISM: Artificial Sequence
<220> FEATURE:
<223> OTHER INFORMATION: Peptide corresponding to residues Asn121-Asp128
      of FC5DIE3IR

<400> SEQUENCE: 108

Asn Thr Leu Glu Ser Glu Glu Asp
1               5

<210> SEQ ID NO 109
<211> LENGTH: 117
<212> TYPE: PRT
<213> ORGANISM: Artificial Sequence
<220> FEATURE:
<223> OTHER INFORMATION: Variable region, heavy chain of the 3A8
      antibody

<400> SEQUENCE: 109

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45
```

```
Gly Glu Ile Asn Pro Ser Asn Gly Arg Ala Asn Tyr Asn Glu Lys Phe
        50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Pro Tyr Gly Tyr Tyr Asp Tyr Trp Gly Gln Gly Thr Thr
                100                 105                 110

Leu Thr Val Ser Ser
            115

<210> SEQ ID NO 110
<211> LENGTH: 112
<212> TYPE: PRT
<213> ORGANISM: Artificial Sequence
<220> FEATURE:
<223> OTHER INFORMATION: Variable region, light chain of the 3A8
      antibody

<400> SEQUENCE: 110

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Leu Leu His Ser
                20                  25                  30

Asn Gly Asn Thr Tyr Phe His Trp Tyr Leu Gln Lys Pro Gly Gln Ser
            35                  40                  45

Pro Lys Leu Leu Ile Tyr Lys Val Ser Asn Arg Phe Phe Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ile
                 85                  90                  95

Thr His Val Pro Leu Thr Phe Gly Ala Gly Thr Lys Leu Glu Leu Lys
                100                 105                 110

<210> SEQ ID NO 111
<211> LENGTH: 121
<212> TYPE: PRT
<213> ORGANISM: Artificial Sequence
<220> FEATURE:
<223> OTHER INFORMATION: Variable region, heavy chain of the 1G5
      antibody

<400> SEQUENCE: 111

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser Tyr
                20                  25                  30

Trp Ile Asn Trp Val Lys Gln Arg Pro Gly Gln Gly Leu Glu Trp Ile
            35                  40                  45

Gly Asn Ile Tyr Pro Gly Asn Ser Asn Thr Asn Tyr Asn Glu Lys Phe
    50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95
```

```
Ala Arg Arg Tyr Tyr Tyr Asp Tyr Asp Asp Ala Met Asp Tyr Trp Gly
            100                 105                 110

Gln Gly Thr Ser Val Thr Val Ser Ser
        115                 120

<210> SEQ ID NO 112
<211> LENGTH: 111
<212> TYPE: PRT
<213> ORGANISM: Artificial Sequence
<220> FEATURE:
<223> OTHER INFORMATION: Variable region, light chain of the 1G5
      antibody

<400> SEQUENCE: 112

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Gly Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Val Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Trp Thr Phe Gly Gly Thr Lys Leu Glu Ile Lys
            100                 105                 110

<210> SEQ ID NO 113
<211> LENGTH: 127
<212> TYPE: PRT
<213> ORGANISM: Artificial Sequence
<220> FEATURE:
<223> OTHER INFORMATION: Heavy chain of the 1B6 antibody without leader
      sequence

<400> SEQUENCE: 113

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Asn Val His Trp Val Arg Gln Pro Pro Gly Lys Gly Leu Glu Trp Leu
        35                  40                  45

Gly Met Ile Trp Gly Gly Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Asn Gly Ala Asn Trp Asp Trp Phe Ala Tyr Trp Gly Gln Gly Thr
            100                 105                 110

Leu Val Thr Val Ser Ala Ala Lys Thr Thr Pro Pro Ser Val Tyr
        115                 120                 125

<210> SEQ ID NO 114
<211> LENGTH: 118
<212> TYPE: PRT
<213> ORGANISM: Artificial Sequence
```

```
<220> FEATURE:
<223> OTHER INFORMATION: Variable region, heavy chain of the 1B6
      antibody

<400> SEQUENCE: 114

Gln Val Gln Leu Lys Glu Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Asn Val His Trp Val Arg Gln Pro Pro Gly Lys Gly Leu Glu Trp Leu
            35                  40                  45

Gly Met Ile Trp Gly Gly Gly Ser Thr Asp Tyr Asn Ser Ala Leu Lys
50                      55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Asn Gly Ala Asn Trp Asp Trp Phe Ala Tyr Trp Gly Gln Gly Thr
            100                 105                 110

Leu Val Thr Val Ser Ala
            115

<210> SEQ ID NO 115
<211> LENGTH: 129
<212> TYPE: PRT
<213> ORGANISM: Artificial Sequence
<220> FEATURE:
<223> OTHER INFORMATION: Light chain of the 1B6 antibody without leader
      sequence

<400> SEQUENCE: 115

Asp Ile Val Met Ser Gln Ser Pro Ser Ser Leu Pro Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
50                      55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Phe Thr Phe Gly Ser Gly Thr Lys Leu Glu Ile
            100                 105                 110

Lys Arg Ala Asp Ala Ala Pro Thr Val Ser Ile Phe Pro Pro Ser Ser
            115                 120                 125

Val

<210> SEQ ID NO 116
<211> LENGTH: 113
<212> TYPE: PRT
<213> ORGANISM: Artificial Sequence
<220> FEATURE:
<223> OTHER INFORMATION: Variable region, light chain of the 1B6
      antibody
```

<400> SEQUENCE: 116

Asp Ile Val Met Ser Gln Ser Pro Ser Leu Pro Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Phe Thr Phe Gly Ser Gly Thr Lys Leu Glu Ile
                100                 105                 110

Lys

<210> SEQ ID NO 117
<211> LENGTH: 130
<212> TYPE: PRT
<213> ORGANISM: Artificial Sequence
<220> FEATURE:
<223> OTHER INFORMATION: Heavy chain of the 2G11 antibody without leader
      sequence

<400> SEQUENCE: 117

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Ala Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Leu Arg Ser Leu Gly Tyr Phe Asp Tyr Trp Gly Gln Gly Thr Thr Leu
                100                 105                 110

Thr Val Ser Ser Ala Lys Thr Thr Ala Pro Ser Val Tyr Pro Leu Ala
            115                 120                 125

Pro Gly
    130

<210> SEQ ID NO 118
<211> LENGTH: 116
<212> TYPE: PRT
<213> ORGANISM: Artificial Sequence
<220> FEATURE:
<223> OTHER INFORMATION: Variable region, heavy chain of the 2G11
      antibody

<400> SEQUENCE: 118

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Thr Tyr
            20                  25                  30

-continued

```
Trp Met His Trp Val Lys Gln Arg Pro Gly Gln Gly Leu Glu Trp Ile
        35                  40                  45

Gly Glu Ile Asn Pro Ser Asn Gly Arg Ala Asn Tyr Asn Glu Lys Phe
 50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Leu Arg Ser Leu Gly Tyr Phe Asp Tyr Trp Gly Gln Gly Thr Thr Leu
                100                 105                 110

Thr Val Ser Ser
            115
```

<210> SEQ ID NO 119
<211> LENGTH: 127
<212> TYPE: PRT
<213> ORGANISM: Artificial Sequence
<220> FEATURE:
<223> OTHER INFORMATION: Light chain of the 2G11 antibody without leader
      sequence

<400> SEQUENCE: 119

```
Asp Val Val Met Thr Gln Ser Pro Leu Ser Leu Pro Val Ser Leu Gly
 1               5                  10                  15

Asp Gln Ala Ser Ile Ser Cys Arg Ser Ser Gln Ser Leu Val His Ser
                 20                  25                  30

Asn Gly Asn Thr Tyr Leu His Trp Tyr Leu Gln Lys Ala Gly Gln Ser
            35                  40                  45

Pro Lys Phe Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Tyr Thr Phe Gly Gly Gly Thr Lys Leu Glu Ile Lys
                100                 105                 110

Arg Ala Asp Ala Ala Pro Thr Val Ser Ile Phe Pro Pro Ser Ser
            115                 120                 125
```

<210> SEQ ID NO 120
<211> LENGTH: 112
<212> TYPE: PRT
<213> ORGANISM: Artificial Sequence
<220> FEATURE:
<223> OTHER INFORMATION: Variable region, light chain of the 2G11
      antibody

<400> SEQUENCE: 120

```
Asp Val Val Met Thr Gln Ser Pro Leu Ser Leu Pro Val Ser Leu Gly
 1               5                  10                  15

Asp Gln Ala Ser Ile Ser Cys Arg Ser Ser Gln Ser Leu Val His Ser
                 20                  25                  30

Asn Gly Asn Thr Tyr Leu His Trp Tyr Leu Gln Lys Ala Gly Gln Ser
            35                  40                  45

Pro Lys Phe Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80
```

```
Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110
```

<210> SEQ ID NO 121
<211> LENGTH: 133
<212> TYPE: PRT
<213> ORGANISM: Artificial Sequence
<220> FEATURE:
<223> OTHER INFORMATION: Heavy chain of the 1H5 antibody without leader
      sequence

<400> SEQUENCE: 121

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Arg Ser Tyr
            20                  25                  30

Ala Met Ser Trp Val Arg Gln Thr Pro Glu Lys Gly Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Gly Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Gly Tyr Asp Gly Tyr Tyr Glu Arg Ile Trp Tyr Tyr Ala Met Asp
            100                 105                 110

Tyr Trp Gly Gln Gly Thr Ser Val Thr Val Ser Ser Ala Lys Thr Thr
        115                 120                 125

Pro Pro Ser Val Tyr
    130
```

<210> SEQ ID NO 122
<211> LENGTH: 124
<212> TYPE: PRT
<213> ORGANISM: Artificial Sequence
<220> FEATURE:
<223> OTHER INFORMATION: Variable region, heavy chain of the 1H5
      antibody

<400> SEQUENCE: 122

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Arg Ser Tyr
            20                  25                  30

Ala Met Ser Trp Val Arg Gln Thr Pro Glu Lys Gly Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Gly Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Gly Tyr Asp Gly Tyr Tyr Glu Arg Ile Trp Tyr Tyr Ala Met Asp
            100                 105                 110

Tyr Trp Gly Gln Gly Thr Ser Val Thr Val Ser Ser
        115                 120
```

```
<210> SEQ ID NO 123
<211> LENGTH: 122
<212> TYPE: PRT
<213> ORGANISM: Artificial Sequence
<220> FEATURE:
<223> OTHER INFORMATION: Light chain of the 1H5 antibody without leader
      sequence

<400> SEQUENCE: 123

Asp Ile Val Met Thr Gln Ser Gln Lys Phe Met Ser Thr Ser Val Gly
1               5                   10                  15

Asp Arg Val Thr Val Ser Cys Lys Ala Ser Gln Asn Val Gly Thr Ile
            20                  25                  30

Val Ala Trp Tyr Gln Gln Lys Pro Gly Gln Ser Pro Lys Ala Leu Ile
        35                  40                  45

Tyr Ser Ala Ser Tyr Arg Phe Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Thr Tyr Pro Leu
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Ser
            115                 120

<210> SEQ ID NO 124
<211> LENGTH: 107
<212> TYPE: PRT
<213> ORGANISM: Artificial Sequence
<220> FEATURE:
<223> OTHER INFORMATION: Variable region, light chain of the 1H5
      antibody

<400> SEQUENCE: 124

Asp Ile Val Met Thr Gln Ser Gln Lys Phe Met Ser Thr Ser Val Gly
1               5                   10                  15

Asp Arg Val Thr Val Ser Cys Lys Ala Ser Gln Asn Val Gly Thr Ile
            20                  25                  30

Val Ala Trp Tyr Gln Gln Lys Pro Gly Gln Ser Pro Lys Ala Leu Ile
        35                  40                  45

Tyr Ser Ala Ser Tyr Arg Phe Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Thr Tyr Pro Leu
                85                  90                  95

Thr Phe Gly Ser Gly Thr Lys Leu Glu Ile Lys
            100                 105

<210> SEQ ID NO 125
<211> LENGTH: 1389
<212> TYPE: DNA
<213> ORGANISM: Artificial Sequence
<220> FEATURE:
<223> OTHER INFORMATION: Nucleotide sequence encoding the heavy chain of
      the recombinant chimeric human-mouse hFc-F233-3A8 antibody
```

<400> SEQUENCE: 125

```
atgcctctgc tgctgctgct gcctctgctg tgggccgggg ctctggctca ggtccagctg      60
cagcagcctg gtgccgaact ggtcaagcca ggcgccagcg tgaagctgtc ttgcaaggct     120
tccggctaca ccttcacaaa ctattggatg cactgggtga agcagaggcc cggacagggc     180
ctggagtgga tcggagagat caaccctagc aatggccggg ccaactacaa tgagaagttt     240
aagtctaagg ctaccctgac agtggacaag tccagctcta ccgcctatat gcagctgtcc     300
agcctgacat ctgaggattc cgccgtgtac tattgtgcta ggtctccata cggttactac     360
gactattggg gcaggggac aactctgact gtgagcagcg ctagcacaaa agggccatcc      420
gtgtttcctc tggctccatc ctcaaaatca acttctgggg ggactgctgc tctgggctgc     480
ctggtgaagg actacttccc agagcccgtc accgtgtcat ggaacagcgg agcactgact     540
agcggagtcc acacctttcc agcagtgctg cagagctccg gactgtactc cctgtctagt     600
gtggtcacag tgccttcaag ctccctgggg actcagacct atatctgcaa cgtgaatcac     660
aagccctcca atactaaggt cgacaaacga gtggagccta gtcttgtga taaaacacat      720
acttgccccc cttgtcctgc accagaactg ctgggaggac ctagcgtgtt cctgttccca     780
cccaagccaa agacacccct gatgattagt agaacccctg aggtcacatg cgtggtcgtg     840
gacgtgagcc acgaggaccc cgaagtcaag ttcaactggt acgtggatgg cgtcgaagtg     900
cataatgcta agacaaaacc ccgggaggaa cagtacaaca gtacctatag agtcgtgtca     960
gtcctgacag tgctgcatca ggattggctg aacgggaaag agtataagtg caaagtgtcc    1020
aataaggccc tgcccgctcc tatcgagaaa actatttcta aggctaaagg ccagccaagg    1080
gaacccccagg tgtacaccct gcctccatca cgcgaggaaa tgacaaagaa ccaggtcagc    1140
ctgacttgtc tggtgaaagg gttctatcca tctgacatcg cagtggagtg ggaaagtaat    1200
ggacagcccg aaaacaatta caagaccaca ccccctgtgc tggactccga tggatctttc    1260
tttctgtata gcaagctgac cgtggataaa tcccggtggc agcagggcaa tgtcttttct    1320
tgtagtgtga tgcacgaagc cctgcataac cattacaccc agaaaagcct gagcctgtcc    1380
cccggcaag                                                            1389
```

<210> SEQ ID NO 126
<211> LENGTH: 463
<212> TYPE: PRT
<213> ORGANISM: Artificial Sequence
<220> FEATURE:
<223> OTHER INFORMATION: Heavy chain of the recombinant chimeric human-mouse hFc-F233-3A8 antibody with signal peptide

<400> SEQUENCE: 126

```
Met Pro Leu Leu Leu Leu Pro Leu Leu Trp Ala Gly Ala Leu Ala
 1               5                  10                  15

Gln Val Gln Leu Gln Gln Pro Gly Ala Glu Leu Val Lys Pro Gly Ala
            20                  25                  30

Ser Val Lys Leu Ser Cys Lys Ala Ser Gly Tyr Thr Phe Thr Asn Tyr
        35                  40                  45

Trp Met His Trp Val Lys Gln Arg Pro Gly Gln Gly Leu Glu Trp Ile
    50                  55                  60

Gly Glu Ile Asn Pro Ser Asn Gly Arg Ala Asn Tyr Asn Glu Lys Phe
65                  70                  75                  80

Lys Ser Lys Ala Thr Leu Thr Val Asp Lys Ser Ser Thr Ala Tyr
                85                  90                  95
```

```
Met Gln Leu Ser Ser Leu Thr Ser Glu Asp Ser Ala Val Tyr Tyr Cys
                100                 105                 110

Ala Arg Ser Pro Tyr Gly Tyr Tyr Asp Tyr Trp Gly Gln Gly Thr Thr
            115                 120                 125

Leu Thr Val Ser Ser Ala Ser Thr Lys Gly Pro Ser Val Phe Pro Leu
        130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
        210                 215                 220

Thr Lys Val Asp Lys Arg Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
        290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
        370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
        450                 455                 460

<210> SEQ ID NO 127
<211> LENGTH: 717
<212> TYPE: DNA
<213> ORGANISM: Artificial Sequence
<220> FEATURE:
<223> OTHER INFORMATION: Nucleotide sequence encoding the light chain of
      the  recombinant chimeric human-mouse hFc-F233-3A8 antibody
```

<400> SEQUENCE: 127

```
atgcggctgc ctgctcagct gctgggcctg ctgatgctgt gggtgtccgg ctcctctggg    60
gatgtgctga tgactcagac tcctctgagc ctgccagtgt ctctgggcga ccaggcctct   120
atctcctgca gatccagcca gtccctgctg cacagcaacg gcaataccta cttccattgg   180
tatctgcaga agcccggcca gtctcctaag ctgctgatct acaaggtgtc caacaggttc   240
tttggcgtgc ccgaccggtt cagcggatct ggatccggca ccgacttcac cctgaagatc   300
agccgcgtgg aggctgaaga cctgggcgtg tattttgtt cacagattac tcatgtcccc   360
ctgacctttg gtgccggtac caaagtggag atcaagcgaa ctgtggccgc tccaagtgtc   420
ttcattttc accctccga cgaacagctg aagagcggaa cagcatctgt ggtctgtctg   480
ctgaacaatt ctaccccag ggaagctaaa gtgcagtgga aggtcgataa cgcactgcag   540
tctggcaata gtcaggagtc agtgacagaa caggactcca agatagcac ttattctctg   600
tctagtaccc tgacactgtc taaggccgac tacgagaagc ataaagtgta tgcttgtgaa   660
gtcactcatc aggggctgtc ttctccagtg accaagtcct tcaatagggg cgaatgt    717
```

<210> SEQ ID NO 128
<211> LENGTH: 239
<212> TYPE: PRT
<213> ORGANISM: Artificial Sequence
<220> FEATURE:
<223> OTHER INFORMATION: Light chain of the recombinant chimeric human-mouse hFc-F233-3A8 antibody with signal peptide

<400> SEQUENCE: 128

```
Met Arg Leu Pro Ala Gln Leu Leu Gly Leu Leu Met Leu Trp Val Ser
1               5                   10                  15

Gly Ser Ser Gly Asp Val Leu Met Thr Gln Thr Pro Leu Ser Leu Pro
            20                  25                  30

Val Ser Leu Gly Asp Gln Ala Ser Ile Ser Cys Arg Ser Ser Gln Ser
        35                  40                  45

Leu Leu His Ser Asn Gly Asn Thr Tyr Phe His Trp Tyr Leu Gln Lys
    50                  55                  60

Pro Gly Gln Ser Pro Lys Leu Leu Ile Tyr Lys Val Ser Asn Arg Phe
65                  70                  75                  80

Phe Gly Val Pro Asp Arg Phe Ser Gly Ser Gly Ser Gly Thr Asp Phe
                85                  90                  95

Thr Leu Lys Ile Ser Arg Val Glu Ala Glu Asp Leu Gly Val Tyr Phe
            100                 105                 110

Cys Ser Gln Ile Thr His Val Pro Leu Thr Phe Gly Ala Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205
```

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 129
<211> LENGTH: 1392
<212> TYPE: DNA
<213> ORGANISM: Artificial Sequence
<220> FEATURE:
<223> OTHER INFORMATION: Nucleotide sequence encoding the heavy chain of
      the recombinant chimeric human-mouse hFc-F236-1B6 antibody

<400> SEQUENCE: 129

```
atgcctctgc tgctgctgct gcctctgctg tgggctgggg ctctggctca ggtccagctg     60
aaagaaagcg gtcccggtct ggtcgcccca tcccagagcc tgtctatcac ctgcacagtg    120
agcggcttct ccctgagcag gtacaacgtg cactgggtgc ggcagccacc tggcaagggc    180
ctggagtggc tgggaatgat ctggggagga ggctctaccg actataattc cgccctgaag    240
agcagactgt ctatctccaa ggataacagc aagtctcagg tgtttctgaa gatgaactcc    300
ctgcagaccg acgatacagc catgtactat tgtgctcgca cggtgccaa ctgggactgg    360 tttgcctact ggggtcaggg aactctggtc actgtcagca gcgctagcac aaaagggcca    420
tccgtgtttc ctctggctcc atcctcaaaa tcaacttctg gggggactgc tgctctgggc    480
tgcctggtga aggactactt cccagagccc gtcaccgtgt catgaacag cggagcactg    540 actagcggag tccacacctt tccagcagtg ctgcagagct ccggactgta ctccctgtct    600
agtgtggtca cagtgccttc aagctccctg gggactcaga cctatatctg caacgtgaat    660
cacaagccct ccaatactaa ggtcgacaaa cgagtggagc taagtcttg tgataaaaca    720 catacttgcc ccccttgtcc tgcaccagaa ctgctgggag acctagcgt gttcctgttt    780 ccacccaagc caaaagacac cctgatgatt agtagaaccc ctgaggtcac atgcgtggtc    840
gtggacgtga gccacgagga ccccgaagtc aagttcaact ggtacgtgga tggcgtcgaa    900
gtgcataatg ctaagacaaa accccgggag aacagtaca acagtaccta tagagtcgtg    960
tcagtcctga cagtgctgca tcaggattgg ctgaacggga agagtataa gtgcaaagtg   1020 tccaataagg ccctgcccgc tcctatcgag aaaactattt ctaaggctaa aggccagcca   1080
agggaacccc aggtgtacac cctgcctcca tcacgcgagg aaatgacaaa gaaccaggtc   1140
agcctgactt gtctggtgaa agggttctat ccatctgaca tcgcagtgga gtgggaaagt   1200
aatggacagc cgaaaacaa ttacaagacc acaccccctg tgctggactc cgatggatct   1260
ttctttctgt atagcaagct gaccgtggat aaatcccggt ggcagcaggg caatgtcttt   1320
tcttgtagtg tgatgcacga agccctgcat aaccattaca cccagaaaag cctgagcctg   1380 tccccggca ag                                                       1392
```

<210> SEQ ID NO 130
<211> LENGTH: 464
<212> TYPE: PRT
<213> ORGANISM: Artificial Sequence
<220> FEATURE:
<223> OTHER INFORMATION: Heavy chain of the recombinant chimeric human-
      mouse hFc-F236-1B6 antibody with signal peptide

```
<400> SEQUENCE: 130

Met Pro Leu Leu Leu Leu Pro Leu Leu Trp Ala Gly Ala Leu Ala
1               5                   10                  15

Gln Val Gln Leu Lys Glu Ser Gly Pro Gly Leu Val Ala Pro Ser Gln
            20                  25                  30

Ser Leu Ser Ile Thr Cys Thr Val Ser Gly Phe Ser Leu Ser Arg Tyr
            35                  40                  45

Asn Val His Trp Val Arg Gln Pro Pro Gly Lys Gly Leu Glu Trp Leu
        50                  55                  60

Gly Met Ile Trp Gly Gly Ser Thr Asp Tyr Asn Ser Ala Leu Lys
65                  70                  75                  80

Ser Arg Leu Ser Ile Ser Lys Asp Asn Ser Lys Ser Gln Val Phe Leu
                85                  90                  95

Lys Met Asn Ser Leu Gln Thr Asp Asp Thr Ala Met Tyr Tyr Cys Ala
            100                 105                 110

Arg Asn Gly Ala Asn Trp Asp Trp Phe Ala Tyr Trp Gly Gln Gly Thr
            115                 120                 125

Leu Val Thr Val Ser Ser Ala Ser Thr Lys Gly Pro Ser Val Phe Pro
            130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
            195                 200                 205

Ser Leu Gly Thr Gln Thr Tyr Ile Cys Asn Val Asn His Lys Pro Ser
            210                 215                 220

Asn Thr Lys Val Asp Lys Arg Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
            275                 280                 285

Glu Val Lys Phe Asn Trp Tyr Val Asp Gly Val Glu Val His Asn Ala
        290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
            355                 360                 365

Pro Pro Ser Arg Glu Glu Met Thr Lys Asn Gln Val Ser Leu Thr Cys
            370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415
```

Ser Asp Gly Ser Phe Phe Leu Tyr Ser Lys Leu Thr Val Asp Lys Ser
                420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 131
<211> LENGTH: 720
<212> TYPE: DNA
<213> ORGANISM: Artificial Sequence
<220> FEATURE:
<223> OTHER INFORMATION: Nucleotide sequence encoding the light chain of
      the recombinant chimeric human-mouse hFc-F236-1B6 antibody

<400> SEQUENCE: 131
atgcgcctgc ctgctcagct gctgggcctg ctgatgctgt gggtctctgg gtcctctggg      60
gatattgtca tgtctcagtc accaagctct ctgccagtgt ccgtgggcga aaggtgacc     120 atgtcctgca agtccagcca gagcctgctg tactcttcca accagaagaa ttacctggcc     180
tggtatcagc agaagcccgg ccagtctcct aagctgctga tctattgggc tagcacaagg     240
gagtctggcg tgcccgaccg gttcaccgga tccggaagcg gcacagactt caccctgaca     300
atcagctctg tgaaggccga ggacctggca gtctattatt gtcagcagta ttacagctat     360
ccattcactt ttggcagcgg taccaaagtg gagatcaagc gaactgtggc cgctccaagt     420
gtcttcattt tccccaccct cgacgaacag ctgaagagcg aacagcatc tgtggtctgt     480 ctgctgaaca atttctaccc cagggaagct aaagtgcagt ggaaggtcga taacgcactg     540
cagtctggca atagtcagga gtcagtgaca gaacaggact ccaaagatag cacttattct     600
ctgtctagta ccctgacact gtctaaggcc gactacgaga agcataaagt gtatgccttgt     660 gaagtcactc atcaggggct gtcttctcca gtgaccaagt ccttcaatag ggcgaatgt     720

<210> SEQ ID NO 132
<211> LENGTH: 240
<212> TYPE: PRT
<213> ORGANISM: Artificial Sequence
<220> FEATURE:
<223> OTHER INFORMATION: Light chain of the recombinant chimeric human-
      mouse hFc-F236-1B6 antibody with signal peptide

<400> SEQUENCE: 132

Met Arg Leu Pro Ala Gln Leu Leu Gly Leu Leu Met Leu Trp Val Ser
1               5                   10                  15

Gly Ser Ser Gly Asp Ile Val Met Ser Gln Ser Pro Ser Ser Leu Pro
            20                  25                  30

Val Ser Val Gly Glu Lys Val Thr Met Ser Cys Lys Ser Ser Gln Ser
        35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Ser Tyr Pro Phe Thr Phe Gly Ser Gly Thr
        115                 120                 125

```
Lys Val Glu Ile Lys Arg Thr Val Ala Ala Pro Ser Val Phe Ile Phe
    130             135             140

Pro Pro Ser Asp Glu Gln Leu Lys Ser Gly Thr Ala Ser Val Val Cys
145             150             155             160

Leu Leu Asn Asn Phe Tyr Pro Arg Glu Ala Lys Val Gln Trp Lys Val
                165             170             175

Asp Asn Ala Leu Gln Ser Gly Asn Ser Gln Glu Ser Val Thr Glu Gln
            180             185             190

Asp Ser Lys Asp Ser Thr Tyr Ser Leu Ser Ser Thr Leu Thr Leu Ser
        195             200             205

Lys Ala Asp Tyr Glu Lys His Lys Val Tyr Ala Cys Glu Val Thr His
    210             215             220

Gln Gly Leu Ser Ser Pro Val Thr Lys Ser Phe Asn Arg Gly Glu Cys
225             230             235             240
```